(12) United States Patent
Buettelmann et al.

(10) Patent No.: US 8,877,782 B2
(45) Date of Patent: *Nov. 4, 2014

(54) ISOXAZOLO-PYRIDINE DERIVATIVES

(71) Applicant: Roche Palo Alto LLC, So. San Francisco, CA (US)

(72) Inventors: Bernd Buettelmann, Schopfheim (DE); Roland Jakob-Roetne, Inzlingen (DE); Henner Knust, Rheinfelden (DE); Matthew C. Lucas, Lexington, MA (US); Andrew Thomas, Binningen (CH)

(73) Assignee: Roche Palo Alto LLC, So. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,191

(22) Filed: Jun. 12, 2013

(65) Prior Publication Data

US 2013/0274468 A1     Oct. 17, 2013

Related U.S. Application Data

(60) Division of application No. 13/370,444, filed on Feb. 10, 2012, now Pat. No. 8,518,974, which is a continuation of application No. 12/325,293, filed on Dec. 1, 2008, now abandoned.

(30) Foreign Application Priority Data

Dec. 4, 2007   (EP) ...................... 07122240

(51) Int. Cl.
| | |
|---|---|
| *A61K 31/4427* | (2006.01) |
| *C07D 413/12* | (2006.01) |
| *C07D 491/10* | (2006.01) |
| *C07D 413/14* | (2006.01) |
| *C07D 487/04* | (2006.01) |
| *C07D 491/08* | (2006.01) |
| *C07D 417/14* | (2006.01) |

(52) U.S. Cl.
CPC ............ *C07D 413/12* (2013.01); *C07D 491/10* (2013.01); *C07D 413/14* (2013.01); *C07D 487/04* (2013.01); *C07D 491/08* (2013.01); *C07D 417/14* (2013.01)
USPC ..................... 514/340; 546/268.1; 546/272.1; 514/336

(58) Field of Classification Search
USPC ..................... 514/336, 340; 546/268.1, 272.1
See application file for complete search history.

(56) References Cited

U.S. PATENT DOCUMENTS

| | | | | |
|---|---|---|---|---|
| 5,080,708 | A * | 1/1992 | Freund et al. .................. | 504/191 |
| 8,518,974 | B2 * | 8/2013 | Buettelmann et al. ........ | 514/340 |
| 2004/0058970 | A1 | 3/2004 | Boase et al. | |
| 2007/0161654 | A1 | 7/2007 | Buettelmann et al. | |
| 2007/0191421 | A1 | 8/2007 | Buettelmann et al. | |

FOREIGN PATENT DOCUMENTS

| | | |
|---|---|---|
| WO | 2007039389 | 4/2007 |
| WO | 2009/071476 | 6/2009 |

OTHER PUBLICATIONS

The Mylaysian Examination Report, issued on Oct. 31, 2013, in the corresponding Mylaysian Patent Application No. PI 2010002566.
The English summary of the Egyptian Office Action, issued on Mar. 4, 2014, in the corresponding Egyptian application No. PCT 929/2010.

* cited by examiner

*Primary Examiner* — Kamal Saeed
*Assistant Examiner* — Janet L Coppins

(57) ABSTRACT

The present invention is concerned with isoxazole-pyridine derivatives of formula I

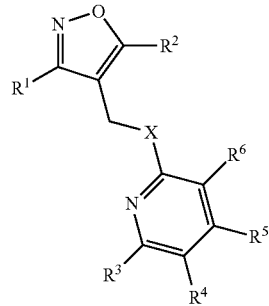

wherein X, $R^1$ to $R^6$ are as described herein. The compounds are active on the GABA A α5 receptor binding site and useful for the treatment of cognitive disorders, such as Alzheimer's disease.

36 Claims, No Drawings

ISOXAZOLO-PYRIDINE DERIVATIVES

CROSS-REFERENCE TO RELATED APPLICATIONS

This application is a divisional application of U.S. application Ser. No. 13/370,444, filed Feb. 10, 2012, which is a continuation of U.S. application Ser. No. 12/325,293, filed Dec. 1, 2008, now abandoned, which claims the benefit of European Patent Application No. 07122240.0, filed Dec. 4, 2007, which. Each of these applications is hereby incorporated by reference herein in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides isoxazole-pyridine derivatives having affinity and selectivity for GABA A α5 receptor binding site, their manufacture, pharmaceutical compositions containing them and their use as cognitive enhancer or for the treatment of cognitive disorders like Alzheimer's disease.

In particular, the present invention provides isoxazole-pyridine derivatives of formula I

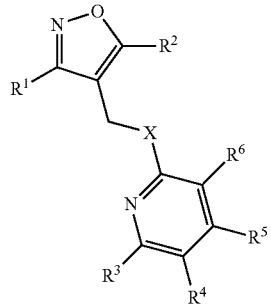

wherein X, $R^1$ to $R^6$ are as described in claim 1.

The most preferred indication in accordance with the present invention is Alzheimer's disease.

DETAILED DESCRIPTION OF THE INVENTION

The following definitions of the general terms used in the present description apply irrespective of whether the terms in question appear alone or in combination.

As used herein, the term "alkyl" denotes a saturated straight- or branched-chain hydrocarbon group containing from 1 to 7 carbon atoms, for example, methyl, ethyl, propyl, isopropyl, n-butyl, iso-butyl, sec-butyl, tert-butyl and the like. Preferred alkyl groups are groups with 1 to 4 carbon atoms.

The term "halo" or "halogen" denotes chloro, iodo, fluoro and bromo.

The term "halo-$C_{1-7}$-alkyl", "$C_{1-7}$-haloalkyl" or "$C_{1-7}$-alkyl optionally substituted with halo" denotes a $C_{1-7}$-alkyl group as defined above wherein at least one of the hydrogen atoms of the alkyl group is replaced by a halogen atom, preferably fluoro or chloro, most preferably fluoro. Examples of halo-$C_{1-7}$-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below. Among the preferred halo-$C_{1-7}$-alkyl groups are difluoro- or trifluoro-methyl or -ethyl.

The term "hydroxy-$C_{1-7}$-alkyl", "$C_{1-7}$-hydroxyalkyl" or "$C_{1-7}$-alkyl optionally substituted with hydroxy" denotes a $C_{1-7}$-alkyl group as defined above wherein at least one of the hydrogen atoms of the alkyl group is replaced by a hydroxy group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one hydroxy group, as well as those groups specifically illustrated by the examples herein below.

The term "cyano-$C_{1-7}$-alkyl", "$C_{1-7}$-cyanoalkyl" or "$C_{1-7}$-alkyl optionally substituted with cyano" denotes a $C_{1-7}$-alkyl group as defined above wherein at least one of the hydrogen atoms of the alkyl group is replaced by a cyano group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more cyano group(s), preferably by one, two or three, and more preferably by one cyano group, as well as those groups specifically illustrated by the examples herein below.

The term "alkoxy" denotes a group —O—R wherein R is alkyl as defined above.

The term "aryl" refers to a monovalent aromatic carbocyclic ring system, preferably to phenyl or naphthyl, and more preferably to phenyl. Aryl is optionally substituted as described herein. If not further indicated, phenyl may optionally be substituted with one or more, in particular with 1, 2, or 3, and more preferably with 1 or 2 substituents selected from halo, CN, NO$_2$, hydroxy, C$_{2-7}$alkyl, C$_{1-7}$alkoxy, C$_{1-7}$haloalkyl, C$_{2-7}$hydroxyalkyl, C$_{1-7}$cyanoalkyl, C$_{1-7}$haloalkoxy, and C$_{3-7}$cycloalkyl.

The term "aromatic" means aromatic according to Hückel's rule. A cyclic molecule follows Hückel's rule when the number of its π-electrons equals 4n+2 where n is zero or any positive integer.

The term "C$_{1-7}$-haloalkoxy" or "halo-C$_{1-7}$-alkoxy" denotes a C$_{1-7}$-alkoxy group as defined above wherein at least one of the hydrogen atoms of the alkoxy group is replaced by a halogen atom, preferably fluoro or chloro, most preferably fluoro. Examples of halo-C$_{1-7}$-alkoxy include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro atoms, as well as those groups specifically illustrated by the examples herein below. Among the preferred halo-C$_{1-7}$-alkoxy groups are difluoro- or trifluoro-methoxy or ethoxy substituted as described above, preferably OCF$_3$.

The term "cycloalkyl" refers to a monovalent saturated cyclic hydrocarbon radical of 3 to 7 ring carbon atoms, preferably 3 to 6 carbon atoms, such as cyclopropyl, cyclobutyl, cyclopentyl, or cyclohexyl.

The term "heterocycloalkyl" refers to a monovalent 3 to 7 membered saturated monocyclic ring containing one, two or three ring heteroatoms selected from N, O and S. One or two ring heteroatoms are preferred. Preferred are 4 to 6 membered heterocycloalkyl or 5 to 6 membered heterocycloalkyl, each containing one or two ring heteroatoms selected from N, O and S. Examples for heterocycloalkyl moieties are tetrahydrofuranyl, tetrahydropyranyl, pyrrolidinyl, morpholinyl, thiomorpholinyl, piperidinyl, or piperazinyl. "Heterocycloalkyl" is hence a subgroup of "heterocyclyl" as defined below. Heterocycloalkyl is optionally substituted as described herein.

The term "heteroaryl" refers to a monovalent aromatic 5- or 6-membered monocyclic ring containing one, two, or three ring heteroatoms selected from N, O, and S, the remaining ring atoms being C. Preferably, the 5- or 6-membered heteroaryl ring contains one or two ring heteroatoms. 6-membered heteroaryl are preferred. Examples for heteroaryl moieties include but are not limited to furanyl, thiophenyl, pyridinyl, pyrimidinyl, pyrazinyl, pyrazolyl, imidazolyl, oxazolyl, isoxazolyl, thiazolyl, isothiazolyl, triazolyl, 1,2,4-oxadiazolyl, or 1,3,4-oxadiazolyl. Preferred heteroaryl groups are pyridinyl, pyrazolyl, isoxazolyl, thiazolyl, or 1,2,4-oxadiazolyl.

The term "heterocyclyl" or "heterocyclyl moiety" refers to a monovalent saturated or partially saturated 3- to 7-membered monocyclic or 9- to 10-membered bicyclic ring system wherein one, two, three or four ring carbon atoms have been replaced by N, O or S, and with the attachment point on the saturated or partially unsaturated ring of said ring system. Such bicyclic heterocyclyl moieties hence include aromatic rings annelated to saturated rings. Where applicable, "heterocyclyl moiety" further includes cases where two residues R' and R" together with the nitrogen to which they are bound form such a heterocyclyl moiety. Examples for heterocyclyl include but are not limited to tetrahydropyridinyl, isochromanyl, chromanyl, oxethanyl, isoxazolidinyl, dihydropyridazinyl, tetrahydrofuranyl, tetrahydropyranyl, tetrahydrothiopyranyl, piperidinyl, piperazinyl, pyrrolidinyl, as well as morpholinyl, thiomorpholinyl, 5,6,7,8-tetrahydro-[1,2,4]triazolo[4,3-a]pyrazinyl, 4,5,6,7-tetrahydro-pyrazolo[1,5-a]pyrimidinyl, hexahydrothiopyranyl, or 6-oxa-3-aza-bicyclo[3.1.1]heptanyl.

Examples for substituted heterocyclyl include, but are not limited to oxetan-3-ol, 3-oxoisazolidinyl, 3-oxo-dihydropyridazinyl, 6-methyl-3-oxo-dihydropyridazinyl, 2,2-dimethyl-tetrahydropyranyl, tetrahydrothiopyranyl dioxide, N-methyl-piperidinyl, N-ethyl-piperidinyl, N-isopropyl-piperidinyl, N-benzyl-piperidinyl, piperidin-1-yl-acetic t-butyl ester, piperidin-1-yl-acetic acid ethyl ester, piperidin-1-yl-acetic acid, N-(1-ethylcarbamoylmethyl-piperidinyl), N-(1-cyclopropylcarbamoylmethylpiperidinyl), N-{1[(2,2,2-trifluoro-ethylcarbamoyl)methyl]piperidinyl}, N-{1-[(2-hydroxyethylcarbamoyl)methyl]piperidinyl}, N-{1-[(tetrahydropyran-4-ylcarbamoyl)methyl]piperidinyl}, as well as 2-oxo-pyrrolidinyl, 4,4-difluoro-piperidinyl, dioxothiomorpholinyl, 3,3-dimethyl-morpholinyl, or 1-methyl-1,2,3,6-tetrahydropyridinyl.

The term "spirocyclic heterocycle" denotes a saturated bicyclic ring system wherein the two rings have one carbon atom in common. The spirocyclic heterocycle may be from 7- to 12-membered, preferably from 7- to 11-membered. As an example for a spirocyclic heterocycle, 2-oxa-6-aza-spiro[3.3]heptyl may be mentioned. The spirocyclic heterocycle may be optionally substituted as described herein.

The term "oxo" when referring to substituents on heterocycloalkyl, heterocyclyl or on a heterocycle means that an oxygen atom is attached to the ring. Thereby, the "oxo" may either replace two hydrogen atoms on a carbon atom, or it may simply be attached to sulfur, so that the sulfur exists in oxidized form, i.e. bearing one or two oxygens.

When indicating the number of substituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In general, the nomenclature used in this application is based on AUTONOM™ v.4.0, a Beilstein Institute computerized system for the generation of IUPAC systematic nomenclature.

In detail, the present invention relates to compounds of the general formula (I)

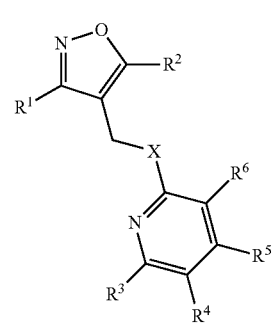

I wherein

X is O or NH;

$R^1$ is phenyl, pyridinyl, or pyrimidinyl, each optionally substituted with 1, 2 or 3 halo, $R^2$ is H, $CH_3$, or $CF_3$;

$R^3$, $R^4$, $R^5$, and $R^6$ each are independently

H, $C_{1-7}$alkyl, optionally substituted with one or more halo, cyano, or hydroxy, $C_{1-7}$alkoxy, optionally substituted with one or more halo,

CN, halo, $NO_2$,

S—$C_{1-7}$alkyl,

S(O)—$C_{1-7}$alkyl benzyloxy, optionally substituted with one or more E,

—C(O)—$R^a$, wherein $R^a$ is hydroxy, $C_{1-7}$alkoxy, $C_{1-7}$alkyl, phenoxy or phenyl, 3- to 7-membered heterocyclyl, optionally substituted with one or more A, —C(O)—$NR^bR^c$, wherein $R^b$ and $R^c$ are each independently

H, $C_{1-7}$alkyl, optionally substituted with one or more halo, methyl, —$(CH_2)_t$-hydroxy, or cyano, —$(CH_2)_t$—$C_{3-7}$cycloalkyl, optionally substituted by one or more B, and t is 0, 1, 2, 3, 4, 5 or 6, —$(CH_2)_u$—O—$C_{1-7}$alkyl, wherein u is 2, 3, 4, 5 or 6, —$CHR^i$—C(O)$OR^{ii}$, wherein $R^i$ is H, benzyl or $C_{1-4}$alkyl, and $R^{ii}$ is H or $C_{1-7}$alkyl, —$S(O)_2$—$C_{1-7}$alkyl, —$S(O)_2$—$C_{3-7}$cycloalkyl, —$(CH_2CH_2O)_vR^{iii}$, wherein v is from 1 to 3, and $R^{iii}$ is H or $C_{1-7}$alkyl, —$(CH_2)_w$-heteroaryl or —$(CH_2)_w$-aryl, each optionally substituted by one or more E, and wherein w is 0, 1, 2, 3, or 4, —$(CH_2)_x$-heterocyclyl, wherein x is 0, 1, 2, 3 or 4, and wherein heterocyclyl is optionally substituted by one or more oxo, $C_{1-7}$alkyl, $C_{3-7}$cycloalkyl, optionally substituted with one or more B,

CN, benzyl, optionally substituted with one or more E,

—$(CH_2)_y$—C(O)$R^{iv}$, wherein y is 0, 1, 2, 3 or 4, and $R^{iv}$ is hydroxy, $C_{1-7}$alkyl, or $C_{1-7}$alkoxy, —$(CH_2)_z$—C(O)$NR^vR^{vi}$, —$(CH_2)_zNR^vR^{vi}$—C(O)—$C_{1-7}$alkyl or —$(CH_2)_zNR^vR^{vi}$—C(O)—O—$C_{1-7}$alkyl, wherein z is 0, 1, 2, 3 or 4, and $R^v$ and $R^{vi}$ are independently hydrogen, $C_{1-7}$alkyl, optionally substituted by one or more halo, OH or CN, $C_{3-7}$cycloalkyl, optionally substituted by one or more B, 5- or 6-membered heterocyclyl, optionally substituted by one or more A, or $R^v$ and $R^{vi}$ together with the nitrogen to which they are bound form a 5- or 6-membered heterocycloalkyl, optionally substituted by one or more A, or $R^b$ and $R^c$ together with the nitrogen to which they are bound form a heterocyclyl or heteroaryl moiety, optionally substituted with one or more A, or $R^b$ and $R^c$ together with the nitrogen to which they are bound form a 7- to 12-membered spirocyclic heterocycle, optionally substituted with one or more A;

with the proviso that $R^b$ and $R^c$ are not simultaneously H,

A is hydroxy, oxo, $C_{1-7}$alkyl, $C_{1-7}$alkoxy, $C_{1-7}$haloalkyl, $C_{1-7}$hydroxyalkyl, halo, or CN;

B is halo, hydroxy, CN, $C_{1-4}$alkyl, benzyloxy, or $C_{1-4}$haloalkyl; and

E is halo, CN, $NO_2$, hydroxy, $C_{1-7}$alkyl, $C_{1-7}$alkoxy, $C_{1-7}$haloalkyl, $C_{1-7}$hydroxyalkyl, $C_{1-7}$cyanoalkyl, $C_{1-7}$haloalkoxy, or $C_{3-7}$cycloalkyl;

or a pharmaceutically acceptable salt thereof.

In certain embodiments of the compound of formula I, X is O or NH. Each of these alternatives may be combined with any other embodiment as disclosed herein.

Further, it is to be understood that every embodiment relating to a specific residue $R^1$ to $R^6$ as disclosed herein may be combined with any other embodiment relating to another residue $R^1$ to $R^6$ as disclosed herein.

In certain embodiments of the compound of formula I, $R^1$ is phenyl, pyridinyl, or pyrimidinyl, each optionally substituted with one, two or three halo. Preferred halo substituents are chloro and fluoro. Preferably, phenyl is optionally substituted with one, two or three, more preferably with one or two halo substituents selected from chloro and fluoro. Thereby, the halo substituents are located at the ortho, meta or para-position or at the meta and para position of the phenyl ring in respect to the attachment to the isoxazole.

In certain embodiments of the compound of formula I, $R^2$ is methyl or trifluoromethyl.

In certain embodiments of the compound of formula I, $R^3$, $R^4$, $R^5$, and $R^6$ are as defined above.

In certain embodiments of the compound of formula I, $R^3$ is H, halo, CN or $C_{1-7}$alkyl. Preferably, $R^3$ is H, CN or $C_{1-4}$alkyl. More preferably, $R^3$ is H, CN or methyl.

In certain embodiments of the compound of formula I, $R^6$ is H, halo, CN or $C_{1-7}$alkyl. Preferably, $R^6$ is H, halo or $C_{1-4}$alkyl, more preferably, $R^6$ is H, Br or $C_{1-4}$alkyl. Even more ore preferably, $R^6$ is H, Br or methyl.

In certain embodiments of the compound of formula I, $R^4$ and $R^5$ are each independently as defined above.

In certain embodiments of the compound of formula I, $R^4$ and $R^5$ are each independently as defined above and $R^3$ and $R^6$ are each independently H, halo, CN or $C_{1-7}$alkyl.

In certain embodiments of the compound of formula I, $R^4$ or $R^5$, and in particular $R^4$ are

H, $C_{1-7}$alkyl, optionally substituted with one or more halo, cyano, or hydroxy, $C_{1-7}$alkoxy, optionally substituted with one or more halo,

CN, halo, $NO_2$,

S—$C_{1-7}$alkyl,

S(O)—$C_{1-7}$alkyl benzyloxy, optionally substituted with one or more E,

—C(O)—$R^a$, wherein $R^a$ is hydroxy, $C_{1-7}$alkoxy, $C_{1-7}$alkyl, phenoxy or phenyl, 3- to 7-membered heterocyclyl, optionally substituted with one or more A, —C(O)—$NR^bR^c$, wherein $R^b$ and $R^c$ are each independently

H, $C_{1-7}$alkyl, optionally substituted with one or more halo, methyl, —$(CH_2)_t$-hydroxy, or cyano, —(CH$_2$)$_t$—C$_{3-7}$cycloalkyl, optionally substituted by one or more B, and t is 0, 1, 2, 3, 4, 5 or 6, —(CH$_2$)$_u$—O—C$_{1-7}$alkyl, wherein it is 2, 3, 4, 5 or 6, —CHR$^i$—C(O)OR$^{ii}$, wherein R$^i$ is H, benzyl or C$_{1-4}$alkyl, and R$^{ii}$ is H or C$_{1-7}$alkyl, —S(O)$_2$—C$_{1-7}$alkyl, —S(O)$_2$—C$_{3-7}$cycloalkyl, —(CH$_2$CH$_2$O)$_v$R$^{iii}$, wherein v is from 1 to 3, and R$^{iii}$ is H or C$_{1-7}$alkyl, —(CH$_2$)$_w$-heteroaryl or —(CH$_2$)$_w$-aryl, each optionally substituted by one or more E, and wherein w is 0, 1, 2, 3, or 4, —(CH$_2$)$_x$-heterocyclyl, wherein x is 0, 1, 2, 3 or 4, and wherein heterocyclyl is optionally substituted by one or more oxo, C$_{1-7}$alkyl, C$_{3-7}$cycloalkyl, optionally substituted with one or more B,

CN, benzyl, optionally substituted with one or more E,

—(CH$_2$)$_y$—C(O)R$^{iv}$, wherein y is 0, 1, 2, 3 or 4, and R$^{iv}$ is hydroxy, C$_{1-7}$alkyl, or C$_{1-7}$alkoxy, —(CH$_2$)$_z$—C(O)NR$^v$R$^{vi}$, —(CH$_2$)$_z$NR$^v$R$^{vi}$—C(O)—C$_{1-7}$alkyl or —(CH$_2$)$_z$NR$^v$R$^{vi}$—C(O)—O—C$_{1-7}$alkyl, wherein z is 0, 1, 2, 3 or 4, and R$^v$ and R$^{vi}$ are independently hydrogen, C$_{1-7}$alkyl, optionally substituted by one or more halo, OH or CN, C$_{3-7}$cycloalkyl, optionally substituted by one or more B, 5- or 6-membered heterocyclyl, optionally substituted by one or more A, or R$^v$ and R$^{vi}$ together with the nitrogen to which they are bound form a 5- or 6-membered heterocycloalkyl, optionally substituted by one or more A, R$^b$ and R$^c$ together with the nitrogen to which they are bound form a heterocyclyl or heteroaryl moiety, optionally substituted with one or more A, or R$^b$ and R$^c$ together with the nitrogen to which they are bound form a 7- to 12-membered spirocyclic heterocycle, optionally substituted with one or more A;

with the proviso that R$^b$ and R$^c$ are not simultaneously H,

A is hydroxy, oxo, C$_{1-7}$alkyl, C$_{1-7}$alkoxy, C$_{1-7}$haloalkyl, C$_{1-7}$hydroxyalkyl, halo, or CN;

B is halo, hydroxy, CN, C$_{1-4}$alkyl, benzyloxy, or C$_{1-4}$haloalkyl; and

E is halo, CN, NO$_2$, hydroxy, C$_{1-7}$alkyl, C$_{1-7}$alkoxy, C$_{1-7}$haloalkyl, C$_{1-7}$hydroxyalkyl, C$_{1-7}$cyanoalkyl, C$_{1-7}$haloalkoxy, or C$_{3-7}$cycloalkyl;

or a pharmaceutically acceptable salt thereof.

In certain embodiments of the compound of formula I, R$^4$ is

H,

C$_{1-7}$alkyl, optionally substituted with one or more halo, cyano, or hydroxy, C$_{1-7}$alkoxy, optionally substituted with one or more halo,

CN, halo,

NO$_2$,

S—C$_{1-7}$alkyl,

S(O)—C$_{1-7}$alkyl, benzyloxy, optionally substituted with one or more E,

—C(O)—R$^a$, wherein R$^a$ is hydroxy, C$_{1-7}$alkoxy, C$_{1-7}$alkyl, phenoxy or phenyl, 3- to 7-membered heterocyclyl, optionally substituted with one or more A, —C(O)—NR$^b$R$^c$, wherein R$^b$ and R$^c$ are each independently

H,

C$_{1-7}$alkyl, optionally substituted with one or more halo, methyl, —(CH$_2$)$_t$-hydroxy, or cyano, —(CH$_2$)$_t$—C$_{3-7}$cycloalkyl, optionally substituted by one or more B, and t is 0, 1, 2, 3, 4, 5 or 6, —(CH$_2$)$_u$—O—C$_{1-7}$alkyl, wherein u is 2, 3, 4, 5 or 6, —CHR$^i$—C(O)OR$^{ii}$, wherein R$^i$ is H, benzyl or C$_{1-4}$alkyl, and R$^{ii}$ is H or C$_{1-7}$alkyl, —S(O)$_2$—C$_{1-7}$alkyl, —S(O)$_2$—C$_{3-7}$cycloalkyl, —(CH$_2$CH$_2$O)$_v$R$^{iii}$, wherein v is from 1 to 3, and R$^{iii}$ is H or C$_{1-7}$alkyl, —(CH$_2$)$_w$-heteroaryl or —(CH$_2$)$_w$-aryl, each optionally substituted by one or more E, and wherein w is 0, 1, 2, 3, or 4, —(CH$_2$)$_x$-heterocyclyl, wherein x is 0, 1, 2, 3 or 4, and wherein heterocyclyl is optionally substituted by one or more oxo, C$_{1-7}$alkyl, C$_{3-7}$cycloalkyl, optionally substituted with one or more B,

CN, benzyl, optionally substituted with one or more E,

—(CH$_2$)$_y$—C(O)R$^{iv}$, wherein y is 0, 1, 2, 3 or 4, and R$^{iv}$ is hydroxy, C$_{1-7}$alkyl, or C$_{1-7}$alkoxy, —(CH$_2$)$_z$—C(O)NR$^v$R$^{vi}$, —(CH$_2$)$_z$NR$^v$R$^{vi}$—C(O)—C$_{1-7}$alkyl or —(CH$_2$)$_z$NR$^v$R$^{vi}$—C(O)—O—C$_{1-7}$alkyl, wherein z is 0, 1, 2, 3 or 4, and R$^v$ and R$^{vi}$ are independently hydrogen, C$_{1-7}$alkyl, optionally substituted by one or more halo, OH or CN, C$_{3-7}$cycloalkyl, optionally substituted by one or more B, 5- or 6-membered heterocyclyl, optionally substituted by one or more A, or R$^v$ and R$^{vi}$ together with the nitrogen to which they are bound form a 5- or 6-membered heterocycloalkyl, optionally substituted by one or more A, R$^b$ and R$^c$ together with the nitrogen to which they are bound form a heterocyclyl or heteroaryl moiety, optionally substituted with one or more A, or R$^b$ and R$^c$ together with the nitrogen to which they are bound form a 7- to 12-membered spirocyclic heterocycle, optionally substituted with one or more A;

with the proviso that R$^b$ and R$^c$ are not simultaneously H,

A is hydroxy, oxo, C$_{1-7}$alkyl, C$_{1-7}$alkoxy, C$_{1-7}$haloalkyl, C$_{1-7}$hydroxyalkyl, halo, or CN;

B is halo, hydroxy, CN, C$_{1-4}$alkyl, benzyloxy, or C$_{1-4}$haloalkyl; and

E is halo, CN, NO$_2$, hydroxy, C$_{1-7}$alkyl, C$_{1-7}$alkoxy, C$_{1-7}$haloalkyl, C$_{1-7}$hydroxyalkyl, C$_{1-7}$cyanoalkyl, C$_{1-7}$haloalkoxy, or C$_{3-7}$cycloalkyl;

or a pharmaceutically acceptable salt thereof.

In certain embodiments of the compound of formula I, R$^4$ is H.

In certain embodiments of the compound of formula I, R$^4$ is C$_{1-7}$alkyl, optionally substituted with one or more halo, cyano, or hydroxy.

In certain embodiments of the compound of formula I, $R^4$ is CN.

In certain embodiments of the compound of formula I, $R^4$ is halo.

In certain embodiments of the compound of formula I, $R^4$ is $NO_2$.

In certain embodiments of the compound of formula I, $R^4$ is —C(O)—$R^a$, wherein $R^a$ is hydroxy, $C_{1-7}$alkoxy, $C_{1-7}$alkyl, phenoxy or phenyl.

In certain embodiments of the compound of formula I, $R^4$ is benzyloxy, optionally substituted with one or more E, wherein E is as described as above.

In certain embodiments of the compound of formula I, $R^4$ is 3- to 7-membered heterocyclyl, optionally substituted with one or more A. Preferably, $R^4$ in such an embodiment is a 3- to 7-membered heterocycloalkyl, optionally substituted with one or more A. A is as described above. As an example for this embodiment, $R^4$ is oxethanyl, substituted with one OH.

In certain embodiments of the compound of formula I, $R^4$ is —C(O)—$NR^bR^c$, wherein $R^b$ is H or $C_{1-7}$alkyl and $R^c$ is
H, with the proviso that $R^b$ and $R^c$ are not simultaneously H,
$C_{1-7}$alkyl, optionally substituted with one or more halo, methyl, —$(CH_2)_t$-hydroxy, or cyano,
—$(CH_2)_t$—$C_{3-7}$cycloalkyl, optionally substituted by one or more B, and t is 0, 1, 2, 3, 4, 5 or 6,
—$(CH_2)_u$—O—$C_{1-7}$alkyl, wherein u is 2, 3, 4, 5 or 6,
—$CHR^i$—C(O)$OR^{ii}$, wherein $R^i$ is H, benzyl or $C_{1-4}$alkyl, and $R^{ii}$ is H or $C_{1-7}$alkyl, —$S(O)_2$—$C_{1-7}$alkyl,
—$S(O)_2$—$C_{3-7}$cycloalkyl,
—$(CH_2CH_2O)_vR^{iii}$, wherein v is from 1 to 3, and $R^{iii}$ is H or $C_{1-7}$alkyl,
—$(CH_2)_w$-heteroaryl or —$(CH_2)_w$-aryl, each optionally substituted by one or more E, and wherein w is 0, 1, 2, 3, or 4,
—$(CH_2)_w$-heterocyclyl, wherein x is 0, 1, 2, 3 or 4, and wherein heterocyclyl is optionally substituted by one or more
oxo,
$C_{1-7}$alkyl,
$C_{3-7}$cycloalkyl, optionally substituted with one or more B,
CN,
benzyl, optionally substituted with one or more E,
—$(CH_2)_y$—C(O)$R^{iv}$, wherein y is 0, 1, 2, 3 or 4, and $R^{iv}$ is hydroxy, $C_{1-7}$alkyl, or $C_{1-7}$alkoxy,
—$(CH_2)_z$—C(O)$NR^vR^{vi}$, —$(CH_2)_z$$NR^vR^{vi}$—C(O)—$C_{1-7}$alkyl or —$(CH_2)_z$$NR^vR^{vi}$—C(O)—O—$C_{1-7}$alkyl, wherein z is 0, 1, 2, 3 or 4,
and $R^v$ and $R^{vi}$ are independently
hydrogen,
$C_{1-7}$alkyl, optionally substituted by one or more halo, OH or CN,
$C_{3-7}$cycloalkyl, optionally substituted by one or more B,
5- or 6-membered heterocyclyl, optionally substituted by one or more A, or
$R^v$ and $R^{vi}$ together with the nitrogen to which they are bound form a 5- or 6-membered heterocycloalkyl, optionally substituted by one or more A,
$R^b$ and $R^c$ together with the nitrogen to which they are bound form a heterocyclyl or heteroaryl moiety, optionally substituted with one or more A, or
$R^b$ and $R^c$ together with the nitrogen to which they are bound form a 7- to 12-membered spirocyclic heterocycle, optionally substituted with one or more A;
with the proviso that $R^b$ and $R^c$ are not simultaneously H, and wherein
A is hydroxy, oxo, $C_{1-7}$alkyl, $C_{1-7}$alkoxy, $C_{1-7}$haloalkyl, $C_{1-7}$hydroxyalkyl, halo, or CN;
B is halo, hydroxy, CN, $C_{1-4}$alkyl, benzyloxy, or $C_{1-4}$haloalkyl; and
E is halo, CN, $NO_2$, hydroxy, $C_{1-7}$alkyl, $C_{1-7}$alkoxy, $C_{1-7}$haloalkyl,
$C_{1-7}$hydroxyalkyl, $C_{1-7}$cyanoalkyl, $C_{1-7}$haloalkoxy, or $C_{3-7}$cycloalkyl.

Examples for heteroaryl in this embodiment comprise pyridinyl, pyrazolyl, isoxazolyl, thiazolyl, or 1,2,4-oxadiazolyl, each optionally substituted by one or more E as defined herein.

Examples for heterocyclyl in —$(CH_2)_x$-heterocyclyl comprise tetrahydropyridinyl, isochromanyl, oxethanyl, isoxazolidinyl, dihydropyridazinyl, tetrahydrofuranyl, tetrahydropyranyl, tetrahydrothiopyranyl, piperidinyl, or pyrrolidinyl, each optionally substituted as described above.

In certain embodiments of the compound of formula I, $R^4$ is —C(O)—$NR^bR^c$, wherein $R^b$ and $R^c$ together with the nitrogen to which they are bound form a heterocyclyl moiety, optionally substituted with one or more A as defined herein.

Examples for the heterocyclyl moiety in this embodiment include morpholinyl, thiomorpholinyl, 5,6,7,8-tetrahydro-[1,2,4]triazolo-[4,3-a]pyrazinyl, or 4,5,6,7-tetrahydro-pyrazolo[1,5-a]pyrimidinyl, each optionally substituted with one or more A as defined herein.

In certain embodiments of the compound of formula I, $R^4$ is —C(O)—$NR^bR^c$, wherein $R^b$ and $R^c$ together with the nitrogen to which they are bound form a 7- to 12-membered spirocyclic heterocycle, optionally substituted with one or more A as defined herein.

Examples for a 7-membered spirocyclic heterocycle comprise 2-oxa-6-aza-spiro[3.3]heptyl, optionally substituted with one or more A as defined herein.

In certain embodiments of the compound of formula I, $R^5$ is
H,
$C_{1-7}$alkyl, optionally substituted by one or more halo, hydroxy or CN,
benzyloxy, optionally substituted with one or more E,
3- to 7-membered heterocyclyl, optionally substituted with one or more A,
—C(O)—$NR^bR^c$, wherein $R^b$ and $R^c$ are each independently
H,
3-7-membered heterocycloalkyl, optionally substituted with one or more A,
A is hydroxy, oxo, $C_{1-7}$alkyl, $C_{1-7}$alkoxy, $C_{1-7}$haloalkyl, $C_{1-7}$hydroxyalkyl, halo, or CN; and
E is halo, CN, $NO_2$, hydroxy, $C_{1-7}$alkyl, $C_{1-7}$alkoxy, $C_{1-7}$hydroxyalkyl,
$C_{1-7}$cyanoalkyl, $C_{1-7}$haloalkoxy, or $C_{3-7}$cycloalkyl.

In certain embodiments of the compound of formula I, $R^5$ is
H,
$CF_3$,
benzyloxy,
tetrahydropyridinyl optionally substituted by one methyl,
—C(O)—$NR^bR^c$, wherein $R^b$ and $R^c$ are each independently H,
or morpholinyl.

In certain embodiments of the invention, $R^4$ is as described in any of the embodiments above, $R^5$ is H or $CF_3$, $R^3$ and $R^6$ are H, halo, CN or $C_{1-7}$alkyl.

In certain embodiments of the invention, $R^3$, $R^4$, $R^5$ and $R^6$ are not simultaneously hydrogen.

A certain embodiment of the invention comprises the compound of formula I

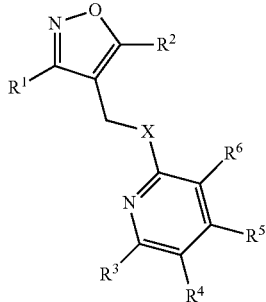

wherein
X is O or NH;
$R^1$ is phenyl, pyridinyl, or pyrimidinyl, each optionally substituted with 1, 2 or 3 halo,
$R^2$ is H or $CH_3$ or $CF_3$;
$R^4$ is
 H,
 $C_{1-7}$alkyl, optionally substituted with one or more halo, cyano, or hydroxy,
 $C_{1-7}$alkoxy, optionally substituted with one or more halo,
 CN,
 halo,
 $NO_2$,
 S—$C_{1-7}$alkyl,
 S(O)—$C_{1-7}$alkyl,
 benzyloxy, optionally substituted with one or more E,
 —C(O)—$R^a$, wherein $R^a$ is hydroxy, $C_{1-7}$alkoxy, $C_{1-7}$alkyl, phenoxy or phenyl,
 3- to 7-membered heterocyclyl, optionally substituted with one or more A,
 —C(O)—$NR^bR^c$, wherein $R^b$ and $R^c$ are each independently
  H,
  $C_{1-7}$alkyl, optionally substituted with one or more halo, methyl, —$(CH_2)_t$-hydroxy, or cyano,
  —$(CH_2)_t$—$C_{3-7}$cycloalkyl, optionally substituted by one or more B, and t is 0, 1, 2, 3, 4, 5 or 6,
  —$(CH_2)_u$—O—$C_{1-2}$alkyl, wherein u is 2, 3, 4, 5 or 6,
  —$CHR^i$—C(O)$OR^{ii}$, wherein $R^i$ is H, benzyl or $C_{1-4}$alkyl, and $R^{ii}$ is H or $C_{1-7}$alkyl,
  —$S(O)_2$—$C_{1-7}$alkyl,
  —$S(O)_2$—$C_{3-7}$cycloalkyl
  —$(CH_2CH_2O)_vR^{iii}$, wherein v is from 1 to 3, and $R^{iii}$ is H or $C_{1-7}$alkyl,
  —$(CH_2)_w$-heteroaryl or —$(CH_2)_w$-aryl, each optionally substituted by one or more E, and wherein w is 0, 1, 2, 3, or 4,
  —$(CH_2)_x$-heterocyclyl, wherein x is 0, 1, 2, 3 or 4, and wherein heterocyclyl is optionally substituted by one or more
   oxo,
   $C_{1-7}$alkyl,
   $C_{3-7}$cycloalkyl, optionally substituted with one or more B,
   CN,
   benzyl, optionally substituted with one or more E,
   —$(CH_2)_y$—C(O)$R^{iv}$, wherein y is 0, 1, 2, 3 or 4, and $R^{iv}$ is hydroxy, $C_{1-7}$alkyl, or $C_{1-7}$alkoxy,
  —$(CH_2)_z$—C(O)$NR^vR^{vi}$, —$(CH_2)_zNR^vR^{vi}$—C(O)—$C_{1-7}$alkyl or —$(CH_2)_zNR^vR^{vi}$—C(O)—O—$C_{1-2}$alkyl, wherein z is 0, 1, 2, 3 or 4,
  and $R^v$ and $R^{vi}$ are independently
   hydrogen,
   $C_{1-7}$alkyl, optionally substituted by one or more halo, OH or CN,
   $C_{3-7}$cycloalkyl, optionally substituted by one or more B,
   5- or 6-membered heterocyclyl, optionally substituted by one or more A, or
   $R^v$ and $R^{vi}$ together with the nitrogen to which they are bound form a 5- or 6-membered heterocycloalkyl, optionally substituted by one or more A,
  $R^b$ and $R^c$ together with the nitrogen to which they are bound form a heterocyclyl or heteroaryl moiety, optionally substituted with one or more A, or
  $R^b$ and $R^c$ together with the nitrogen to which they are bound form a 7- to 12-membered spirocyclic heterocycle, optionally substituted with one or more A;
  with the proviso that $R^b$ and $R^c$ are not simultaneously H,
A is hydroxy, oxo, $C_{1-7}$alkyl, $C_{1-7}$alkoxy, $C_{1-7}$haloalkyl, $C_{1-7}$hydroxyalkyl, halo, or CN;
B is halo, hydroxy, CN, $C_{1-4}$alkyl, benzyloxy, or $C_{1-4}$haloalkyl;
E is halo, CN, $NO_2$, hydroxy, $C_{1-7}$alkyl, $C_{1-7}$alkoxy, $C_{1-7}$haloalkyl,
 $C_{1-7}$hydroxyalkyl, $C_{1-7}$cyanoalkyl, $C_{1-7}$haloalkoxy, or $C_{3-7}$cycloalkyl;
$R^5$ is H,
 $C_{1-7}$alkyl, optionally substituted by one or more halo, hydroxy or CN,
 benzyloxy, optionally substituted with one or more E,
 3- to 7-membered heterocyclyl, optionally substituted with one or more A,
 —C(O)—$NR^bR^c$, wherein $R^b$ and $R^c$ are each independently
 H, with the proviso that $R^b$ and $R^c$ are not simultaneously H,
 3-7-membered heterocycloalkyl, optionally substituted with one or more A,
$R^3$ and $R^6$ are H, halo, CN or $C_{1-7}$alkyl;
A is hydroxy, oxo, $C_{1-7}$alkyl, $C_{1-7}$alkoxy, $C_{1-7}$haloalkyl, $C_{1-7}$hydroxyalkyl, halo, or CN;
B is halo, hydroxy, CN, $C_{1-4}$alkyl, or $C_{1-4}$haloalkyl; and
E is halo, CN, $NO_2$, hydroxy, $C_{1-7}$alkyl, $C_{1-7}$alkoxy, $C_{1-7}$hydroxyalkyl,
 $C_{1-7}$cyanoalkyl, $C_{1-7}$haloalkoxy, or $C_{3-7}$cycloalkyl,
or a pharmaceutically acceptable salt thereof.

A further embodiment of the invention are compounds of formula I

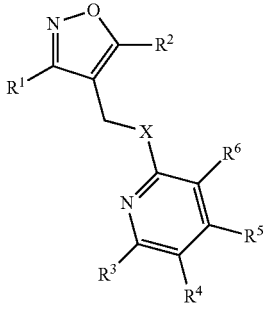

wherein

X is O or NH;

$R^1$ is phenyl, pyridinyl, or pyrimidinyl, each optionally substituted with 1, 2 or 3 halo, $R^2$ is $C_{1-4}$alkyl or $C_{1-4}$haloalkyl;

$R^3$, $R^4$, $R^5$, and $R^6$ each are independently

H, $C_{1-7}$alkyl, optionally substituted with one or more halo, cyano, or hydroxy, $C_{1-7}$alkoxy, optionally substituted with one or more halo,

CN, halo, $NO_2$, benzyloxy, optionally substituted with one or more E,

—C(O)—$R^a$, wherein $R^a$ is hydroxy, $C_{1-7}$alkoxy, $C_{1-7}$alkyl, phenoxy or phenyl, 3- to 7-membered heterocyclyl, optionally substituted with one or more A, —C(O)—$NR^bR^c$, wherein $R^b$ and $R^c$ are each independently

H, $C_{1-7}$alkyl, optionally substituted with one or more halo, hydroxy, or cyano, —$(CH_2)_t$—$C_{3-7}$cycloalkyl, optionally substituted by one or more B, and t is 0, 1, 2, 3 or 4, —$(CH_2)_u$—O—$C_{1-7}$alkyl, wherein it is 2, 3, 4, 5 or 6, —$CHR^i$—C(O)$OR^{ii}$, wherein $R^i$ is H or $C_{1-4}$alkyl, and $R^{ii}$ is H or $C_{1-7}$alkyl, —$(CH_2CH_2O)_vR^{iii}$, wherein v is from 1 to 3, and IV is $R^{iii}$ or $C_{1-7}$alkyl, —$(CH_2)_w$-heteroaryl or —$(CH_2)_w$-aryl, each optionally substituted by one or more E, and wherein w is 0, 1, 2, 3, or 4, —$(CH_2)_x$-heterocyclyl, wherein x is 0, 1, 2, 3 or 4, and wherein heterocyclyl is optionally substituted by one or more oxo, $C_{1-7}$alkyl, $C_{3-7}$cycloalkyl, optionally substituted with one or more B,

CN, benzyl, optionally substituted with one or more E,

—$(CH_2)_y$—C(O)$R^{iv}$, wherein y is 0, 1, 2, 3 or 4, and $R^{iv}$ is hydroxy, $C_{1-7}$alkyl, or $C_{1-7}$alkoxy, —$(CH_2)_z$—C(O)$NR^vR^{vi}$, wherein z is 0, 1, 2, 3 or 4, and $R^v$ and $R^{vi}$ are independently hydrogen, $C_{1-7}$alkyl, optionally substituted by one or more halo, OH or CN, $C_{3-7}$cycloalkyl, optionally substituted by one or more B, 5- or 6-membered heterocyclyl, optionally substituted by one or more A, or $R^v$ and $R^{vi}$ together with the nitrogen to which they are bound form a 5- or 6-membered heterocycloalkyl, optionally substituted by one or more A, $R^b$ and $R^c$ together with the nitrogen to which they are bound form a heterocyclyl moiety, optionally substituted with one or more A, or $R^b$ and $R^c$ together with the nitrogen to which they are bound form a 7- to 12-membered spirocyclic heterocycle, optionally substituted with one or more A;

—$NR^dR^e$, wherein $R^d$ and $R^e$ are each independently hydrogen, $C_{1-7}$alkyl, —C(O)$C_{1-7}$alkyl, optionally substituted with one or more halo, —C(O)$(CH_2)_m$—O—$C_{1-7}$alkyl, wherein m is 0, 1, 2, 3, 4, 5 or 6, —C(O)C(O)$OC_{1-7}$-alkyl, —C(O)$CH_2$C(O)$OC_{1-7}$-alkyl, —C(O)$R^{vii}$, wherein $R^{vii}$ is phenyl or 5- to 6-membered heteroaryl, each optionally substituted with one or more E, —C(O)—$C_{3-7}$cycloalkyl, optionally substituted with one or more B, —C(O)—$R^{viii}$, wherein $R^{viii}$ is 3- to 7-membered heterocyclkyl, optionally substituted by one or more A;

A is hydroxy, oxo, $C_{1-7}$alkyl, $C_{4-7}$alkoxy, $C_{1-7}$hydroxyalkyl, halo, or CN;

B is halo, hydroxy, CN, $C_{1-4}$alkyl, or $C_{1-4}$haloalkyl; and

E is halo, CN, $NO_2$, hydroxy, $C_{1-7}$alkyl, $C_{1-7}$alkoxy, $C_{1-7}$hydroxyalkyl, $C_{1-7}$cyanoalkyl, $C_{1-7}$haloalkoxy, or $C_{3-7}$cycloalkyl;

or a pharmaceutically acceptable salt thereof.

Preferred compounds of formula I of present invention are those exemplified in examples given below. Particularly preferred are:

2-methyl-6-(5-methyl-3-phenyl-isoxazol-4-ylmethoxy)-pyridine,

N-methyl-6-(5-methyl-3-phenyl-isoxazol-4-ylmethoxy)-nicotinamide,

N-ethyl-6-(5-methyl-3-phenyl-isoxazol-4-ylmethoxy)-nicotinamide,

N-(2-fluoro-ethyl)-6-(5-methyl-3-phenyl-isoxazol-4-ylmethoxy)-nicotinamide,

N-(2,2-difluoro-ethyl)-6-(5-methyl-3-phenyl-isoxazol-4-ylmethoxy)-nicotinamide, 6-(5-methyl-3-phenyl-isoxazol-4-ylmethoxy)-N-(2,2,2-trifluoro-ethyl)-nicotinamide, N-(2-hydroxy-ethyl)-6-(5-methyl-3-phenyl-isoxazol-4-ylmethoxy)-nicotinamide, (R,S)—N-(2-hydroxy-propyl)-6-(5-methyl-3-phenyl-isoxazol-4-ylmethoxy)-nicotin amide, N-(3-methoxy-propyl)-6-(5-methyl-3-phenyl-isoxazol-4-ylmethoxy)-nicotinamide, N-cyclopropylmethyl-6-(5-methyl-3-phenyl-isoxazol-4-ylmethoxy)-nicotinamide, N-(2-ethyl-butyl)-6-(5-methyl-3-phenyl-isoxazol-4-ylmethoxy)-nicotinamide, N-(4-cyano-thiazol-2-ylmethyl)-6-(5-methyl-3-phenyl-isoxazol-4-ylmethoxy)-nicotinamide, 6-(5-methyl-3-phenyl-isoxazol-4-ylmethoxy)-N-pyridin-2-ylmethyl-nicotinamide, N-(6-methyl-3-oxo-2,3-dihydro-pyridazin-4-ylmethyl)-6-(5-methyl-3-phenyl-isoxazol-4-ylmethoxy)-nicotinamide, N-isopropyl-6-(5-methyl-3-phenyl-isoxazol-4-ylmethoxy)-nicotinamide, N-cyclopropyl-6-(5-methyl-3-phenyl-isoxazol-4-ylmethoxy)-nicotinamide, N-cyclobutyl-6-(5-methyl-3-phenyl-isoxazol-4-ylmethoxy)-nicotinamide, N-cyclopentyl-6-(5-methyl-3-phenyl-isoxazol-4-ylmethoxy)-nicotinamide, 6-(5-methyl-3-phenyl-isoxazol-4-ylmethoxy)-N-(tetrahydro-pyran-4-yl)-nicotinamide, (R,S)—N-(2,2-dimethyl-tetrahydro-pyran-4-yl)-6-(5-methyl-3-phenyl-isoxazol-4-ylmethoxy)-nicotinamide, N-(1,1-dioxo-hexahydro-1,6-thiopyran-4-yl)-6-(5-methyl-3-phenyl-isoxazol-4-ylmethoxy)-nicotinamide, 6-(5-methyl-3-phenyl-isoxazol-4-ylmethoxy)-N-(1-methyl-piperidin-4-yl)-nicotinamide, N-(1-ethyl-piperidin-4-yl)-6-(5-methyl-3-phenyl-isoxazol-4-ylmethoxy)-nicotin amide,
N-(1-isopropyl-piperidin-4-yl)-6-(5-methyl-3-phenyl-isoxazol-4-ylmethoxy)-nicotinamide,
N-(1-benzyl-piperidin-4-yl)-6-(5-methyl-3-phenyl-isoxazol-4-ylmethoxy)-nicotinamide,
N-(1-ethyl-piperidin-3-yl)-6-(5-methyl-3-phenyl-isoxazol-4-ylmethoxy)-nicotin amide,
(3-{[6-(5-methyl-3-phenyl-isoxazol-4-ylmethoxy)-pyridine-3-carbonyl]-amino}-piperidin-1-yl)-acetic acid,
6-(5-methyl-3-phenyl-isoxazol-4-ylmethoxy)-N-{1-[(2,2,2-trifluoro-ethylcarbamoyl)-methyl]-piperidin-3-yl}-nicotinamide,
N-{1-[(2-hydroxy-ethylcarbamoyl)-methyl]-piperidin-3-yl}-6-(5-methyl-3-phenyl-isoxazol-4-ylmethoxy)-nicotinamide,
N-(4-fluoro-phenyl)-6-(5-methyl-3-phenyl-isoxazol-4-ylmethoxy)-nicotinamide,
4-benzyloxy-2-(5-methyl-3-phenyl-isoxazol-4-ylmethoxy)-pyridine,
1-methyl-2'-(5-methyl-3-phenyl-isoxazol-4-ylmethoxy)-1,2,3,6-tetrahydro-[4,4']bipyridinyl,
2-(5-methyl-3-phenyl-isoxazol-4-ylmethoxy)-N-(2,2,2-trifluoro-ethyl)-isonicotinamide,
6-(5-methyl-3-phenyl-isoxazol-4-ylmethoxy)-N-(tetrahydro-pyran-4-yl)-4-trifluoromethyl-nicotinamide,
5-methyl-6-(5-methyl-3-phenyl-isoxazol-4-ylmethoxy)-N-(tetrahydro-pyran-4-yl)-nicotinamide,
N-isopropyl-5-methyl-6-(5-methyl-3-phenyl-isoxazol-4-ylmethoxy)-nicotinamide,
6-(5-methyl-3-phenyl-isoxazol-4-ylmethoxy)-N-(tetrahydro-furan-3-ylmethyl)-nicotinamide,
[6-(5-methyl-3-phenyl-isoxazol-4-ylmethoxy)-pyridin-3-yl]-(2-oxa-6-aza-spiro[3.3]hept-6-yl)-methanone,
6-(5-methyl-3-phenyl-isoxazol-4-ylmethoxy)-nicotinic acid isopropyl ester,
6-[3-(2-fluoro-phenyl)-5-methyl-isoxazol-4-ylmethoxy]-N-(2,2,2-trifluoro-ethyl)-nicotinamide,
6-[3-(2-fluoro-phenyl)-5-methyl-isoxazol-4-ylmethoxy]-N-(2,2,3,3,3-pentafluoro-propyl)-nicotinamide,
6-[3-(2-fluoro-phenyl)-5-methyl-isoxazol-4-ylmethoxy]-N-isopropyl-nicotinamide,
6-[3-(2-fluoro-phenyl)-5-methyl-isoxazol-4-ylmethoxy]-N-(tetrahydro-pyran-4-yl)-nicotinamide,
6-[3-(3-fluoro-phenyl)-5-methyl-isoxazol-4-ylmethoxy]-N-(2,2,2-trifluoro-ethyl)-nicotinamide,
N-cyclopropylmethyl-6-[3-(3-fluoro-phenyl)-5-methyl-isoxazol-4-ylmethoxy]-nicotinamide,
6-[3-(3-fluoro-phenyl)-5-methyl-isoxazol-4-ylmethoxy]-N-isopropyl-nicotinamide,
6-[3-(3-fluoro-phenyl)-5-methyl-isoxazol-4-ylmethoxy]-N-(tetrahydro-pyran-4-yl)-nicotinamide,
6-[3-(3-chloro-phenyl)-5-methyl-isoxazol-4-ylmethoxy]-N-(2,2,2-trifluoro-ethyl)-nicotinamide,
6-[3-(3-chloro-phenyl)-5-methyl-isoxazol-4-ylmethoxy]-N-cyclopropylmethyl-nicotinamide,
6-[3-(3-chloro-phenyl)-5-methyl-isoxazol-4-ylmethoxy]-N-cyclopropyl-nicotinamide,
6-[3-(3-chloro-phenyl)-5-methyl-isoxazol-4-ylmethoxy]-N-(tetrahydro-pyran-4-yl)-nicotinamide,
6-[3-(4-fluoro-phenyl)-5-methyl-isoxazol-4-ylmethoxy]-N-(2,2,2-trifluoro-ethyl)-nicotinamide,
N-cyclopropylmethyl-6-[3-(4-fluoro-phenyl)-5-methyl-isoxazol-4-ylmethoxy]-nicotinamide,
6-[3-(4-fluoro-phenyl)-5-methyl-isoxazol-4-ylmethoxy]-N-isopropyl-nicotinamide,
N-cyclopropyl-6-[3-(4-fluoro-phenyl)-5-methyl-isoxazol-4-ylmethoxy]-nicotinamide,
6-[3-(4-fluoro-phenyl)-5-methyl-isoxazol-4-ylmethoxy]-N-(tetrahydro-pyran-4-yl)-nicotinamide,
(1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone,
3-{6-[3-(4-fluoro-phenyl)-5-methyl-isoxazol-4-ylmethoxy]-pyridin-3-yl}-oxetan-3-ol,
6-[3-(4-chloro-phenyl)-5-methyl-isoxazol-4-ylmethoxy]-nicotinic acid methyl ester,
6-[3-(4-chloro-phenyl)-5-methyl-isoxazol-4-ylmethoxy]-N-(2,2,2-trifluoro-ethyl)-nicotinamide,
6-[3-(4-chloro-phenyl)-5-methyl-isoxazol-4-ylmethoxy]-N-cyclopropylmethyl-nicotinamide,
6-[3-(4-chloro-phenyl)-5-methyl-isoxazol-4-ylmethoxy]-N-isopropyl-nicotinamide,
6-[3-(4-chloro-phenyl)-5-methyl-isoxazol-4-ylmethoxy]-N-cyclopropyl-nicotinamide,
6-[3-(4-chloro-phenyl)-5-methyl-isoxazol-4-ylmethoxy]-N-(tetrahydro-pyran-4-yl)-nicotinamide,
{6-[3-(4-chloro-phenyl)-5-methyl-isoxazol-4-ylmethoxy]-pyridin-3-yl}-(1,1-dioxo-1λ6-thiomorpholin-4-yl)-methanone,
{6-[3-(4-chloro-phenyl)-5-methyl-isoxazol-4-ylmethoxy]-pyridin-3-yl}-morpholin-4-yl-methanone,
{6-[3-(4-chloro-phenyl)-5-methyl-isoxazol-4-ylmethoxy]-pyridin-3-yl}-thiomorpholin-4-yl-methanone,
6-[3-(3,4-difluoro-phenyl)-5-methyl-isoxazol-4-ylmethoxy]-N-(2,2,2-trifluoro-ethyl)-nicotinamide,
6-[3-(3,4-difluoro-phenyl)-5-methyl-isoxazol-4-ylmethoxy]-N-isopropyl-nicotinamide,
6-[3-(3,4-difluoro-phenyl)-5-methyl-isoxazol-4-ylmethoxy]-N-(tetrahydro-pyran-4-yl)-nicotinamide,
6-[3-(4-fluoro-phenyl)-5-trifluoromethyl-isoxazol-4-ylmethoxy]-N-(tetrahydro-pyran-4-yl)-nicotinamide,
6-(5-methyl-3-pyridin-4-yl-isoxazol-4-ylmethoxy)-N-(2,2,2-trifluoro-ethyl)-nicotinamide,
N-cyclopropylmethyl-6-(5-methyl-3-pyridin-4-yl-isoxazol-4-ylmethoxy)-nicotinamide,
N-cyclopropyl-6-(5-methyl-3-pyridin-4-yl-isoxazol-4-ylmethoxy)-nicotinamide,
N-isopropyl-6-(5-methyl-3-pyridin-4-yl-isoxazol-4-ylmethoxy)-nicotinamide,
6-(5-methyl-3-pyridin-4-yl-isoxazol-4-ylmethoxy)-N-(tetrahydro-pyran-4-yl)-nicotinamide,
N-isopropyl-6-[(5-methyl-3-phenyl-isoxazol-4-ylmethyl)-amino]-nicotinamide,
6-[(5-methyl-3-phenyl-isoxazol-4-ylmethyl)-amino]-N-(tetrahydro-pyran-4-yl)-nicotinamide,
6-{[3-(4-fluoro-phenyl)-5-methyl-isoxazol-4-ylmethyl]-amino}-N-(2,2,2-trifluoro-ethyl)-nicotinamide,
N-cyclopropylmethyl-6-{[3-(4-fluoro-phenyl)-5-methyl-isoxazol-4-ylmethyl]-amino}-nicotinamide,
6-{[3-(4-fluoro-phenyl)-5-methyl-isoxazol-4-ylmethyl]-amino}-N-isopropyl-nicotinamide,
N-cyclopropyl-6-{[3-(4-fluoro-phenyl)-5-methyl-isoxazol-4-ylmethyl]-amino}-nicotinamide,
6-{[3-(4-fluoro-phenyl)-5-methyl-isoxazol-4-ylmethyl]-amino}-N-(tetrahydro-pyran-4-yl)-nicotinamide,
N-(2-hydroxy-1,1-dimethyl-ethyl)-6-(5-methyl-3-phenyl-isoxazol-4-ylmethoxy)-nicotinamide,
N-(2-methoxy-ethyl)-6-(5-methyl-3-phenyl-isoxazol-4-ylmethoxy)-nicotinamide,
N-(1,1-dioxo-tetrahydro-thiophen-3-yl)-6-(5-methyl-3-phenyl-isoxazol-4-ylmethoxy)-nicotinamide, 6-(5-methyl-3-phenyl-isoxazol-4-ylmethoxy)-N-(3,3,3-trifluoro-2-hydroxy-propyl)-nicotinamide,
(4-hydroxy-piperidin-1-yl)-[6-(5-methyl-3-phenyl-isoxazol-4-ylmethoxy)-pyridin-3-yl]-methanone,
N-(3-hydroxy-2,2-dimethyl-propyl)-6-(5-methyl-3-phenyl-isoxazol-4-ylmethoxy)-nicotinamide,
N-(2-isopropoxy-ethyl)-6-(5-methyl-3-phenyl-isoxazol-4-ylmethoxy)-nicotinamide,
N-(2-hydroxy-1-methyl-ethyl)-6-(5-methyl-3-phenyl-isoxazol-4-ylmethoxy)-nicotinamide,
(3-hydroxy-azetidin-1-yl)-[6-(5-methyl-3-phenyl-isoxazol-4-ylmethoxy)-pyridin-3-yl]-methanone,
N-(2-hydroxy-cyclohexyl)-6-(5-methyl-3-phenyl-isoxazol-4-ylmethoxy)-nicotinamide,
N-(2-hydroxy-2-methyl-propyl)-6-(5-methyl-3-phenyl-isoxazol-4-ylmethoxy)-nicotinamide,
N-(1-hydroxy-cyclopropylmethyl)-6-(5-methyl-3-phenyl-isoxazol-4-ylmethoxy)-nicotinamide,
N—((R)-2-hydroxy-1-methyl-ethyl)-6-(5-methyl-3-phenyl-isoxazol-4-ylmethoxy)-nicotinamide,
N—((S)-2-hydroxy-1-methyl-ethyl)-6-(5-methyl-3-phenyl-isoxazol-4-ylmethoxy)-nicotinamide,
N-((1R,2R)-2-hydroxy-cyclohexyl)-6-(5-methyl-3-phenyl-isoxazol-4-ylmethoxy)-nicotinamide,
N-((1S,2S)-2-hydroxy-cyclohexyl)-6-(5-methyl-3-phenyl-isoxazol-4-ylmethoxy)-nicotinamide,
N-((1S,2R) and (1R,2S)-2-hydroxy-cyclohexyl)-6-(5-methyl-3-phenyl-isoxazol-4-ylmethoxy)-nicotinamide,
N-(2-hydroxy-cyclopentyl)-6-(5-methyl-3-phenyl-isoxazol-4-ylmethoxy)-nicotinamide,
N-(2-hydroxy-1-hydroxymethyl-ethyl)-6-(5-methyl-3-phenyl-isoxazol-4-ylmethoxy)-nicotinamide,
6-(5-methyl-3-phenyl-isoxazol-4-ylmethoxy)-N—(S)-tetrahydro-furan-3-yl-nicotinamide,
N-((1R,2S)-2-hydroxy-cyclohexyl)-6-(5-methyl-3-phenyl-isoxazol-4-ylmethoxy)-nicotinamide
or N-((1S,2R)-2-hydroxy-cyclohexyl)-6-(5-methyl-3-phenyl-isoxazol-4-ylmethoxy)-nicotinamide,
N-((1S,2R)-2-hydroxy-cyclohexyl)-6-(5-methyl-3-phenyl-isoxazol-4-ylmethoxy)-nicotinamide
or N-((1R,2S)-2-hydroxy-cyclohexyl)-6-(5-methyl-3-phenyl-isoxazol-4-ylmethoxy)-nicotinamide,
N-(2-acetylamino-ethyl)-6-(5-methyl-3-phenyl-isoxazol-4-ylmethoxy)-nicotinamide,
N—((S)-1-hydroxymethyl-2-methyl-propyl)-6-(5-methyl-3-phenyl-isoxazol-4-ylmethoxy)-nicotinamide,
N—((S)-1-hydroxymethyl-3-methyl-butyl)-6-(5-methyl-3-phenyl-isoxazol-4-ylmethoxy)-nicotinamide,
N—((S)-1-hydroxymethyl-propyl)-6-(5-methyl-3-phenyl-isoxazol-4-ylmethoxy)-nicotinamide,
N—((R)-1-hydroxymethyl-propyl)-6-(5-methyl-3-phenyl-isoxazol-4-ylmethoxy)-nicotinamide,
N-((1R,2S)-2-hydroxy-cyclopentyl)-6-(5-methyl-3-phenyl-isoxazol-4-ylmethoxy)-nicotinamide
or N-((1S,2R)-2-hydroxy-cyclopentyl)-6-(5-methyl-3-phenyl-isoxazol-4-ylmethoxy)-nicotinamide,
N-((1S,2R)-2-hydroxy-cyclopentyl)-6-(5-methyl-3-phenyl-isoxazol-4-ylmethoxy)-nicotinamide
or N-((1R,2S)-2-hydroxy-cyclopentyl)-6-(5-methyl-3-phenyl-isoxazol-4-ylmethoxy)-nicotinamide,
N-((1S,2S)-2-hydroxy-cyclopentyl)-6-(5-methyl-3-phenyl-isoxazol-4-ylmethoxy)-nicotinamide
or N-((1R,2R)-2-hydroxy-cyclopentyl)-6-(5-methyl-3-phenyl-isoxazol-4-ylmethoxy)-nicotinamide,
N-((1R,2R)-2-hydroxy-cyclopentyl)-6-(5-methyl-3-phenyl-isoxazol-4-ylmethoxy)-nicotinamide
or N-((1S,2S)-2-hydroxy-cyclopentyl)-6-(5-methyl-3-phenyl-isoxazol-4-ylmethoxy)-nicotinamide,
6-(5-methyl-3-phenyl-isoxazol-4-ylmethoxy)-N-[2-(2-oxo-imidazolidin-1-yl)-ethyl]-nicotinamide,
N-(3-hydroxy-butyl)-6-(5-methyl-3-phenyl-isoxazol-4-ylmethoxy)-nicotinamide,
3-{[6-(5-methyl-3-phenyl-isoxazol-4-ylmethoxy)-pyridine-3-carbonyl]-amino}-azetidine-1-carboxylic acid tert-butyl ester,
(2-{[6-(5-methyl-3-phenyl-isoxazol-4-ylmethoxy)-pyridine-3-carbonyl]-amino}-ethyl)-carbamic acid tert-butyl ester,
N-(2,3-dihydroxy-propyl)-6-(5-methyl-3-phenyl-isoxazol-4-ylmethoxy)-nicotinamide,
N-(3-hydroxy-propyl)-6-(5-methyl-3-phenyl-isoxazol-4-ylmethoxy)-nicotinamide,
N-(4-hydroxy-butyl)-6-(5-methyl-3-phenyl-isoxazol-4-ylmethoxy)-nicotinamide,
N-(5-hydroxy-pentyl)-6-(5-methyl-3-phenyl-isoxazol-4-ylmethoxy)-nicotinamide,
N-(6-hydroxy-hexyl)-6-(5-methyl-3-phenyl-isoxazol-4-ylmethoxy)-nicotinamide,
(3-hydroxy-pyrrolidin-1-yl)-[6-(5-methyl-3-phenyl-isoxazol-4-ylmethoxy)-pyridin-3-yl]-methanone,
((S)-2-hydroxymethyl-pyrrolidin-1-yl)-[6-(5-methyl-3-phenyl-isoxazol-4-ylmethoxy)-pyridin-3-yl]-methanone,
((R)-2-hydroxymethyl-pyrrolidin-1-yl)-[6-(5-methyl-3-phenyl-isoxazol-4-ylmethoxy)-pyridin-3-yl]-methanone,
N-(3-benzyloxy-cyclobutyl)-6-(5-methyl-3-phenyl-isoxazol-4-ylmethoxy)-nicotinamide,
[6-(5-methyl-3-phenyl-isoxazol-4-ylmethoxy)-pyridin-3-yl]-(2-methyl-pyrrolidin-1-yl)-methanone,
[6-(5-methyl-3-phenyl-isoxazol-4-ylmethoxy)-pyridin-3-yl]-pyrrolidin-1-yl-methanone,
(S)-2-{[6-(5-methyl-3-phenyl-isoxazol-4-ylmethoxy)-pyridine-3-carbonyl]-amino}-3-phenyl-propionic acid methyl ester,
(cis or trans)-N-(3-benzyloxy-cyclobutyl)-6-(5-methyl-3-phenyl-isoxazol-4-ylmethoxy)-nicotinamide,
(S)-2-{[6-(5-methyl-3-phenyl-isoxazol-4-ylmethoxy)-pyridine-3-carbonyl]-amino}-3-phenyl-propionic acid,
N-(3-methyl-oxetan-3-yl)-6-(5-methyl-3-phenyl-isoxazol-4-ylmethoxy)-nicotinamide,
butane-1-sulfonic acid [6-(5-methyl-3-phenyl-isoxazol-4-ylmethoxy)-pyridine-3-carbonyl]-amide,
6-(5-methyl-3-phenyl-isoxazol-4-ylmethoxy)-N-(2,2,2-trifluoro-1-methyl-ethyl)-nicotinamide,
6-(5-methyl-3-phenyl-isoxazol-4-ylmethoxy)-N—((S)-2,2,2-trifluoro-1-methyl-ethyl)-nicotinamide,
cyclopropanesulfonic acid methyl-[6-(5-methyl-3-phenyl-isoxazol-4-ylmethoxy)-pyridine-3-carbonyl]-amide,
6-(5-methyl-3-phenyl-isoxazol-4-ylmethoxy)-N-(1-methyl-1H-pyrazol-4-yl)-nicotinamide,
1-[6-(5-methyl-3-phenyl-isoxazol-4-ylmethoxy)-pyridine-3-carbonyl]-1,2-dihydro-pyrazol-3-one,
N-(1-methyl-cyclopropyl)-6-(5-methyl-3-phenyl-isoxazol-4-ylmethoxy)-nicotinamide,
azetidin-1-yl-[6-(5-methyl-3-phenyl-isoxazol-4-ylmethoxy)-pyridin-3-yl]-methanone,
(3-methoxy-azetidin-1-yl)-[6-(5-methyl-3-phenyl-isoxazol-4-ylmethoxy)-pyridin-3-yl]-methanone,
[6-(5-methyl-3-phenyl-isoxazol-4-ylmethoxy)-pyridin-3-yl]-thiazolidin-3-yl-methanone,
N-(1-cyano-cyclopropyl)-6-(5-methyl-3-phenyl-isoxazol-4-ylmethoxy)-nicotinamide,
6-(5-methyl-3-phenyl-isoxazol-4-ylmethoxy)-N-(1-methyl-1H-pyrazol-3-yl)-nicotinamide, 5-(3-methyl-[1,2,4]oxadiazol-5-yl)-2-(5-methyl-3-phenyl-isoxazol-4-ylmethoxy)-pyridine,
2-(5-methyl-3-phenyl-isoxazol-4-ylmethoxy)-5-(5-methyl-4H-[1,2,4]triazol-3-yl)-pyridine,
2-(5-methyl-3-phenyl-isoxazol-4-ylmethoxy)-5-methylsulfanyl-pyridine,
5-methanesulfinyl-2-(5-methyl-3-phenyl-isoxazol-4-ylmethoxy)-pyridine,
6-(5-methyl-3-m-tolyl-isoxazol-4-ylmethoxy)-N-(tetrahydro-pyran-4-yl)-nicotinamide
N-isopropyl-6-(5-methyl-3-m-tolyl-isoxazol-4-ylmethoxy)-nicotinamide,
6-(5-methyl-3-p-tolyl-isoxazol-4-ylmethoxy)-N-(tetrahydro-pyran-4-yl)-nicotinamide
N-Isopropyl-6-(5-methyl-3-p-tolyl-isoxazol-4-ylmethoxy)-nicotinamide,
6-[3-(2-fluoro-4-methyl-phenyl)-5-methyl-isoxazol-4-ylmethoxy]-N-isopropyl-nicotinamide,
6-[3-(4-chloro-phenyl)-5-methyl-isoxazol-4-ylmethoxy]-N-(2-hydroxy-1,1-dimethyl-ethyl)-nicotinamide,
6-[3-(4-chloro-phenyl)-5-methyl-isoxazol-4-ylmethoxy]-N-(1-methyl-1H-pyrazol-4-yl)-nicotinamide,
6-[3-(4-chloro-phenyl)-5-methyl-isoxazol-4-ylmethoxy]-N—((R)-2-hydroxy-1-methyl-ethyl)-nicotinamide,
6-[3-(4-chloro-phenyl)-5-methyl-isoxazol-4-ylmethoxy]-N—((S)-2-hydroxy-1-methyl-ethyl)-nicotinamide,
6-[3-(4-chloro-phenyl)-5-methyl-isoxazol-4-ylmethoxy]-N—((S)-2,2,2-trifluoro-1-methyl-ethyl)-nicotinamide,
6-[3-(4-chloro-phenyl)-5-methyl-isoxazol-4-ylmethoxy]-N-((1R,2R)-2-hydroxy-cyclopentyl)-nicotinamide
or 6-[3-(4-chloro-phenyl)-5-methyl-isoxazol-4-ylmethoxy]-N-((1S,2S)-2-hydroxy-cyclopentyl)-nicotinamide,
6-[3-(4-chloro-phenyl)-5-methyl-isoxazol-4-ylmethoxy]-N-((1S,2S)-2-hydroxy-cyclopentyl)-nicotinamide
or 6-[3-(4-chloro-phenyl)-5-methyl-isoxazol-4-ylmethoxy]-N-((1R,2R)-2-hydroxy-cyclopentyl)-nicotinamide,
6-[3-(2,3-difluoro-phenyl)-5-methyl-isoxazol-4-ylmethoxy]-N-isopropyl-nicotinamide,
6-[3-(2,3-difluoro-phenyl)-5-methyl-isoxazol-4-ylmethoxy]-N-(tetrahydro-pyran-4-yl)-nicotinamide,
6-[3-(2,4-difluoro-phenyl)-5-methyl-isoxazol-4-ylmethoxy]-N-isopropyl-nicotinamide,
6-[3-(2,4-difluoro-phenyl)-5-methyl-isoxazol-4-ylmethoxy]-N-(tetrahydro-pyran-4-yl)-nicotinamide,
6-[3-(2,5-difluoro-phenyl)-5-methyl-isoxazol-4-ylmethoxy]-N-isopropyl-nicotinamide,
6-[3-(2,5-difluoro-phenyl)-5-methyl-isoxazol-4-ylmethoxy]-N-(tetrahydro-pyran-4-yl)-nicotinamide,
6-[3-(3,4-difluoro-phenyl)-5-methyl-isoxazol-4-ylmethoxy]-N-(2-hydroxy-1,1-dimethyl-ethyl)-nicotinamide,
6-[3-(3,4-difluoro-phenyl)-5-methyl-isoxazol-4-ylmethoxy]-N-(3-hydroxy-2,2-dimethyl-propyl)-nicotinamide,
6-[3-(3,4-difluoro-phenyl)-5-methyl-isoxazol-4-ylmethoxy]-N-(2-hydroxy-2-methyl-propyl)-nicotinamide,
6-[3-(4-chloro-2-fluoro-phenyl)-5-methyl-isoxazol-4-ylmethoxy]-N-isopropyl-nicotinamide,
6-(5-methyl-3-pyridin-2-yl-isoxazol-4-ylmethoxy)-nicotinic acid methyl ester,
6-(5-methyl-3-pyridin-2-yl-isoxazol-4-ylmethoxy)-N-(tetrahydro-pyran-4-yl)-nicotinamide,
N-isopropyl-6-(5-methyl-3-pyridin-2-yl-isoxazol-4-ylmethoxy)-nicotinamide,
[6-(5-methyl-3-pyridin-2-yl-isoxazol-4-ylmethoxy)-pyridin-3-yl]-morpholin-4-yl-methanone,
6-(5-methyl-3-pyridin-2-yl-isoxazol-4-ylmethoxy)-N-(2,2,2-trifluoro-ethyl)-nicotinamide,
(1,1-dioxo-1,6-thiomorpholin-4-yl)-[6-(5-methyl-3-pyridin-2-yl-isoxazol-4-ylmethoxy)-pyridin-3-yl]-methanone,
N-cyclopropylmethyl-6-(5-methyl-3-pyridin-2-yl-isoxazol-4-ylmethoxy)-nicotinamide,
N-cyclopropyl-6-(5-methyl-3-pyridin-2-yl-isoxazol-4-ylmethoxy)-nicotinamide,
methyl-6-(5-methyl-3-pyridin-2-yl-isoxazol-4-ylmethoxy)-nicotinamide,
ethyl-6-(5-methyl-3-pyridin-2-yl-isoxazol-4-ylmethoxy)-nicotinamide,
(2-hydroxy-1,1-dimethyl-ethyl)-6-(5-methyl-3-pyridin-2-yl-isoxazol-4-ylmethoxy)-nicotinamide,
[6-(5-methyl-3-pyridin-2-yl-isoxazol-4-ylmethoxy)-pyridin-3-yl]-thiomorpholin-4-yl-methanone,
6-(5-methyl-3-pyridin-2-yl-isoxazol-4-ylmethoxy)-nicotinic acid,
(2-hydroxy-ethyl)-6-(5-methyl-3-pyridin-2-yl-isoxazol-4-ylmethoxy)-nicotinamide,
(2-methoxy-ethyl)-6-(5-methyl-3-pyridin-2-yl-isoxazol-4-ylmethoxy)-nicotinamide,
6-[3-(5-fluoro-pyridin-2-yl)-5-methyl-isoxazol-4-ylmethoxy]-nicotinic acid methyl ester,
6-[3-(5-fluoro-pyridin-2-yl)-5-methyl-isoxazol-4-ylmethoxy]-nicotinic acid,
6-[3-(5-fluoro-pyridin-2-yl)-5-methyl-isoxazol-4-ylmethoxy]-(tetrahydro-pyran-4-yl)-nicotinamide,
6-[3-(5-fluoro-pyridin-2-yl)-5-methyl-isoxazol-4-ylmethoxy]-isopropyl-nicotinamide,
cyclopropyl-6-[3-(5-fluoro-pyridin-2-yl)-5-methyl-isoxazol-4-ylmethoxy]-nicotinamide,
6-[3-(5-fluoro-pyridin-2-yl)-5-methyl-isoxazol-4-ylmethoxy](2-hydroxy-1,1-dimethyl-ethyl)-nicotinamide,
cyclopropylmethyl-6-[3-(5-fluoro-pyridin-2-yl)-5-methyl-isoxazol-4-ylmethoxy]-nicotinamide,
(1,1-dioxo-1,6-thiomorpholin-4-yl)-{6-[3-(5-fluoro-pyridin-2-yl)-5-methyl-isoxazol-4-ylmethoxy]-pyridin-3-yl}-methanone,
6-[3-(5-fluoro-pyridin-2-yl)-5-methyl-isoxazol-4-ylmethoxy]-2,2,2-trifluoro-ethyl)-nicotinamide,
6-[3-(5-fluoro-pyridin-2-yl)-5-methyl-isoxazol-4-ylmethoxy]-(2-hydroxy-ethyl)-nicotinamide,
{6-[3-(5-fluoro-pyridin-2-yl)-5-methyl-isoxazol-4-ylmethoxy]-pyridin-3-yl}-morpholin-4-yl-methanone,
ethyl-6-[3-(5-fluoro-pyridin-2-yl)-5-methyl-isoxazol-4-ylmethoxy]-nicotinamide,
6-[3-(5-fluoro-pyridin-2-yl)-5-methyl-isoxazol-4-ylmethoxy]-methyl-nicotinamide,
6-[3-(5-fluoro-pyridin-2-yl)-5-methyl-isoxazol-4-ylmethoxy]-N—((S)-2,2,2-trifluoro-1-methyl-ethyl)-nicotinamide,
6-[3-(5-chloro-pyridin-2-yl)-5-methyl-isoxazol-4-ylmethoxy]-nicotinic acid methyl ester,
6-[3-(5-chloro-pyridin-2-yl)-5-methyl-isoxazol-4-ylmethoxy]-(tetrahydro-pyran-4-yl)-nicotinamide,
6-[3-(5-chloro-pyridin-2-yl)-5-methyl-isoxazol-4-ylmethoxy]-isopropyl-nicotinamide,
6-[3-(5-chloro-pyridin-2-yl)-5-methyl-isoxazol-4-ylmethoxy]-cyclopropyl-nicotinamide,
6-[3-(5-chloro-pyridin-2-yl)-5-methyl-isoxazol-4-ylmethoxy]-nicotinic acid,
6-[3-(5-chloro-pyridin-2-yl)-5-methyl-isoxazol-4-ylmethoxy]-(2-hydroxy-1,1-dimethyl-ethyl)-nicotinamide,
6-[3-(5-chloro-pyridin-2-yl)-5-methyl-isoxazol-4-ylmethoxy]-cyclopropylmethyl-nicotinamide, {6-[3-(5-chloro-pyridin-2-yl)-5-methyl-isoxazol-4-yl-methoxy]-pyridin-3-yl}-(1,1-dioxo-1,6-thiomorpholin-4-yl)-methanone, 6-[3-(5-chloro-pyridin-2-yl)-5-methyl-isoxazol-4-yl-methoxy]-(2,2,2-trifluoro-ethyl)-nicotinamide, {6-[3-(5-chloro-pyridin-2-yl)-5-methyl-isoxazol-4-yl-methoxy]-pyridin-3-yl}-morpholin-4-yl-methanone, {6-[3-(5-chloro-pyridin-2-yl)-5-methyl-isoxazol-4-yl-methoxy]-pyridin-3-yl}-thiomorpholin-4-yl-methanone, 6-[3-(5-chloro-pyridin-2-yl)-5-methyl-isoxazol-4-yl-methoxy]-(2-hydroxy-ethyl)-nicotinamide, 6-(5-methyl-3-pyrimidin-4-yl-isoxazol-4-ylmethoxy)-nicotinic acid methyl ester, N-isopropyl-6-(5-methyl-3-pyrimidin-4-yl-isoxazol-4-yl-methoxy)-nicotinamide, N-cyclopropyl-6-(5-methyl-3-pyrimidin-4-yl-isoxazol-4-yl-methoxy)-nicotinamide, N-(2-hydroxy-1,1-dimethyl-ethyl)-6-(5-methyl-3-pyrimidin-4-yl-isoxazol-4-ylmethoxy)-nicotinamide,

[6-(5-methyl-3-pyrimidin-4-yl-isoxazol-4-ylmethoxy)-pyridin-3-yl]-morpholin-4-yl-methanone, N-ethyl-6-(5-methyl-3-pyrimidin-4-yl-isoxazol-4-yl-methoxy)-nicotinamide, N-methyl-6-(5-methyl-3-pyrimidin-4-yl-isoxazol-4-yl-methoxy)-nicotinamide,

[6-(5-methyl-3-pyrimidin-4-yl-isoxazol-4-ylmethoxy)-pyridin-3-yl]-thiomorpholin-4-yl-methanone, N-(2-hydroxy-ethyl)-6-(5-methyl-3-pyrimidin-4-yl-isoxazol-4-ylmethoxy)-nicotinamide, N-isopropyl-6-(3-phenyl-isoxazol-4-ylmethoxy)-nicotinamide, 6-(3-phenyl-isoxazol-4-ylmethoxy)-N-(tetrahydro-pyran-4-yl)-nicotinamide, 6-[3-(4-fluoro-phenyl)-isoxazol-4-ylmethoxy]-N-isopropyl-nicotinamide, 6-[3-(4-fluoro-phenyl)-isoxazol-4-ylmethoxy]-N-(tetrahydro-pyran-4-yl)-nicotinamide, 6-[3-(4-fluoro-phenyl)-isoxazol-4-ylmethoxy]-N-(2-hydroxy-1-methyl-ethyl)-nicotinamide, 6-[3-(4-fluoro-phenyl)-isoxazol-4-ylmethoxy]-N—((R)-2-hydroxy-1-methyl-ethyl)-nicotinamide, 6-[3-(4-fluoro-phenyl)-isoxazol-4-ylmethoxy]-N—((S)-2-hydroxy-1-methyl-ethyl)-nicotinamide, N-cyclopropylmethyl-6-[3-(4-fluoro-phenyl)-isoxazol-4-ylmethoxy]-nicotinamide, N-cyclopropyl-6-[3-(4-fluoro-phenyl)-isoxazol-4-yl-methoxy]-nicotinamide, 6-[3-(4-fluoro-phenyl)-isoxazol-4-ylmethoxy]-N-(2,2,2-trifluoro-ethyl)-nicotinamide, 6-[3-(4-fluoro-phenyl)-isoxazol-4-ylmethoxy]-N-((1S,2S)-2-hydroxy-cyclopentyl)-nicotinamide, 6-[3-(4-fluoro-phenyl)-isoxazol-4-ylmethoxy]-N-((1R,2R)-2-hydroxy-cyclopentyl)-nicotinamide or 6-[3-(4-fluoro-phenyl)-isoxazol-4-ylmethoxy]-N-((1S,2S)-2-hydroxy-cyclopentyl)-nicotinamide, 6-[3-(4-fluoro-phenyl)-isoxazol-4-ylmethoxy]-N-(2-hydroxy-1-hydroxymethyl-ethyl)-nicotinamide, N-(2-acetylamino-ethyl)-6-[3-(4-fluoro-phenyl)-isoxazol-4-ylmethoxy]-nicotinamide, 6-[3-(4-fluoro-phenyl)-isoxazol-4-ylmethoxy]-N-(2-methoxy-ethyl)-nicotinamide, 6-[3-(4-fluoro-phenyl)-isoxazol-4-ylmethoxy]-N—((R)-2-hydroxy-propyl)-nicotinamide, 6-[3-(4-fluoro-phenyl)-isoxazol-4-ylmethoxy]-N-(2-hydroxy-ethyl)-nicotinamide, 6-[3-(4-fluoro-phenyl)-isoxazol-4-ylmethoxy]-N-(1-hydroxy-cyclopropylmethyl)-nicotinamide, N-(1,1-dioxo-tetrahydro-1,6-thiophen-3-yl)-6-[3-(4-fluoro-phenyl)-isoxazol-4-ylmethoxy]-nicotinamide, 6-[3-(4-fluoro-phenyl)-isoxazol-4-ylmethoxy]-N-((1R,2R)-2-hydroxy-cyclopentyl)-nicotinamide or 6-[3-(4-fluoro-phenyl)-isoxazol-4-ylmethoxy]-N-((1S,2S)-2-hydroxy-cyclopentyl)-nicotinamide, 6-[3-(4-chloro-phenyl)-isoxazol-4-ylmethoxy]-N-(2,2,2-trifluoro-ethyl)-nicotinamide, 6-[3-(4-chloro-phenyl)-isoxazol-4-ylmethoxy]-N-cyclopropyl-nicotinamide, 6-[3-(4-chloro-phenyl)-isoxazol-4-ylmethoxy]-N-isopropyl-nicotinamide, 6-[3-(4-chloro-phenyl)-isoxazol-4-ylmethoxy]-N-(tetrahydro-pyran-4-yl)-nicotinamide, 6-[3-(4-chloro-phenyl)-isoxazol-4-ylmethoxy]-N-(2-hydroxy-ethyl)-nicotinamide, 6-[3-(4-chloro-phenyl)-isoxazol-4-ylmethoxy]-N-(2-hydroxy-propyl)-nicotinamide, 6-[3-(4-chloro-phenyl)-isoxazol-4-ylmethoxy]-N-(3-hydroxy-propyl)-nicotinamide, 6-[3-(4-chloro-phenyl)-isoxazol-4-ylmethoxy]-N-(2-hydroxy-1,1-dimethyl-ethyl)-nicotinamide, 6-[3-(4-chloro-phenyl)-isoxazol-4-ylmethoxy]-N-(3-hydroxy-2,2-dimethyl-propyl)-nicotinamide, 3-({6-[3-(4-chloro-phenyl)-isoxazol-4-ylmethoxy]-pyridine-3-carbonyl}-amino)-azetidine-1-carboxylic acid tert-butyl ester, 6-[3-(4-chloro-phenyl)-isoxazol-4-ylmethoxy]-N-((1S,2S)-2-hydroxy-cyclopentyl)-nicotinamide and 6-[3-(4-chloro-phenyl)-isoxazol-4-ylmethoxy]-N-((1R,2R)-2-hydroxy-cyclopentyl)-nicotinamide, 6-[3-(4-chloro-phenyl)-isoxazol-4-ylmethoxy]-N-(2-hydroxy-1-hydroxymethyl-ethyl)-nicotinamide, 6-[3-(4-chloro-phenyl)-isoxazol-4-ylmethoxy]-N—((R)-2-hydroxy-1-methyl-ethyl)-nicotinamide, 6-[3-(4-chloro-phenyl)-isoxazol-4-ylmethoxy]-N—((S)-2-hydroxy-1-methyl-ethyl)-nicotinamide, N-(2-acetylamino-ethyl)-6-[3-(4-chloro-phenyl)-isoxazol-4-ylmethoxy]-nicotinamide, 6-[3-(4-chloro-phenyl)-isoxazol-4-ylmethoxy]-N—((S)-2,2,2-trifluoro-1-methyl-ethyl)-nicotinamide, 6-(3-pyridin-2-yl-isoxazol-4-ylmethoxy)-N-(tetrahydro-pyran-4-yl)-nicotinamide, N-isopropyl-6-(3-pyridin-2-yl-isoxazol-4-ylmethoxy)-nicotinamide, N-cyclopropyl-6-(3-pyridin-2-yl-isoxazol-4-ylmethoxy)-nicotinamide, N-cyclopropylmethyl-6-(3-pyridin-2-yl-isoxazol-4-yl-methoxy)-nicotinamide, 6-(3-pyridin-2-yl-isoxazol-4-ylmethoxy)-N-(2,2,2-trifluoro-ethyl)-nicotinamide, N-(2-hydroxy-ethyl)-6-(3-pyridin-2-yl-isoxazol-4-yl-methoxy)-nicotinamide, N-ethyl-6-(3-pyridin-2-yl-isoxazol-4-ylmethoxy)-nicotinamide, 6-[3-(5-fluoro-pyridin-2-yl)-isoxazol-4-ylmethoxy]-(tetrahydro-pyran-4-yl)-nicotinamide, 6-[3-(5-fluoro-pyridin-2-yl)-isoxazol-4-ylmethoxy]-isopropyl-nicotinamide, cyclopropyl-6-[3-(5-fluoro-pyridin-2-yl)-isoxazol-4-yl-methoxy]-nicotinamide, 6-[3-(5-fluoro-pyridin-2-yl)-isoxazol-4-ylmethoxy]-(2-hydroxy-1,1-dimethyl-ethyl)-nicotinamide, 6-[3-(5-fluoro-pyridin-2-yl)-isoxazol-4-ylmethoxy]-(2,2,2-trifluoro-ethyl)-nicotinamide, 6-[3-(5-fluoro-pyridin-2-yl)-isoxazol-4-ylmethoxy]-(2-hydroxy-ethyl)-nicotinamide, ethyl-6-[3-(5-fluoro-pyridin-2-yl)-isoxazol-4-ylmethoxy]-nicotinamide, or 6-[3-(5-fluoro-pyridin-2-yl)-isoxazol-4-ylmethoxy]-methyl-nicotinamide.

The present compounds of formula I (X=O) and their pharmaceutically acceptable salts can be prepared by a process comprising a) reacting a compound of formula II (R=halo, a=0, 1, 2, or 3):

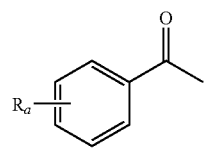

II with ethyl trifluoroacetate in a suitable solvent, such as tert-butylmethylether, in the presence of a base, such as sodium methoxide, to give a compound of formula III:

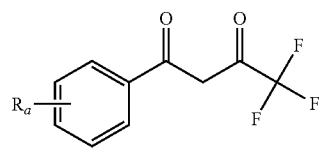

III b) reacting the compound of formula III with hydroxylamine hydrochloride in the presence of a suitable base, such as sodium hydroxide, in a suitable solvent, such as ethanol, to give a compound of formula IV:

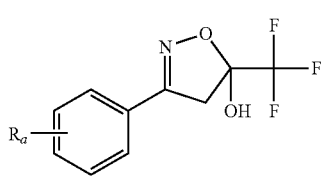

IV c) reacting the compound of formula IV with trifluoroacetic acid, to give a compound of formula V:

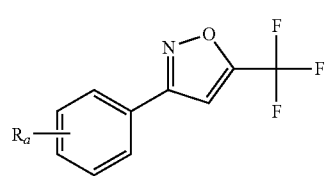

V d) reacting the compound of formula V with a base, such as BuLi and 2,2,6,6-tetramethylpiperidine in a suitable solvent, such as THF, followed by carbon dioxide, to give a compound of formula VI:

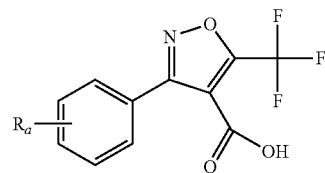

VI e) reacting the compound of formula VI with a base, such as triethylamine, in a suitable solvent, such as THF, followed by reaction with ethyl chloroformate and a reducing agent, such as sodiumborohydride, to give a compound of formula VII:

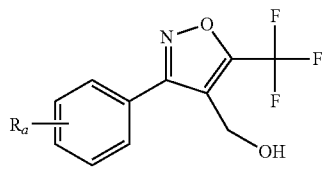

VII or alternatively, f) reacting a compound of formula VIII:

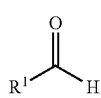

VIII with hydroxylamine hydrochloride in a suitable solvent, such as ethanol and water, in the presence of a base, such as aqueous sodium hydroxide, to give a compound of formula IX:

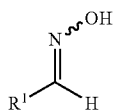

IX g) reacting the compound of formula IX with a chlorinating agent, such as N-chlorosuccinimide, in a suitable solvent, such as DMF, to give a compound of formula X:

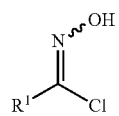

X h1) and then either reacting the compound of formula X with a compound of formula XI:

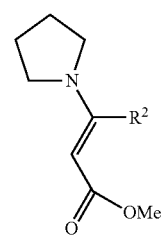

XI in the presence of a suitable base, such as triethylamine, in a suitable solvent, such as chloroform, or alternatively h2) reacting the compound of formula X with a compound of formula XII:

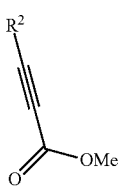

in the presence of a suitable base, such as triethylamine, in a suitable solvent, such as diethylether, or alternatively h3) reacting the compound of formula X with a compound of formula XIII:

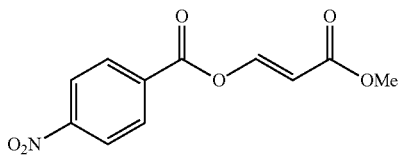

to give a compound of formula XIV:

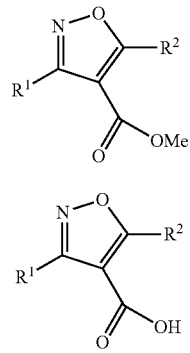

i) reacting a compound of formula XIVa with a reducing agent, such as lithiumaluminiumhydride, in a suitable solvent, such as THF, to give a compound of formula XV or reacting a compound of formula XIV with a hydrolytic agent, such as NaOH or LiOH, in a suitable solvent, such as THF, MeOH or EtOH, water to give a compound of formula XIVb followed by reacting a compound of formula XIVb with a reducing agent, such as lithiumaluminiumhydride or ethylchloroformate, in the presence of sodiumborohydride in a suitable solvent, such as THF or water, to give a compound of formula XV;

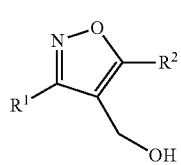

j1) reacting compounds of formula VII or XIVa or XIVb with a compounds of formula XVI:

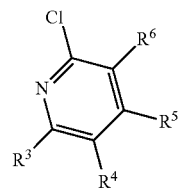

in the presence of a suitable base, such as sodium hydride, in a suitable solvent, such as THF, or alternatively j2) reacting compounds of formula VII or XIV with a compounds of formula XVII:

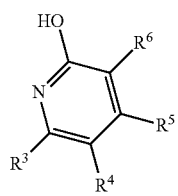

in the presence of triphenylphosphine and diethylazodicarboxylate, in a suitable solvent, such as THF, to give a compound of formula I-a (X=O):

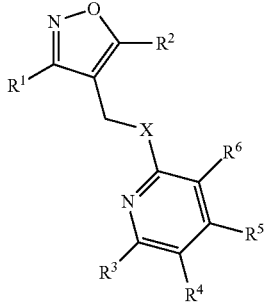

wherein $R^1$ to $R^3$ are as described for formula I hereinabove, and, if desired, converting a compound of formula I into a pharmaceutically acceptable salt.

The present compounds of formula I (X=NH) and their pharmaceutically acceptable salts can be prepared by a process comprising:

k) reacting a compound of formula XV or VII:

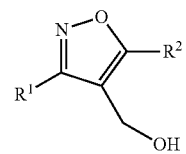

with thionyl chloride in a suitable solvent, such as dichloromethane, to give a compound of formula XVIII:

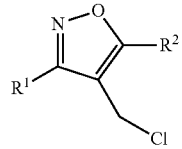

XVIII l) reacting a compound of formula XVIII in the presence of a suitable base, such as KHMDS, with 2-aminopyridine in a suitable solvent, such as THF, to give a compound of formula 1-b (X=NH, $R^{3-6}$=H)):

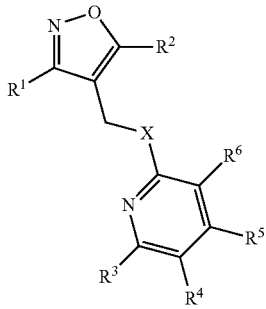

I-b m) reacting a compound of formula XIV:

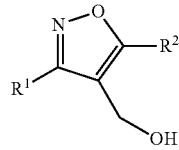

XV with phthalimide in the presence of triphenylphosphine and diethylazodicarboxylate, in a suitable solvent, such as THF to give a compound of formula XIX:

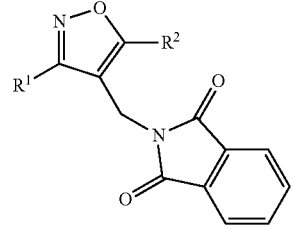

XIX n) reacting the compound of formula XIX with hydrazine, to give a compound of formula XX:

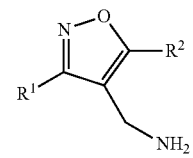

XX o) reacting the compound of formula XX with methyl 6-chloronicotinate, in the presence of a suitable base, such as N,N-diisopropyl ethyl amine, in a suitable solvent, such as DMSO, under microwave irradiation at elevated temperatures, such as 160° C., to give a compound of formula I-c':

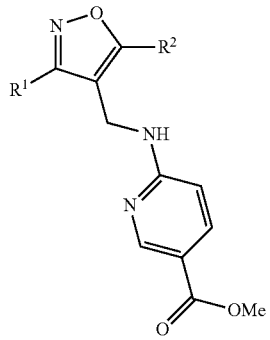

I-c'

In accordance with Schemes 1-5, compounds of formula I can be prepared following standard methods.

Scheme 1

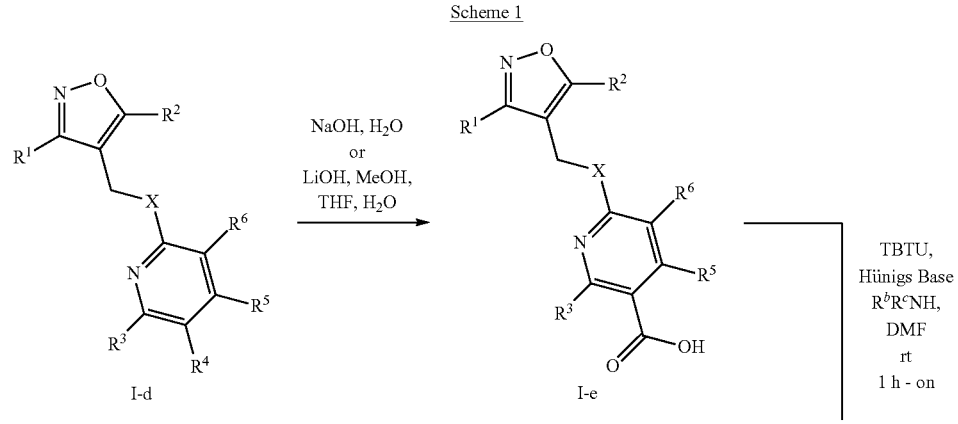

-continued
Me₃Al,
R^b R^c NH
dioxane
85-95° C.
1 h - on
or TBD,
R^b R^c NH
toluene
r.t. -50° C.
1 h -72 h
or
CDI,
30 min, 80° C.
R^b R^c NH,
DMF, 80° C.
1 h - on
or
EDAC, HOBt,
DIPEA, r.t.
R^b R^c NH
DCM,
1 h - on
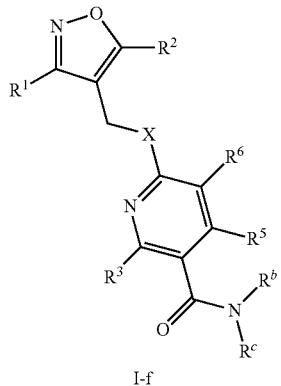
I-f
R⁴ = CO₂Me
Scheme 2
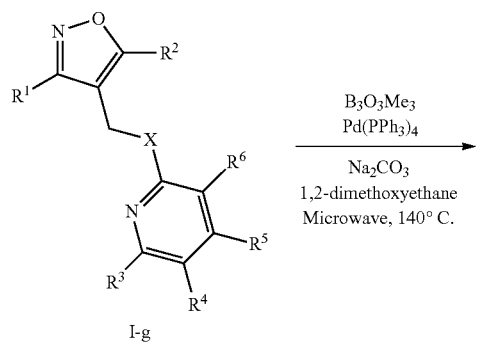
I-g
B₃O₃Me₃
Pd(PPh₃)₄
Na₂CO₃
1,2-dimethoxyethane
Microwave, 140° C.
Scheme 3
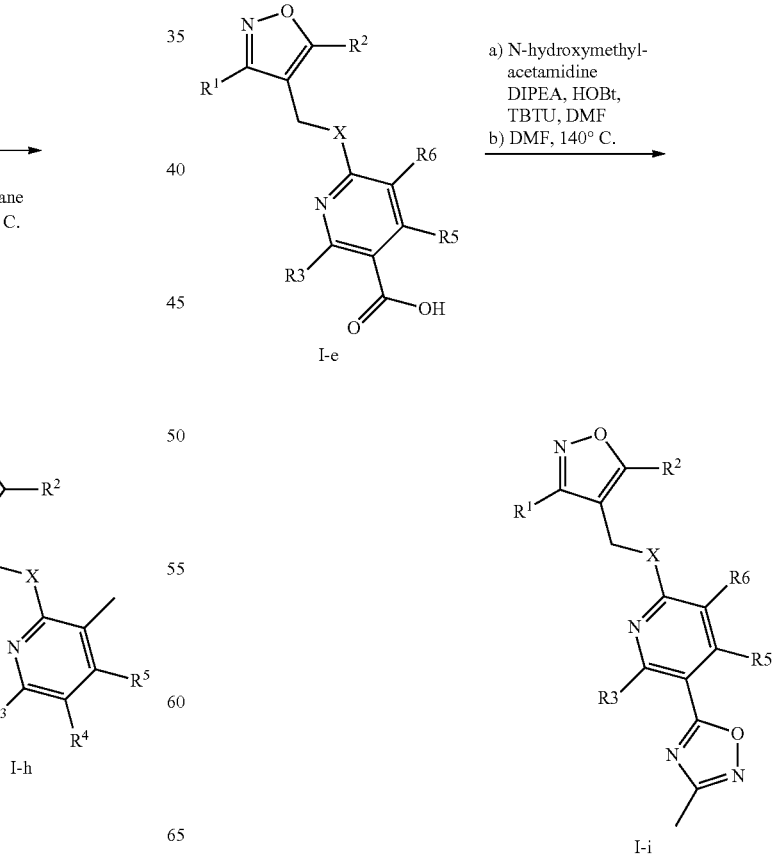
a) N-hydroxymethyl-
acetamidine
DIPEA, HOBt,
TBTU, DMF
b) DMF, 140° C.
I-e
I-h
R⁶ = Br
I-i

Scheme 4

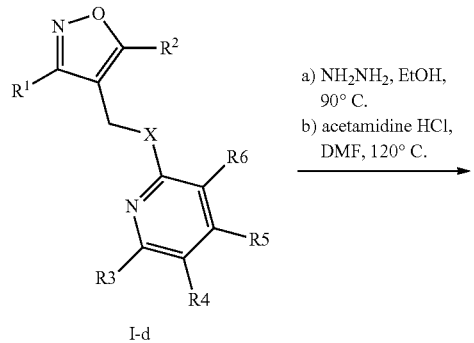

a) NH$_2$NH$_2$, EtOH, 90° C.
b) acetamidine HCl, DMF, 120° C.

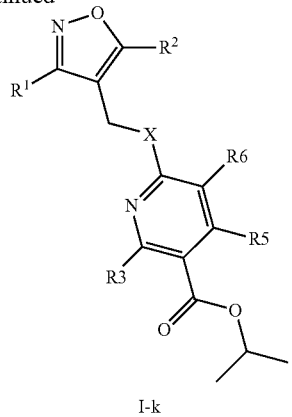

on = overnight
rt = room temperature
DMF = N,N-dimethylformamide
TBTU = O-(Benzotriazol-1-yl)-N,N,N',N'-tetramethyluronium tetrafluoroborate
HOBt = N1-hydroxybenzotriazole
DIPEA = N,N-diisopropylethylamine
DCM = dichloromethane
DMAP = N,N-dimethylamino-4-pyridine
EtOH = ethanol
EDAC = 1-ethyl-3-(3-dimethylaminopropyl) carbodiimide hydrochloride
TBD = 1,5,7-triazabicyclo[4.4.0]dec-5-ene
CDI = 1,1'-carbonyldiimidazole As mentioned earlier, the compounds of formula I and their pharmaceutically usable salts possess valuable pharmacological properties. Compounds of the present invention are ligands for GABA A receptors containing the α5 subunit and are therefore useful in the therapy where cognition enhancement is required.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell memebranes, [3H]flumazenil at a concentration of 1 nM for α1, α2, α3 subunits and 0.5 nM for α5 subunits and the test compound in the range of $10$-$10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ky values were calculated using Excel-Fit (Microsoft) and are the means of two determinations.

R$^4$ = CO$_2$Me

Scheme 5

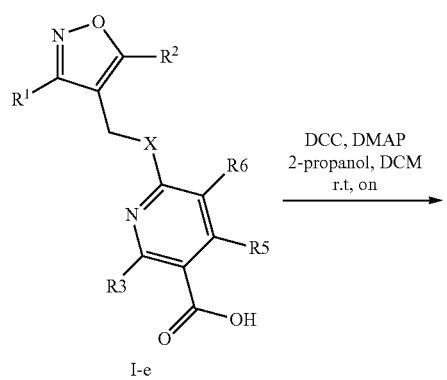

DCC, DMAP
2-propanol, DCM
r.t, on

The compounds of the accompanying examples were tested in the above described assay, and the preferred compounds were found to possess a Ki value for displacement of [$^3$H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit.

| Example | hKi GABAAa5 | Example | hKi GABAAa5 | Example | hKi GABAAa5 | Example | hKi GABAAa5 |
|---|---|---|---|---|---|---|---|
| 1 | 36.5 | 14 | 2.5 | 27 | 2.7 | 40 | 13.8 |
| 2 | 3.1 | 15 | 5.2 | 28 | 2.8 | 41 | 9.3 |
| 3 | 31.1 | 16 | 3.9 | 29 | 3.9 | 42 | 13.7 |
| 4 | 60.8 | 17 | 7.7 | 30 | 13.1 | 43 | 12.3 |
| 5 | 13.1 | 18 | 19.4 | 31 | 2.1 | 44 | 10.1 |
| 6 | 22.2 | 19 | 13.1 | 32 | 8 | 45 | 8.4 |
| 7 | 14.2 | 20 | 21.6 | 33 | 4.9 | 46 | 13.1 |
| 8 | 4.3 | 21 | 2.8 | 34 | 6.3 | 47 | 11.8 |
| 9 | 2.9 | 22 | 4.6 | 35 | 9.4 | 48 | 38 |
| 10 | 4.4 | 23 | 6.5 | 36 | 9.9 | 49 | 12.1 |
| 11 | 2 | 24 | 35 | 37 | 7.3 | 50 | 20.2 |
| 12 | 2.2 | 25 | 20.2 | 38 | 43.5 | 51 | 50.8 |
| 13 | 2.6 | 26 | 1.3 | 39 | 5 | 52 | 16.8 |
| 53 | 23.6 | 73 | 20.9 | 93 | 1.7 | 113 | 20.9 |
| 54 | 25.6 | 74 | 28.1 | 94 | 48.1 | 114 | 42.6 |
| 55 | 22.8 | 75 | 29.9 | 95 | 45.6 | 115 | 4.5 |
| 56 | 35.1 | 76 | 11.7 | 96 | 13.4 | 116 | 22.3 |
| 57 | 32.1 | 77 | 4.6 | 97 | 27.4 | 117 | 2.1 |
| 58 | 37.8 | 78 | 40.7 | 98 | 7.8 | 118 | 1.3 |
| 59 | 55.4 | 79 | 68.1 | 99 | 8.1 | 119 | 0.7 |
| 60 | 38.7 | 80 | 44.4 | 100 | 7.6 | 120 | 1.1 |
| 61 | 18.4 | 81 | 15.1 | 101 | 3.9 | 121 | 0.8 |
| 62 | 14.6 | 82 | 16.8 | 102 | 19.5 | 122 | 2.9 |
| 63 | 10.7 | 83 | 4.7 | 103 | 16.2 | 123 | 5.4 |
| 64 | 34.4 | 84 | 4.5 | 104 | 39.5 | 124 | 7.5 |
| 65 | 24.4 | 85 | 9.8 | 105 | 1.2 | 125 | 2.7 |
| 66 | 1.4 | 86 | 3.6 | 106 | 1.5 | 126 | 4.7 |
| 67 | 47.3 | 87 | 4.6 | 107 | 0.7 | 127 | 2.4 |
| 68 | 18.6 | 88 | 17.4 | 108 | 1.1 | 128 | 88.5 |
| 69 | 2.95 | 89 | 3 | 109 | 0.8 | 129 | 24.3 |
| 70 | 53.1 | 90 | 3.2 | 110 | 13 | 130 | 30.8 |
| 71 | 80.8 | 91 | 2.3 | 111 | 10.4 | 131 | 34 |
| 72 | 19.3 | 92 | 41.3 | 112 | 4.7 | 132 | 28.3 |
| 133 | 41.6 | 153 | 65.7 | 173 | 5.9 | 193 | 2.3 |
| 134 | 23.8 | 154 | 53.2 | 174 | 7.6 | 194 | 2.1 |
| 135 | 22.1 | 155 | 24 | 175 | 3.7 | 195 | 1.7 |
| 136 | 57 | 156 | 29.8 | 176 | 7.4 | 196 | 0.7 |
| 137 | 19.8 | 157 | 26.3 | 177 | 6.5 | 197 | 11 |
| 138 | 33.3 | 158 | 31.7 | 178 | 29.2 | 198 | 6.5 |
| 139 | 16.5 | 159 | 27.9 | 179 | 9.4 | 199 | 2.8 |
| 140 | 57.8 | 160 | 87.3 | 180 | 7.2 | 200 | 3.9 |
| 141 | 22.5 | 161 | 27.4 | 181 | 19.2 | 201 | 1.7 |
| 142 | 33.5 | 162 | 10.4 | 182 | 10.1 | 202 | 1.6 |
| 143 | 38.4 | 163 | 37.3 | 183 | 10 | 203 | 4.8 |
| 144 | 12.5 | 164 | 5.9 | 184 | 7.8 | 204 | 4.4 |
| 145 | 58.9 | 165 | 10.6 | 185 | 4.5 | 205 | 4 |
| 146 | 5.9 | 166 | 8.8 | 186 | 2.3 | 206 | 1.8 |
| 147 | 4.1 | 167 | 69.3 | 187 | 73.4 | 207 | 10.9 |
| 148 | 7.1 | 168 | 17.8 | 188 | 7.7 | 208 | 0.7 |
| 149 | 4.5 | 169 | 15.4 | 189 | 41.3 | 209 | 2.3 |
| 150 | 5.6 | 170 | 19.4 | 190 | 1 | 210 | 5 |
| 151 | 84.5 | 171 | 14.9 | 191 | 5 | 211 | 2.7 |
| 152 | 39.7 | 172 | 25.9 | 192 | 2.9 | 212 | 2 |
| 213 | 1.6 | 233 | 32.2 | 253 | 0.8 | 273 | 0.6 |
| 214 | 4.3 | 234 | 0.6 | 254 | 4.1 | 274 | 14.6 |
| 215 | 2.3 | 235 | 1.9 | 255 | 0.8 | 275 | 1.1 |
| 216 | 4.5 | 236 | 36.7 | 256 | 0.8 | 276 | 10.1 |
| 217 | 8.4 | 237 | 1.1 | 257 | 0.5 | 277 | 1.5 |
| 218 | 2 | 238 | 34.9 | 258 | 1.3 | 278 | 1.6 |
| 219 | 2.2 | 239 | 3.6 | 259 | 0.7 | 279 | 1.3 |
| 220 | 2.6 | 240 | 13.9 | 260 | 0.5 | 280 | 1.1 |
| 221 | 4.1 | 241 | 16 | 261 | 26.5 | 281 | 4 |
| 222 | 8.2 | 242 | 37.3 | 262 | 5.2 | 282 | 6.8 |
| 223 | 26.1 | 243 | 2.9 | 263 | 2.4 | 283 | 22.3 |
| 224 | 41.9 | 244 | 5.1 | 264 | 2.3 | 284 | 0.5 |
| 225 | 20.2 | 245 | 3.3 | 265 | 27.3 | 285 | 1.1 |
| 226 | 2.6 | 246 | 1.1 | 266 | 4.3 | 286 | 2 |
| 227 | 48 | 247 | 17.7 | 267 | 9.3 | 287 | 19.2 |
| 228 | 37.1 | 248 | 28.1 | 268 | 3.3 | 288 | 0.4 |

-continued

| Example | hKi GABAAa5 | Example | hKi GABAAa5 | Example | hKi GABAAa5 | Example | hKi GABAAa5 |
|---|---|---|---|---|---|---|---|
| 229 | 47.7 | 249 | 3.2 | 269 | 6.7 | 289 | 0.3 |
| 230 | 1.2 | 250 | 3.1 | 270 | 0.4 | 290 | 0.6 |
| 231 | 28 | 251 | 0.9 | 271 | 3.8 | 291 | 1.2 |
| 232 | 1.4 | 252 | 1 | 272 | 1.1 | 292 | 0.4 |
| 293 | 1.2 | 313 | 3 | 333 | 13.1 | 353 | 5.5 |
| 294 | 0.3 | 314 | 5.6 | 334 | 21.2 | 354 | 10.7 |
| 295 | 0.4 | 315 | 8.1 | 335 | 37.6 | 355 | 4.3 |
| 296 | 4.1 | 316 | 36.2 | 336 | 40.7 | 356 | 13.1 |
| 297 | 0.5 | 317 | 3.1 | 337 | 9.5 | 357 | ~20 |
| 298 | 0.6 | 318 | 4.8 | 338 | 23.3 | 358 | 17.8 |
| 299 | 0.5 | 319 | 20.2 | 339 | 23.1 | 359 | 13.1 |
| 300 | 1.6 | 320 | 6 | 340 | 19.4 | 360 | 18.9 |
| 301 | 0.3 | 321 | 21.4 | 341 | 29.2 | 361 | 19 |
| 302 | 0.3 | 322 | 17.7 | 342 | 15.1 | 362 | 8 |
| 303 | 0.3 | 323 | 7.3 | 343 | 12.4 | 363 | 19.9 |
| 304 | 3.8 | 324 | 10.6 | 344 | 5.6 | 364 | 13.6 |
| 305 | 0.6 | 325 | 9 | 345 | 6.4 | 365 | 8 |
| 306 | 0.3 | 326 | 27.7 | 346 | 10.9 | 366 | 6.8 |
| 307 | 0.6 | 327 | 13.9 | 347 | 7.1 | 367 | 13.5 |
| 308 | 0.2 | 328 | 17.4 | 348 | 10.3 | 368 | 44.9 |
| 309 | 0.6 | 329 | 12.9 | 349 | 39.9 | 369 | 9.3 |
| 310 | 0.4 | 330 | 15.1 | 350 | 22.9 | 370 | 21.4 |
| 311 | 0.1 | 331 | 17.8 | 351 | 55.5 | 371 | 14.1 |
| 312 | 11.3 | 332 | 22.6 | 352 | 8 | 372 | 18.5 |

"h" in hKi means "human"

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula I should be appropriate, although the above upper limit can also be exceeded when necessary.

The following examples illustrate the present invention without limiting it. All temperatures are given in degrees Celsius.

Example A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch firstly can be mixed in a mixer and then in a comminuting machine. The mixture can be returned to the mixer; the talc then can be added thereto and mixed thoroughly. The mixture can be filled by machine into hard gelatine capsules.

Example C

Suppositories of the following composition can be manufactured:

|  | mg/supp. |
|---|---|
| Active substance | 15 |
| Suppository mass | 1285 |
| Total | 1300 |

The suppository mass can melted in a glass or steel vessel, mixed thoroughly and cooled to 45° C. Thereupon, the finely powdered active substance can be added thereto and stirred until it has dispersed completely. The mixture then can be poured into suppository moulds of suitable size and left to cool; the suppositories then can be removed from the moulds and packed individually in wax paper or metal foil.

The following examples 1-372 are provided for illustration of the invention. They should not be considered as limiting the scope of the invention, but merely as being representative thereof.

Example 1

2-(5-Methyl-3-phenyl-isoxazol-4-ylmethoxy)-pyridine

To a solution of (5-methyl-3-phenyl-isoxazol-4-yl)-methanol (100 mg, 0.53 mmol) in THF (6 mL) was added 2-hydroxypyridine (50 mg, 0.53 mmol) and tributyl phosphine (206 µL, 0.79 mmol) at ambient temperature under an argon atmosphere. After cooling to 0° C., N,N,N',N'-tetramethylazodicarboxamide (137 mg, 0.79 mmol) was added. The resulting orange solution was stirred for 16 h at ambient temperature followed by 2.5 h at 50° C. Then triphenylphosphine (208 mg, 0.79 mmol), 2-hydroxypyridine (50 mg, 0.53 mmol) and diethyl azodicarboxylate (127 µL, 0.79 mmol) were added and the reaction mixture was stirred for 4 h at 50° C. The reaction mixture was then evaporated. Purification by chromatography (SiO$_2$, heptane:ethyl acetate=95:5 to 0:100) afforded the title compound (36 mg, 25%) as a colourless oil. MS: m/e=267.2 [M+H]$^+$.

Example 2

2-Methyl-6-(5-methyl-3-phenyl-isoxazol-4-ylmethoxy)-pyridine

To a suspension of sodium hydride (55% dispersion in mineral oil, 48 mg, 1.1 mmol) in THF (1.5 mL) was added a solution of (5-methyl-3-phenyl-isoxazol-4-yl)-methanol (189 mg, 1.0 mmol) in THF (3 mL) at 0° C. and the reaction mixture warmed to room temperature over 30 min. Then a solution of 2-fluoro-6-methylpyridine (122 mg, 1.1 mmol) in THF (3 mL) was added dropwise at 0° C. and the reaction mixture was stirred at room temperature overnight. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography (SiO$_2$, heptane:ethyl acetate=100:0 to 4:1) afforded the title compound (135 mg, 48%) which was obtained as a yellow oil. MS: m/e=281.1 [M+H]$^+$.

Example 3

5-Bromo-2-(5-methyl-3-phenyl-isoxazol-4-yl-methoxy)-pyridine

To a solution of (5-methyl-3-phenyl-isoxazol-4-yl)-methanol (189 mg, 1.0 mmol) in THF (12 mL) was added 2-hydroxy-5-bromopyridine (191 mg, 1.1 mmol) and triphenylphosphine (393 mg, 1.5 mmol) at ambient temperature under an argon atmosphere. Then diethyl azodicarboxylate (233 µL, 1.5 mmol) was added and the reaction mixture was stirred for 3 h at room temperature. Concentration and purification by chromatography (SiO$_2$, heptane:ethyl acetate=100:0 to 1:1) afforded the title compound (144 mg, 42%) as a colourless gum. MS: m/e=345.0/347.1 [M+H]$^+$.

Example 4

2-(5-Methyl-3-phenyl-isoxazol-4-ylmethoxy)-5-trifluoromethyl-pyridine

To a solution of (5-methyl-3-phenyl-isoxazol-4-yl)-methanol (95 mg, 0.50 mmol) in THF (6 mL) was added 2-hydroxy-5-trifluoromethylpyridine (90 mg, 0.55 mmol) and triphenylphosphine (197 mg, 0.75 mmol) at ambient temperature under an argon atmosphere. Then diethyl azodicarboxylate (120 µL, 0.75 mmol) was added and the reaction mixture was stirred for 2.5 h at 50° C. Concentration and purification by chromatography (SiO$_2$, heptane:ethyl acetate=95:5 to 0:100) afforded the title compound (86 mg, 51%) as a colourless oil. MS: m/e=335.3 [M+H]$^+$.

Example 5

6-(5-Methyl-3-phenyl-isoxazol-4-ylmethoxy)-nicotinonitrile

To a solution of (5-methyl-3-phenyl-isoxazol-4-yl)-methanol (220 mg, 1.16 mmol) in THF (2 mL) was added sodium hydride (55% dispersion in mineral oil, 996 mg, 22.8 mmol). After stirring for 0.5 h at ambient temperature 6-chloronicotinonitrile (161 mg, 1.16 mmol) was added and the reaction mixture was stirred for 5 h at ambient temperature. It was diluted with ethyl acetate (10 mL), washed with aqueous citric acid (10%, 10 mL), water (10 mL) and aqueous sodium chloride (saturated, 10 mL). The combined aqueous layers were extracted with ethyl acetate (10 mL). After drying over sodium sulfate and concentration purification by chromatography (SiO$_2$, heptane:ethyl acetate=90:10 to 60:40) afforded the title compound (307 mg, 91%) as a white solid. MS: m/e=292.1 [M+H]$^+$.

Example 6

2-(5-Methyl-3-phenyl-isoxazol-4-ylmethoxy)-5-nitro-pyridine

As described for example 4, (5-methyl-3-phenyl-isoxazol-4-yl)-methanol (200 mg, 1.06 mmol) was converted using 2-hydroxy-5-nitro-pyridine instead of 2-hydroxy-5-trifluoromethylpyridine to the title compound (SiO$_2$, heptane:ethyl acetate:dichloromethane=80:0:20 to 50:30:20, 122 mg, 37%) which was obtained as a white solid. MS: m/e=312.2 [M+H]$^+$.

Example 7

6-(5-Methyl-3-phenyl-isoxazol-4-ylmethoxy)-nicotinic acid methyl ester

As described for example 5, (5-methyl-3-phenyl-isoxazol-4-yl)-methanol (200 mg, 1.06 mmol) was converted using methyl 6-chloronicotinate instead of 6-chloronicotinonitrile to the title compound (SiO$_2$, heptane:ethyl acetate=100:0 to 70:30, 191 mg, 42%) which was obtained as a colourless oil. MS: m/e=325.3 [M+H]$^+$.

Example 8

N-Methyl-6-(5-methyl-3-phenyl-isoxazol-4-ylmethoxy)-nicotinamide a) 6-(5-Methyl-3-phenyl-isoxazol-4-ylmethoxy)-nicotinic acid

To a solution of 6-(5-methyl-3-phenyl-isoxazol-4-ylmethoxy)-nicotinic acid methyl ester (3.89 g, 120 mmol) in ethanol (40 mL) was added aqueous sodium hydroxide (1 M, 36.0 mL, 36.0 mmol). After heating at reflux for 2 h it was cooled to ambient temperature and concentrated. Addition of aqueous sodium hydroxide (1 M, 50 mL) was followed by washing with tert-butylmethylether (100 mL). The aqueous phase was acidified with aqueous hydrogen chloride (conc.) to pH=1 and extracted with tert-butylmethylether (100 mL). The organic layer was washed with water (50 mL) and aqueous sodium chloride (saturated, 50 mL). Drying over sodium sulfate and concentration afforded the title compound (1.68 g, 45%) as an off white solid. MS: m/e=309.3 [M−H]$^−$.

b) N-Methyl-6-(5-methyl-3-phenyl-isoxazol-4-ylmethoxy)-nicotinamide

To a solution of 6-(5-methyl-3-phenyl-isoxazol-4-ylmethoxy)-nicotinic acid (100 mg, 0.32 mmol) in DMF (2 mL) were added 2-(1H-benzotriazole-1-yl)-1,1,3,3-tetramethyluronium tetrafluoroborate (114 mg, 0.35 mmol), N,N-diisopropyl ethyl amine (275 µL, 1.6 mmol) and methylamine (1 M solution in MeOH, 3544, 0.35 mmol). The resulting reaction mixture was stirred overnight at room temperature. Concentration and purification by chromatography (SiO$_2$, heptane:ethyl acetate=100:0 to 1:1) afforded the title compound (40 mg, 33%) as an off white solid. MS: m/e=324.4 [M+H]$^+$.

Example 9

N-Ethyl-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using ethylamine instead of methylamine, to the title compound (90 mg, 83%) which was obtained as a white solid. MS: m/e=338.4 [M+H]$^+$.

Example 10

N-(2-Fluoro-ethyl)-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using 2-fluoroethylamine hydrochloride instead of methylamine, to the title compound (109 mg, 95%) which was obtained as a white solid. MS: m/e=356.3 [M+H]$^+$.

Example 11

N-(2,2-Difluoro-ethyl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (100 mg, 0.32 mmol) was converted, using 2,2-diflitoroethylamine instead of methylamine, to the title compound (96 mg, 80%) which was obtained as an off white solid. MS: m/e=374.1 [M+H]$^+$.

Example 12

6-(5-Methyl-3-phenyl-isoxazol-4-ylmethoxy)-N-(2,2,2-trifluoro-ethyl)-nicotinamide To a solution of 6-(5-methyl-3-phenyl-isoxazol-4-ylmethoxy)-nicotinic acid (200 mg, 0.64 mmol) in DMF (2 mL) were added 2-(1H-benzotriazole-1-yl)-1,1,3,3-tetramethyluronium tetrafluoroborate (228 mg, 0.71 mmol), N,N-diisopropyl ethyl amine (552 µL, 3.22 mmol) and 2,2,2-trifluoroethylamine 77 µL, 0.77 mmol). The resulting reaction mixture was stirred for 12 h at ambient temperature. After dilution with ethyl acetate (20 mL) it was washed with water (20 mL) and aqueous sodium carbonate (saturated, 40 mL). The organic layer was dried over sodium sulfate and concentrated. Purification by chromatography (SiO$_2$, heptane:ethyl acetate=80:20 to 20:80) afforded the title compound (213 mg, 84%) as a white solid. MS: m/e=392.2 [M+H]$^+$.

Example 13

N-(2-Hydroxy-ethyl)-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using ethanolamine instead of methylamine, to the title compound (92 mg, 81%) which was obtained as a white solid. MS: m/e=354.4 [M+H]$^+$.

Example 14

(R,S)—N-(2-Hydroxy-propyl)-6-(5-methyl-3-phenyl-isoxazol-4-ylmethoxy)-nicotinamide As described for example 12, 6-(5-methyl-3-phenyl-isoxazol-4-ylmethoxy)-nicotinic acid (200 mg, 0.64 mmol) was converted using (R,S)-1-amino-2-propanol instead of 2,2,2-trifluoroethylamine to the title compound (SiO$_2$, heptane:ethyl acetate:methanol=50:50:0 to 0:95:5, 142 mg, 60%) which was obtained as a white solid. MS: m/e=368.1 [M+H]$^+$.

Example 15

N-(3-Methoxy-propyl)-6-(5-methyl-3-phenyl-isoxazol-4-ylmethoxy)-nicotinamide To a solution of 6-(5-methyl-3-phenyl-isoxazol-4-ylmethoxy)-nicotinic acid (100 mg, 0.32 mmol) in DMF (2 mL) were added 2-(1H-benzotriazole-1-yl)-1,1,3,3-tetramethyluronium tetrafluoroborate (114 mg, 0.35 mmol), N,N-diisopropyl ethyl amine (275 µL, 1.6 mmol) and 3-methoxypropylamine (36 μL, 0.35 mmol). The resulting reaction mixture was stirred overnight at room temperature. Concentration and purification by preparative HPLC on reversed phase eluting with acetonitrile/water [0.1% aq NH$_3$ (25%)] afforded the title compound (101 mg, 82%) which was obtained as a white solid. MS: m/e=382.5 [M+H]$^+$.

Example 16

N-Cyclopropylmethyl-6-(5-methyl-3-phenyl-isoxazol-4-ylmethoxy)-nicotinamide

As described for example 12, 6-(5-methyl-3-phenyl-isoxazol-4-ylmethoxy)-nicotinic acid (155 mg, 0.50 mmol) was converted using aminomethylcyclopropane instead of 2,2,2-trifluoroethylamine to the title compound (SiO$_2$, heptane:ethyl acetate=80:20 to 50:50, 142 mg, 78%) which was obtained as a white foam. MS: m/e=364.3 [M+H]$^+$.

Example 17

N-(2-Ethyl-butyl)-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using 2-ethylbutylamine instead of methylamine, to the title compound (121 mg, 95%) which was obtained as an off white solid. MS: m/e=394.4 [M+H]$^+$.

Example 18

(R,S) 6-(5-Methyl-3-phenyl-isoxazol-4-ylmethoxy)-N-(3-oxo-isoxazolidin-5-ylmethyl)-nicotinamide To a solution of 6-(5-methyl-3-phenyl-isoxazol-4-ylmethoxy)-nicotinic acid (200 mg, 0.64 mmol) in DMF (2 mL) was added 1,1'-carbonyl-diimidazole (115 mg, 0.71 mmol) and the reaction mixture was stirred for 0.5 h at 80° C. After cooling to ambient temperature 5-aminomethyl-isoxazolidin-3-one (82 mg, 0.71 mmol) was added and stirring was continued for 1 h at this temperature and for 2 h at 80° C. It was diluted with ethyl acetate (10 mL) and washed with water (10 mL) and aqueous sodium chloride (saturated, 10 mL). The organic layer was dried over sodium sulfate and concentrated. Purification by chromatography (SiO$_2$, heptane:ethyl acetate:methanol=40:60:0 to 0:90:10) afforded the title compound (13 mg, 5%) as a white solid. MS: m/e=409.3 [M+H]$^+$.

Example 19

N-(3-Cyclopropyl-[1,2,4]oxadiazol-5-ylmethyl)-6-(5-methyl-3-phenyl-isoxazol-4-ylmethoxy)-nicotinamide As described for example 18, 6-(5-methyl-3-phenyl-isoxazol-4-ylmethoxy)-nicotinic acid (200 mg, 0.64 mmol) was converted using (3-cyclopropyl-[1,2,4]oxadiazol-5-yl)-methylamine instead of aminomethyl-isoxazolidin-3-one to the title compound (SiO$_2$, heptane:ethyl acetate=90:10 to 40:60, 97 mg, 34%) which was obtained as a light brown oil. MS: m/e=432.3 [M+H]$^+$.

Example 20

N-(5-Cyclopropyl-1H-pyrazol-3-ylmethyl)-6-(5-methyl-3-phenyl-isoxazol-4-ylmethoxy)-nicotinamide As described for example 18, 6-(5-methyl-3-phenyl-isoxazol-4-ylmethoxy)-nicotinic acid (200 mg, 0.64 mmol) was converted using (5-cyclopropyl-1H-pyrazol-3-yl)-methylamine instead of aminomethyl-isoxazolidin-3-one to the title compound (SiO$_2$, heptane:ethyl acetate:methanol=30:70:0 to 0:95:5, 97 mg, 35%) which was obtained as a colourless oil. MS: m/e=430.2 [M+H]$^+$.

Example 21

N-(4-Cyano-thiazol-2-ylmethyl)-6-(5-methyl-3-phenyl-isoxazol-4-ylmethoxy)-nicotinamide As described for example 18, 6-(5-methyl-3-phenyl-isoxazol-4-ylmethoxy)-nicotinic acid (200 mg, 0.64 mmol) was converted using 2-aminomethyl-thiazole-4-carbonitrile instead of aminomethyl-isoxazolidin-3-one to the title compound (SiO$_2$, heptane:ethyl acetate=90:10 to 40:60, 188 mg, 68%) which was obtained as a white solid. MS: m/e=432.3 [M+H]$^+$.

Example 22

6-(5-Methyl-3-phenyl-isoxazol-4-ylmethoxy)-N-pyridin-2-ylmethyl-nicotinamide

As described for example 12, 6-(5-methyl-3-phenyl-isoxazol-4-ylmethoxy)-nicotinic acid (200 mg, 0.64 mmol) was converted using 2-(aminomethyl)pyridine instead of 2,2,2-trifluoroethylamine to the title compound (SiO$_2$, heptane:ethyl acetate:methanol=50:50:0 to 0:95:5, 191 mg, 74%) which was obtained as a white solid. MS: m/e=401.2 [M+H]$^+$.

Example 23

N-(6-Methyl-3-oxo-2,3-dihydro-pyridazin-4-ylmethyl)-6-(5-methyl-3-phenyl-isoxazol-4-ylmethoxy)-nicotinamide As described for example 18, 6-(5-methyl-3-phenyl-isoxazol-4-ylmethoxy)-nicotinic acid (200 mg, 0.64 mmol) was converted using 4-aminomethyl-6-methyl-2H-pyridazin-3-one instead of aminomethyl-isoxazolidin-3-one to the title compound (SiO$_2$, heptane:ethyl acetate:methanol=20:80:0 to 0:90:10, 231 mg, 83%) which was obtained as a white solid. MS: m/e=432.3 [M+H]$^+$.

Example 24

{[6-(5-Methyl-3-phenyl-isoxazol-4-ylmethoxy)-pyridine-3-carbonyl]-amino}-acetic acid tert-butyl ester As described for example 15, 6-(5-methyl-3-phenyl-isoxazol-4-ylmethoxy)-nicotinic acid (100 mg, 0.32 mmol) was converted, using glycine tert-butylester hydrochloride instead of 3-methoxypropylamine, to the title compound (111 mg, 81%) which was obtained as an off white foam. MS: m/e=424.3 [M+H]$^+$.

Example 25

2-{[6-(5-Methyl-3-phenyl-isoxazol-4-ylmethoxy)-pyridine-3-carbonyl]-amino}-propionic acid ethyl ester As described for example 15, 6-(5-methyl-3-phenyl-isoxazol-4-ylmethoxy)-nicotinic acid (100 mg, 0.32 mmol) was converted, using DL-alanine ethylester hydrochloride instead of 3-methoxypropylamine, to the title compound (23 mg, 17%) which was obtained as a light yellow gum. MS: m/e=410.1 [M+H]$^+$.

Example 26

N-Isopropyl-6-(5-methyl-3-phenyl-isoxazol-4-yl-methoxy)-nicotinamide

As described for example 8b, 6-(5-methyl-3-phenyl-isoxazol-4-ylmethoxy)-nicotinic acid (100 mg, 0.32 mmol) was converted, using isopropylamine (1 M in DMF) instead of methylamine, to the title compound (110 mg, 97%) which was obtained as an off white solid. MS: m/e=352.5 [M+H]$^+$.

Example 27

N-Cyclopropyl-6-(5-methyl-3-phenyl-isoxazol-4-ylmethoxy)-nicotinamide

As described for example 12, 6-(5-methyl-3-phenyl-isoxazol-4-ylmethoxy)-nicotinic acid (200 mg, 0.64 mmol) was converted using cyclopropylamine instead of 2,2,2-trifluoroethylamine to the title compound (SiO$_2$, heptane:ethyl acetate=80:20 to 20:80, 148 mg, 68%) which was obtained as a white solid. MS: m/e=350.2 [M+H]$^+$.

Example 28

N-Cyclobutyl-6-(5-methyl-3-phenyl-isoxazol-4-yl-methoxy)-nicotinamide

As described for example 8b, 6-(5-methyl-3-phenyl-isoxazol-4-ylmethoxy)-nicotinic acid (100 mg, 0.32 mmol) was converted, using cyclobutylamine (1 M in DMF) instead of methylamine, to the title compound (66 mg, 56%) which was obtained as a white solid. MS: m/e=364.4 [M+H]$^+$.

Example 29

N-Cyclopentyl-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using cyclopentylamine (1 M in DMF) instead of methylamine, to the title compound (98 mg, 81%) which was obtained as a white solid. MS: m/e=378.4 [M+H]$^+$.

Example 30

N-Cyclohexyl-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using cyclohexylamine instead of methylamine, to the title compound (126 mg, 100%) which was obtained as a white solid. MS: m/e=392.3 [M+H]$^+$.

Example 31

6-(5-Methyl-3-phenyl-isoxazol-4-ylmethoxy)-N-(tetrahydro-pyran-4-yl)-nicotinamide As described for example 12, 6-(5-methyl-3-phenyl-isoxazol-4-ylmethoxy)-nicotinic acid (200 mg, 0.64 mmol) was converted using 4-aminotetrahydropyran instead of 2,2,2-trifluoroethylamine to the title compound (SiO$_2$, heptane:ethyl acetate=80:20 to 20:80, 231 mg, 91%) which was obtained as a white solid. MS: m/e=394.1 [M+H]$^+$.

Example 32

(R,S)—N-(2,2-Dimethyl-tetrahydro-pyran-4-yl)-6-(5-methyl-3-phenyl-isoxazol-4-ylmethoxy)-nicotinamide As described for example 12, 6-(5-methyl-3-phenyl-isoxazol-4-ylmethoxy)-nicotinic acid (200 mg, 0.64 mmol) was converted using (R,S)-2,2-dimethyl-4-aminotetrahydropyran instead of 2,2,2-trifluoroethylamine to the title compound (SiO$_2$, heptane:ethyl acetate=70:30 to 30:70, 140 mg, 52%) which was obtained as a colourless solid. MS: m/e=422.2 [M+H]$^+$.

Example 33

N-(1,1-Dioxo-hexahydro-1,6-thiopyran-4-yl)-6-(5-methyl-3-phenyl-isoxazol-4-ylmethoxy)-nicotinamide As described for example 18, 6-(5-methyl-3-phenyl-isoxazol-4-ylmethoxy)-nicotinic acid (200 mg, 0.64 mmol) was converted using 4-amino-tetrahydro-thiopyran 1,1-dioxide instead of aminomethyl-isoxazolidin-3-one to the title compound (164 mg, 58%) which was obtained as a white solid. MS: m/e=442.2 [M+H]$^+$.

Example 34

6-(5-Methyl-3-phenyl-isoxazol-4-ylmethoxy)-N-(1-methyl-piperidin-4-yl)-nicotinamide To a solution of 6-(5-methyl-3-phenyl-isoxazol-4-ylmethoxy)-nicotinic acid (100 mg, 0.32 mmol) in DMF (2 mL) were added 2-(1H-benzotriazole-1-yl)-1,1,3,3-tetramethyluronium tetrafluoroborate (114 mg, 0.35 mmol), N,N-diisopropyl ethyl amine (275 μL, 1.6 mmol) and 1-methylpiperidin-4-amine (41 mg, 0.35 mmol). The resulting reaction mixture was stirred overnight at room temperature. Concentration and purification by preparative HPLC on reversed phase eluting with acetonitrile/water [0.1% aq NH$_3$ (25%)]. Then the residue was partitioned with ethyl acetate and water, the organic extract was washed with aqueous sodium hydrogen carbonate (saturated) dried over sodium sulfate and concentrated to afford the title compound (94 mg, 72%) which was obtained as a white solid. MS: m/e=407.5 [M+H]$^+$.

Example 35

N-(1-Ethyl-piperidin-4-yl)-6-(5-methyl-3-phenyl-isoxazol-4-ylmethoxy)-nicotinamide As described for example 34, 6-(5-methyl-3-phenyl-isoxazol-4-ylmethoxy)-nicotinic acid (100 mg, 0.32 mmol) was converted, using 1-ethylpiperidin-4-amine instead of 1-methylpiperidin-4-amine, to the title compound (99 mg, 73%) which was obtained as an off white solid. MS: m/e=421.1 [M+H]$^+$.

Example 36

N-(1-Isopropyl-piperidin-4-yl)-6-(5-methyl-3-phenyl-isoxazol-4-ylmethoxy)-nicotinamide As described for example 34, 6-(5-methyl-3-phenyl-isoxazol-4-ylmethoxy)-nicotinic acid (100 mg, 0.32 mmol) was converted, using N-isopropyl-4-aminopiperidine instead of 1-methylpiperidin-4-amine, to the title compound (110 mg, 73%) which was obtained as a white foam. MS: m/e=435.4 [M+H]$^+$.

Example 37

N-(1-Benzyl-piperidin-4-yl)-6-(5-methyl-3-phenyl-isoxazol-4-ylmethoxy)-nicotinamide As described for example 34, 6-(5-methyl-3-phenyl-isoxazol-4-ylmethoxy)-nicotinic acid (100 mg, 0.32 mmol) was converted, using 4-amino-1-benzylpiperidine instead of 1-methylpiperidin-4-amine, to the title compound (120 mg, 77%) which was obtained as an off white foam. MS: m/e=483.3 [M+H]$^+$.

Example 38

3-{[6-(5-Methyl-3-phenyl-isoxazol-4-ylmethoxy)-pyridine-3-carbonyl]-amino}-piperidine-1-carboxylic acid tert-butyl ester As described for example 34, 6-(5-methyl-3-phenyl-isoxazol-4-ylmethoxy)-nicotinic acid (100 mg, 0.32 mmol) was converted, using (+/−)-3-amino-1-N-Boc-piperidine instead of 1-methylpiperidin-4-amine, to the title compound (96 mg, 61%) which was obtained as a white foam. MS: m/e=493.3 [M+H]$^+$.

Example 39

N-(1-Ethyl-piperidin-3-yl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (100 mg, 0.32 mmol) was converted, using 3-amino-N-ethylpiperidine (1 M in DMF) instead of methylamine, to the title compound (64 mg, 95%) which was obtained as an off white foam. MS: m/e=421.3 [M+H]$^+$.

Example 40

(3-{[6-(5-Methyl-3-phenyl-isoxazol-4-ylmethoxy)-pyridine-3-carbonyl]-amino}-piperidin-1-yl)-acetic acid ethyl ester To a solution of 6-(5-methyl-3-phenyl-isoxazol-4-ylmethoxy)-nicotinic acid (500 mg, 1.6 mmol) in DMF (10 mL) were added 2-(1H-benzotriazole-1-yl)-1,1,3,3-tetramethyluronium tetrafluoroborate (569 mg, 1.8 mmol), N,N-diisopropyl ethyl amine (1.38 mL, 8.1 mmol) and (3-amino-piperidin-1-yl)-acetic acid ethyl ester hydrochloride (459 mg, 1.8 mmol). The resulting reaction mixture was stirred overnight at room temperature. Concentration and purification by chromatography (SiO$_2$, heptane:ethyl acetate=100:0 to 1:1 and then dichloromethane:methanol=9:1) afforded the title compound (622 mg, 81%) as a light brown gum. MS: m/e=479.1 [M+H]$^+$.

Example 41

(3-{[6-(5-Methyl-3-phenyl-isoxazol-4-ylmethoxy)-pyridine-3-carbonyl]-amino}-piperidin-1-yl)-acetic acid To a solution of (3-{[6-(5-methyl-3-phenyl-isoxazol-4-ylmethoxy)-pyridine-3-carbonyl]-amino}-piperidin-1-yl)-acetic acid ethyl ester (538 mg, 1.1 mmol) in THF (5 mL) was added a solution of lithium hydroxide monohydrate (94 mg, 2.2 mmol) in water (5 mL) and methanol (1 mL) added and the resulting mixture stirred at room temperature overnight. The mixture was acidified to pH 4 with HCl (25%, 3 drops) and methanol (2 drops) added. A gum began to form and the mixture was cooled at 0° C. for 1.5 h and then the aqueous layer decanted off. Trituration with diethylether and hexane afforded the title compound (420 mg, 83%) which was obtained as an off white solid. MS: m/e=449.0 [M−H]$^-$.

Example 42

N-(1-Ethylcarbamoylmethyl-piperidin-3-yl)-6-(5-methyl-3-phenyl-isoxazol-4-ylmethoxy)-nicotinamide As described for example 8b, (3-{[6-(5-methyl-3-phenyl-isoxazol-4-ylmethoxy)-pyridine-3-carbonyl]-amino}-piperidin-1-yl)-acetic acid (70 mg, 0.16 mmol) instead of 6-(5-methyl-3-phenyl-isoxazol-4-ylmethoxy)-nicotinic acid was converted, using ethylamine (1 M in DMF) instead of methylamine, to the title compound (47 mg, 63%) which was obtained as an off white solid after trituration with water. MS: m/e=478.3 [M+H]$^+$.

Example 43

N-(1-Cyclopropylcarbamoylmethyl-piperidin-3-yl)-6-(5-methyl-3-phenyl-isoxazol-4-ylmethoxy)-nicotinamide As described for example 42, (3-{[6-(5-methyl-3-phenyl-isoxazol-4-ylmethoxy)-pyridine-3-carbonyl]-amino}-piperidin-1-yl)-acetic acid (70 mg, 0.16 mmol) was converted, using cyclopropylamine instead of methylamine, to the title compound (52 mg, 63%) which was obtained as a white solid. MS: m/e=490.5 [M+H]$^+$.

Example 44

6-(5-Methyl-3-phenyl-isoxazol-4-ylmethoxy)-N-{1-[(2,2,2-trifluoro-ethylcarbamoyl)-methyl]-piperidin-3-yl}-nicotinamide As described for example 42, (3-{[6-(5-methyl-3-phenyl-isoxazol-4-ylmethoxy)-pyridine-3-carbonyl]-amino}-piperidin-1-yl)-acetic acid (70 mg, 0.16 mmol) was converted, using 2,2,2-trifluoroethylamine instead of methylamine, to the title compound (51 mg, 62%) which was obtained as an off white solid. MS: m/e=532.0 [M+H]$^+$.

Example 45

N-{1-[(2-Hydroxy-ethylcarbamoyl)-methyl]-piperidin-3-yl}-6-(5-methyl-3-phenyl-isoxazol-4-yl-methoxy)-nicotinamide As described for example 42, (3-{[6-(5-methyl-3-phenyl-isoxazol-4-ylmethoxy)-pyridine-3-carbonyl]-amino}-piperidin-1-yl)-acetic acid (70 mg, 0.16 mmol) was converted, using ethanolamine instead of methylamine, to the title compound (52 mg, 67%) which was obtained as an off white solid. MS: m/e=494.3 [M+H]$^+$.

Example 46

6-(5-Methyl-3-phenyl-isoxazol-4-ylmethoxy)-N-{1-[(tetrahydro-pyran-4-ylcarbamoyl)-methyl]-piperidin-3-yl}-nicotinamide As described for example 42, (3-{[6-(5-methyl-3-phenyl-isoxazol-4-ylmethoxy)-pyridine-3-carbonyl]-amino}-piperidin-1-yl)-acetic acid (70 mg, 0.16 mmol) was converted, using 4-aminotetrahydropyran instead of methylamine, to the title compound (61 mg, 74%) which was obtained as an off white solid. MS: m/e=534.2 [M+H]$^+$.

Example 47

N-tert-Butyl-6-(5-methyl-3-phenyl-isoxazol-4-yl-methoxy)-nicotinamide

As described for example 15, 6-(5-methyl-3-phenyl-isoxazol-4-ylmethoxy)-nicotinic acid (100 mg, 0.32 mmol) was converted, using tert-butylamine instead of 3-methoxypropylamine, to the title compound (89 mg, 76%) which was obtained as an off white solid. MS: m/e=366.3 [M+H]'.

Example 48

6-(5-Methyl-3-phenyl-isoxazol-4-ylmethoxy)-N-phenyl-nicotinamide

As described for example 15, 6-(5-methyl-3-phenyl-isoxazol-4-ylmethoxy)-nicotinic acid (100 mg, 0.32 mmol) was converted, using aniline instead of 3-methoxypropylamine, to the title compound (87 mg, 70%) which was obtained as an off white solid. MS: m/e=386.4 [M+H]$^+$.

Example 49

N-(4-Fluoro-phenyl)-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using 4-fluoroaniline (1 M in DMF) instead of methylamine, to the title compound (109 mg, 84%) which was obtained as a white solid. MS: m/e=404.4 [M+H]$^+$.

Example 50

N-Methyl-6-(5-methyl-3-phenyl-isoxazol-4-yl-methoxy)-N-(tetrahydro-pyran-4-yl)-nicotinamide To a solution of 6-(5-methyl-3-phenyl-isoxazol-4-yl-methoxy)-N-(tetrahydro-pyran-4-yl)-nicotinamide (200 mg, 0.51 mmol) in THF (2 mL) was added at 0° C. potassium bis(trimethylsilyl)amide (0.91 M in THF, 614 µL, 0.56 mmol) over a period of 2 min. After stirring for 0.5 h at this temperature iodomethane (41 µL, 0.66 mmol) was added and the resulting suspension was stirred for 2 h at ambient temperature. Concentration and purification by chromatography (SiO$_2$, heptane:ethyl acetate=50:50 to 0:100) afforded the title compound (91 mg, 44%) as a white foam. MS: m/e=408.5 [M+H]$^+$.

Example 51

[6-(5-Methyl-3-phenyl-isoxazol-4-ylmethoxy)-pyridin-3-yl]-piperidin-1-yl-methanone As described for example 15, 6-(5-methyl-3-phenyl-isoxazol-4-ylmethoxy)-nicotinic acid (100 mg, 0.32 mmol) was converted, using piperidine instead of 3-methoxypropylamine, to the title compound (91 mg, 75%) which was obtained as a yellow gum. MS: m/e=378.5 [M+H]$^+$.

Example 52

(4,4-Difluoro-piperidin-1-yl)-[6-(5-methyl-3-phenyl-isoxazol-4-ylmethoxy)-pyridin-3-yl]-methanone As described for example 8b, 6-(5-methyl-3-phenyl-isoxazol-4-ylmethoxy)-nicotinic acid (100 mg, 0.32 mmol) was converted, using 4,4-difluoropiperidine hydrochloride (1 M in DMF) instead of methylamine, to the title compound (131 mg, 98%) which was obtained as a light yellow gum. MS: m/e=414.4 [M+H]$^+$.

Example 53

[6-(5-Methyl-3-phenyl-isoxazol-4-ylmethoxy)-pyridin-3-yl]-morpholin-4-yl-methanone As described for example 12, 6-(5-methyl-3-phenyl-isoxazol-4-ylmethoxy)-nicotinic acid (200 mg, 0.64 mmol) was converted using morpholine instead of 2,2,2-trifluoroethylamine to the title compound (SiO$_2$, heptane:ethyl acetate=80:20 to 20:80, 165 mg, 67%) which was obtained as a white solid. MS: m/e=380.3 [M+H]$^+$.

Example 54

[6-(5-Methyl-3-phenyl-isoxazol-4-ylmethoxy)-pyridin-3-yl]-thiomorpholin-4-yl-methanone As described for example 12, 6-(5-methyl-3-phenyl-isoxazol-4-ylmethoxy)-nicotinic acid (450 mg, 1.45 mmol) was converted using thiomorpholine instead of 2,2,2-trifluoroethylamine to the title compound (SiO$_2$, heptane:ethyl acetate=80:20 to 20:80, 560 mg, 97%) which was obtained as a white solid. MS: m/e=396.1 [M+H]$^+$.

Example 55

(1,1-Dioxo-1,6-thiomorpholin-4-yl)-[6-(5-methyl-3-phenyl-isoxazol-4-ylmethoxy)-pyridin-3-yl]-methanone To solution of [6-(5-methyl-3-phenyl-isoxazol-4-yl-methoxy)-pyridin-3-yl]-thiomorpholin-4-yl-methanone (423 mg, 1.07 mmol) in a mixture of dichloromethane (4.5 mL), methanol (4.5 mL) and water (65 µL) was added potassium monopersulfate triple salt (1.32 g, 2.14 mmol) and the reaction mixture was heated at reflux for 8 h. After cooling it was poured onto aqueous sodium bisulfite (38%, 10 mL) and stirred for 45 min at ambient temperature. Extraction with dichloromethane (50 mL) was followed by washing the organic layers with aqueous sodium carbonate (50 mL). Drying over sodium sulfate, concentration and purification of the residue by chromatography (SiO$_2$, ethyl acetate:dichloromethane=80:20 to 20:80) afforded the title compound (15 mg, 3%) as a colourless oil. MS: m/e=427.5 [M+H]$^+$ Example 56

4-Benzyloxy-2-(5-methyl-3-phenyl-isoxazol-4-ylmethoxy)-pyridine

As described for example 4, (5-methyl-3-phenyl-isoxazol-4-yl)-methanol (95 mg, 0.50 mmol) was converted using 4-benzyloxy-2(1H)-pyridone instead of 2-hydroxy-5-trifluoromethylpyridine to the title compound (SiO$_2$, heptane:ethyl acetate=95:5 to 0:100, 52 mg, 28%) which was obtained as a colourless oil. MS: m/e=373.1 [M+H]$^+$.

Example 57

1-Methyl-2'-(5-methyl-3-phenyl-isoxazol-4-ylmethoxy)-1,2,3,6-tetrahydro-[4,4']bipyridinyl As described for example 4, (5-methyl-3-phenyl-isoxazol-4-yl)-methanol (135 mg, 0.72 mmol) was converted using 1'-methyl-1',2',3',6'-tetrahydro-1H-[4,4']bipyridinyl-2-one instead of 2-hydroxy-5-trifluoromethylpyridine to the title compound (SiO$_2$, heptane:ethyl acetate:methanol=95:5:0 to 0:80:20, 45 mg, 17%) which was obtained as a yellow oil. MS: m/e=362.3 [M+H]$^+$.

Example 58

2-(5-Methyl-3-phenyl-isoxazol-4-ylmethoxy)-N-(2,2,2-trifluoro-ethyl)-isonicotinamide a) 2-(5-Methyl-3-phenyl-isoxazol-4-ylmethoxy)-isonicotinic acid methyl ester To a solution of (5-methyl-3-phenyl-isoxazol-4-yl)-methanol (1.5 g, 8.0 mmol) in THF (79 mL) was added 2-hydroxy-isonicotinic acid methyl ester (1.8 g, 12.0 mmol) and triphenylphosphine (2.8 g, 11 mmol) at room temperature under an argon atmosphere. Then diethyl azodicarboxylate (1.64 mL, 11 mmol) was added and the reaction mixture was stirred overnight at room temperature. Then 2-hydroxy-isonicotinic acid methyl ester (0.2 g, 0.17 mmol) was added and the resulting mixture stirred at room temperature for 1 h and then heated at 60° C. for 1 h. After cooling to room temperature, concentration and purification by chromatography (SiO$_2$, heptane:ethyl acetate=100:0 to 1:1) afforded the title compound (0.99 g, 38%) as a light yellow solid. MS: m/e=325.1 [M+H]$^+$.

b) 2-(5-Methyl-3-phenyl-isoxazol-4-ylmethoxy)-isonicotinic acid

To a suspension of 2-(5-methyl-3-phenyl-isoxazol-4-ylmethoxy)-isonicotinic acid methyl ester (759 mg, 2.3 mmol) in THF (6.3 mL) was added a solution of lithium hydroxide monohydrate (196 mg, 4.7 mmol) in water (6.3 mL) and methanol (1.4 mL) added and the resulting mixture stirred at room temperature for 2 h. The mixture was acidified to pH 4 with HCl (25%, 3 drops and the resulting precipitate filtered off and dried to afford the title compound (641 mg, 88%) which was obtained as a white solid. MS: m/e=309.5 [M−H]$^-$.

c) 2-(5-Methyl-3-phenyl-isoxazol-4-ylmethoxy)-N-(2,2,2-trifluoro-ethyl)-isonicotinamide As described for example 8b, 2-(5-methyl-3-phenyl-isoxazol-4-ylmethoxy)-isonicotinic acid (78 mg, 0.3 mmol), instead of 6-(5-methyl-3-phenyl-isoxazol-4-ylmethoxy)-nicotinic acid, was converted, using 2,2,2-trifluoroethylamine instead of methylamine, to the title compound (49 mg, 51%) which was obtained as a white solid. MS: m/e=392.3 [M+H]$^+$.

Example 59

2-(5-Methyl-3-phenyl-isoxazol-4-ylmethoxy)-N-(tetrahydro-pyran-4-yl)-isonicotinamide As described for example 58c, 2-(5-methyl-3-phenyl-isoxazol-4-ylmethoxy)-isonicotinic acid (78 mg, 0.3 mmol) was converted, using 4-aminotetrahydropyran instead of 2,2,2-trifluoroethylamine, to the title compound (61 mg, 62%) which was obtained as a white solid. MS: m/e=394.3 [M+H]$^+$.

Example 60

2-Methyl-6-(5-methyl-3-phenyl-isoxazol-4-ylmethoxy)-N-(tetrahydro-pyran-4-yl)-nicotinamide To a solution of 5-bromo-2-methyl-6-(5-methyl-3-phenyl-isoxazol-4-ylmethoxy)-N-(tetrahydro-pyran-4-yl)-nicotinamide (150 mg, 0.37 mmol) in methanol (3 mL) and THF (3 mL) was added under an argon atmosphere palladium on charcoal (10%, 20 mg) and ammonium formate (70 mg, 1.12 mmol). The reaction mixture was stirred for 6 h at ambient temperature. Filtration over Hyflo® and washing with THF afforded the title compound (29 mg, 20%) which was obtained as a light brown semi-solid. MS: m/e=408.3 [M+H]$^+$.

Example 61

6-(5-Methyl-3-phenyl-isoxazol-4-ylmethoxy)-4-trifluoromethyl-nicotinic acid a) 6-(5-Methyl-3-phenyl-isoxazol-4-ylmethoxy)-4-trifluoromethyl-nicotinic acid methyl ester As described for example 5, (5-methyl-3-phenyl-isoxazol-4-yl)-methanol (3.47 g, 18.4 mmol) was converted using methyl 6-chloro-4-(trifluoromethyl)nicotinate instead of 6-chloronicotinonitrile to the title compound which was used directly in the next transformation without further purification.

b) 6-(5-Methyl-3-phenyl-isoxazol-4-ylmethoxy)-4-trifluoromethyl-nicotinic acid

As described for example 8a, 6-(5-methyl-3-phenyl-isoxazol-4-ylmethoxy)-4-trifluoromethyl-nicotinic acid methyl ester (example 61a) instead of 6-(5-methyl-3-phenyl-isoxazol-4-ylmethoxy)-nicotinic acid methyl ester was converted to the title compound (3.61 g, 52%) which was obtained as a white solid. MS: m/e=377.4 [M–H]⁻.

Example 62

N-Isopropyl-6-(5-methyl-3-phenyl-isoxazol-4-yl-methoxy)-4-trifluoromethyl-nicotinamide As described for example 12, 6-(5-methyl-3-phenyl-isoxazol-4-ylmethoxy)-4-trifluoromethyl-nicotinic acid (200 mg, 0.53 mmol) instead of 6-(5-methyl-3-phenyl-isoxazol-4-ylmethoxy)-nicotinic acid was converted using isopropylamine instead of 2,2,2-trifluoroethylamine to the title compound (SiO$_2$, ethyl acetate:dichloromethane=100:0 to 50:50, 60 mg, 27%) which was obtained as an off white solid. MS: m/e=420.1 [M+H]⁺.

Example 63

6-(5-Methyl-3-phenyl-isoxazol-4-ylmethoxy)-N-(tetrahydro-pyran-4-yl)-4-trifluoromethyl-nicotinamide As described for example 12, 6-(5-methyl-3-phenyl-isoxazol-4-ylmethoxy)-4-trifluoromethyl-nicotinic acid (200 mg, 0.53 mmol) instead of 6-(5-methyl-3-phenyl-isoxazol-4-ylmethoxy)-nicotinic acid was converted using 4-aminotetrahydropyran instead of 2,2,2-trifluoroethylamine to the title compound (SiO$_2$, ethyl acetate:dichloromethane=50:50 to 100:0, 109 mg, 45%) which was obtained as a white solid. MS: m/e=462.2 [M+H]⁺.

Example 64

5-Bromo-6-(5-methyl-3-phenyl-isoxazol-4-yl-methoxy)-nicotinic acid methyl ester

As described for example 5, (5-methyl-3-phenyl-isoxazol-4-yl)-methanol (3.60 mg, 19.0 mmol) was converted using methyl 5-bromo-6-chloronicotinate instead of 6-chloronicotinonitrile to the title compound (SiO$_2$, heptane:ethyl acetate=90:10 to 60:40, 2.83 g, 37%) which was obtained as a white solid. MS: m/e=403.3/405.2 [M+H]'.

Example 65

5-Bromo-6-(5-methyl-3-phenyl-isoxazol-4-yl-methoxy)-N-(tetrahydro-pyran-4-yl)-nicotinamide a) 5-Bromo-6-(5-methyl-3-phenyl-isoxazol-4-yl-methoxy)-nicotinic acid As described for example 8a, 5-bromo-6-(5-methyl-3-phenyl-isoxazol-4-ylmethoxy)-nicotinic acid methyl ester (2.71 g, 6.49 mmol) instead of 6-(5-methyl-3-phenyl-isoxazol-4-ylmethoxy)-nicotinic acid methyl ester was converted to the title compound (2.55 g, 99%) which was obtained as a white solid. MS: m/e=386.9/389.0 [M–H]⁻.

b) 5-Bromo-6-(5-methyl-3-phenyl-isoxazol-4-yl-methoxy)-N-(tetrahydro-pyran-4-yl)-nicotinamide As described for example 31, 5-bromo-6-(5-methyl-3-phenyl-isoxazol-4-ylmethoxy)-nicotinic acid (2.28 g, 5.86 mmol) instead of 6-(5-methyl-3-phenyl-isoxazol-4-ylmethoxy)-nicotinic acid was converted to the title compound (2.47 g, 89%) which was obtained as a white solid. MS: m/e=471.9/473.9 [M+H]⁺.

Example 66

5-Methyl-6-(5-methyl-3-phenyl-isoxazol-4-yl-methoxy)-N-(tetrahydro-pyran-4-yl)-nicotinamide To a suspension of 5-bromo-6-(5-methyl-3-phenyl-isoxazol-4-ylmethoxy)-N-(tetrahydro-pyran-4-yl)-nicotinamide (200 mg, 0.42 mmol) in 1,2-dimethoxyethane (1 mL) was added trimethylboroxine (88 µL, 0.64 mmol), aqueous sodium carbonate (1 M, 0.64 mL, 0.64 mmol) and tetrakis (triphenylphosphine)palladium(0) (49 mg, 0.04 mmol). The reaction mixture was then irradiated in the microwave for 20 min at 140° C. under an argon atmosphere. It was diluted with ethyl acetate (10 mL) and washed with water (10 mL) and brine (10 mL). The aqueous layers were extracted with ethyl acetate (10 mL) and the combined organic layers were dried over sodium sulfate. Trituration from tert-butylmethylether afforded the title compound (87 mg, 50%) which was obtained as a white solid. MS: m/e=408.4 [MA-1]+

Example 67

5-Bromo-2-methyl-6-(5-methyl-3-phenyl-isoxazol-4-ylmethoxy)-N-(tetrahydro-pyran-4-yl)-nicotinamide a) 5-Bromo-2-methyl-6-(5-methyl-3-phenyl-isoxazol-4-ylmethoxy)-nicotinic acid ethyl ester As described for example 4, (5-methyl-3-phenyl-isoxazol-4-yl)-methanol (402 mg, 2.12 mmol) was converted using 5-bromo-6-hydroxy-2-methyl-nicotinic acid ethyl ester instead of 2-hydroxy-5-trifluoromethylpyridine to the title compound (SiO$_2$, heptane:ethyl acetate=100:0 to 50:50, 700 mg, 76%) which was obtained as a colourless oil. MS: m/e=431.1/433.2 [M+H]⁺.

b) 5-Bromo-2-methyl-6-(5-methyl-3-phenyl-isoxazol-4-ylmethoxy)-nicotinic acid

As described for example 8a, 5-bromo-2-methyl-6-(5-methyl-3-phenyl-isoxazol-4-ylmethoxy)-nicotinic acid ethyl ester (650 mg, 1.51 mmol) instead of 6-(5-methyl-3-phenyl-isoxazol-4-ylmethoxy)-nicotinic acid methyl ester was converted to the title compound (542 mg, 89%) which was obtained as a white solid. MS: m/e=401.3/403.4 [M–H]⁻.

c) 5-Bromo-2-methyl-6-(5-methyl-3-phenyl-isoxazol-4-ylmethoxy)-N-(tetrahydro-pyran-4-yl)-nicotinamide As described for example 31, 5-bromo-2-methyl-6-(5-methyl-3-phenyl-isoxazol-4-ylmethoxy)-nicotinic acid (488 mg, 1.21 mmol) instead of 6-(5-methyl-3-phenyl-isoxazol-4-ylmethoxy)-nicotinic acid was converted to the title compound (450 mg, 76%) which was obtained as a light brown solid. MS: m/e=486.3/488.2 [M+H]⁺.

Example 68

5-Bromo-N-isopropyl-6-(5-methyl-3-phenyl-isoxazol-4-ylmethoxy)-nicotinamide

As described for example 8b, 5-bromo-6-(5-methyl-3-phenyl-isoxazol-4-ylmethoxy)-nicotinic acid (240 mg, 0.6 mmol), instead of 6-(5-methyl-3-phenyl-isoxazol-4-yl-methoxy)-nicotinic acid, was converted, using isopropylamine instead of methylamine, to the title compound (229 mg, 86%) which was obtained as an off white foam. MS: m/e=430.3/432.2 [M+H]+.

Example 69

N-Isopropyl-5-methyl-6-(5-methyl-3-phenyl-isoxazol-4-ylmethoxy)-nicotinamide

As described for example 66, 5-bromo-N-isopropyl-6-(5-methyl-3-phenyl-isoxazol-4-ylmethoxy)-nicotinamide (150 mg, 0.35 mmol), instead of 5-bromo-6-(5-methyl-3-phenyl-isoxazol-4-ylmethoxy)-N-(tetrahydro-pyran-4-yl)-nicotinamide was converted to the title compound (73 mg, 52%) which was obtained as an off white gum. MS: m/e=366.0 [M+H]+.

Example 70

N-Isopropyl-N-methyl-6-(5-methyl-3-phenyl-isoxazol-4-ylmethoxy)-nicotinamide

As described for example 50, N-isopropyl-6-(5-methyl-3-phenyl-isoxazol-4-ylmethoxy)-nicotinamide (200 mg, 0.6 mmol), instead of 6-(5-methyl-3-phenyl-isoxazol-4-yl-methoxy)-N-(tetrahydro-pyran-4-yl)-nicotinamide, was converted to the title compound (69 mg, 33%) which was obtained as a colourless gum. MS: m/e=366.3 [M+H]+.

Example 71

(3,3-Dimethyl-morpholin-4-yl)-[6-(5-methyl-3-phenyl-isoxazol-4-ylmethoxy)-pyridin-3-yl]-methanone As described for example 12, 6-(5-methyl-3-phenyl-isoxazol-4-ylmethoxy)-nicotinic acid (124 mg, 0.40 mmol) was converted using 3,3-dimethyl-morpholine instead of 2,2,2-trifluoroethylamine to the title compound (SiO2, heptane:ethyl acetate=80:20 to 30:70, 41 mg, 25%) which was obtained as a light brown oil. MS: m/e=408.1 [M+H]+.

Example 72

2-Methyl-6-(5-methyl-3-phenyl-isoxazol-4-ylmethoxy)-nicotinic acid ethyl ester

As described for example 4, (5-methyl-3-phenyl-isoxazol-4-yl)-methanol (313 mg, 1.66 mmol) was converted using 6-hydroxy-2-methyl-nicotinic acid ethyl ester instead of 2-hydroxy-5-trifluoromethylpyridine to the title compound (SiO2, heptane:ethyl acetate=60:40 to 10:90, 322 mg, 55%) which was obtained as a colourless oil. MS: m/e=353.2 [M+H]+.

Example 73

6-(5-Methyl-3-phenyl-isoxazol-4-ylmethoxy)-pyridine-2-carbonitrile

To a solution of (5-methyl-3-phenyl-isoxazol-4-yl)-methanol (189 mg, 1.0 mmol) and 6-chloropyridine-2-carbonitrile (150 mg, 1.0 mmol) in toluene (10 mL) was added sodium hydride (55% dispersion in mineral oil, 100 mg, 2.0 mmol) and the mixture heated at 50° C. for 6 h. Then 18-crown-6 (18 mg) was added and the mixture heated at 100° C. overnight. The mixture was then diluted with ethyl acetate and washed with water. The aqueous layers were extracted with ethyl acetate (10 mL) and the combined organic layers were dried over sodium sulfate. Purification by chromatography (SiO2, heptane:ethyl acetate=7:3) afforded the title compound (70 mg, 24%) as a white solid after trituration with diisopropylether. MS: m/e=292.0 [M+H]+.

Example 74

3-[6-(5-Methyl-3-phenyl-isoxazol-4-ylmethoxy)-pyridin-3-yl]-oxetan-3-ol

A solution of 5-bromo-2-(5-methyl-3-phenyl-isoxazol-4-ylmethoxy)-pyridine (100 mg, 0.29 mmol) THF (3 mL) was treated with n-butyl lithium (1.6 M in hexanes, 0.18 mL, 0.29 mmol) at −75° C. Then a solution of 3-oxetanone (22.0 mg, 0.29 mmol) in THF (1 mL) was added and the mixture was stirred for 10 min. Methanol was then added and the mixture was allowed to warm to room temperature. Purification by chromatography (SiO2, ethylacetate/heptane 2:8 to 1:1) afforded the title compound (65 mg, 66%) as a white solid. MS: m/e=339.1 [M+H]+.

Example 75

(5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone As described for example 40, 6-(5-methyl-3-phenyl-isoxazol-4-ylmethoxy)-nicotinic acid (100 mg, 0.32 mmol) was converted, using 5,6,7,8-tetrahydro-(1,2,4)triazolo(4,3-a)-pyrazine hydrochloride instead of (3-amino-piperidin-1-yl)-acetic acid ethyl ester hydrochloride, to the title compound (121 mg, 86%) which was obtained as a white foam. MS: m/e=417.4 [M+H]+.

Example 76

6-(5-Methyl-3-phenyl-isoxazol-4-ylmethoxy)-N-(tetrahydro-pyran-3-ylmethyl)-nicotinamide As described for example 8b, 6-(5-methyl-3-phenyl-isoxazol-4-ylmethoxy)-nicotinic acid (100 mg, 0.32 mmol) was converted, using (tetrahydro-2-H-pyran-3-yl)methanamine hydrochloride instead of methylamine, to the title compound (33 mg, 25%) which was obtained as a white solid after crystallisation from ethyl acetate:hexane. MS: m/e=408.4 [M+H]+.

Example 77

6-(5-Methyl-3-phenyl-isoxazol-4-ylmethoxy)-N-(tetrahydro-furan-3-ylmethyl)-nicotinamide As described for example 8b, 6-(5-methyl-3-phenyl-isoxazol-4-ylmethoxy)-nicotinic acid (100 mg, 0.32 mmol) was converted, using (tetrahydrofuran-3-yl)methanamine hydrochloride instead of methylamine, to the title compound (103 mg, 81%) which was obtained as a white solid. MS: m/e=394.3 [M+H]+.

Example 78

(6,7-Dihydro-5H-pyrazolo[1,5-a]pyrimidin-4-yl)-[6-(5-methyl-3-phenyl-isoxazol-4-ylmethoxy)-pyridin-3-yl]-methanone As described for example 8b, 6-(5-methyl-3-phenyl-isoxazol-4-ylmethoxy)-nicotinic acid (100 mg, 0.32 mmol) was converted, using 4,5,6,7-tetrahydropyrazolo(1,5-a)-pyrimidine hydrochloride instead of methylamine, to the title compound (41 mg, 31%) which was obtained as a light yellow solid after crystallisation from ethyl acetate:hexane. MS: m/e=416.4 [M+H]'.

Example 79

N-Isochroman-4-yl-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (100 mg, 0.32 mmol) was converted, using rac-3,4-dihydro-1H-isochromen-4-amine hydrochloride instead of methylamine, to the title compound (136 mg, 96%) which was obtained as an off white solid. MS: m/e=442.3 [M+H]$^+$.

Example 80

N-(3-Isopropyl-isoxazol-5-ylmethyl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (100 mg, 0.32 mmol) was converted, using 5-aminomethyl-3-isopropylisoxazole TFA instead of methylamine, to the title compound (112 mg, 81%) which was obtained as a colourless gum. MS: m/e=433.3 [M+H]$^+$.

Example 81

[6-(5-Methyl-3-phenyl-isoxazol-4-ylmethoxy)-pyridin-3-yl]-(2-oxa-6-aza-spiro[3.3]hept-6-yl)-methanone As described for example 8b, 6-(5-methyl-3-phenyl-isoxazol-4-ylmethoxy)-nicotinic acid (100 mg, 0.32 mmol) was converted, using 2-oxa-6-aza-spiro[3.3]heptane oxalate instead of methylamine, to the title compound (96 mg, 76%) which was obtained as an off white solid. MS: m/e=392.4 [M+H]$^+$.

Example 82

[6-(5-Methyl-3-phenyl-isoxazol-4-ylmethoxy)-pyridin-3-yl]-(6-oxa-1-aza-spiro[3.3]hept-1-yl)-methanone As described for example 15, 6-(5-methyl-3-phenyl-isoxazol-4-ylmethoxy)-nicotinic acid (33 mg, 0.1 mmol) was converted, using 6-oxa-1-aza-spiro[3.3]heptane instead of 3-methoxypropylamine, to the title compound (15 mg, 35%) which was obtained as a colourless gum. MS: m/e=392.3 [M+H]$^+$.

Example 83

6-(5-Methyl-3-phenyl-isoxazol-4-ylmethoxy)-nicotinic acid isopropyl ester

A solution of N,N-dicyclohexylcarbodiimide (258 mg, 1.25 mmol) and 4-dimethylaminopyridine (12 mg, 0.10 mmol) in dichloromethane (4 mL) was added dropwise to a solution of 6-(5-methyl-3-phenyl-isoxazol-4-ylmethoxy)-nicotinic acid (310 mg, 1.0 mmol) and 2-propanol (0.06 g, 1.0 mmol) in dichloromethane (4 mL) at room temperature. After 15 h, the mixture was filtered and the filtrate was concentrated and purified by chromatography (SiO$_2$, heptane:ethyl acetate 100:0 to 8:2) to give the title compound (270 mg, 77%) as a colourless oil. MS: m/e=353.1 [M+H]$^+$.

Example 84

6-[3-(2-Fluoro-phenyl)-5-methyl-isoxazol-4-ylmethoxy]-N-(2,2,2-trifluoro-ethyl)-nicotinamide a) 2-Fluoro-benzaldehyde oxime To a suspension of 2-fluorobenzaldehyde (63.3 g, 495 mmol) and hydroxylamine hydrochloride (38.2 g, 544 mmol) in ethanol (36 mL) and water (69 mL) was added ice (205 g). Then an aqueous solution of sodium hydroxide (32%, 115 mL, 1.24 mol) was added dropwise within a 10 min period (temperature rises from −8° C. to +7° C.) whereupon most of the solid dissolves. After 1 h stirring at room temperature the resulting mixture was then acidified with HCl (5 N). The mixture was then extracted with dichloromethane to afford the title compound (66.8 g, 97%) which was obtained as a light yellow solid. MS m/e (EI): 139.0 [M].

b) (E)- and/or (Z)—N-Hydroxy-2-fluoro-benzenecarboximidoyl chloride

To a solution of (E)- and/or (Z)-2-fluoro-benzaldehyde oxime (66.8 g, 480 mmol) in DMF (334 mL) was added N-chlorosuccinimide (29.4 g, 211 mmol) portionwise and after 10 min, keeping the temperature below 50° C., N-chlorosuccinimide (44.1 g, 317 mmol) was added portionwise. The reaction mixture was stirred at room temperature for 2 h and then extracted with tert-butyl methyl ether to afford the title compound (91.9 g, 91%) which was obtained as a yellow oil. 1H-NMR (CDCl$_3$): 7.10-7.25 (m, 2H), 7.40-7.50 (m, 1H), 7.64-7.70 (m, 3H), 8.99 (s, 1H).

c) 3-(2-Fluoro-phenyl)-5-methyl-isoxazole-4-carboxylic acid ethyl ester

To a solution of ethyl 2-butynoate (65.5 mL, 562 mmol) and triethylamine (80.7 mL, 576 mmol) in ethanol (600 mL) was added, at 0-4° C. over 2 h, 500 mL of a solution of (E)- and/or (Z)—N-hydroxy-2-fluoro-benzenecarboximidoyl chloride (83.3 g 480 mmol) in ethanol (900 mL). Ethyl 2-butynoate (44.6 ml, 383 mmol) in ethanol (125 mL) was added at 0° C., then the remaining 400 ml of the (E)- and/or (Z)—N-hydroxy-2-fluoro-benzenecarboximidoyl chloride solution were added over a 1 h period. The resulting mixture was then stirred for 48 h at room temperature and evaporated. The mixture was then poured onto HCl (1.2 L), and extracted with tert-butyl methyl ether. The combined organic layers were then washed with water and brine, dried over sodium sulfate and evaporated. Purification by chromatography (SiO$_2$, heptane:ethyl acetate=100:0 to 9:1) afforded the title product (73.6 g, 62%) which was obtained as a yellow oil, MS: m/e=250.1 [M+H]⁺.

d) [3-(2-Fluoro-phenyl)-5-methyl-isoxazol-4-yl]-methanol

To a solution of 3-(2-fluoro-phenyl)-5-methyl-isoxazole-4-carboxylic acid ethyl ester (73.6 g, 295 mmol) in THF (977 mL) was added portionwise lithiumaluminiumhydride (6.48 g, 162 mmol) over 20 min, at 0° C., and the reaction mixture was stirred at room temperature for 2.5 h. The mixture was then cooled to 0° C. and water (7.5 mL) added followed by sodium hydroxide (15% solution, 7.5 mL) and then again with water (21 mL). The precipitate was then filtered off and washed with THF. The combined washings and filtrate were then evaporated. Purification by chromatography (SiO₂, heptane:ethyl acetate=75:25) afforded the title compound (34.7 g, 57%) which was obtained as a light yellow oil. MS: m/e=208.0 [M+H]⁺.

e) 6-[3-(2-Fluoro-phenyl)-5-methyl-isoxazol-4-yl-methoxy]-nicotinic acid methyl ester To a suspension of sodium hydride (55% dispersion in mineral oil, 1.16 g, 26.5 mmol) in THF (30 mL) was added a solution of [3-(2-fluoro-phenyl)-5-methyl-isoxazol-4-yl]-methanol (5.0 g, 24.1 mmol) in THF (60 mL) at 0° C. and the reaction mixture warmed to room temperature over 30 min. Then a solution of methyl 6-chloronicotinate (4.65 g, 26.5 mmol) in THF (60 mL) was added dropwise at 0° C. and the reaction mixture was stirred at room temperature for 2 h. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography (SiO₂, heptane:ethyl acetate=4:1 to 2:1) afforded the title compound (4.0 g, 49%) which was obtained as a white solid. MS: m/e=343.0 [M+H]⁺.

f) 6-[3-(2-Fluoro-phenyl)-5-methyl-isoxazol-4-yl-methoxy]-N-(2,2,2-trifluoro-ethyl)-nicotinamide A solution of trimethylaluminium (2 M in toluene, 1.17 mL, 2.3 mmol) was added dropwise (exothermic) to a solution of 2,2,2-trifluoroethylamine (188 µL, 2.3 mmol) in dioxane (15 mL) and the resulting mixture was stirred at room temperature for 1.5 h. Then 6-[3-(2-fluoro-phenyl)-5-methyl-isoxazol-4-ylmethoxy]-nicotinic acid methyl ester (200 mg, 0.58 mmol) was added. The resulting mixture was then heated at 85° C. for 2 h and then cooled to room temperature and then poured into water and extracted with ethyl acetate which was then washed with brine, dried over sodium sulfate and evaporated. Purification by chromatography (SiO₂, heptane:ethyl acetate=2:1 to 1:1) afforded the title compound (210 mg, 88%) which was obtained as a colourless oil. MS: m/e=410.4 [M+H]⁺.

Example 85

6-[3-(2-Fluoro-phenyl)-5-methyl-isoxazol-4-yl-methoxy]-N-(2,2,3,3,3-pentafluoro-propyl)-nicotinamide As described for example 84f, 6-[3-(2-fluoro-phenyl)-5-methyl-isoxazol-4-ylmethoxy]-nicotinic acid methyl ester (100 mg, 0.292 mmol) was converted, using 2,2,3,3,3-pentafluoropropylamine instead of 2,2,2-trifluoroethylamine, to the title compound (100 mg, 75%) which was obtained as a white solid. MS: m/e=460.1 [M+H]⁺.

Example 86

6-[3-(2-Fluoro-phenyl)-5-methyl-isoxazol-4-yl-methoxy]-N-isopropyl-nicotinamide

As described for example 84f, 6-[3-(2-fluoro-phenyl)-5-methyl-isoxazol-4-ylmethoxy]-nicotinic acid methyl ester (200 mg, 0.58 mmol) was converted, using isopropylamine instead of 2,2,2-trifluoroethylamine, to the title compound (180 mg, 83%) which was obtained as a colourless oil. MS: m/e=370.1 [M+H]⁺.

Example 87

6-[3-(2-Fluoro-phenyl)-5-methyl-isoxazol-4-yl-methoxy]-N-(tetrahydro-pyran-4-yl)-nicotinamide As described for example 84f, 6-[3-(2-fluoro-phenyl)-5-methyl-isoxazol-4-ylmethoxy]-nicotinic acid methyl ester (100 mg, 0.29 mmol) was converted, using 4-aminotetrahydropyran instead of 2,2,2-trifluoroethylamine, to the title compound (110 mg, 92%) which was obtained as a colourless oil. MS: m/e=412.2 [M+H]⁺.

Example 88

6-[3-(3-Fluoro-phenyl)-5-methyl-isoxazol-4-yl-methoxy]-nicotinic acid methyl ester a) (E)- and/or (Z)-3-Fluoro-benzaldehyde oxime

To a suspension of 3-fluorobenzaldehyde (6.75 g, 54 mmol) and hydroxylamine hydrochloride (4.16 g, 60 mmol) in ethanol (4.3 mL) and water (13 mL) was added ice (25 g). Then a solution of sodium hydroxide (5.5 g, 138 mmol) in water (6.5 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with HCl (4 N). The white precipitate was then filtered off, washed with water and dried under high vacuum to afford the title compound (7.0 g, 93%) which was obtained as a white solid. MS m/e (EI): 139.1 [M].

b) (E)- and/or (Z)—N-Hydroxy-3-fluoro-benzenecarboximidoyl chloride

To a solution of (E)- and/or (Z)-3-fluoro-benzaldehyde oxime (6.9 g, 50 mmol) in DMF (50 mL) was added N-chlorosuccinimide (6.6 g, 50 mmol) portionwise over 1 h, keeping the temperature below 35° C. The reaction mixture was stirred at room temperature for 1 h. The mixture was then poured onto ice-water, and extracted with ethyl acetate. The combined organic layers were then washed with water and brine, dried over sodium sulfate and evaporated to afford the title compound (6.3 g, 73%) which was obtained as an off white solid. MS m/e (EI): 173.1 [M].

c) 3-(3-Fluoro-phenyl)-5-methyl-isoxazole-4-carboxylic acid ethyl ester

To a solution of (E)- and/or (Z)—N-hydroxy-3-fluoro-benzenecarboximidoyl chloride (11.1 g, 64 mmol) in diethylether (151 mL) was added ethyl 2-butynoate (7.2 g, 7.5 mL, 64 mmol) at 0° C. followed by the dropwise addition of triethylamine (7.8 g, 10.7 mL, 77 mmol) and the resulting mixture allowed to warm up to room temperature overnight. The mixture was then poured onto ice-water, and extracted with diethylether. The combined organic layers were then washed with water and brine, dried over sodium sulfate and evaporated. Purification by chromatography ($SiO_2$, heptane: ethyl acetate=100:0 to 1:1) afforded the title compound (6.3 g, 39%) which was obtained as a white solid. MS: m/e=250.1 $[M+H]^+$.

d) [3-(3-Fluoro-phenyl)-5-methyl-isoxazol-4-yl]-methanol

To a solution of 3-(3-fluoro-phenyl)-5-methyl-isoxazole-4-carboxylic acid ethyl ester (6.18 g, 25 mmol) in THF (320 mL) was added portionwise lithiumaluminiumhydride (528 mg, 14 mmol) at 0° C. and the reaction mixture was stirred at room temperature for 3 h. The mixture was then cooled to 0° C. and water (518 µL) added followed by sodium hydroxide (15% solution, 518 µL) and then again water (1.5 mL) and the mixture then stirred overnight at room temperature. The precipitate was then filtered off and washed with THF. The combined washings and filtrate were then evaporated. Purification by chromatography ($SiO_2$, heptane:ethyl acetate=100:0 to 1:1) afforded the title compound (3.9 g, 75%) which was obtained as a yellow solid. MS: m/e=208.3 $[M+H]^+$.

e) 6-[3-(3-Fluoro-phenyl)-5-methyl-isoxazol-4-yl-methoxy]-nicotinic acid methyl ester To a suspension of sodium hydride (55% dispersion in mineral oil, 852 mg, 20 mmol) in THF (27 mL) was added a solution of [3-(3-fluoro-phenyl)-5-methyl-isoxazol-4-yl]-methanol (3.68 g, 18 mmol) in THF (54 mL) at 0° C. and the reaction mixture warmed to room temperature over 30 min. Then a solution of methyl 6-chloronicotinate (3.35 g, 20 mmol) in THF (1.5 mL) was added dropwise at 0° C. and the reaction mixture was stirred at room temperature overnight. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography ($SiO_2$, heptane:ethyl acetate=7:3) afforded the title compound (4.1 g, 68%) which was obtained as a white solid. MS: m/e=343.1 $[M+H]^+$.

Example 89

6-[3-(3-Fluoro-phenyl)-5-methyl-isoxazol-4-yl-methoxy]-N-(2,2,2-trifluoro-ethyl)-nicotinamide A solution of trimethylaluminium (2 M in toluene, 600 µL, 1.2 mmol) was added dropwise (exothermic) to a solution of 2,2,2-trifluoroethylamine (119 mg, 94 µL, 1.2 mmol) in dioxane (7.5 mL) and the resulting mixture was stirred at room temperature for 1 h. Then a solution of 6-[3-(3-fluoro-phenyl)-5-methyl-isoxazol-4-ylmethoxy]-nicotinic acid methyl ester (103 mg, 0.3 mmol) in dioxane (4 mL) was added. The resulting mixture was then heated at 85-95° C. for 2 h and then cooled to room temperature and then poured into water and extracted with ethyl acetate which was then washed with brine, dried over sodium sulfate and evaporated. Purification by chromatography ($SiO_2$, heptane:ethyl acetate=100:0 to 1:1) afforded the title compound (122 mg, 99%) which was obtained as a white solid. MS: m/e=410.1 $[M+H]^+$.

Example 90

N-Cyclopropylmethyl-6-[3-(3-fluoro-phenyl)-5-methyl-isoxazol-4-ylmethoxy]-nicotinamide A solution of trimethylaluminium (2 M in toluene, 600 µL, 1.2 mmol) was added dropwise (exothermic) to a solution of cyclopropylmethylamine (85 mg, 103 µL, 1.2 mmol) in dioxane (7.5 mL) and the resulting mixture was stirred at room temperature for 1 h. Then a solution of 6-[3-(3-fluoro-phenyl)-5-methyl-isoxazol-4-ylmethoxy]-nicotinic acid methyl ester (103 mg, 0.3 mmol) in dioxane (4 mL) was added. The resulting mixture was then heated at 85-95° C. overnight and then cooled to room temperature and then poured into water and extracted with ethyl acetate which was then washed with brine, dried over sodium sulfate and evaporated. Purification by chromatography ($SiO_2$, heptane:ethyl acetate=100:0 to 1:1) afforded the title compound (78 mg, 68%) which was obtained as an off white solid. MS: m/e=382.3 $[M+H]^+$.

Example 91

6-[3-(3-Fluoro-phenyl)-5-methyl-isoxazol-4-yl-methoxy]-N-isopropyl-nicotinamide a) 6-[3-(3-Fluoro-phenyl)-5-methyl-isoxazol-4-yl-methoxy]-nicotinic acid As described for example 41a, 6-[3-(3-fluoro-phenyl)-5-methyl-isoxazol-4-ylmethoxy]-nicotinic acid methyl ester (3.3 g, 10 mmol), instead of (3-{[6-(5-methyl-3-phenyl-isoxazol-4-ylmethoxy)-pyridine-3-carbonyl]-amino}-piperidin-1-yl)-acetic acid ethyl ester, was converted, to the title compound (3.0 g, 95%) which was obtained as an off white solid. MS: m/e=327.4 $[M-H]^-$.

b) 6-[3-(3-Fluoro-phenyl)-5-methyl-isoxazol-4-yl-methoxy]-N-isopropyl-nicotinamide To a solution of 6-[3-(3-fluoro-phenyl)-5-methyl-isoxazol-4-ylmethoxy]-nicotinic acid (98.5 mg, 0.3 mmol) in DMF (1.5 mL) were added 2-(1H-benzotriazole-1-yl)-1,1,3,3-tetramethyluronium tetrafluoroborate (106 mg, 0.33 mmol), N,N-diisopropyl ethyl amine (257 µL, 1.5 mmol) and isopropylamine (28.3 µL, 0.33 mmol). The resulting reaction mixture was stirred overnight at room temperature. Concentration and purification by chromatography ($SiO_2$, heptane: ethyl acetate=100:0 to 0:100) afforded the title compound 57 mg, 51%) as an off white solid. MS: m/e=370.1 $[M+H]^+$.

Example 92

N-Cyclopropyl-6-[3-(3-fluoro-phenyl)-5-methyl-isoxazol-4-ylmethoxy]-nicotinamide A solution of trimethylaluminium (2 M in toluene, 600 µL, 1.2 mmol) was added dropwise (exothermic) to a solution of cyclopropylamine (69 mg, 84 µL, 1.2 mmol) in dioxane (7.5 mL) and the resulting mixture was stirred at room temperature for 1 h. Then a solution of 6-[3-(3-fluoro-phenyl)-5-methyl-isoxazol-4-ylmethoxy]-nicotinic acid methyl ester (103 mg, 0.3 mmol) in dioxane (4 mL) was added. The resulting mixture was then heated at 85-95° C. for 3 h and then cooled to room temperature and then poured into water and extracted with ethyl acetate which was then washed with brine, dried over sodium sulfate and evaporated. Purification by chromatography (SiO$_2$, heptane:ethyl acetate=100:0 to 1:1) afforded the title compound (100 mg, 91%) which was obtained as a white solid. MS: m/e=368.0 [M+H]$^+$.

Example 93

6-[3-(3-Fluoro-phenyl)-5-methyl-isoxazol-4-yl-methoxy]-N-(tetrahydro-pyran-4-yl)-nicotinamide As described for example 92, 6-[3-(3-fluoro-phenyl)-5-methyl-isoxazol-4-ylmethoxy]-nicotinic acid methyl ester (103 mg, 0.3 mmol) was converted, using 4-aminotetrahydro-pyran instead of cyclopropylamine, to the title compound (105 mg, 85%) which was obtained as a white solid. MS: m/e=412.5 [M+H]$^+$.

Example 94

{6-[3-(3-Fluoro-phenyl)-5-methyl-isoxazol-4-yl-methoxy]-pyridin-3-yl}-morpholin-4-yl-methanone As described for example 90, 6-[3-(3-fluoro-phenyl)-5-methyl-isoxazol-4-ylmethoxy]-nicotinic acid methyl ester (103 mg, 0.3 mmol) was converted, using morpholine instead of cyclopropylmethylamine, to the title compound (60 mg, 50%) which was obtained as a colourless gum. MS: m/e=398.3 [M+H]$^+$.

Example 95

{6-[3-(3-Fluoro-phenyl)-5-methyl-isoxazol-4-yl-methoxy]-pyridin-3-yl}-thiomorpholin-4-yl-methanone A solution of trimethylaluminium (2 M in toluene, 600 µL, 1.2 mmol) was added dropwise (exothermic) to a solution of thiomorpholine (124 mg, 120 µL, 1.2 mmol) in dioxane (7.5 mL) and the resulting mixture was stirred at room temperature for 1 h. Then a solution of 6-[3-(3-fluoro-phenyl)-5-methyl-isoxazol-4-ylmethoxy]-nicotinic acid methyl ester (103 mg, 0.3 mmol) in dioxane (4 mL) was added. The resulting mixture was then heated at 85-95° C. for 4 h and then cooled to room temperature and then poured into water and extracted with ethyl acetate which was then washed with brine, dried over sodium sulfate and evaporated. Purification by chromatography (SiO$_2$, heptane:ethyl acetate=100:0 to 1:3) afforded the title compound (124 mg, 100%) which was obtained as a light yellow gum. MS: m/e=414.4 [M+H]$^+$.

Example 96

(1,1-Dioxo-1λ6-thiomorpholin-4-yl)-{6-[3-(3-fluoro-phenyl)-5-methyl-isoxazol-4-ylmethoxy]-pyridin-3-yl}-methanone As described for example 95, 6-[3-(3-fluoro-phenyl)-5-methyl-isoxazol-4-ylmethoxy]-nicotinic acid methyl ester (103 mg, 0.3 mmol) was converted, using thiomorpholine-S,S-dioxide instead of thiomorpholine, to the title compound (133 mg, 100%) which was obtained as a white foam. MS: m/e=446.0 [M+H]$^+$.

Example 97

6-[3-(3-Chloro-phenyl)-5-methyl-isoxazol-4-yl-methoxy]-nicotinic acid methyl ester a) (E)- and/or (Z)-3-Chloro-benzaldehyde oxime To a suspension of 3-chlorobenzaldehyde (50 g, 355 mmol) and hydroxylamine hydrochloride (38 g, 543 mmol) in ethanol (200 mL) containing sodium acetate (46 g, 558 mmol) was heated under reflux for 3 h. After 30 min stirring at room temperature a white solid precipitated and the resulting mixture was then diluted with water and acidified with HCl (4 N). The white precipitate was then filtered off, washed with water and dried under high vacuum to afford the title compound (54 g, 98%) which was obtained as a white solid. Mp: 64-66° C.

b) (E)- and/or (Z)—N-Hydroxy-3-chloro-benzenecarboximidoyl chloride

To a solution of (E)- and/or (Z)-3-chloro-benzaldehyde oxime (54 g, 347 mmol) in DMF (800 mL) was added HCl (conc., 17 mL) and the mixture cooled to room temperature. Then potassium monopersulfate triple salt (247 g, 400 mmol) and the reaction mixture was stirred at room temperature for 1 h. The mixture was then poured onto ice-water, and extracted with ethyl acetate. The combined organic layers were then washed with water and brine, dried over sodium sulfate and evaporated to afford the title compound (66 g, 100%) which was obtained as a white solid. Mp: 58-60° C.

c) 3-(3-Chloro-phenyl)-5-methyl-isoxazole-4-carboxylic acid ethyl ester

To a suspension of sodium (2.67 g, 116 mmol) in methanol (100 mL) was added ethyl acetoacetate (12.8 g, 11.9 mL, 110 mmol) at room temperature over 15 minutes and then a solution of (E)- and/or (Z)—N-hydroxy-3-chloro-benzenecarboximidoyl chloride (19.0 g, 100 mmol) in methanol (100 mL) was added over 20 minutes and the resulting mixture allowed to stir for 4 h at room temperature. The mixture was then poured onto water and cooled to 5° C., filtered and evaporated. Purification by recrystallisation from ethanol afforded the title compound (10.1 g, 40%) which was obtained as a white solid. Mp: 71-73° C.

d) 3-(3-Chloro-phenyl)-5-methyl-isoxazole-4-carboxylic acid

To a solution of 3-(3-chloro-phenyl)-5-methyl-isoxazole-4-carboxylic acid ethyl ester (9.1 g, 36 mmol) in ethanol (50 mL) was added aqueous sodium hydroxide (4 N, 10 mL). After heating at reflux for 1 h the mixture was cooled to room temperature and acidified with HCl (4 N, 10 mL) and water (10 mL) at 0° C. Purification by filtration and drying afforded the title compound (8.3 g, 97%) which was obtained as a white solid. Mp: 171-173° C.

e) [3-(3-Chloro-phenyl)-5-methyl-isoxazol-4-yl]-methanol

To a solution of 3-(3-chloro-phenyl)-5-methyl-isoxazole-4-carboxylic acid (4.8 g, 20 mmol in THF (50 mL) at −10° C. was added triethylamine (2.9 mL, 21 mmol) and then a solution of ethylchloroformate (1.96 mL, 20 mmol) in THF (10 mL) added keeping the temperature below −5° C. After 1 h the mixture was filtered and the filtrate cooled to −10° C. and a suspension of sodiumborohydride (2.0 g, 50 mmol) in water (10 mL) added over 15 minutes keeping the temperature below −5° C. The mixture was then allowed to warm up to room temperature over 2 h and diluted with sodium hydroxide (2 N, 30 mL) and extracted with ethyl acetate. The combined organic layers were then washed with water and brine, dried over sodium sulfate and evaporated to afford the title compound (3.5 g, 78%) which was obtained as a clear oil which solidified with time as a white solid. Mp: 66-68° C.

f) 6-[3-(3-Chloro-phenyl)-5-methyl-isoxazol-4-yl-methoxy]-nicotinic acid methyl ester As described for example 88e, [3-(3-chloro-phenyl)-5-methyl-isoxazol-4-yl]-methanol (224 mg, 1.0 mmol), instead of [3-(3-fluoro-phenyl)-5-methyl-isoxazol-4-yl]-methanol, was converted, to the title compound (185 mg, 52%) which was obtained as all off-white solid. MS: m/e=359.4 [M+H]$^+$.

Example 98

6-[3-(3-Chloro-phenyl)-5-methyl-isoxazol-4-yl-methoxy]-N-(2,2,2-trifluoro-ethyl)-nicotinamide a) 6-[3-(3-Chloro-phenyl)-5-methyl-isoxazol-4-yl-methoxy]-nicotinic acid As described for example 91a, 6-[3-(3-chloro-phenyl)-5-methyl-isoxazol-4-ylmethoxy]-nicotinic acid methyl ester (734 mg, 2.1 mmol), instead of 6-[3-(3-fluoro-phenyl)-5-methyl-isoxazol-4-ylmethoxy]-nicotinic acid methyl ester, was converted, to the title compound (592 mg, 84%) which was obtained as a white solid. MS: m/e=343.4 [M−H]$^-$.

b) 6-[3-(3-Chloro-phenyl)-5-methyl-isoxazol-4-yl-methoxy]-N-(2,2,2-trifluoro-ethyl)-nicotinamide To a solution of 6-[3-(3-chloro-phenyl)-5-methyl-isoxazol-4-ylmethoxy]-nicotinic acid (69 mg, 0.2 mmol) in DMF (300 μL) were added 2-(1H-benzotriazole-1-yl)-1,1,3,3-tetramethyluronium tetrafluoroborate (71 mg, 0.22 mmol), N,N-diisopropyl ethyl amine (171 μL, 1.0 mmol) and 2,2,2-trifluoroethylamine (17.3 μL, 0.22 mmol). The resulting reaction mixture was stirred for 1 h at room temperature. Concentration and purification by chromatography (SiO$_2$, heptane:ethyl acetate=100:0 to 1:1) afforded the title compound (30 mg, 35%) as a white solid. MS: m/e=426.1 [M+H]$^+$.

Example 99

6-[3-(3-Chloro-phenyl)-5-methyl-isoxazol-4-yl-methoxy]-N-cyclopropylmethyl-nicotinamide As described for example 98b, 6-[3-(3-chloro-phenyl)-5-methyl-isoxazol-4-ylmethoxy]-nicotinic acid (69 mg, 0.2 mmol) was converted, using cyclopropanemethylamine instead of 2,2,2-trifluoroethylamine, to the title compound (39 mg, 49%) which was obtained as a white solid. MS: m/e=398.0 [M+H]$^+$.

Example 100

6-[3-(3-Chloro-phenyl)-5-methyl-isoxazol-4-yl-methoxy]-N-cyclopropyl-nicotinamide As described for example 98b, 6-[3-(3-chloro-phenyl)-5-methyl-isoxazol-4-ylmethoxy]-nicotinic acid (69 mg, 0.2 mmol) was converted, using cyclopropylamine instead of 2,2,2-trifluoroethylamine, to the title compound (55 mg, 72%) which was obtained as a white solid. MS: m/e=384.0 [M+H]$^+$.

Example 101

6-[3-(3-Chloro-phenyl)-5-methyl-isoxazol-4-yl-methoxy]-N-(tetrahydro-pyran-4-yl)-nicotinamide As described for example 98b, 6-[3-(3-chloro-phenyl)-5-methyl-isoxazol-4-ylmethoxy]-nicotinic acid (69 mg, 0.2 mmol) was converted, using 4-aminotetrahydropyran instead of 2,2,2-trifluoroethylamine, to the title compound (76 mg, 89%) which was obtained as a white solid. MS: m/e=428.5 [M+H]$^+$.

Example 102

{6-[3-(3-Chloro-phenyl)-5-methyl-isoxazol-4-yl-methoxy]-pyridin-3-yl}-(1,1-dioxo-1λ6-thiomorpholin-4-yl)-methanone As described for example 98b, 6-[3-(3-chloro-phenyl)-5-methyl-isoxazol-4-ylmethoxy]-nicotinic acid (69 mg, 0.2 mmol) was converted, using thiomorpholine-S,S-dioxide instead of 2,2,2-trifluoroethylamine, to the title compound (80 mg, 87%) which was obtained as a white solid. MS: m/e=462.1 [M+H]$^+$.

Example 103

6-[3-(4-Fluoro-phenyl)-5-methyl-isoxazol-4-yl-methoxy]-nicotinic acid methyl ester a) (E)- and/or (Z)-4-Fluoro-benzaldehyde oxime As described for example 88a, 4-fluorobenzaldehyde (24.8 g, 200 mmol) was converted, instead of 3-fluorobenzaldehyde, to the title compound (23.3 g, 84%) which was obtained as a white solid. MS: m/e=139.1 [M]$^+$.

b) (E)- and/or (Z)—N-Hydroxy-4-fluoro-benzenecarboximidoyl chloride

As described for example 88b, (E)- and/or (Z)-4-fluoro-benzaldehyde oxime 4-fluorobenzaldehyde (23.3 g, 167 mmol) was converted, instead of (E)- and/or (Z)-3-fluoro-benzaldehyde oxime, to the title compound (25.9 g, 89%) which was obtained as an off white solid. MS: m/e=173.0 [M]$^+$.

c) 3-(4-Fluoro-phenyl)-5-methyl-isoxazole-4-carboxylic acid ethyl ester

As described for example 88c, (E)- and/or (Z)—N-hydroxy-4-fluoro-benzenecarboximidoyl chloride (15.4 g, 89 mmol) was converted, instead of (E)- and/or (Z)—N-hydroxy-3-fluoro-benzenecarboximidoyl chloride, to the title compound (9.8 g, 44%) which was obtained as an off white solid. MS: m/e=250.1 [M+H]$^+$.

d) [3-(4-Fluoro-phenyl)-5-methyl-isoxazol-4-yl]-methanol

As described for example 88d, 3-(4-fluoro-phenyl)-5-methyl-isoxazole-4-carboxylic acid ethyl ester (3.0 g, 12 mmol)

was converted, instead of 3-(3-fluoro-phenyl)-5-methyl-isoxazole-4-carboxylic acid ethyl ester, to the title compound (1.8 g, 71%) which was obtained as a white solid. MS: m/e=208.1 [M+H]+.

e) 6-[3-(4-Fluoro-phenyl)-5-methyl-isoxazol-4-yl-methoxy]-nicotinic acid methyl ester As described for example 88e, [3-(4-fluoro-phenyl)-5-methyl-isoxazol-4-yl]-methanol (103 mg, 0.55 mmol) was converted, instead of [3-(3-fluoro-phenyl)-5-methyl-isoxazol-4-yl]-methanol, to the title compound (81 mg, 47%) which was obtained as a light yellow solid. MS: m/e=343.3 [M+H]+.

Example 104

6-[3-(4-Fluoro-phenyl)-5-methyl-isoxazol-4-yl-methoxy]-nicotinic acid

As described for example 91a, 6-[3-(4-fluoro-phenyl)-5-methyl-isoxazol-4-ylmethoxy]-nicotinic acid methyl ester (1.4 g, 4.2 mmol), instead of 6-[3-(3-fluoro-phenyl)-5-methyl-isoxazol-4-ylmethoxy]-nicotinic acid methyl ester, was converted, to the title compound (1.1 g, 78%) which was obtained as a white solid. MS: m/e=327.3 [M−H]−.

Example 105

6-[3-(4-Fluoro-phenyl)-5-methyl-isoxazol-4-yl-methoxy]-N-(2,2,2-trifluoro-ethyl)-nicotinamide As described for example 98b, 6-[3-(4-fluoro-phenyl)-5-methyl-isoxazol-4-ylmethoxy]-nicotinic acid (99 mg, 0.33 mmol), instead of 6-[3-(3-chloro-phenyl)-5-methyl-isoxazol-4-ylmethoxy]-nicotinic acid, was converted, to the title compound (61 mg, 50%) which was obtained as a white solid. MS: m/e=410.4 [M+H]+.

Example 106

N-Cyclopropylmethyl-6-[3-(4-fluoro-phenyl)-5-methyl-isoxazol-4-ylmethoxy]-nicotinamide As described for example 105, 6-[3-(4-fluoro-phenyl)-5-methyl-isoxazol-4-ylmethoxy]-nicotinic acid (99 mg, 0.33 mmol) was converted, using cyclopropanemethylamine instead of 2,2,2-trifluoroethylamine, to the title compound (74 mg, 65%) which was obtained as a white solid. MS: m/e=382.4 [M+H]+.

Example 107

6-[3-(4-Fluoro-phenyl)-5-methyl-isoxazol-4-yl-methoxy]-N-isopropyl-nicotinamide

As described for example 105, 6-[3-(4-fluoro-phenyl)-5-methyl-isoxazol-4-ylmethoxy]-nicotinic acid (99 mg, 0.33 mmol) was converted, using isopropylamine instead of 2,2,2-trifluoroethylamine, to the title compound (87 mg, 79%) which was obtained as an off white solid. MS: m/e=370.0 [M+H]+.

Example 108

N-Cyclopropyl-6-[3-(4-fluoro-phenyl)-5-methyl-isoxazol-4-ylmethoxy]-nicotinamide As described for example 105, 6-[3-(4-fluoro-phenyl)-5-methyl-isoxazol-4-ylmethoxy]-nicotinic acid (99 mg, 0.33 mmol) was converted, using cyclopropylamine instead of 2,2,2-trifluoroethylamine, to the title compound (47 mg, 43%) which was obtained as a white solid. MS: m/e=368.0 [M+H]+.

Example 109

6-[3-(4-Fluoro-phenyl)-5-methyl-isoxazol-4-yl-methoxy]-N-(tetrahydro-pyran-4-yl)-nicotinamide As described for example 105, 6-[3-(4-fluoro-phenyl)-5-methyl-isoxazol-4-ylmethoxy]-nicotinic acid (99 mg, 0.33 mmol) was converted, using 4-aminotetrahydropyran instead of 2,2,2-trifluoroethylamine, to the title compound (105 mg, 85%) which was obtained as a white solid. MS: m/e=412.5 [M+H]+.

Example 110

{6-[3-(4-Fluoro-phenyl)-5-methyl-isoxazol-4-yl-methoxy]-pyridin-3-yl}-morpholin-4-yl-methanone As described for example 105, 6-[3-(4-fluoro-phenyl)-5-methyl-isoxazol-4-ylmethoxy]-nicotinic acid (99 mg, 0.33 mmol) was converted, using morpholine instead of 2,2,2-trifluoroethylamine, to the title compound (16 mg, 13%) which was obtained as a white solid. MS: m/e=398.3 [M+H]+.

Example 111

{6-[3-(4-Fluoro-phenyl)-5-methyl-isoxazol-4-yl-methoxy]-pyridin-3-yl}-thiomorpholin-4-yl-methanone As described for example 105, 6-[3-(4-fluoro-phenyl)-5-methyl-isoxazol-4-ylmethoxy]-nicotinic acid (99 mg, 0.33 mmol) was converted, using thiomorpholine instead of 2,2,2-trifluoroethylamine, to the title compound (46 mg, 37%) which was obtained as a light yellow solid. MS: m/e=414.4 [M+H]+.

Example 112

(1,1-Dioxo-1λ6-thiomorpholin-4-yl)-{6-[3-(4-fluoro-phenyl)-5-methyl-isoxazol-4-ylmethoxy]-pyridin-3-yl}-methanone As described for example 105, 6-[3-(4-fluoro-phenyl)-5-methyl-isoxazol-4-ylmethoxy]-nicotinic acid (99 mg, 0.33 mmol) was converted, using thiomorpholine-S,S-dioxide instead of 2,2,2-trifluoroethylamine, to the title compound (73 mg, 55%) which was obtained as a white solid. MS: m/e=446.1 [M+H]+.

Example 113

3-{6-[3-(4-Fluoro-phenyl)-5-methyl-isoxazol-4-yl-methoxy]-pyridin-3-yl}-oxetan-3-ol a) 5-Bromo-2-[3-(4-fluoro-phenyl)-5-methyl-isoxazol-4-ylmethoxy]-pyridine To a solution of [3-(4-fluoro-phenyl)-5-methyl-isoxazol-4-yl]-methanol (500 mg, 2.41 mmol) in THF (5 mL) at room temperature was added sodium hydride (55% dispersion in mineral oil, 137 mg, 3.1 mmol) and the reaction mixture stirred at room temperature for 1 h. Then a solution of 2-chloro-5-bromo-pyridine (484 mg, 2.41 mmol) in THF (5 mL) was added at room temperature and the reaction mixture was stirred at room temperature for 2 h. The reaction mixture was then diluted with methanol and water and the mixture was extracted with ethyl acetate. The combined organic layers were then washed with water and brine and then dried over sodium sulfate, filtered and evaporated. Purification by chromatography (SiO$_2$, heptane:ethyl acetate=9:1 to 4:1) afforded the title compound (128 mg, 15%) which was obtained as a colourless oil. MS: m/e=363.1/365.1 [M+H]$^+$.

b) 3-{6-[3-(4-Fluoro-phenyl)-5-methyl-isoxazol-4-ylmethoxy]-pyridin-3-yl}-oxetan-3-ol A solution of 5-bromo-2-[3-(4-fluoro-phenyl)-5-methyl-isoxazol-4-ylmethoxy]-pyridine (110 mg, 0.3 mmol) in THF (3 mL) was treated at −78° C. with n-butyllithium (1.6 M solution in hexanes, 189 µL, 0.3 mmol) and then with 3-oxetanone (23.0 mg, 0.3 mmol). After 20 minutes methanol was added and the mixture was warmed to room temperature. Concentration and purification by chromatography (silicagel, heptane:ethyl acetate=85:15 to 8:3) to afforded the title product (32 mg, 30%) which was obtained as a colourless oil. MS: m/e=357.1 [M+H]$^+$.

Example 114

{6-[3-(4-Fluoro-phenyl)-5-methyl-isoxazol-4-ylmethoxy]-pyridin-3-yl}-(1R,5S)-6-oxa-3-aza-bicyclo[3.1.1]hept-3-yl-methanone As described for example 105, 6-[3-(4-fluoro-phenyl)-5-methyl-isoxazol-4-ylmethoxy]-nicotinic acid (36 mg, 0.11 mmol) was converted, using rac-6-oxa-3-aza-bicyclo[3.1.1]heptane instead of 2,2,2-trifluoroethylamine, to the title compound (10 mg, 22%) which was obtained as a colourless gum. MS: m/e=410.4 [M+H]$^+$.

Example 115

6-[3-(4-Chloro-phenyl)-5-methyl-isoxazol-4-ylmethoxy]-nicotinic acid methyl ester a) (E)- and/or (Z)-4-Chloro-benzaldehyde oxime As described for example 88a, 4-chlorobenzaldehyde (25.0 g, 178 mmol) was converted, instead of 3-fluorobenzaldehyde, to the title compound (27.0 g, 97%) which was obtained as an off white solid. MS: m/e=155.1 [M]$^+$.

b) (E)- and/or (Z)—N-Hydroxy-4-chloro-benzenecarboximidoyl chloride

As described for example 88b, (E)- and/or (Z)-4-chlorobenzaldehyde oxime 4-fluorobenzaldehyde (27.0 g, 173 mmol) was converted, instead of (E)- and/or (Z)-3-fluorobenzaldehyde oxime, to the title compound (28.4 g, 86%) which was obtained as a light yellow solid. MS: m/e=189.1 [M]$^+$.

c) 3-(4-Chloro-phenyl)-5-methyl-isoxazole-4-carboxylic acid ethyl ester

As described for example 88c, (E)- and/or (Z)—N-hydroxy-4-chloro-benzenecarboximidoyl chloride (26.0 g, 137 mmol) was converted, instead of (E)- and/or (Z)—N-hydroxy-3-fluoro-benzenecarboximidoyl chloride, to the title compound (15.2 g, 42%) which was obtained as a light yellow solid. MS: m/e=266.1 [M+H]$^+$.

d) [3-(4-Chloro-phenyl)-5-methyl-isoxazol-4-yl]-methanol

As described for example 88d, 3-(4-chloro-phenyl)-5-methyl-isoxazole-4-carboxylic acid ethyl ester (373 mg, 1.4 mmol) was converted, instead of 3-(3-fluoro-phenyl)-5-methyl-isoxazole-4-carboxylic acid ethyl ester, to the title compound (204 mg, 65%) which was obtained as a white solid. MS: m/e=224.1 [M+H]$^+$.

e) 6-[3-(4-Chloro-phenyl)-5-methyl-isoxazol-4-ylmethoxy]-nicotinic acid methyl ester As described for example 88e, [3-(4-chloro-phenyl)-5-methyl-isoxazol-4-yl]-methanol (2.0 g, 9 mmol) was converted, instead of [3-(3-fluoro-phenyl)-5-methyl-isoxazol-4-yl]-methanol, to the title compound (2.4 g, 74%) which was obtained as a light yellow solid. MS: m/e=359.0 [M+H]$^+$.

Example 116

6-[3-(4-Chloro-phenyl)-5-methyl-isoxazol-4-ylmethoxy]-nicotinic acid

As described for example 91a, 6-[3-(4-chloro-phenyl)-5-methyl-isoxazol-4-ylmethoxy]-nicotinic acid methyl ester (880 mg, 4.2 mmol), instead of 6-[3-(3-fluoro-phenyl)-5-methyl-isoxazol-4-ylmethoxy]-nicotinic acid methyl ester, was converted, to the title compound (832 mg, 98%) which was obtained as an off white solid. MS: m/e=343.1 [M−H]$^-$.

Example 117

6-[3-(4-Chloro-phenyl)-5-methyl-isoxazol-4-ylmethoxy]-N-(2,2,2-trifluoro-ethyl)-nicotinamide A solution of trimethylaluminium (2 M in toluene, 401 µL, 0.8 mmol) was added dropwise (exothermic) to a solution of 2,2,2-trifluoroethylamine (79 mg, 63 µL, 0.8 mmol) in dioxane (5 mL) and the resulting mixture was stirred at room temperature for 1 h. Then a solution of 6-[3-(4-chloro-phenyl)-5-methyl-isoxazol-4-ylmethoxy]-nicotinic acid methyl ester (72 mg, 0.2 mmol) in dioxane (2.5 mL) was added. The resulting mixture was then heated at 85-95° C. for 1 h and then cooled to room temperature and then poured into water and extracted with ethyl acetate which was then washed with brine, dried over sodium sulfate and evaporated. Purification by chromatography (SiO$_2$, heptane:ethyl acetate=100:0 to 1:1) afforded the title compound (66 mg, 77%) which was obtained as a white solid. MS: m/e=426.0 [M+H]$^+$.

Example 118

6-[3-(4-Chloro-phenyl)-5-methyl-isoxazol-4-ylmethoxy]-N-cyclopropylmethyl-nicotinamide As described for example 117, 6-[3-(4-chloro-phenyl)-5-methyl-isoxazol-4-ylmethoxy]-nicotinic acid methyl ester (144 mg, 0.4 mmol) was converted, using cyclopropanemethylamine instead of 2,2,2-trifluoroethylamine, to the title

Example 119

6-[3-(4-Chloro-phenyl)-5-methyl-isoxazol-4-yl-methoxy]-N-isopropyl-nicotinamide

As described for example 8b, 6-[3-(4-chloro-phenyl)-5-methyl-isoxazol-4-ylmethoxy]-nicotinic acid (103 mg, 0.3 mmol), instead of 6-(5-methyl-3-phenyl-isoxazol-4-yl-methoxy)-nicotinic acid, was converted, using isopropylamine instead of methylamine, to the title compound (88 mg, 76%) which was obtained as an off white solid. MS: m/e=368.0 [M+H]$^+$.

Example 120

6-[3-(4-Chloro-phenyl)-5-methyl-isoxazol-4-yl-methoxy]-N-cyclopropyl-nicotinamide As described for example 117, 6-[3-(4-chloro-phenyl)-5-methyl-isoxazol-4-ylmethoxy]-nicotinic acid methyl ester (108 mg, 0.3 mmol) was converted, using cyclopropylamine instead of 2,2,2-trifluoroethylamine, to the title compound (93 mg, 81%) which was obtained as a white solid. MS: m/e=384.1 [M+H]$^+$.

Example 121

6-[3-(4-Chloro-phenyl)-5-methyl-isoxazol-4-yl-methoxy]-N-(tetrahydro-pyran-4-yl)-nicotinamide As described for example 117, 6-[3-(4-chloro-phenyl)-5-methyl-isoxazol-4-ylmethoxy]-nicotinic acid methyl ester (108 mg, 0.3 mmol) was converted, using 4-aminotetrahydropyran instead of 2,2,2-trifluoroethylamine, to the title compound (99 mg, 77%) which was obtained as a white solid. MS: m/e=428.1 [M+H]$^+$.

Example 122

{6-[3-(4-Chloro-phenyl)-5-methyl-isoxazol-4-yl-methoxy]-pyridin-3-yl}-(1,1-dioxo-1,6-thiomorpholin-4-yl)-methanone As described for example 117, 6-[3-(4-chloro-phenyl)-5-methyl-isoxazol-4-ylmethoxy]-nicotinic acid methyl ester (108 mg, 0.3 mmol) was converted, using thiomorpholine-S,S-dioxide instead of 2,2,2-trifluoroethylamine, to the title compound (137 mg, 99%) which was obtained as a white solid. MS: m/e=462.1 [M+H]$^+$.

Example 123

{6-[3-(4-Chloro-phenyl)-5-methyl-isoxazol-4-yl-methoxy]-pyridin-3-yl}-morpholin-4-yl-methanone As described for example 89, 6-[3-(4-chloro-phenyl)-5-methyl-isoxazol-4-ylmethoxy]-nicotinic acid methyl ester (144 mg, 0.4 mmol), instead of 6-[3-(3-fluoro-phenyl)-5-methyl-isoxazol-4-ylmethoxy]-nicotinic acid methyl ester, was converted, using morpholine instead of 2,2,2-trifluoroethylamine, to the title compound (142 mg, 85%) which was obtained as a white solid. MS: m/e=414.1 [M+H]$^+$.

Example 124

{6-[3-(4-Chloro-phenyl)-5-methyl-isoxazol-4-yl-methoxy]-pyridin-3-yl}-thiomorpholin-4-yl-methanone As described for example 117, 6-[3-(4-chloro-phenyl)-5-methyl-isoxazol-4-ylmethoxy]-nicotinic acid methyl ester (72 mg, 0.2 mmol) was converted, using thiomorpholine instead of 2,2,2-trifluoroethylamine, to the title compound (82 mg, 95%) which was obtained as a white solid. MS: m/e=430.5 [M+H]'.

Example 125

6-[3-(3,4-Difluoro-phenyl)-5-methyl-isoxazol-4-ylmethoxy]-N-(2,2,2-trifluoro-ethyl)-nicotinamide a) (E)- and/or (Z)-3,4-Difluoro-benzaldehyde oxime As described for example 88a, 3,4-difluorobenzaldehyde (50.0 g, 338 mmol), instead of 2-fluorobenzaldehyde, was converted to the title compound (53.1 g, 85%) which was obtained as a light yellow solid. MS: m/e=156.0 [M–H]$^-$.

b) (E)- and/or (Z)-3,4-Difluoro-N-hydroxy-benzenecarboximidoyl chloride

As described for example 88b, (E)- and/or (Z)-3,4-difluoro-benzaldehyde oxime (44.8 g, 285 mmol), instead of (E)- and/or (Z)-2-fluoro-benzaldehyde oxime, was converted to the title compound (54.6 g, 100%) which was obtained as a yellow solid. MS: m/e=191.1 [M]$^+$.

c) 3-(3,4-Difluoro-phenyl)-5-methyl-isoxazole-4-carboxylic acid ethyl ester

As described for example 88c, (E)- and/or (Z)-3,4-difluoro-N-hydroxy-benzenecarboximidoyl chloride (54.6 g, 285 mmol), instead of (E)- and/or (Z)—N-hydroxy-2-fluoro-benzenecarboximidoyl chloride, was converted to the title compound (29.5 g, 39%) which was obtained as an off white solid. MS: m/e=268.2 [M+H]$^+$.

d) [3-(3,4-Difluoro-phenyl)-5-methyl-isoxazol-4-yl]-methanol

As described for example 88d, 3-(3,4-difluoro-phenyl)-5-methyl-isoxazole-4-carboxylic acid ethyl ester (28.5 g, 107 mmol), instead of 3-(3-fluoro-phenyl)-5-methyl-isoxazole-4-carboxylic acid ethyl ester, was converted to the title compound (24.0 g, 48%) which was obtained as a light yellow solid. MS: m/e=226.2 [M+H]'.

e) 6-[3-(3,4-Difluoro-phenyl)-5-methyl-isoxazol-4-ylmethoxy]-nicotinic acid methyl ester As described for example 88e, [3-(3,4-difluoro-phenyl)-5-methyl-isoxazol-4-yl]methanol (5.0 g, 22.2 mmol), instead of [3-(3-fluoro-phenyl)-5-methyl-isoxazol-4-yl]-methanol, was converted to the title compound (5.2 g, 65%) which was obtained as a white solid. MS: m/e=361.2 [M+H]$^+$.

f) 6-[3-(3,4-Difluoro-phenyl)-5-methyl-isoxazol-4-ylmethoxy]-N-(2,2,2-trifluoro-ethyl)-nicotinamide A solution of trimethylaluminium (2 M in toluene, 1.1 mL, 2.2 mmol) was added dropwise (exothermic) to a solution of 2,2,2-trifluoroethylamine (250 mg, 2.2 mmol) in dioxane (10 mL) and the resulting mixture was stirred at room temperature for 1 h. Then a solution of 6-[3-(3,4-difluoro-phenyl)-5-methyl-isoxazol-4-ylmethoxy]-nicotinic acid methyl ester (200 mg, 0.56 mmol) in dioxane (10 mL) was added. The resulting mixture was then heated at 85-95° C. for 16 h and then cooled to room temperature and then poured into water and extracted with ethyl acetate which was then washed with brine, dried over sodium sulfate and evaporated. Purification by chromatography (SiO$_2$, heptane:ethyl acetate=95:5 to 1:1) afforded the title compound (150 mg, 63%) which was obtained as a white solid. MS: m/e=482.2 [M+H]'.

Example 126

6-[3-(3,4-Difluoro-phenyl)-5-methyl-isoxazol-4-ylmethoxy]-N-isopropyl-nicotinamide As described for example 125, 6-[3-(3,4-difluoro-phenyl)-5-methyl-isoxazol-4-ylmethoxy]-nicotinic acid methyl ester (200 mg, 0.56 mmol) was converted, using isopropylamine instead of 2,2,2-trifluoroethylamine, to the title compound (160 mg, 74%), which was obtained as a white solid. MS: m/e=386.5 [M−H]$^−$.

Example 127

6-[3-(3,4-Difluoro-phenyl)-5-methyl-isoxazol-4-ylmethoxy]-N-(tetrahydro-pyran-4-yl)-nicotinamide As described for example 125, 6-[3-(3,4-difluoro-phenyl)-5-methyl-isoxazol-4-ylmethoxy]-nicotinic acid methyl ester (200 mg, 0.56 mmol) was converted, using 4-aminotetrahydropyran instead of 2,2,2-trifluoroethylamine, to the title compound (120 mg, 50%) which was obtained as a white solid. MS: m/e=430.3 [M+H]$^+$.

Example 128

6-(3-Phenyl-5-trifluoromethyl-isoxazol-4-ylmethoxy)-nicotinic acid methyl ester a) rac-3-Phenyl-5-hydroxy-5-(trifluoromethyl)isoxazoline Prepared according to J. Org. Chem., 1995, 60, 3907. A solution of benzoyltrifluoroacetone (21 g, 97 mmol) was added dropwise over 1 h, at 20-30° C., to a solution of hydroxylamine HCl (6.82 g, 98 mmol) containing sodium hydroxide (2 N, 51 mL, 102 mmol) and the resulting mixture heated under reflux for 45 min. After cooling to room temperature, the mixture was poured into ice-water (500 mL), the precipitate was filtered off, washed with water and dried under vacuum to afford the title compound (20.51 g, 91%) which was obtained as a white solid. MS: m/e=230.2 [M−H]$^−$.

b) 3-Phenyl-4-(1-phenyl-1H-imidazol-4-yl)-5-trifluoromethyl-isoxazole

Prepared according to J. Org. Chem., 1995, 60, 3907. A solution of rac-3-phenyl-5-hydroxy-5-(trifluoromethyl)isoxazoline (20.4 g, 88 mmol) in trifluoroacetic acid (602 g, 404 mL, 5.3 mol) was heated under reflux for 24 h. After cooling to room temperature, the mixture was added carefully to a sodium carbonate solution (3 N, 880 mL) under ice-bath cooling until the reaction mixture was pH 7. The mixture was then extracted with tert-butylmethylether and the combined organic layers dried over sodium sulfate, filtered and evaporated. The residue was then evaporated and triturated with water to afford the title compound (17.3 g, 92%) which was obtained as a white solid. MS: m/e=214.1 [M+H]$^+$.

c) 3-Phenyl-5-trifluoromethyl-isoxazole-4-carboxylic acid

To a solution of 2,2,6,6-tetramethylpiperidine (7.7 g, 9.24 mL, 54 mmol) in dry THF (62 mL) was added BuLi (1.6 M in hexane, 30.7 mL, 49 mmol) at 0° C. and the resulting mixture stirred at 0° C. for 30 min. Then a solution of 3-phenyl-4-(1-phenyl-1H-imidazol-4-yl)-5-trifluoromethyl-isoxazole (8.72 g, 41 mmol) in dry THF (41 mL) was added dropwise at 0° C. and the resulting mixture stirred at 0° C. for 1 h. The mixture was then quenched with carbon dioxide gas and the resulting mixture stirred at 0° C. for 1 h. The mixture was then poured into HCl (1 N) and the mixture was extracted with ethyl acetate and the combined organic layers dried over sodium sulfate, filtered and evaporated to afford the title compound (10.32 g, 98%) which was obtained as a light brown solid. MS: m/e=256.1 [M−H]$^−$.

d) (3-Phenyl-5-trifluoromethyl-isoxazol-4-yl)-methanol

To a solution of 3-phenyl-5-trifluoromethyl-isoxazole-4-carboxylic acid (5.0 g, 19 mmol in THF (60 mL) at −10° C. was added triethylamine (2.0 g, 2.71 mL, 19 mmol) and then a solution of ethylchloroformate (2.1 g, 1.9 mL, 19 mmol) in THF (10 mL) added keeping the temperature below −5° C. After 30 min the mixture was filtered and the filtrate cooled to −10° C. and a suspension of sodiumborohydride (1.8 g, 49 mmol) in water (20 mL) added over 15 minutes keeping the temperature below −5° C. The mixture was then allowed to warm up to room temperature overnight and diluted with HCl (1 N) and extracted with ethyl acetate. The combined organic layers were then washed with water and brine, dried over sodium sulfate and evaporated. Purification by chromatography (SiO$_2$, heptane:ethyl acetate=100:0 to 1:1) afforded the title compound (3.1 g, 66%) as a white solid. MS: m/e=243.1 [M]'.

e) 6-(3-Phenyl-5-trifluoromethyl-isoxazol-4-ylmethoxy)-nicotinic acid methyl ester To a solution of (3-phenyl-5-trifluoromethyl-isoxazol-4-yl)-methanol (100 mg, 0.41 mmol) in THF (5 mL) was added 6-hydroxy-nicotinic acid methyl ester (69.3 mg, 0.45 mmol) and triphenylphosphine (162 mg, 0.62 mmol) at ambient temperature under an argon atmosphere. Then diethyl azodicarboxylate (96 µL, 0.62 mmol) was added and the reaction mixture was heated at 50° C. for 2 h. After cooling to room temperature the mixture was evaporated. Purification by chromatography (SiO$_2$, heptane:ethyl acetate=100:0 to 1:1) afforded the title compound (66 mg, 42%) as all off-whit solid. MS: m/e=379.5 [M+H]$^+$.

Example 129

N-Methyl-6-(3-phenyl-5-trifluoromethyl-isoxazol-4-ylmethoxy)-nicotinamide

As described for example 90, 6-(3-phenyl-5-trifluoromethyl-isoxazol-4-ylmethoxy)-nicotinic acid methyl ester (100 mg, 0.26 mmol), instead of 6-[3-(3-fluoro-phenyl)-5-

Example 130

N-Ethyl-6-(3-phenyl-5-trifluoromethyl-isoxazol-4-ylmethoxy)-nicotinamide

As described for example 117, 6-(3-phenyl-5-trifluoromethyl-isoxazol-4-ylmethoxy)-nicotinic acid methyl ester (100 mg, 0.26 mmol), 6-[3-(4-chloro-phenyl)-5-methyl-isoxazol-4-ylmethoxy]-nicotinic acid methyl ester (144 mg, 0.4 mmol) was converted, using ethylamine (2 M in THF) instead of 2,2,2-trifluoroethylamine, to the title compound (80 mg, 77 which was obtained as a white solid. MS: m/e=392.3 [M+H]$^+$.

Example 131

N-(2-Hydroxy-ethyl)-6-(3-phenyl-5-trifluoromethyl-isoxazol-4-ylmethoxy)-nicotinamide As described for example 129, 6-(3-phenyl-5-trifluoromethyl-isoxazol-4-ylmethoxy)-nicotinic acid methyl ester (100 mg, 0.26 mmol) was converted, using ethanolamine instead of methylamine (2 M in THF), to the title compound (26 mg, 24%) which was obtained as an off white solid. MS: m/e=408.3 [M+H]$^+$.

Example 132

N-Cyclopropylmethyl-6-(3-phenyl-5-trifluoromethyl-isoxazol-4-ylmethoxy)-nicotinamide A solution of trimethylaluminium (2 M in toluene, 529 µL, 1.1 mmol) was added dropwise (exothermic) to a solution of cyclopropanemethylamine (75 mg, 91 µL, 1.1 mmol) in dioxane (7 mL) and the resulting mixture was stirred at room temperature for 1 h. Then a solution of 6-(3-phenyl-5-trifluoromethyl-isoxazol-4-ylmethoxy)-nicotinic acid methyl ester (100 mg, 0.26 mmol) in dioxane (4 mL) was added. The resulting mixture was then heated at 85-95° C. for 6 h and then cooled to room temperature and then poured into water and extracted with ethyl acetate which was then washed with brine, dried over sodium sulfate and evaporated. Purification by chromatography (SiO$_2$, heptane:ethyl acetate=100:0 to 1:1) afforded the title compound (92 mg, 83%) which was obtained as an off white solid. MS: m/e=418.3 [M+H]$^+$.

Example 133

N-Isopropyl-6-(3-phenyl-5-trifluoromethyl-isoxazol-4-ylmethoxy)-nicotinamide

A solution of trimethylaluminium (2 M in toluene, 529 µL, 1.1 mmol) was added dropwise (exothermic) to a solution of isopropylamine (63 mg, 91 µL, 1.1 mmol) in dioxane (7 mL) and the resulting mixture was stirred at room temperature for 1 h. Then a solution of 6-(3-phenyl-5-trifluoromethyl-isoxazol-4-ylmethoxy)-nicotinic acid methyl ester (100 mg, 0.26 mmol) in dioxane (4 mL) was added. The resulting mixture was then heated at 85-95° C. for 5 h and then cooled to room temperature and then poured into water and extracted with ethyl acetate which was then washed with brine, dried over sodium sulfate and evaporated. Purification by chromatography (SiO$_2$, heptane:ethyl acetate=100:0 to 1:1) afforded the title compound (102 mg, 95%) which was obtained as a white solid. MS: m/e=406.4 [M+H]$^+$.

Example 134

N-Cyclopropyl-6-(3-phenyl-5-trifluoromethyl-isoxazol-4-ylmethoxy)-nicotinamide

As described for example 89, 6-(3-phenyl-5-trifluoromethyl-isoxazol-4-ylmethoxy)-nicotinic acid methyl ester (100 mg, 0.26 mmol), instead of 6-[3-(4-chloro-phenyl)-5-methyl-isoxazol-4-ylmethoxy]-nicotinic acid methyl ester, was converted, using cylopropylamine instead of morpholine, to the title compound (100 mg, 94%) which was obtained as a white solid. MS: m/e=404.5 [M+H]$^+$.

Example 135

6-(3-Phenyl-5-trifluoromethyl-isoxazol-4-ylmethoxy)-N-(tetrahydro-pyran-4-yl)-nicotinamide As described for example 90, 6-(3-phenyl-5-trifluoromethyl-isoxazol-4-ylmethoxy)-nicotinic acid methyl ester (100 mg, 0.26 mmol), instead of 6-[3-(3-fluoro-phenyl)-5-methyl-isoxazol-4-ylmethoxy]-nicotinic acid methyl ester was converted, using 4-aminotetrahydropyran instead of cyclopropylmethylamine, to the title compound (111 mg, 94%) which was obtained as a white solid. MS: m/e=448.3 [M+H]$^+$.

Example 136

6-[3-(4-Fluoro-phenyl)-5-trifluoromethyl-isoxazol-4-ylmethoxy]-nicotinic acid methyl ester a) 4,4,4-Trifluoro-1-(4-fluoro-phenyl)-butane-1,3-dione To a solution of ethyl trifluoroacetate (23.9 mL, 199 mmol) in tertbutylmethylether (230 mL) containing sodium methoxide (5.4 M, 39.6 mL, 214 mmol) was added 4-fluoroacetophenone (25 g, 181 mmol) and the resulting mixture stirred at room temperature for 3 h and then poured into ice-water. The mixture was then diluted with HCl (2 N, 200 mL) and then extracted with ethyl acetate. The combined organic extracts were then dried over sodium sulfate and evaporated to afford the title compound (40.9 g, 97%) which was obtained as an orange oil. MS: m/e=232.9 [M–H]$^-$.

b) rac-3-(4-Fluoro-phenyl)-5-trifluoromethyl-4,5-dihydro-isoxazol-5-ol

As described for example 128a, 4,4,4-trifluoro-1-(4-fluoro-phenyl)-butane-1,3-dione (12.39 g, 174.7 mmol), instead of benzoyltrifluoroacetone, was converted to the title compound (39.6 g, 92%) which was obtained as a light brown solid. MS: m/e=247.9 [M–H]$^-$.

c) 3-(4-Fluoro-phenyl)-5-trifluoromethyl-isoxazole

As described for example 128b, rac-3-(4-fluoro-phenyl)-5-trifluoromethyl-4,5-dihydro-isoxazol-5-ol (35.6 g, 142.9 mmol), instead of 3-phenyl-5-hydroxy-5-(trifluoromethyl)

isoxazoline, was converted to the title compound (32.2 g, 98%) which was obtained as a light brown solid. MS: m/e=298.1 [M+H]$^+$.

d) 3-(4-Fluoro-phenyl)-5-trifluoromethyl-isoxazole-4-carboxylic acid

As described for example 128c, 3-(4-fluoro-phenyl)-5-trifluoromethyl-isoxazole (40 g, 173 mmol), instead of 3-phenyl-4-(1-phenyl-1H-imidazol-4-yl)-5-trifluoromethyl-isoxazole, was converted to the title compound (23.1 g, 49%) which was obtained as a yellow solid. MS: m/e=294.0 [M−H]$^−$.

e) [3-(4-Fluoro-phenyl)-5-trifluoromethyl-isoxazol-4-yl]-methanol

As described for example 128d, 3-(4-fluoro-phenyl)-5-trifluoromethyl-isoxazole-4-carboxylic acid (3.0 g, 11 mmol), instead of 3-phenyl-5-trifluoromethyl-isoxazole-4-carboxylic acid, was converted to the title compound (1.58 g, 56%) which was obtained as a yellow solid. MS: m/e=262.0 [M+H]$^+$.

f) 6-[3-(4-Fluoro-phenyl)-5-trifluoromethyl-isoxazol-4-ylmethoxy]-nicotinic acid methyl ester As described for Example 128e, [3-(4-fluoro-phenyl)-5-trifluoromethyl-isoxazol-4-yl]-methanol (100 mg, 0.38 mmol), instead of (3-phenyl-5-trifluoromethyl-isoxazol-4-yl)-methanol, was converted to the title compound (54 mg, 36%) which was obtained as a white solid. MS: m/e=397.0 [M+H]$^+$.

Example 137

6-[3-(4-Fluoro-phenyl)-5-trifluoromethyl-isoxazol-4-ylmethoxy]-N-methyl-nicotinamide As described for example 129, 6-[3-(4-fluoro-phenyl)-5-trifluoromethyl-isoxazol-4-ylmethoxy]-nicotinic acid methyl ester (100 mg, 0.25 mmol), instead of 6-(3-phenyl-5-trifluoromethyl-isoxazol-4-ylmethoxy)-nicotinic acid methyl ester, was converted to the title compound (66 mg, 66%) which was obtained as an off white solid. MS: m/e=396.1 [M+H]$^+$.

Example 138

N-Ethyl-6-[3-(4-fluoro-phenyl)-5-trifluoromethyl-isoxazol-4-ylmethoxy]-nicotinamide As described for example 137, 6-[3-(4-fluoro-phenyl)-5-trifluoromethyl-isoxazol-4-ylmethoxy]-nicotinic acid methyl ester (100 mg, 0.25 mmol) was converted, using ethylamine instead of methylamine, to the title compound (75 mg, 72%) which was obtained as a white solid. MS: m/e=410.4 [M+H]$^+$.

Example 139

6-[3-(4-Fluoro-phenyl)-5-trifluoromethyl-isoxazol-4-ylmethoxy]-N-(2-hydroxy-ethyl)-nicotinamide As described for example 137, 6-[3-(4-fluoro-phenyl)-5-trifluoromethyl-isoxazol-4-ylmethoxy]-nicotinic acid methyl ester (100 mg, 0.25 mmol) was converted, using ethanolamine instead of methylamine to the title compound (19 mg, 18%) which was obtained as a white solid. MS: m/e=426.1 [M+H]$^+$.

Example 140

6-[3-(4-Fluoro-phenyl)-5-trifluoromethyl-isoxazol-4-ylmethoxy]-N-(2,2,2-trifluoro-ethyl)-nicotinamide As described for example 92, 6-[3-(4-fluoro-phenyl)-5-trifluoromethyl-isoxazol-4-ylmethoxy]-nicotinic acid methyl ester (100 mg, 0.25 mmol), instead of 6-[3-(3-fluoro-phenyl)-5-methyl-isoxazol-4-ylmethoxy]-nicotinic acid methyl ester, was converted, using 2,2,2-trifluoroethylamine instead of cyclopropylamine, to the title compound (115 mg, 98%) which was obtained as a white solid. MS: m/e=464.3 [M+H]$^+$.

Example 141

N-Cyclopropylmethyl-6-[3-(4-fluoro-phenyl)-5-trifluoromethyl-isoxazol-4-ylmethoxy]-nicotinamide As described for example 137, 6-[3-(4-fluoro-phenyl)-5-trifluoromethyl-isoxazol-4-ylmethoxy]-nicotinic acid methyl ester (100 mg, 0.25 mmol) was converted, using cyclopropanemethylamine instead of methylamine, to the title compound (96 mg, 87%) which was obtained as an off white solid. MS: m/e=436.0 [M+H]$^+$.

Example 142

6-[3-(4-Fluoro-phenyl)-5-trifluoromethyl-isoxazol-4-ylmethoxy]-N-isopropyl-nicotinamide As described for example 137, 6-[3-(4-fluoro-phenyl)-5-trifluoromethyl-isoxazol-4-ylmethoxy]-nicotinic acid methyl ester (100 mg, 0.25 mmol) was converted, using isopropylamine instead of methylamine, to the title compound (104 mg, 97%) which was obtained as an off white solid. MS: m/e=424.1 [M+H]$^+$.

Example 143

N-Cyclopropyl-6-[3-(4-fluoro-phenyl)-5-trifluoromethyl-isoxazol-4-ylmethoxy]-nicotinamide As described for example 89, 6-[3-(4-fluoro-phenyl)-5-trifluoromethyl-isoxazol-4-ylmethoxy]-nicotinic acid methyl ester (100 mg, 0.25 mmol), instead of 6-[3-(3-fluoro-phenyl)-5-methyl-isoxazol-4-ylmethoxy]-nicotinic acid methyl ester, was converted, using cylopropylamine instead of 2,2,2-trifluoroethylamine, to the title compound (90 mg, 54%) which was obtained as a white solid. MS: m/e=422.1 [M+H]$^+$.

Example 144

6-[3-(4-Fluoro-phenyl)-5-trifluoromethyl-isoxazol-4-ylmethoxy]-N-(tetrahydro-pyran-4-yl)-nicotinamide As described for example 137, 6-[3-(4-fluoro-phenyl)-5-trifluoromethyl-isoxazol-4-ylmethoxy]-nicotinic acid methyl ester (100 mg, 0.25 mmol) was converted, using 4-aminotetrahydropyran instead of methylamine (2 M in THF), to the title compound (94 mg, 80%) which was obtained as a white solid. MS: m/e=466.0 [M+H]$^+$.

Example 145

(1,1-Dioxo-1λ6-thiomorpholin-4-yl)-{6-[3-(4-fluoro-phenyl)-5-trifluoromethyl-isoxazol-4-yl-methoxy]-pyridin-3-yl}-methanone A solution of trimethylaluminium (2 M in toluene, 504 µL, 1.0 mmol) was added dropwise (exothermic) to a solution of thiomorpholine-S,S-dioxide (136 mg, 1.0 mmol) in dioxane (7 mL) and the resulting mixture was stirred at room temperature for 1 h. Then a solution of 6-[3-(4-fluoro-phenyl)-5-trifluoromethyl-isoxazol-4-ylmethoxy]-nicotinic acid methyl ester (100 mg, 0.25 mmol) in dioxane (4 mL) was added. The resulting mixture was then heated at 85-95° C. for 4 days and then cooled to room temperature and then poured into water and extracted with ethyl acetate which was then washed with brine, dried over sodium sulfate and evaporated. Purification by chromatography (SiO$_2$, heptane:ethyl acetate=100:0 to 1:1) afforded the title compound (32 mg, 25%) which was obtained as an off white solid. MS: m/e=500.0 [M+H]$^+$.

Example 146

6-(5-Methyl-3-pyridin-4-yl-isoxazol-4-ylmethoxy)-N-(2,2,2-trifluoro-ethyl)-nicotinamide a) 5-Methyl-3-pyridin-4-yl-isoxazole-4-carboxylic acid ethyl ester To a suspension of N-chlorosuccinimide (10.9 g, 81.9 mmol) in chloroform (50 mL) was added pyridine (0.66 mL, 8.2 mmol) and a solution of pyridine-4-carboxaldoxime (10.0 g, 81.2 mmol) in chloroform (150 mL) during 15 min at ambient temperature. After stirring for 30 min at this temperature a solution of ethyl(E)-3-(1-pyrrolidino)-2-butenoate (15.0 g, 81.9 mmol) in chloroform (10 mL) was added. The resulting suspension was warmed to 50° C. and a solution of triethylamine (12 mL, 86 mmol) in chloroform (10 mL) was added dropwise over a period of 1 h. Stirring was continued for 0.5 h at 50° C. and for 30 h at ambient temperature. The dark brown solution was washed with water (100 mL) and the aqueous layers were extracted with dichloromethane (50 mL) and dried over sodium sulfate. Concentration was followed by trituration of the residue in a mixture of tert-butylmethyl-ether and heptane (1:1, 20 mL) affording the title compound (8.09 g, 24%) as a brown solid. MS: m/e=233.1 [M+H]$^+$.

b) (5-Methyl-3-pyridin-4-yl-isoxazol-4-yl)-methanol

To a solution of 5-methyl-3-pyridin-4-yl-isoxazole-4-carboxylic acid ethyl ester (7.06 g, 17.3 mmol) in THF (350 mL) was added at 5° C. lithiumaluminumhydride (635 mg, 16.7 mmol). After stirring for 2 h at this temperature further lithiumaluminumhydride (318 mg, 8.4 mmol) was added and stirred for 1 h at 5° C. Water (1.9 mL) was added carefully followed by aqueous sodium hydroxide (15%, 1.9 mL) and water (0.540 mL). The resulting suspension was stirred for 15 min at ambient temperature and filtered over Hyflo®. Concentration and purification by chromatography (SiO$_2$, heptane:ethyl acetate=50:50 to 0:100) afforded the title compound (2.15 g, 65%) as a light yellow solid. MS: m/e=191.2 [M+H]$^+$.

c) 6-(5-Methyl-3-pyridin-4-yl-isoxazol-4-yl-methoxy)-nicotinic acid

A solution of (5-methyl-3-pyridin-4-yl-isoxazol-4-yl)-methanol (1.00 g, 5.26 mmol) in THF (15 mL) was cooled to 0° C. and sodium hydride (55% dispersion in mineral oil, 252 mg, 5.78 mmol) was added carefully under an atmosphere of nitrogen. After the resulting suspension was stirred for 0.5 h at ambient temperature methyl 6-chloronicotinate (1.08 g, 6.31 mmol) was added and the suspension was stirred for 18 h at this temperature.

The reaction mixture was treated with a aqueous sodium hydroxide (1 N, 15.8 mL, 15.8 mmol) and stirred for 0.5 h at 70° C. The solution was cooled to ambient temperature, diluted with water (15 mL) and washed with tert-butylmethylether (15 mL). The organic layers were extracted with water (20 mL) and the combined aqueous layers were acified to pH=4 with a aqueous hydrochloric acid (25%). After the resulting suspension was stirred for 0.5 h at ambient temperature it was filtered off and washed with water (20 mL) affording the title compound (1.60 g, 97%) which was obtained as a white solid MS: m/e=310.2 [M+H]$^+$.

d) 6-(5-Methyl-3-pyridin-4-yl-isoxazol-4-yl-methoxy)-N-(2,2,2-trifluoro-ethyl)-nicotinamide As described for example 92, 6-(5-methyl-3-pyridin-4-yl-isoxazol-4-ylmethoxy)-nicotinic acid (93 mg, 0.3 mmol), instead of 6-[3-(3-fluoro-phenyl)-5-methyl-isoxazol-4-yl-methoxy]-nicotinic acid methyl ester (103 mg, 0.3 mmol) was converted, using 2,2,2-trifluoroethylamine instead of cyclopropylamine, to the title compound (16 mg, 14%) which was obtained as a light brown solid. MS: m/e=393.3 [M+H]$^+$.

Example 147

N-Cyclopropylmethyl-6-(5-methyl-3-pyridin-4-yl-isoxazol-4-ylmethoxy)-nicotinamide As described for example 90, 6-(5-methyl-3-pyridin-4-yl-isoxazol-4-ylmethoxy)-nicotinic acid (93 mg, 0.3 mmol), instead of 6-[3-(3-fluoro-phenyl)-5-methyl-isoxazol-4-yl-methoxy]-nicotinic acid methyl ester, was converted to the title compound (69 mg, 63%) which was obtained as an off white solid. MS: m/e=365.1 [M+H]'.

Example 148

N-Cyclopropyl-6-(5-methyl-3-pyridin-4-yl-isoxazol-4-ylmethoxy)-nicotinamide

As described for example 146d, 6-(5-methyl-3-pyridin-4-yl-isoxazol-4-ylmethoxy)-nicotinic acid (200 mg, 0.64 mol) was converted, using cyclopropylamine instead of 2,2,2-trifluoroethylamine, to the title compound (trituration with tert-butylmethylether, 194 mg, 86%) which was obtained as a white solid. MS: m/e=351.3 [M+H]$^+$.

Example 149

N-Isopropyl-6-(5-methyl-3-pyridin-4-yl-isoxazol-4-ylmethoxy)-nicotinamide

As described for example 12, 6-(5-methyl-3-pyridin-4-yl-isoxazol-4-ylmethoxy)-nicotinic acid (200 mg, 0.64 mol) instead of 6-(5-methyl-3-phenyl-isoxazol-4-ylmethoxy)-nicotinic acid was converted using isopropylamine instead of

Example 150

6-(5-Methyl-3-pyridin-4-yl-isoxazol-4-ylmethoxy)-N-(tetrahydro-pyran-4-yl)-nicotinamide As described for example 12, 6-(5-methyl-3-pyridin-4-yl-isoxazol-4-ylmethoxy)-nicotinic acid (200 mg, 0.64 mol) instead of 6-(5-methyl-3-phenyl-isoxazol-4-ylmethoxy)-nicotinic acid was converted using 4-aminotetrahydropyran instead of 2,2,2-trifluoroethylamine to the title compound (trituration with tert-butylmethylether, 178 mg, 70%) which was obtained as a white solid. MS: m/e=395.2 [M+H]$^+$.

Example 151

[6-(5-Methyl-3-pyridin-4-yl-isoxazol-4-ylmethoxy)-pyridin-3-yl]-morpholin-4-yl-methanone As described for example 147, 6-(5-methyl-3-pyridin-4-yl-isoxazol-4-ylmethoxy)-nicotinic acid (93 mg, 0.3 mmol) was converted, using morpholine instead of cyclopropylmethylamine, to the title compound (58 mg, 51%) which was obtained as an off white solid. MS: m/e=381.0 [M+H]$^+$.

Example 152

[6-(5-Methyl-3-pyridin-4-yl-isoxazol-4-ylmethoxy)-pyridin-3-yl]-thiomorpholin-4-yl-methanone As described for example 147, 6-(5-methyl-3-pyridin-4-yl-isoxazol-4-ylmethoxy)-nicotinic acid (93 mg, 0.3 mmol) was converted, using thiomorpholine instead of cyclopropylmethylamine, to the title compound (56 mg, 47%) which was obtained as an off white solid. MS: m/e=397.3 [M+H]$^+$.

Example 153

(1,1-Dioxo-1λ6-thiomorpholin-4-yl)-[6-(5-methyl-3-pyridin-4-yl-isoxazol-4-ylmethoxy)-pyridin-3-yl]-methanone As described for example 147, 6-(5-methyl-3-pyridin-4-yl-isoxazol-4-ylmethoxy)-nicotinic acid (93 mg, 0.3 mmol) was converted, using thiomorpholine-S,S-dioxide instead of cyclopropylmethylamine, to the title compound (75 mg, 58%) which was obtained as an off white solid. MS: m/e=429.4 [M+H]$^+$.

Example 154

6-(5-Methyl-3-pyridin-3-yl-isoxazol-4-ylmethoxy)-nicotinic acid methyl ester a) (E)- and/or (Z)—N-Hydroxy-3-pyridinecarboximidoyl chloride As described for example 88b, 3-pyridinealdoxime (25.0 g, 205 mmol), instead of (E)- and/or (Z)-3-fluoro-benzaldehyde oxime, was converted, to the title compound (18.8 g, 59%) which was obtained as a light brown solid. MS: m/e=157.0 [M+H]'.

b) 5-Methyl-3-pyridin-3-yl-isoxazole-4-carboxylic acid ethyl ester

As described for example 88c, (E)- and/or (Z)—N-hydroxy-3-pyridinecarboximidoyl chloride (18.6 g, 119 mmol), instead of (E)- and/or (Z)—N-hydroxy-3-fluoro-benzenecarboximidoyl chloride, was converted, to the title compound (8.1 g, 29%) which was obtained as an off white solid. MS: m/e=233.1 [M+H]$^+$.

c) (5-Methyl-3-pyridin-3-yl-isoxazol-4-yl)-methanol

As described for example 88d, 5-methyl-3-pyridin-3-yl-isoxazole-4-carboxylic acid ethyl ester (7.9 g, 34 mmol), instead of 3-(3-fluoro-phenyl)-5-methyl-isoxazole-4-carboxylic acid ethyl ester, was converted, to the title compound (4.3 g, 67%) which was obtained as a light yellow liquid. MS: m/e=191.3 [M+H]$^+$.

d) 6-(5-Methyl-3-pyridin-3-yl-isoxazol-4-ylmethoxy)-nicotinic acid methyl ester

As described for example 88e, 5-methyl-3-pyridin-3-yl-isoxazole-4-carboxylic acid ethyl ester (190 mg, 1.0 mmol), instead of [3-(3-fluoro-phenyl)-5-methyl-isoxazol-4-yl]-methanol, was converted, to the title compound (174 mg, 53%) which was obtained as a white solid. MS: m/e=326.0 [M+H]$^+$.

Example 155

6-(5-Methyl-3-pyridin-3-yl-isoxazol-4-ylmethoxy)-N-(2,2,2-trifluoro-ethyl)-nicotinamide As described for example 92, 6-(5-methyl-3-pyridin-3-yl-isoxazol-4-ylmethoxy)-nicotinic acid methyl ester (130 mg, 0.4 mmol), instead of 6-[3-(3-fluoro-phenyl)-5-methyl-isoxazol-4-ylmethoxy]-nicotinic acid methyl ester, was converted, using 2,2,2-trifluoroethylamine instead of cyclopropylamine, to the title compound (139 mg, 89%) which was obtained as an off white solid. MS: m/e=393.1 [M+H]$^+$.

Example 156

N-Cyclopropylmethyl-6-(5-methyl-3-pyridin-3-yl-isoxazol-4-ylmethoxy)-nicotinamide As described for example 90, 6-(5-methyl-3-pyridin-3-yl-isoxazol-4-ylmethoxy)-nicotinic acid methyl ester (130 mg, 0.4 mmol), instead of 6-[3-(3-fluoro-phenyl)-5-methyl-isoxazol-4-ylmethoxy]-nicotinic acid methyl ester, was converted to the title compound (98 mg, 67%) which was obtained as a light yellow solid. MS: m/e=365.1 [M+H]$^+$.

Example 157

N-Cyclopropyl-6-(5-methyl-3-pyridin-3-yl-isoxazol-4-ylmethoxy)-nicotinamide

As described for example 89, 6-(5-methyl-3-pyridin-3-yl-isoxazol-4-ylmethoxy)-nicotinic acid methyl ester (130 mg, 0.4 mmol), instead of 6-[3-(3-fluoro-phenyl)-5-methyl-isoxazol-4-ylmethoxy]-nicotinic acid methyl ester, using cyclopropylamine instead of 2,2,2-trifluoroethylamine, was converted to the title compound (117 mg, 83%) which was obtained as an off white solid. MS: m/e=351.4 [M+H]$^+$.

Example 158

N-Isopropyl-6-(5-methyl-3-pyridin-3-yl-isoxazol-4-ylmethoxy)-nicotinamide

As described for example 155, 6-(5-methyl-3-pyridin-3-yl-isoxazol-4-ylmethoxy)-nicotinic acid methyl ester (130 mg, 0.4 mmol), was converted, using isopropylamine instead of 2,2,2-trifluoroethylamine, to the title compound (112 mg, 83%) which was obtained as an off white solid. MS: m/e=353.0 [M+H]$^+$.

Example 159

6-(5-Methyl-3-pyridin-3-yl-isoxazol-4-ylmethoxy)-N-(tetrahydro-pyran-4-yl)-nicotinamide As described for example 89, 6-(5-methyl-3-pyridin-3-yl-isoxazol-4-ylmethoxy)-nicotinic acid methyl ester (130 mg, 0.4 mmol), instead of 6-[3-(3-fluoro-phenyl)-5-methyl-isoxazol-4-ylmethoxy]-nicotinic acid methyl ester, using 4-aminotetrahydropyran instead of 2,2,2-trifluoroethylamine, was converted to the title compound (117 mg, 83%) which was obtained as an off white solid. MS: m/e=395.1 [M+H]$^+$.

Example 160

(5-Methyl-3-phenyl-isoxazol-4-ylmethyl)-pyridin-2-yl-amine a) 4-Chloromethyl-5-methyl-3-phenyl-isoxazole To a solution of (5-methyl-3-phenyl-isoxazol-4-yl)-methanol (4.5 g, 236 mmol) in dichloromethane (50 mL) was added at 0° C. thionyl chloride (3.6 g, 2.7 mL, 306 mmol) dropwise over 3 min and the solution stirred at 0° C. for 2 h. After this time, the mixture was diluted with water (50 mL) and the organic phase separated and washed with brine. The aqueous phase was extracted with dichloromethane and the combined extracts dried over sodium sulfate, filtered and evaporated to afford the title compound (4.6 g, 93%) which was obtained as a light brown liquid. MS: m/e=208.1 [M+H]$^+$.

b) (5-Methyl-3-phenyl-isoxazol-4-ylmethyl)-pyridin-2-yl-amine

To a solution of 2-aminopyridine (109 mg, 1.2 mmol) in THF (2 mL) was added potassium bis(trimethylsilyl)amide (0.9 M in THF, 1.2 mL, 1.1 mmol) at 0° C. under argon. After 10 min, a solution of 4-chloromethyl-5-methyl-3-phenyl-isoxazole (200 mg, 1.0 mmol) in THF (1 mL) was added and the resulting mixture stirred at 0° C. for 1 h. The mixture was then diluted with ethyl acetate (10 mL) and washed with water (10 mL) and brine (10 mL). The aqueous phase was extracted with ethyl acetate and the combined extracts dried over sodium sulfate, filtered and evaporated. Purification by chromatography (SiO$_2$, heptane:ethyl acetate=4:1: to 1:1) afforded the title compound (45 mg, 18%) as an off white solid. MS: m/e=266.2 [M+H]$^+$.

Example 161

6-[(5-Methyl-3-phenyl-isoxazol-4-ylmethyl)-amino]-nicotinic acid methyl ester

A mixture of (5-methyl-3-phenyl-4-isoxazolyl)-methylamine (200 mg, 1.06 mmol), methyl 6-chloronicotinate (182 mg, 1.06 mmol), N,N-diisopropyl ethyl amine (364 µL, 2.13 mmol) and DMSO (2 mL) was heated in the microwave to 160° C. for 0.5 h. It was diluted with ethyl acetate (8 mL) and washed with aqueous sodium carbonate (saturated, 8 mL), water (8 mL) and brine (8 mL). The combined aqueous layers were extracted with ethyl acetate (10 mL) and the combined organic layers were dried over sodium sulfate. Concentration and purification by chromatography (SiO$_2$, heptane:ethyl acetate=100:0 to 50:50) afforded the title compound (158 mg, 46%) as a light yellow oil. MS: m/e=324.3 [M+H]$^+$.

Example 162

N-(2-Hydroxy-ethyl)-6-[(5-methyl-3-phenyl-isoxazol-4-ylmethyl)-amino]-nicotinamide a) 6-[(5-Methyl-3-phenyl-isoxazol-4-ylmethyl)-amino]-nicotinic acid To a suspension of 6-[(5-methyl-3-phenyl-isoxazol-4-ylmethyl)-amino]-nicotinic acid methyl ester (1.86 g, 5.50 mmol) in ethanol (100 mL) was added aqueous sodium hydroxide (1 N, 17 mL, 17 mmol) and the resulting suspension was heated to 80° C. for 0.5 h. After the solution was cooled to ambient temperature the solvent was distilled off and the residue was diluted with water (50 mL) and washed with tert-butylmethylether (50 mL). The organic layers were extracted with aqueous sodium hydroxide (1 N, 20 mL) and the combined aqueous layers were acified with aqueous hydrochloric acid (25%) to pH=3 and were extracted with a mixture of ethyl acetate and methanol (4:1, 30 mL). Drying over sodium sulfate and concentration afforded the title compound (1.55 g, 91%) which was obtained as a white solid. MS: m/e=310.3 [M+H]$^+$.

b) N-(2-Hydroxy-ethyl)-6-[(5-methyl-3-phenyl-isoxazol-4-ylmethyl)-amino]-nicotinamide To a mixture of 6-[(5-methyl-3-phenyl-isoxazol-4-ylmethyl)-amino]-nicotinic acid (200 mg, 0.65 mmol) and 2-(1H-benzotriazole-1-yl)-1,1,3,3-tetramethyluronium tetrafluoroborate (228 mg, 0.71 mmol) was added DMF (2 mL). After stirring for 2 min at ambient temperature N,N-diisopropyl ethyl amine (553 µL, 3.23 mmol) and ethanolamine (47 µl, 0.78 mmol) were added and the resulting solution was stirred for 2 h at this temperature. It was diluted with ethyl acetate (15 mL) and washed with water (20 mL) and brine (15 mL). The aqueous layers were extracted with ethyl acetate and the combined organic layers were dried over sodium sulfate. Concentration and purification by chromatography (SiO$_2$, heptane:ethyl acetate:methanol=30:70:0 to 0:95:5) afforded the title compound (200 mg, 88%) as a white solid. MS: m/e=353.2 [M+H]$^+$.

Example 163

6-[(5-Methyl-3-phenyl-isoxazol-4-ylmethyl)-amino]-N-[2-(2-oxo-pyrrolidin-1-yl)-ethyl]-nicotinamide As described for example 162b, 6-[(5-methyl-3-phenyl-isoxazol-4-ylmethyl)-amino]-nicotinic acid (200 mg, 0.65 mmol) was converted using 1-(2-amino-ethyl)-pyrrolidin-2-one instead of ethanolamine to the title compound (trituration with tert-butylmethylether, 224 mg, 83%) which was obtained as a white solid. MS: m/e=420.2 [M+H]$^+$.

Example 164

N-Isopropyl-6-[(5-methyl-3-phenyl-isoxazol-4-ylmethyl)-amino]-nicotinamide

As described for example 162b, 6-[(5-methyl-3-phenyl-isoxazol-4-ylmethyl)-amino]-nicotinic acid (200 mg, 0.65 mmol) was converted using isopropylamine instead of ethanolamine to the title compound (SiO$_2$, heptane:ethyl acetate=50:50 to 0:100, 185 mg, 82%) which was obtained as a white solid. MS: m/e=351.3 [M+H]$^+$.

Example 165

N-Cyclopropyl-6-[(5-methyl-3-phenyl-isoxazol-4-ylmethyl)-amino]-nicotinamide

As described for example 162b, 6-[(5-methyl-3-phenyl-isoxazol-4-ylmethyl)-amino]-nicotinic acid (200 mg, 0.65 mmol) was converted using cyclopropylamine instead of ethanolamine to the title compound (SiO$_2$, heptane:ethyl acetate=70:30 to 0:100, 201 mg, 89%) which was obtained as a white solid. MS: m/e=349.3 [M+H]$^+$.

Example 166

6-[(5-Methyl-3-phenyl-isoxazol-4-ylmethyl)-amino]-N-(tetrahydro-pyran-4-yl)-nicotinamide As described for example 162b, 6-[(5-methyl-3-phenyl-isoxazol-4-ylmethyl)-amino]-nicotinic acid (200 mg, 0.65 mmol) was converted using 4-amino-tetrahydropyran instead of ethanolamine to the title compound (trituration with tert-butylmethylether, 168 mg, 66%) which was obtained as a white solid. MS: m/e=393.3 [M+H]$^+$.

Example 167

6-{[3-(3-Fluoro-phenyl)-5-methyl-isoxazol-4-ylmethyl]-amino}-nicotinic acid methyl ester a) 2-[3-(3-Fluoro-phenyl)-5-methyl-isoxazol-4-ylmethyl]-isoindole-1,3-dione To a solution of [3-(3-fluoro-phenyl)-5-methyl-isoxazol-4-yl]-methanol (5.8 g, 28 mmol) in THF (339 mL) was added phthalimide (5.5 g, 37 mmol) and triphenylphosphine (9.8 g, 37 mmol) at ambient temperature under an argon atmosphere. Then a solution of diethyl azodicarboxylate (40% in toluene, 14.6 mL, 37 mmol) was added and the reaction mixture was stirred for 1 h at room temperature. Concentration and repeated trituration with ethyl acetate afforded the title compound (6.3 g, 66%) as a white solid. MS: m/e=337.1 [M+H]$^+$.

b) C-[3-(3-Fluoro-phenyl)-5-methyl-isoxazol-4-yl]-methylamine

To a solution of 2-[3-(3-fluoro-phenyl)-5-methyl-isoxazol-4-ylmethyl]-isoindole-1,3-dione (6.3 g, 19 mmol) in THF (252 mL) and ethanol (22 mL) at 0° C. was added hydrazine hydrate (7.0 g, 6.8 mL, 140 mmol) and the resulting mixture stirred at room temperature overnight. The mixture was then filtered and the filtrate diluted with HCl (1 N) and extracted with ethyl acetate. The combined organic extracts were then washed with HCl (1 N) and the aqueous layer made basic with NaOH (6 N). The aqueous layers were extracted with ethyl acetate and the combined organic layers washed with brine and dried over sodium sulfate. Concentration and purification by chromatography (NH$_2$—SiO$_2$, dichloromethane) afforded the title compound (3.0 g, 77%) as a yellow oil. MS: m/e=207.3 [M+H]$^+$.

c) 6-{[3-(3-Fluoro-phenyl)-5-methyl-isoxazol-4-ylmethyl]-amino}-nicotinic acid methyl ester A mixture of C-[3-(3-fluoro-phenyl)-5-methyl-isoxazol-4-yl]-methylamine (530 mg, 2.6 mmol), methyl 6-chloronicotinate (440 mg, 2.6 mmol), N,N-diisopropyl ethyl amine (880 µL, 5.1 mmol) and DMSO (5.1 mL) was heated in the microwave to 160° C. for 2×0.5 h and 1 h. The mixture was then diluted with ice-water and extracted with ethyl acetate. The combined organic extracts were then washed with brine and dried over sodium sulfate. Concentration and purification by chromatography (SiO$_2$, heptane:ethyl acetate=100:0 to 1:1) afforded the title compound (335 mg, 38%) as a yellow gum. MS: m/e=342.1 [M+H]$^+$.

Example 168

6-{[3-(3-Fluoro-phenyl)-5-methyl-isoxazol-4-ylmethyl]-amino}-N-(2,2,2-trifluoro-ethyl)-nicotinamide A solution of trimethylaluminium (2 M in toluene, 500 µL, 1.0 mmol) was added dropwise (exothermic) to a solution of 2,2,2-trifluoroethylamine (99 mg, 79 µL, 1.0 mmol) in dioxane (4 mL) and the resulting mixture was stirred at room temperature for 1 h. Then a solution of 6-{[3-(3-fluoro-phenyl)-5-methyl-isoxazol-4-ylmethyl]-amino}-nicotinic acid methyl ester (85 mg, 0.25 mmol) in dioxane (3 mL) was added. The resulting mixture was then heated at 85-95° C. for 2 h and then cooled to room temperature and then poured into a sodium potassium tartrate solution and extracted with ethyl acetate which was then washed with brine, dried over sodium sulfate and evaporated. Purification by chromatography (SiO$_2$, heptane:ethyl acetate=100:0 to 0:100) afforded the title compound (88 mg, 86%) which was obtained as a white solid. MS: m/e=409.1 [M+H]$^+$.

Example 169

6-{[3-(3-Fluoro-phenyl)-5-methyl-isoxazol-4-ylmethyl]-amino}-N-isopropyl-nicotinamide As described for example 168, 6-{[3-(3-fluoro-phenyl)-5-methyl-isoxazol-4-ylmethyl]-amino}-nicotinic acid methyl ester (85 mg, 0.25 mmol) was converted using isopropylamine instead of 2,2,2-trifluoroethylamine to the title compound (30 mg, 33%) which was obtained as an off white foam. MS: m/e=369.1 [M+H]$^+$.

Example 170

N-Cyclopropyl-6-{[3-(3-fluoro-phenyl)-5-methyl-isoxazol-4-ylmethyl]-amino}-nicotinamide As described for example 168, 6-{[3-(3-fluoro-phenyl)-5-methyl-isoxazol-4-ylmethyl]-amino}-nicotinic acid methyl ester (90 mg, 0.26 mmol) was converted using cyclopropylamine instead of 2,2,2-trifluoroethylamine to the title compound (81 mg, 84%) which was obtained as an off white solid. MS: m/e=367.4 [M+H]$^+$.

Example 171

6-{[3-(3-Fluoro-phenyl)-5-methyl-isoxazol-4-ylmethyl]-amino}-N-(tetrahydro-pyran-4-yl)-nicotinamide

As described for example 169, 6-{[3-(3-fluoro-phenyl)-5-methyl-isoxazol-4-ylmethyl]-amino}-nicotinic acid methyl ester (90 mg, 0.26 mmol) was converted using 4-amiontetrahydropyran instead of 2,2,2-trifluoroethylamine to the title compound (80 mg, 74%) which was obtained as a white solid. MS: m/e=411.4 [M+H]$^+$.

Example 172

6-{[3-(4-Fluoro-phenyl)-5-methyl-isoxazol-4-ylmethyl]-amino}-nicotinic acid methyl ester a) 2-[3-(4-Fluoro-phenyl)-5-methyl-isoxazol-4-ylmethyl]-isoindole-1,3-dione

To a solution of [3-(3-fluoro-phenyl)-5-methyl-isoxazol-4-yl]-methanol (5.0 g, 24 mmol) in THF (290 mL) was added phthalimide (4.7 g, 32 mmol) and triphenylphosphine (8.4 g, 32 mmol) at ambient temperature under an argon atmosphere. Then a solution of diethyl azodicarboxylate (40% in toluene, 12.5 mL, 32 mmol) was added and the reaction mixture was stirred for 1 h at room temperature. Concentration and repeated trituration and then purification by chromatography (SiO$_2$, heptane:ethyl acetate=100:0 to 1:1) afforded the title compound (6.0 g, 74%) as a white solid. MS: m/e=337.1 [M+H]$^+$.

b) C-[3-(4-Fluoro-phenyl)-5-methyl-isoxazol-4-yl]-methylamine

As described for example 167b, 2-[3-(4-fluoro-phenyl)-5-methyl-isoxazol-4-ylmethyl]-isoindole-1,3-dione (5.9 mg, 18 mmol), instead of 2-[3-(3-fluoro-phenyl)-5-methyl-isoxazol-4-ylmethyl]-isoindole-1,3-dione, was converted to the title compound (2.0 g, 54%) which was obtained as a light yellow oil. MS: m/e=190.3 [M+H]$^+$.

c) 6-{[3-(4-Fluoro-phenyl)-5-methyl-isoxazol-4-ylmethyl]-amino}-nicotinic acid methyl ester A mixture of C-[3-(4-fluoro-phenyl)-5-methyl-isoxazol-4-yl]-methylamine (620 mg, 3.0 mmol), methyl 6-chloronicotinate (516 mg, 3.0 mmol), N,N-diisopropyl ethyl amine (1.0 mL, 6.0 mmol) and DMSO (6 mL) was heated in the microwave to 160° C. for 2 h. The mixture was then diluted with ice-water and extracted with ethyl acetate. The combined organic extracts were then washed with brine and dried over sodium sulfate. Concentration and purification by chromatography (SiO$_2$, heptane:ethyl acetate=100:0 to 1:1 then dichloromethane:methanol 97:3) afforded the title compound (335 mg, 33%) as a white foam. MS: m/e=342.1 [M+H]$^+$.

Example 173

6-{[3-(4-Fluoro-phenyl)-5-methyl-isoxazol-4-ylmethyl]-amino}-N-(2,2,2-trifluoro-ethyl)-nicotinamide

As described for example 168, 6-{[3-(4-fluoro-phenyl)-5-methyl-isoxazol-4-ylmethyl]-amino}-nicotinic acid methyl ester (70 mg, 0.2 mmol), instead of 6-{[3-(3-fluoro-phenyl)-5-methyl-isoxazol-4-ylmethyl]-amino}-nicotinic acid methyl ester (85 mg, 0.25 mmol) was converted to the title compound (63 mg, 75%) which was obtained as a white solid. MS: m/e=409.3 [M+H]$^+$.

Example 174

N-Cyclopropylmethyl-6-{[3-(4-fluoro-phenyl)-5-methyl-isoxazol-4-ylmethyl]-amino}-nicotinamide

As described for example 173, 6-{[3-(4-fluoro-phenyl)-5-methyl-isoxazol-4-ylmethyl]-amino}-nicotinic acid methyl ester (70 mg, 0.2 mmol) was converted, using aminomethylcyclopropane instead of 2,2,2-trifluoroethylamine, to the title compound (80 mg, 83%) which was obtained as an off white foam. MS: m/e=381.4 [M+H]$^+$.

Example 175

6-{[3-(4-Fluoro-phenyl)-5-methyl-isoxazol-4-ylmethyl]-amino}-N-isopropyl-nicotinamide

A solution of trimethylaluminium (2 M in toluene, 410 μL, 0.8 mmol) was added dropwise (exothermic) to a solution of isopropylamine (48 mg, 70 μL, 0.8 mmol) in dioxane (5 mL) and the resulting mixture was stirred at room temperature for 1 h. Then a solution of 6-{[3-(4-fluoro-phenyl)-5-methyl-isoxazol-4-ylmethyl]-amino}-nicotinic acid methyl ester (70 mg, 0.2 mmol) in dioxane (2.5 mL) was added. The resulting mixture was then heated at 85-95° C. for 5 h and then cooled to room temperature and then poured into a sodium potassium tartrate solution and extracted with ethyl acetate which was then washed with brine, dried over sodium sulfate and evaporated. Purification by chromatography (SiO$_2$, heptane:ethyl acetate=100:0 to 0:100) afforded the title compound (53 mg, 70%) which was obtained as an off white foam. MS: m/e=369.4 [M+H]$^+$.

Example 176

N-Cyclopropyl-6-{[3-(4-fluoro-phenyl)-5-methyl-isoxazol-4-ylmethyl]-amino}-nicotinamide

A solution of trimethylaluminium (2 M in toluene, 410 μL, 0.8 mmol) was added dropwise (exothermic) to a solution of cyclopropylamine (47 mg, 58 μL, 0.8 mmol) in dioxane (5 mL) and the resulting mixture was stirred at room temperature for 1 h. Then a solution of 6-{[3-(4-fluoro-phenyl)-5-methyl-isoxazol-4-ylmethyl]-amino}-nicotinic acid methyl ester (70 mg, 0.2 mmol) in dioxane (2.5 mL) was added. The resulting mixture was then heated at 85-95° C. for 5 h and then cooled to room temperature and then poured into a sodium potassium tartrate solution and extracted with ethyl acetate which was then washed with brine, dried over sodium sulfate and evaporated. Purification by chromatography (SiO$_2$, heptane:ethyl acetate=100:0 to 0:100) afforded the title compound (45 mg, 60%) which was obtained as an off white foam. MS: m/e=367.0 [M+H]$^+$.

Example 177

6-{[3-(4-Fluoro-phenyl)-5-methyl-isoxazol-4-ylmethyl]-amino}-N-(tetrahydro-pyran-4-yl)-nicotinamide

As described for example 176, 6-{[3-(4-fluoro-phenyl)-5-methyl-isoxazol-4-ylmethyl]-amino}-nicotinic acid methyl ester (70 mg, 0.2 mmol) was converted, using 4-aminotetrahydropyran instead of 2,2,2-trifluoroethylamine, to the title compound (69 mg, 82%) which was obtained as a white foam. MS: m/e=411.4 [M+H]$^+$.

Example 178

(1,1-Dioxo-1,6-thiomorpholin-4-yl)-(6-{[3-(4-fluoro-phenyl)-5-methyl-isoxazol-4-ylmethyl]-amino}-pyridin-3-yl)-methanone As described for example 176, 6-{[3-(4-fluoro-phenyl)-5-methyl-isoxazol-4-ylmethyl]-amino}-nicotinic acid methyl ester (86 mg, 0.25 mmol) was converted, using thiomorpholine-S,S-dioxide instead of 2,2,2-trifluoroethylamine, to the title compound (76 mg, 68%) which was obtained as a white foam. MS: m/e=445.4 [M+H]$^+$.

Example 179

Not Encompassed by the Present Invention

N-[6-(5-Methyl-3-phenyl-isoxazol-4-ylmethoxy)-pyridin-3-yl]-acetamide a) 6-(5-Methyl-3-phenyl-isoxazol-4-ylmethoxy)-pyridin-3-ylamine To a suspension of 2-(5-methyl-3-phenyl-isoxazol-4-ylmethoxy)-5-nitro-pyridine (2.6 g, 83.5 mmol) in methanol (45 mL) was added ammonium chloride (2.23 g, 417.6 mmol) and Zinc (dust, 10.92 g, 167 mmol) and the resulting mixture heated at 70° C. for 1 h. After cooling to room temperature the mixture was filtered and the filtrate evaporated. Purification by chromatography (SiO$_2$, heptane:ethyl acetate=100:0 to 4:1) afforded the title compound (2.0 g, 85%) which was obtained as a light yellow oil. MS: m/e=282.0 [M+H]$^+$.

b) N-[6-(5-Methyl-3-phenyl-isoxazol-4-ylmethoxy)-pyridin-3-yl]-acetamide

To a solution of 6-(5-methyl-3-phenyl-isoxazol-4-ylmethoxy)-pyridin-3-ylamine (150 mg, 0.53 mmol) in THF (4 mL) was added triethylamine (65 mg, 90 μL, 0.64 mmol) and the resulting mixture cooled to 0° C. with ice. Then a solution of acetyl chloride (50 mg, 50 μL) in THF (1 mL) was added and the resulting mixture allowed to warm up to room temperature over 1 h. The mixture was then filtered and the filtrate evaporated before being diluted with methanol and potassium carbonate (10 mg) added. After one hour at room temperature the mixture was extracted with dichloromethane. The combined organic layers were then washed with water and then dried over sodium sulfate, filtered and evaporated to afford the title compound (145 mg, 84%) which was obtained as white crystals. MS: m/e=324.0 [M+H]$^+$.

Example 180

Not Encompassed by the Present Invention

N-[6-(5-Methyl-3-phenyl-isoxazol-4-ylmethoxy)-pyridin-3-yl]-oxalamic acid methyl ester As described for example 179b, 6-(5-methyl-3-phenyl-isoxazol-4-ylmethoxy)-pyridin-3-ylamine (150 mg, 0.53 mmol) was converted, using methyloxalylchloride instead of acetyl chloride, to the title compound (118 mg, 60%) which was obtained as a white solid after purification by chromatography (SiO$_2$, dichloromethane:methanol=100:0 to 9:1). MS: m/e=368.0 [M+H]$^+$.

Example 181

Not Encompassed by the Present Invention

N-[6-(5-Methyl-3-phenyl-isoxazol-4-ylmethoxy)-pyridin-3-yl]-isobutyramide

As described for example 179b, 6-(5-methyl-3-phenyl-isoxazol-4-ylmethoxy)-pyridin-3-ylamine (150 mg, 0.53 mmol) was converted, using isobutyrylchloride instead of acetyl chloride, to the title compound (170 mg, 91%) which was obtained as a white solid after trituration with diisopropylether. MS: m/e=352.0 [M+H]$^+$.

Example 182

Not Encompassed by the Present Invention

Cyclopropanecarboxylic acid [6-(5-methyl-3-phenyl-isoxazol-4-ylmethoxy)-pyridin-3-yl]-amide As described for example 179b, 6-(5-methyl-3-phenyl-isoxazol-4-ylmethoxy)-pyridin-3-ylamine (150 mg, 0.53 mmol) was converted, using cyclopropanecarbonylchloride instead of acetyl chloride, to the title compound (132 mg, 71%) which was obtained as a white solid after trituration with diisopropylether. MS: m/e=350.0 [M+H]$^+$.

Example 183

N-(2-Hydroxy-1,1-dimethyl-ethyl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (200 mg, 0.65 mmol) was converted, using 2-amino-2-methyl-1-propanol instead of methylamine, to the title compound (130 mg, 53%) which was obtained as an off white solid. MS: m/e=380.5 [M−H]$^-$.

Example 184

N-(2-Methoxy-ethyl)-6-(5-methyl-3-phenyl-isoxazol-4-ylmethoxy)-nicotinamide

A solution of trimethylaluminium (2 M in toluene, 2.0 mL, 4.0 mmol) was added dropwise (exothermic) to a solution of 2-methoxyethylamine (300 mg, 4.0 mmol) in dioxane (3 mL) and the resulting mixture was stirred at room temperature for 1 h. Then a solution of 6-(5-methyl-3-phenyl-isoxazol-4-ylmethoxy)-nicotinic acid (310 mg, 1.0 mmol) in dioxane (3 mL) was added. The resulting mixture was then heated at 85-95° C. for 4 days and then cooled to room temperature and then poured into water and extracted with ethyl acetate which was then washed with brine, dried over sodium sulfate and evaporated. Purification by chromatography (SiO$_2$, dichloromethane:methanol=100:0 to 9:1) afforded the title compound (280 mg, 76%) which was obtained as a colourless oil. MS: m/e=368.1 [M+H]'.

Example 185

N-(1,1-Dioxo-tetrahydro-thiophen-3-yl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (200 mg, 0.65 mmol) was converted, using 1,1-dioxo-tetrahydro-thiophen-3-ylamine instead of methylamine, to the title compound (150 mg, 54%) which was obtained as a white solid. MS: m/e=428.2 [M+H]$^+$.

Example 186

6-(5-Methyl-3-phenyl-isoxazol-4-ylmethoxy)-N-(3,3,3-trifluoro-2-hydroxy-propyl)-nicotinamide As described for example 8b, 6-(5-methyl-3-phenyl-isoxazol-4-ylmethoxy)-nicotinic acid (200 mg, 0.65 mmol) was converted, using 3-amino-1,1,1-trifluoropropan-2-ol instead of methylamine, to the title compound (124 mg, 46%) which was obtained as a white solid. MS: m/e=420.1 [M−H]$^−$.

Example 187

(4-Hydroxy-piperidin-1-yl)-[6-(5-methyl-3-phenyl-isoxazol-4-ylmethoxy)-pyridin-3-yl]-methanone As described for example 8b, 6-(5-methyl-3-phenyl-isoxazol-4-ylmethoxy)-nicotinic acid (155 mg, 0.50 mmol) was converted, using 4-hydroxypiperidine instead of methylamine, to the title compound (145 mg, 73%) which was obtained as a white solid. MS: m/e=394.2 [M+H]$^+$.

Example 188

N-(3-Hydroxy-2,2-dimethyl-propyl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (310 mg, 1.0 mmol) was converted, using 3-amino-2,2-dimethyl-1-propanol instead of methylamine, to the title compound (235 mg, 59%) which was obtained as a white solid. MS: m/e=396.2 [M+H]$^+$.

Example 189

N-(2-Isopropoxy-ethyl)-6-(5-methyl-3-phenyl-isoxazol-4-ylmethoxy)-nicotinamide

As described for example 8b, 6-(5-methyl-3-phenyl-isoxazol-4-ylmethoxy)-nicotinic acid (200 mg, 0.65 mmol) was converted, using 2-aminoethyl isopropylether instead of methylamine, to the title compound (190 mg, 74%) which was obtained as a white solid. MS: m/e=454.1 [M+OAc]$^−$.

Example 190

N-(2-Hydroxy-1-methyl-ethyl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (150 mg, 0.5 mmol) was converted, using rac-2-amino-1-propanol instead of methylamine, to the title compound (158 mg, 89%) which was obtained as a white solid. MS: m/e=368.2 [M+H]$^+$.

Example 191

(3-Hydroxy-azetidin-1-yl)-[6-(5-methyl-3-phenyl-isoxazol-4-ylmethoxy)-pyridin-3-yl]-methanone To a solution of 6-(5-methyl-3-phenyl-isoxazol-4-ylmethoxy)-nicotinic acid (200 mg, 0.65 mmol) and azetidin-3-ol hydrochloride (70.7 mg, 0.65 mmol) in THF (6 mL) at 0° C. were added 1-hydroxybenzotriazole hydrate (100.8 mg, 0.65 mmol), N-ethyldiisopropylamine (281.7 µl, 1.613 mmol) and N-(3-dimethylaminopropy)-N'-ethylcarbodiimidazole hydrochloride (126.2 mg, 0.65 mmol). The resulting reaction mixture was stirred overnight at room temperature. Concentration and purification by chromatography (SiO$_2$, heptane:ethyl acetate=3:1 to 1:4) afforded the title compound (215 mg, 91%) as a colourless oil. MS: m/e=366.2 [M+H]$^+$.

Example 192

N-(2-Hydroxy-cyclohexyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using rac-(cis and trans)-2-aminocyclohexanol instead of 2-aminoethyl isopropylether, to the title compound (130 mg, 50%) which was obtained as a white solid. MS: m/e=408.4 [M+H]$^+$.

Example 193

N-(2-Hydroxy-2-methyl-propyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using 1-amino-2-methyl-propan-2-ol instead of 2-aminoethyl isopropylether, to the title compound (215 mg, 49%) which was obtained as a white solid. MS: m/e=380.0 [M−H]$^−$.

Example 194

N-(1-Hydroxy-cyclopropylmethyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using 1-(aminomethyl)-cyclopropan-2-ol instead of 2-aminoethyl isopropylether, to the title compound (140 mg, 57%) which was obtained as a white solid. MS: m/e=378.3 [M−H]$^−$.

Example 195

N—((R)-2-Hydroxy-1-methyl-ethyl)-6-(5-methyl-3-phenyl-isoxazol-4-ylmethoxy)-nicotinamide The stereoisomers of N-(2-hydroxy-1-methyl-ethyl)-6-(5-methyl-3-phenyl-isoxazol-4-ylmethoxy)-nicotinamide (example 192, 500 mg) in ethanol:heptane (1:1, 8 mL) were separated using a 5×50 cm Chiralpak AD column at room temperature using an isopropanol:heptane (2:8) mobile phase with UV detection at 220 nM. The least polar component (+ve sign of rotation) was obtained as a white solid (168 mg).

Example 196

N—((S)-2-Hydroxy-1-methyl-ethyl)-6-(5-methyl-3-phenyl-isoxazol-4-ylmethoxy)-nicotinamide The stereoisomers of N-(2-hydroxy-1-methyl-ethyl)-6-(5-methyl-3-phenyl-isoxazol-4-ylmethoxy)-nicotinamide (example 192, 500 mg) in ethanol:heptane (1:1, 8 mL) were separated using a 5×50 cm Chiralpak AD column at room temperature using an isopropanol:heptane (2:8) mobile phase with UV detection at 220 nM. The most polar component (−ve sign of rotation) was obtained as a white solid (172 mg).

Example 197

N-((1R,2R)-2-Hydroxy-cyclohexyl)-6-(5-methyl-3-phenyl-isoxazol-4-ylm ethoxy)-nicotinamide As described for example 191, 6-(5-methyl-3-phenyl-isoxazol-4-ylmethoxy)-nicotinic acid (200 mg, 0.65 mmol) was converted, using (1R,2R)-2-amino-cyclohexanol hydrochloride (1:1) instead of 2-aminoethyl isopropylether, to the title compound (240 mg, 91%) which was obtained as a white solid. MS: m/e=406.2 [M−H]−.

Example 198

N-((1S,2S)-2-Hydroxy-cyclohexyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using (1S,2S)-2-amino-cyclohexanol hydrochloride (1:1) instead of 2-aminoethyl isopropylether, to the title compound (240 mg, 91%) which was obtained as a white solid. MS: m/e=408.3 [M+H]+.

Example 199

N-((1S,2R) and (1R,2S)-2-Hydroxy-cyclohexyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (800 mg, 2.58 mmol) was converted, using rac-cis-2-amino-cyclohexanol hydrochloride (1:1) instead of 2-aminoethyl isopropylether, to the title compound (995 mg, 95%) which was obtained as a white solid. MS: m/e=406.2 [M−H]−.

Example 200

N-(2-Hydroxy-cyclopentyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using 2-amino cyclopentanol instead of 2-aminoethyl isopropylether, to the title compound (80 mg, 31%) which was obtained as a white solid. MS: m/e=494.2 [M+H]+.

Example 201

N-(2-Hydroxy-1-hydroxymethyl-ethyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using 2-amino-1,3-propandiol instead of 2-aminoethyl isopropylether, to the title compound (215 mg, 87%) which was obtained as a colourless oil. MS: m/e=384.0 [M+H]+.

Example 202

6-(5-Methyl-3-phenyl-isoxazol-4-ylmethoxy)-N—(S)-tetrahydro-furan-3-yl-nicotinamide As described for example 168, 6-(5-methyl-3-phenyl-isoxazol-4-ylmethoxy)-nicotinic acid methyl ester (200 mg, 0.65 mmol) was converted, instead of 6-{[3-(3-fluoro-phenyl)-5-methyl-isoxazol-4-ylmethyl]-amino}-nicotinic acid methyl ester, was converted, using (S)-tetrahydrofuran-3-amine hydrochloride instead of 2,2,2-trifluoroethylamine, to the title compound (121 mg, 52%) which was obtained as a white solid. MS: m/e=380.1 [M+H]+.

Example 203

N-((1R,2S)-2-Hydroxy-cyclohexyl)-6-(5-methyl-3-phenyl-isoxazol-4-ylmethoxy)-nicotinamide or
N-((1S,2R)-2-Hydroxy-cyclohexyl)-6-(5-methyl-3-phenyl-isoxazol-4-ylmethoxy)-nicotinamide The stereoisomers N-((1S,2R) and (1R,2S)-2-hydroxy-cyclohexyl)-6-(5-methyl-3-phenyl-isoxazol-4-ylmethoxy)-nicotinamide (example 199, 910 mg) in ethanol:heptane (1:1, 8 mL) were separated using a 5×50 cm Chiralpak AD column at room temperature using an ethanol:heptane (3:7) mobile phase with UV detection at 220 nM. The least polar component (+ve sign of rotation) was obtained as a white solid (270 mg).

Example 204

N-((1S,2R)-2-Hydroxy-cyclohexyl)-6-(5-methyl-3-phenyl-isoxazol-4-ylmethoxy)-nicotinamide or
N-((1R,2S)-2-Hydroxy-cyclohexyl)-6-(5-methyl-3-phenyl-isoxazol-4-ylmethoxy)-nicotinamide The stereoisomers N-((1S,2R) and (1R,2S)-2-hydroxy-cyclohexyl)-6-(5-methyl-3-phenyl-isoxazol-4-ylmethoxy)-nicotinamide (example 199, 910 mg) in ethanol:heptane (1:1, 8 mL) were separated using a 5×50 cm Chiralpak AD column at room temperature using an ethanol:heptane (3:7) mobile phase with UV detection at 220 nM. The most polar component (−ve sign of rotation) was obtained as a white solid (320 mg).

Example 205

N-(2-Acetylamino-ethyl)-6-(5-methyl-3-phenyl-isoxazol-4-ylmethoxy)-nicotinamide

As described for example 191, 6-(5-methyl-3-phenyl-isoxazol-4-ylmethoxy)-nicotinic acid (200 mg, 0.65 mmol) was converted, using N-acetylethylendiamine instead of 2-aminoethyl isopropylether, to the title compound (170 mg, 67%) which was obtained as a white solid. MS: m/e=395.1 [M+H]+.

Example 206

N—((S)-1-Hydroxymethyl-2-methyl-propyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using L-valinol instead of 2-aminoethyl isopropylether, to the title compound (220 mg, 86%) which was obtained as a white solid. MS: m/e=394.2 [M−H]⁻.

Example 207

N—((S)-1-Hydroxymethyl-3-methyl-butyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using (R)-(−)-leucinol instead of 2-aminoethyl isopropylether, to the title compound (130 mg, 49%) which was obtained as a white solid. MS: m/e=408.4 [M−H]⁻.

Example 208

N—((S)-1-Hydroxymethyl-propyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using (S)-(+)-2-amino-1-butanol instead of 2-aminoethyl isopropylether, to the title compound (210 mg, 85%) which was obtained as a white solid. MS: m/e=380.2 [M−H]⁻.

Example 209

N—((R)-1-Hydroxymethyl-propyl)-6-(5-methyl-3-phenyl-isoxazol-4-ylmethoxy)-nicotinamide As described for example 208, 6-(5-methyl-3-phenyl-isoxazol-4-ylmethoxy)-nicotinic acid (200 mg, 0.65 mmol) was converted, using (R)-(+)-2-amino-1-butanol instead of (S)-(+)-2-amino-1-butanol, to the title compound (210 mg, 85%) which was obtained as a white solid. MS: m/e=380.2 [M−H]⁻.

Example 210

N-((1R,2S)-2-Hydroxy-cyclopentyl)-6-(5-methyl-3-phenyl-isoxazol-4-ylmethoxy)-nicotinamide or N-((1S,2R)-2-hydroxy-cyclopentyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (800 mg, 2.58 mmol) was converted, using rac cis-2-amino cyclopentanol hydrochloride instead of 2-aminoethyl isopropylether, to the title compound (830 mg, 82%) which was obtained as a white solid. MS: m/e=392.1 [M−H]⁻.

The stereoisomers N-((1R,2S) and (1S,2R)-2-hydroxy-cyclopentyl)-6-(5-methyl-3-phenyl-isoxazol-4-ylmethoxy)-nicotinamide (750 mg) in ethanol (9 mL) were separated using a 5×50 cm Chiralpak AD column at room temperature using an ethanol:heptane (3:7) mobile phase with UV detection at 220 nM. The least polar component (−ve sign of rotation) was obtained as a white solid (210 mg).

Example 211

N-((1S,2R)-2-Hydroxy-cyclopentyl)-6-(5-methyl-3-phenyl-isoxazol-4-ylmethoxy)-nicotinamide or N-((1R,2S)-2-hydroxy-cyclopentyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (800 mg, 2.58 mmol) was converted, using rac cis-2-amino cyclopentanol hydrochloride instead of 2-aminoethyl isopropylether, to the title compound (830 mg, 82%) which was obtained as a white solid. MS: m/e=392.1 [M−H]⁻.

The stereoisomers N-((1R,2S) and (1S,2R)-2-hydroxy-cyclopentyl)-6-(5-methyl-3-phenyl-isoxazol-4-ylmethoxy)-nicotinamide (750 mg) in ethanol (9 mL) were separated using a 5×50 cm Chiralpak AD column at room temperature using an ethanol:heptane (3:7) mobile phase with UV detection at 220 nM. The most polar component (−ve sign of rotation) was obtained as a white solid (400 mg).

Example 212

N-((1S,2S)-2-Hydroxy-cyclopentyl)-6-(5-methyl-3-phenyl-isoxazol-4-ylmethoxy)-nicotinamide or N-((1R,2R)-2-hydroxy-cyclopentyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (800 mg, 2.58 mmol) was converted, using rac trans-2-amino cyclopentanol hydrochloride instead of 2-aminoethyl isopropylether, to the title compound (820 mg, 81%) which was obtained as a white solid. MS: m/e=392.2 [M−H]⁻.

The stereoisomers N-((1S,2S) and (1R,2R)-2-hydroxy-cyclopentyl)-6-(5-methyl-3-phenyl-isoxazol-4-ylmethoxy)-nicotinamide (750 mg) in ethanol (9 mL) were separated using a 5×50 cm Chiralpak AD column at room temperature using an ethanol:heptane (3:7) mobile phase with UV detection at 220 nM. The least polar component (−ve sign of rotation) was obtained as a white solid (310 mg).

Example 213

N-((1R,2R)-2-Hydroxy-cyclopentyl)-6-(5-methyl-3-phenyl-isoxazol-4-ylmethoxy)-nicotinamide or N-((1S,2S)-2-hydroxy-cyclopentyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (800 mg, 2.58 mmol) was converted, using rac trans-2-amino cyclopentanol hydrochloride instead of 2-aminoethyl isopropylether, to the title compound (820 mg, 81%) which was obtained as a white solid. MS: m/e=392.2 [M−H]⁻.

The stereoisomers N-((1S,2S) and (1R,2R)-2-hydroxy-cyclopentyl)-6-(5-methyl-3-phenyl-isoxazol-4-ylmethoxy)-nicotinamide (750 mg) in ethanol (9 mL) were separated using a 5×50 cm Chiralpak AD column at room temperature using an ethanol:heptane (3:7) mobile phase with UV detection at 220 nM. The most polar component (+ve sign of rotation) was obtained as a white solid (310 mg).

Example 214

6-(5-Methyl-3-phenyl-isoxazol-4-ylmethoxy)-N-[2-(2-oxo-imidazolidin-1-yl)-ethyl]-nicotinamide As described for example 191, 6-(5-methyl-3-phenyl-isoxazol-4-ylmethoxy)-nicotinic acid (200 mg, 0.65 mmol) was converted, using (1-(2-aminoethyl)imidazoidin-2-one instead of 2-aminoethyl isopropylether, to the title compound (175 mg, 64%) which was obtained as a white solid. MS: m/e=422.1 [M+H]⁺.

Example 215

N-(3-Hydroxy-butyl)-6-(5-methyl-3-phenyl-isoxazol-4-ylmethoxy)-nicotinamide

As described for example 191, 6-(5-methyl-3-phenyl-isoxazol-4-ylmethoxy)-nicotinic acid (200 mg, 0.65 mmol) was converted, using 4-amino-2-butanol instead of 2-aminoethyl isopropylether, to the title compound (221 mg, 90%) which was obtained as a white solid. MS: m/e=380.3 [M−H]⁻.

Example 216

3-{[6-(5-Methyl-3-phenyl-isoxazol-4-ylmethoxy)-pyridine-3-carbonyl]-amino}-azetidine-1-carboxylic acid tert-butyl ester As described for example 191, 6-(5-methyl-3-phenyl-isoxazol-4-ylmethoxy)-nicotinic acid (200 mg, 0.65 mmol) was converted, using 3-amino-1-N-Boc-azetidine instead of 2-aminoethyl isopropylether, to the title compound (257 mg, 86%) which was obtained as a white solid. MS: m/e=463.3 [M−H]⁻.

Example 217

(2-{[6-(5-Methyl-3-phenyl-isoxazol-4-ylmethoxy)-pyridine-3-carbonyl]-amino}-ethyl)-carbamic acid tert-butyl ester As described for example 191, 6-(5-methyl-3-phenyl-isoxazol-4-ylmethoxy)-nicotinic acid (200 mg, 0.65 mmol) was converted, using N-Boc-ethylenediamine instead of 2-aminoethyl isopropylether, to the title compound (261 mg, 90%) which was obtained as a white solid. MS: m/e=511.5 [M+OAc]⁻.

Example 218

N-(2,3-Dihydroxy-propyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (200 mg, 0.65 mmol) was converted, using (R,S)-3-amino-1,2-propandiol instead of 2-aminoethyl isopropylether, to the title compound (91 mg, 37%) which was obtained as a white solid. MS: m/e=382.3 [M−H]⁻.

Example 219

N-(3-Hydroxy-propyl)-6-(5-methyl-3-phenyl-isoxazol-4-ylmethoxy)-nicotinamide

As described for example 191, 6-(5-methyl-3-phenyl-isoxazol-4-ylmethoxy)-nicotinic acid (200 mg, 0.65 mmol) was converted, using 3-amino-1-propanol instead of 2-aminoethyl isopropylether, to the title compound (200 mg, 84%) which was obtained as a colourless oil. MS: m/e=368.0 [M+H]⁺.

Example 220

N-(4-Hydroxy-butyl)-6-(5-methyl-3-phenyl-isoxazol-4-ylmethoxy)-nicotinamide

To a solution of 6-(5-methyl-3-phenyl-isoxazol-4-ylmethoxy)-nicotinic acid methyl ester (180 mg, 0.55 mmol) and 4-amino-1-butanol (59 mg, 0.66 mmol) in toluene (1 mL) was added 1,5,7-triazabicyclo[4.4.0]dec-5-ene (23 mg, 0.17 mmol) and the reaction stirred under argon for 6 h at room temperature. Saturated aqueous sodium bicarbonate (1 mL) was then added and the resulting mixture was extracted with ethyl acetate (3×5 mL). The combined organic extracts were then dried over sodium sulfate and evaporated. Purification by chromatography (SiO₂, dichloromethane:methanol=100:0 to 9:1) afforded the title compound (78 mg, 37%) which was obtained as a white solid. MS: m/e=382.2 [M+H]⁺.

Example 221

N-(5-Hydroxy-pentyl)-6-(5-methyl-3-phenyl-isoxazol-4-ylmethoxy)-nicotinamide

As described for example 220, 6-(5-methyl-3-phenyl-isoxazol-4-ylmethoxy)-nicotinic acid methyl ester (180 mg, 0.55 mmol) was converted, using 5-amino-1-pentanol instead of 3-amino-1-propanol, to the title compound (31 mg, 14%) which was obtained as a white solid. MS: m/e=396.1 [M+H]⁺.

Example 222

N-(6-Hydroxy-hexyl)-6-(5-methyl-3-phenyl-isoxazol-4-ylmethoxy)-nicotinamide

As described for example 220, 6-(5-methyl-3-phenyl-isoxazol-4-ylmethoxy)-nicotinic acid methyl ester (180 mg, 0.55 mmol) was converted, using 6-amino-1-hexanol instead of 3-amino-1-propanol, to the title compound (45 mg, 20%) which was obtained as a white solid. MS: m/e=410.3 [M+H]⁺.

Example 223

(3-Hydroxy-pyrrolidin-1-yl)-[6-(5-methyl-3-phenyl-isoxazol-4-ylmethoxy)-pyridin-3-yl]-methanone As described for example 220, 6-(5-methyl-3-phenyl-isoxazol-4-ylmethoxy)-nicotinic acid methyl ester (120 mg, 0.37 mmol) was converted, using 3-pyrrolidinol instead of 3-amino-1-propanol, to the title compound (122 mg, 87%) which was obtained as a colourless oil. MS: m/e=380.3 [M+H]⁺.

Example 224

((S)-2-Hydroxymethyl-pyrrolidin-1-yl)-[6-(5-methyl-3-phenyl-isoxazol-4-ylmethoxy)-pyridin-3-yl]-methanone As described for example 220, 6-(5-methyl-3-phenyl-isoxazol-4-ylmethoxy)-nicotinic acid methyl ester (120 mg, 0.37 mmol) was converted, using L-prolinol instead of 3-amino-1-propanol, to the title compound (122 mg, 84%) which was obtained as a colourless oil. MS: m/e=394.1 [M+H]⁺.

Example 225

((R)-2-Hydroxymethyl-pyrrolidin-1-yl)-[6-(5-methyl-3-phenyl-isoxazol-4-ylmethoxy)-pyridin-3-yl]-methanone As described for example 223, 6-(5-methyl-3-phenyl-isoxazol-4-ylmethoxy)-nicotinic acid methyl ester (120 mg, 0.37 mmol) was converted, using D-prolinol instead of L-prolinol, to the title compound (139 mg, 96%) which was obtained as a colourless oil. MS: m/e=394.1 [M+H]'.

Example 226

N-(3-Benzyloxy-cyclobutyl)-6-(5-methyl-3-phenyl-isoxazol-4-ylmethoxy)-nicotinamide As described for example 191, 6-(5-methyl-3-phenyl-isoxazol-4-ylmethoxy)-nicotinic acid (300 mg, 0.97 mmol) was converted, using rac 3-benzyloxy-cyclobutylamine instead of 2-aminoethyl isopropylether, to the title compound (350 mg, 43%) which was obtained as a white solid. MS: m/e=470.2 [M+H]$^+$.

Example 227

[6-(5-Methyl-3-phenyl-isoxazol-4-ylmethoxy)-pyridin-3-yl]-(2-methyl-pyrrolidin-1-yl)-methanone As described for example 191, 6-(5-methyl-3-phenyl-isoxazol-4-ylmethoxy)-nicotinic acid (200 mg, 0.64 mmol) was converted, using 2-methyl-pyrrolidine instead of 2-aminoethyl isopropylether, to the title compound (240 mg, 99%) which was obtained as a colourless. MS: m/e=378.3 [M+H]$^+$.

Example 228

[6-(5-Methyl-3-phenyl-isoxazol-4-ylmethoxy)-pyridin-3-yl]-pyrrolidin-1-yl-methanone As described for example 191, 6-(5-methyl-3-phenyl-isoxazol-4-ylmethoxy)-nicotinic acid (200 mg, 0.64 mmol) was converted, using pyrrolidine instead of 2-aminoethyl isopropylether, to the title compound (229 mg, 98%) which was obtained as a colourless. MS: m/e=364.3 [M+H]'.

Example 229

(S)-2-{[6-(5-Methyl-3-phenyl-isoxazol-4-ylmethoxy)-pyridine-3-carbonyl]-amino}-3-phenyl-propionic acid methyl ester As described for example 191, 6-(5-methyl-3-phenyl-isoxazol-4-ylmethoxy)-nicotinic acid (111 mg, 0.36 mmol) was converted, using L-phenylalanine methylester hydrochloride instead of 2-aminoethyl isopropylether, to the title compound (148 mg, 88%) which was obtained as a white solid. MS: m/e=470.1 [M–H]$^-$.

Example 230

(cis or trans)-N-(3-Benzyloxy-cyclobutyl)-6-(5-methyl-3-phenyl-isoxazol-4-ylmethoxy)-nicotinamide The stereoisomers N-(3-benzyloxy-cyclobutyl)-6-(5-methyl-3-phenyl-isoxazol-4-ylmethoxy)-nicotinamide (example 228, 350 mg) in ethanol (9 mL) were separated using a 5×50 cm Chiralpak AD column at room temperature using an ethanol:heptane (3:7) mobile phase with UV detection at 220 nM. The least polar component (–ve sign of rotation) was obtained as a white solid (160 mg).

Example 231

(S)-2-{[6-(5-Methyl-3-phenyl-isoxazol-4-ylmethoxy)-pyridine-3-carbonyl]-amino}-3-phenyl-propionic acid To a suspension of (S)-2-{[6-(5-methyl-3-phenyl-isoxazol-4-ylmethoxy)-pyridine-3-carbonyl]-amino}-3-phenyl-propionic acid methyl ester (100 mg, 0.21 mmol) in THF (1 mL) and methanol (0.29 mL) was added a solution of lithium hydroxide monohydrate (25.4 mg, 1.0 mmol) in water (0.74 mL) added and the resulting mixture stirred at room temperature for 2 h. The mixture was acidified to pH 4 with HCl (1 N, 30 mL) and the resulting mixture extracted with ethyl acetate. The combined organic layers were then washed with water and brine, dried over sodium sulfate and evaporated to afford the title compound (92 mg, 95%) which was obtained as a white solid. MS: m/e=470.1 [M–H]$^-$.

Example 232

N-(3-Methyl-oxetan-3-yl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (200 mg, 0.64 mmol) was converted, using 3-methyl-3-oxetanamine instead of methylamine, to the title compound (22 mg, 8%) which was obtained as a white solid. MS: m/e=380.2 [M+H]$^+$.

Example 233

Butane-1-sulfonic acid [6-(5-methyl-3-phenyl-isoxazol-4-ylmethoxy)-pyridine-3-carbonyl]-amide To a solution of 6-(5-methyl-3-phenyl-isoxazol-4-ylmethoxy)-nicotinic acid (100 mg, 0.32 mmol) in dichloromethane (5 mL) was added butane-1-sulfonic acid amide (44.2 mg, 0.32 mmol), N,N-dicyclohexylcarbodiimide (67.1 mg, 322 mmol) and 4-dimethylaminopyridine (40.1 mg, 0.32 mmol). The resulting mixture was stirred at room temperature overnight. The mixture was then filtered and the filtrate was concentrated and purified by chromatography (SiO$_2$, heptane:ethyl acetate 100:0 to 0:100) to give the title compound (17 mg, 12%) as a white solid. MS: m/e=428.1 [M–H]$^-$.

Example 234

6-(5-Methyl-3-phenyl-isoxazol-4-ylmethoxy)-N-(2,2,2-trifluoro-1-methyl-ethyl)-nicotinamide As described for example 8b, 6-(5-methyl-3-phenyl-isoxazol-4-ylmethoxy)-nicotinic acid (100 mg, 0.32 mmol) was converted, using 2,2,2-trifluoro-1-methyl-ethylamine (ABCR FO7820EFA) instead of methylamine, to the title compound (66 mg, 47%) which was obtained as a light yellow solid. MS: m/e=404.5 [M–H]$^-$.

Example 235

6-(5-Methyl-3-phenyl-isoxazol-4-ylmethoxy)-N—((S)-2,2,2-trifluoro-1-methyl-ethyl)-nicotinamide As described for example 234, 6-(5-methyl-3-phenyl-isoxazol-4-ylmethoxy)-nicotinic acid (100 mg, 0.32 mmol) was converted, using L-2,2,2-trifluoro-1-methyl-ethylamine (ABCR AB146651) instead of 2,2,2-trifluoro-1-methyl-ethylamine, to the title compound (69 mg, 53%) which was obtained as an off white solid. MS: m/e=404.5 [M−H]⁻.

Example 236

Cyclopropanesulfonic acid methyl-[6-(5-methyl-3-phenyl-isoxazol-4-ylmethoxy)-pyridine-3-carbonyl]-amide a) Cyclopropanesulfonic acid [6-(5-methyl-3-phenyl-isoxazol-4-ylmethoxy)-pyridine-3-carbonyl]-amide As described for example 233, 6-(5-methyl-3-phenyl-isoxazol-4-ylmethoxy)-nicotinic acid (128 mg, 0.41 mmol) was converted, using cyclopropanesulfonic acid amide instead of butane-1-sulfonic acid amide, to the title compound (96 mg, 56%) which was obtained as an off white solid. MS: m/e=412.1 [M−H]⁻.

b) Cyclopropanesulfonic acid methyl-[6-(5-methyl-3-phenyl-isoxazol-4-ylmethoxy)-pyridine-3-carbonyl]-amide To a solution of mixture of iodomethane (120 μL, 1.91 mmol), triethylamine (245 μL, 1.75 mmol) and anhydrous sodium carbonate (36.9 mg, 0.35 mmol) in DMF (0.5 mL) was added cyclopropanesulfonic acid [6-(5-methyl-3-phenyl-isoxazol-4-ylmethoxy)-pyridine-3-carbonyl]-amide (44 mg, 0.11 mmol). The reaction mixture was then heated in the microwave for 40 min at 100° C. The mixture was then cooled and evaporated and the residue was purified by chromatography (SiO₂, heptane:ethyl acetate 2:1 to 1:1) to give the title compound (3.9 mg, 9%) as a yellow solid. MS: m/e=486.3 [M+OAc]⁻.

Example 237

6-(5-Methyl-3-phenyl-isoxazol-4-ylmethoxy)-N-(1-methyl-1H-pyrazol-4-yl)-nicotinamide As described for example 191, 6-(5-methyl-3-phenyl-isoxazol-4-ylmethoxy)-nicotinic acid (200 mg, 0.65 mmol) was converted, using 1-methyl-1H-pyrazol-4-ylamine instead of 2-aminoethyl isopropylether, to the title compound (102 mg, 41%) which was obtained as a white solid. MS: m/e=388.1 [M−H]⁻.

Example 238

1-[6-(5-Methyl-3-phenyl-isoxazol-4-ylmethoxy)-pyridine-3-carbonyl]-1,2-dihydro-pyrazol-3-one As described for example 191, 6-(5-methyl-3-phenyl-isoxazol-4-ylmethoxy)-nicotinic acid (200 mg, 0.65 mmol) was converted, using 3-pyrazolidinone hydrochloride instead of 2-aminoethyl isopropylether, to the title compound (12 mg, 5%) which was obtained as a white solid. MS: m/e=375.0 [M−H]⁻.

Example 239

N-(1-Methyl-cyclopropyl)-6-(5-methyl-3-phenyl-isoxazol-4-ylmethoxy)-nicotinamide As described for example 8b, 6-(5-methyl-3-phenyl-isoxazol-4-ylmethoxy)-nicotinic acid (100 mg, 0.32 mmol) was converted, using 1-methylcyclopropylamine hydrochloride instead of methylamine, to the title compound (97 mg, 83%) which was obtained as a white solid. MS: m/e=362.5 [M−H]⁻.

Example 240

Azetidin-1-yl-[6-(5-methyl-3-phenyl-isoxazol-4-ylmethoxy)-pyridin-3-yl]-methanone As described for example 8b, 6-(5-methyl-3-phenyl-isoxazol-4-ylmethoxy)-nicotinic acid (100 mg, 0.32 mmol) was converted, using azetidine instead of methylamine, to the title compound (32 mg, 28%) which was obtained as a light yellow oil. MS: m/e=350.3 [M+H]'.

Example 241

(3-Methoxy-azetidin-1-yl)-[6-(5-methyl-3-phenyl-isoxazol-4-ylmethoxy)-pyridin-3-yl]-methanone As described for example 8b, 6-(5-methyl-3-phenyl-isoxazol-4-ylmethoxy)-nicotinic acid (100 mg, 0.32 mmol) was converted, using 3-methoxyazetidine hydrochloride instead of methylamine, to the title compound (75 mg, 61%) which was obtained as a light yellow oil. MS: m/e=380.3 [M+H]⁺.

Example 242

[6-(5-Methyl-3-phenyl-isoxazol-4-ylmethoxy)-pyridin-3-yl]-thiazolidin-3-yl-methanone As described for example 191, 6-(5-methyl-3-phenyl-isoxazol-4-ylmethoxy)-nicotinic acid (200 mg, 0.65 mmol) was converted, using thiazolidine instead of 2-aminoethyl isopropylether, to the title compound (68 mg, 28%) which was obtained as a white solid. MS: m/e=382.2 [M+H]'.

Example 243

N-(1-Cyano-cyclopropyl)-6-(5-methyl-3-phenyl-isoxazol-4-ylmethoxy)-nicotinamide

As described for example 191, 6-(5-methyl-3-phenyl-isoxazol-4-ylmethoxy)-nicotinic acid (100 mg, 0.32 mmol) was converted, using 1-amino-1-cyclopropanecarbonitrile instead of 2-aminoethyl isopropylether, to the title compound (61 mg, 51%) which was obtained as a white solid. MS: m/e=375.2 [M+H]⁺.

Example 244

6-(5-Methyl-3-phenyl-isoxazol-4-ylmethoxy)-N-(1-methyl-1H-pyrazol-3-yl)-nicotinamide As described for example 191, 6-(5-methyl-3-phenyl-isoxazol-4-ylmethoxy)-nicotinic acid (100 mg, 0.32 mmol) was converted, using 1-methyl-1H-pyrazol-3-ylamine instead of 2-aminoethyl isopropylether, to the title compound (110 mg, 87%) which was obtained as a colourless oil. MS: m/e=390.2 [M+H]⁺.

Example 245

5-(3-Methyl-[1,2,4]oxadiazol-5-yl)-2-(5-methyl-3-phenyl-isoxazol-4-ylmethoxy)-pyridine To a stirred solution of 6-(5-methyl-3-phenyl-isoxazol-4-ylmethoxy)-nicotinic acid (500 mg, 1.6 mmol), N-ethyldiisopropylamine (1.04 g, 2.0 mmol) and 1-hydroxybenzotriazole hydrate (40 mg, 0.3 mmol) in DMF (16 mL) at ambient temperature and under argon was added 2-(1H-benzotriazole-1-yl)-1,1,3,3-tetramethyluronium tetrafluoroborate (517 mg, 1.6 mmol) followed by N-hydroxymethylacetamidine (149 mg, 2.0 mmol). After 14 h the mixture was diluted with water (15 mL) and extracted with EtOAc (3×25 mL). The combined extracts were washed with 10% aqueous LiCl solution (2×10 mL) then dried over sodium sulfate, filtered and concentrated. The residue was then dissolved in DMF (16 mL) and heated at 140° C. for 3 h then cooled, diluted with EtOAc (60 mL), washed with 10% aqueous LiCl (3×100 mL), then dried over sodium sulfate, filtered and concentrated. Purification by chromatography ($SiO_2$, heptane:ethyl acetate 8:2 to 0:1) afforded the title compound (385 mg, 69%) as a yellow solid. MS: m/e=349.4 $[M+H]^+$.

Example 246

2-(5-Methyl-3-phenyl-isoxazol-4-ylmethoxy)-5-(5-methyl-4H-[1,2,4]triazol-3-yl)-pyridine a) 6-(5-Methyl-3-phenyl-isoxazol-4-ylmethoxy)-nicotinic acid hydrazide A mixture of 6-(5-methyl-3-phenyl-isoxazol-4-ylmethoxy)-nicotinic acid methyl ester (1.0 g, 3 mmol), hydrazine (3.09 g, 62 mmol) and ethanol (1 mL) was heated at 90° C. for 5 h.

The mixture was then cooled to room temperature and concentrated to give a white residue that was triturated with chloroform and filtered. The filtrates were concentrated to afford the title compound (743 mg, 15.1 mmol) in 66% purity. This material was used directly without further purification. MS: m/e=325.4 $[M+H]^+$.

b) 2-(5-Methyl-3-phenyl-isoxazol-4-ylmethoxy)-5-(5-methyl-4H-[1,2,4]triazol-3-yl)-pyridine A mixture of 6-(5-methyl-3-phenyl-isoxazol-4-ylmethoxy)-nicotinic acid hydrazide (300 mg, 0.6 mmol) and acetamidine hydrochloride (87 mg, 0.9 mmol) in DMF (6 mL) was heated at 120° C. for 2 h. A second portion of acetamidine hydrochloride (174 mg, 1.8 mmol) was added. After 8 h the mixture was cooled to room temperature and diluted with ethylacetate (40 mL). The mixture was filtered and the filtrates collected and washed with water (3×10 mL) and brine (10 mL) then dried over sodium sulfate, filtered and concentrated. Purification by chromatography ($SiO_2$, 0-5% dichloromethane:methanol=100:0 to 95:5) followed by purification by HPLC (acetonitrile:water=2:8) gave the title compound (42 mg, 20%) as a white solid. MS: m/e=348.2 $[M+H]^+$.

Example 247

2-(5-Methyl-3-phenyl-isoxazol-4-ylmethoxy)-5-methylsulfanyl-pyridine

To a solution of 5-bromo-2-(5-methyl-3-phenyl-isoxazol-4-ylmethoxy)-pyridine (300 mg, 0.87 mmol) in THF (3 mL) was added n-butyllithium (1.6 M, 543.1 µL, 0.87 mmol) and the resulting mixture stirred at −78° C. for 30 min. Then methyl disulfide (78.7 µL, 0.87 mmol) was added and the resulting mixture stirred overnight. The mixture was then evaporated. Purification by chromatography ($SiO_2$, heptane: ethyl acetate 8:2 to 1:3) afforded the title compound (136 mg, 50%) as a light yellow oil. MS: m/e=313.1 $[M+H]^+$.

Example 248

5-Methanesulfinyl-2-(5-methyl-3-phenyl-isoxazol-4-ylmethoxy)-pyridine

To a solution of 2-(5-methyl-3-phenyl-isoxazol-4-ylmethoxy)-5-methylsulfanyl-pyridine (70 mg, 0.22 mmol) in dichloromethane (2.1 mL) was added 2-benzenesulfonyl-3-phenyl-oxaziridine (58.5 mg, 0.22 mmol) and the reaction mixture was stirred overnight at room temperature. The mixture was then evaporated. Purification by chromatography ($SiO_2$, heptane:ethyl acetate 8:2 to 1:3) afforded the title compound (70 mg, 95%) as a white solid. MS: m/e=329.2 $[M+H]^+$.

Example 249

6-(5-Methyl-3-m-tolyl-isoxazol-4-ylmethoxy)-N-(tetrahydro-pyran-4-yl)-nicotinamide a) (E)- and/or (Z)-3-Methyl-benzaldehyde oxime As described for example 84a, m-tolualdehyde (15.0 g, 118.6 mmol) was converted, instead of 2-fluorobenzaldehyde, to the title compound (16.0 g, 100%) which was obtained as a yellow liquid. MS: m/e=135.0 $[M]^+$.

b) (E)- and/or (Z)-3-Methyl-N-hydroxy-benzenecarboximidoyl chloride

As described for example 84b, (E)- and/or (Z)-3-methyl-benzaldehyde oxime (17.4 g, 128.7 mmol) was converted, instead of (E)- and/or (Z)-2-fluoro-benzaldehyde oxime, to the title compound (21.8 g, 100%) which was obtained as a yellow liquid. MS: m/e=169.1 $[M]^+$.

c) 5-Methyl-3-m-tolyl-isoxazole-4-carboxylic acid ethyl ester

As described for example 84c, (E)- and/or (Z)-3-methyl-N-hydroxy-benzenecarboximidoyl chloride (10 g, 44.2 mmol) was converted, instead of (E)- and/or (Z)—N-hydroxy-2-fluoro-benzenecarboximidoyl chloride, to the title compound (5.1 g, 47%) which was obtained as a light yellow oil. MS: m/e=246.3 $[M+H]^+$.

d) (5-Methyl-3-m-tolyl-isoxazol-4-yl)-methanol

As described for example 84d, 5-methyl-3-m-tolyl-isoxazole-4-carboxylic acid ethyl ester (5.1 g, 20.8 mmol) was converted, instead of 3-(2-fluoro-phenyl)-5-methyl-isoxazole-4-carboxylic acid ethyl ester, to the title compound (3.2 g, 77%) which was obtained as a light yellow oil. MS: m/e=262.3 $[M+OAc]^-$.

e) 6-(5-Methyl-3-m-tolyl-isoxazol-4-ylmethoxy)-nicotinic acid methyl ester

As described for example 84e, (5-methyl-3-m-tolyl-isoxazol-4-yl)-methanol (3.2 g, 15.9 mmol) was converted, instead of [3-(2-fluoro-phenyl)-5-methyl-isoxazol-4-yl]-methanol, to the title compound (1.8 g, 33%) which was obtained as a colourelss oil. MS: m/e=339.3 $[M+H]^+$.

f) 6-(5-Methyl-3-m-tolyl-isoxazol-4-ylmethoxy)-N-(tetrahydro-pyran-4-yl)-nicotinamide As described for example 84f, 6-(5-methyl-3-m-tolyl-isoxazol-4-ylmethoxy)-nicotinic acid methyl ester (200 mg, 0.6 mmol) was converted, instead of [6-[3-(2-fluoro-phenyl)-5-methyl-isoxazol-4-ylmethoxy]-nicotinic acid methyl ester, using 4-aminotetrahydropyran instead of 2,2,2-trifluoroethylamine, to the title compound (190 mg, 79%) which was obtained as a white solid. MS: m/e=408.4 [M+H]$^+$.

Example 250

N-Isopropyl-6-(5-methyl-3-m-tolyl-isoxazol-4-ylmethoxy)-nicotinamide

As described for example 249f, 6-(5-methyl-3-m-tolyl-isoxazol-4-ylmethoxy)-nicotinic acid methyl ester (200 mg, 0.6 mmol) was converted, using isopropylamine instead of 4-aminotetrahydropyran, to the title compound (160 mg, 74%) which was obtained as a white solid. MS: m/e=366.1 [M+H]$^+$.

Example 251

6-(5-Methyl-3-p-tolyl-isoxazol-4-ylmethoxy)-N-(tetrahydro-pyran-4-yl)-nicotinamide a) (E)- and/or (Z)-4-Methyl-benzaldehyde oxime As described for example 249a, p-tolualdehyde (50.0 g, 408 mmol) was converted, instead of m-tolualdehyde, to the title compound (45.1 g, 82%) which was obtained as a white solid. 1H-NMR (CDCl$_3$): 2.38 (s, 3H), 7.20-7.25 (m, 2H), 7.45-7.50 (m, 2H), 8.12 (s, 1H), 8.40-8.60 (br s, 1H).

b) (E)- and/or (Z)-4-Methyl-N-hydroxy-benzenecarboximidoyl chloride

As described for example 249b, (E)- and/or (Z)-4-methyl-benzaldehyde oxime (45.0 g, 333 mmol) was converted, instead of (E)- and/or (Z)-3-methyl-benzaldehyde oxime, to the title compound (73.2 g, 100%, 77% purity) which was obtained as a yellow liquid. MS: m/e=1H-NMR (CDCl$_3$): 2.38 (s, 3H), 7.20-7.25 (m, 2H), 7.65-7.70 (m, 2H), 8.80-9.10 (br s, 1H).

c) 5-Methyl-3-p-tolyl-isoxazole-4-carboxylic acid ethyl ester

As described for example 249c, (E)- and/or (Z)-4-methyl-N-hydroxy-benzenecarboximidoyl chloride (10 g, 45.4 mmol, 77% purity) was converted, instead of E)- and/or (Z)-3-methyl-N-hydroxy-benzenecarboximidoyl chloride, to the title compound (12.6 g, 100%, 80% purity) which was obtained as a light yellow liquid. MS: m/e=246.2 [M+H]$^+$.

d) (5-Methyl-3-p-tolyl-isoxazol-4-yl)-methanol

As described for example 249d, 5-methyl-3-p-tolyl-isoxazole-4-carboxylic acid ethyl ester (12.6 g, 51.4 mmol) was converted, instead of 5-methyl-3-m-tolyl-isoxazole-4-carboxylic acid ethyl ester, to the title compound (3.95 g, 38%) which was obtained as a white solid. MS: m/e=204.2 [M+H]$^+$.

e) 6-(5-Methyl-3-p-tolyl-isoxazol-4-ylmethoxy)-nicotinic acid methyl ester

As described for example 249e, (5-methyl-3-p-tolyl-isoxazol-4-yl)-methanol (3.0 g, 14.8 mmol) was converted, instead of, (5-methyl-3-m-tolyl-isoxazol-4-yl)-methanol, to the title compound (3.9 g, 78%) which was obtained as a yellow solid. MS: m/e=339.3 [M+H]$^+$.

f) 6-(5-Methyl-3-p-tolyl-isoxazol-4-ylmethoxy)-N-(tetrahydro-pyran-4-yl)-nicotinamide As described for example 249f, 6-(5-methyl-3-p-tolyl-isoxazol-4-ylmethoxy)-nicotinic acid methyl ester (250 mg, 0.73 mmol) was converted, instead of 6-(5-methyl-3-m-tolyl-isoxazol-4-ylmethoxy)-nicotinic acid methyl ester, to the title compound (260 mg, 84%) which was obtained as a white solid. MS: m/e=408.4 [M+H]$^+$.

Example 252

N-Isopropyl-6-(5-methyl-3-p-tolyl-isoxazol-4-ylmethoxy)-nicotinamide

As described for example 250, 6-(5-methyl-3-p-tolyl-isoxazol-4-ylmethoxy)-nicotinic acid methyl ester (250 mg, 0.73 mmol) was converted, instead of 6-(5-methyl-3-m-tolyl-isoxazol-4-ylmethoxy)-nicotinic acid methyl ester, to the title compound (210 mg, 78%) which was obtained as a white solid. MS: m/e=366.3 [M+H]$^+$.

Example 253

6-[3-(2-Fluoro-4-methyl-phenyl)-5-methyl-isoxazol-4-ylmethoxy]-N-isopropyl-nicotinamide a) (E)- and/or (Z)-2-Fluoro-4-methyl-benzaldehyde oxime As described for example 84a, 2-fluoro-4-methyl-benzaldehyde (25.0 g, 172 mmol) was converted, instead of 2-fluorobenzaldehyde, to the title compound (26.4 g, 100%) which was obtained as a white solid. MS: m/e=154.0 [M+H]$^+$.

b) (E)- and/or (Z)-2-Fluoro-4-methyl-N-hydroxy-benzenecarboximidoyl chloride

As described for example 84b, (E)- and/or (Z)-2-fluoro-4-methyl-benzaldehyde oxime (26.3 g, 172 mmol) was converted, instead of (E)- and/or (Z)-2-fluoro-benzaldehyde oxime, to the title compound (37.2 g, 100%, purity 87%) which was obtained as a white solid. MS: m/e=187.0 [M]$^+$.

c) 3-(2-Fluoro-4-methyl-phenyl)-5-methyl-isoxazole-4-carboxylic acid ethyl ester As described for example 84c, (E)- and/or (Z)-2-fluoro-4-methyl-N-hydroxy-benzenecarboximidoyl chloride (18.5 g, 85.6 mmol) was converted, instead of (E)- and/or (Z)—N-hydroxy-2-fluoro-benzenecarboximidoyl chloride, to the title compound (18.8 g, 83%) which was obtained as a light yellow oil. MS: m/e=264.0 [M+H]$^+$.

d) [3-(2-Fluoro-4-methyl-phenyl)-5-methyl-isoxazol-4-yl]-methanol

As described for example 84d, 3-(2-fluoro-4-methyl-phenyl)-5-methyl-isoxazole-4-carboxylic acid ethyl ester (18.5 g, 70.3 mmol) was converted, instead of 3-(2-fluoro-phenyl)-5-methyl-isoxazole-4-carboxylic acid ethyl ester, to the title compound (15.5 g, 100%) which was obtained as a light yellow oil. MS: m/e=280.1 [M+OAc]⁻.

e) 6-[3-(2-Fluoro-4-methyl-phenyl)-5-methyl-isoxazol-4-ylmethoxy]-nicotinic acid methyl ester As described for example 84e, [3-(2-fluoro-4-methyl-phenyl)-5-methyl-isoxazol-4-yl]-methanol (6.64 g, 30 mmol) was converted, instead of [3-(2-fluoro-phenyl)-5-methyl-isoxazol-4-yl]-methanol, to the title compound (6.52 g, 61%) which was obtained as a yellow solid. MS: m/e=357.1 [M+H]⁺.

f) 6-[3-(2-Fluoro-4-methyl-phenyl)-5-methyl-isoxazol-4-ylmethoxy]-N-isopropyl-nicotinamide As described for example 84f, 6-[3-(2-fluoro-4-methyl-phenyl)-5-methyl-isoxazol-4-ylmethoxy]-nicotinic acid methyl ester (200 mg, 0.56 mmol) was converted, instead of [6-[3-(2-fluoro-phenyl)-5-methyl-isoxazol-4-ylmethoxy]-nicotinic acid methyl ester, using isopropylamine instead of 2,2,2-trifluoroethylamine, to the title compound (90 mg, 42%) which was obtained as a white solid. MS: m/e=384.3 [M+H]⁺.

Example 254

6-[3-(4-Chloro-phenyl)-5-methyl-isoxazol-4-ylmethoxy]-N-(2-hydroxy-1,1-dimethyl-ethyl)-nicotinamide As described for example 191, 6-[3-(4-chloro-phenyl)-5-methyl-isoxazol-4-ylmethoxy]-nicotinic acid (100 mg, 0.29 mmol) was converted, instead of 6-(5-methyl-3-phenyl-isoxazol-4-ylmethoxy)-nicotinic acid, using 2-amino-2-methyl-1-propanol instead of 2-aminoethyl isopropylether, to the title compound (37 mg, 30%) which was obtained as a white solid. MS: m/e=416.2 [M+H]⁺.

Example 255

6-[3-(4-Chloro-phenyl)-5-methyl-isoxazol-4-ylmethoxy]-N-(1-methyl-1H-pyrazol-4-yl)-nicotinamide As described for example 254, 6-[3-(4-chloro-phenyl)-5-methyl-isoxazol-4-ylmethoxy]-nicotinic acid (100 mg, 0.29 mmol) was converted, using 1-methyl-1H-pyrazol-4-ylamine instead of 2-amino-2-methyl-1-propanol, to the title compound (90 mg, 73%) which was obtained as a white solid. MS: m/e=424.2 [M+H]⁺.

Example 256

6-[3-(4-Chloro-phenyl)-5-methyl-isoxazol-4-ylmethoxy]-N—((R)-2-hydroxy-1-methyl-ethyl)-nicotinamide As described for example 254, 6-[3-(4-chloro-phenyl)-5-methyl-isoxazol-4-ylmethoxy]-nicotinic acid (100 mg, 0.29 mmol) was converted, using D-alaninol instead of 2-amino-2-methyl-1-propanol, to the title compound (100 mg, 94%) which was obtained as a white solid. MS: m/e=402.2 [M+H]⁺.

Example 257

6-[3-(4-Chloro-phenyl)-5-methyl-isoxazol-4-ylmethoxy]-N—((S)-2-hydroxy-1-methyl-ethyl)-nicotinamide As described for example 254, 6-[3-(4-chloro-phenyl)-5-methyl-isoxazol-4-ylmethoxy]-nicotinic acid (100 mg, 0.29 mmol) was converted, using L-alaninol instead of 2-amino-2-methyl-1-propanol, to the title compound (110 mg, 94%) which was obtained as a white solid. MS: m/e=402.3 [M+H]⁺.

Example 258

6-[3-(4-Chloro-phenyl)-5-methyl-isoxazol-4-ylmethoxy]-N—((S)-2,2,2-trifluoro-1-methyl-ethyl)-nicotinamide As described for example 254, 6-[3-(4-chloro-phenyl)-5-methyl-isoxazol-4-ylmethoxy]-nicotinic acid (100 mg, 0.29 mmol) was converted, using L-2,2,2-trifluoro-1-methyl-ethylamine (ABCR AB146651) instead of 2-amino-2-methyl-1-propanol, to the title compound (91 mg, 71%) which was obtained as a white solid. MS: m/e=440.2 [M+H]⁺.

Example 259

6-[3-(4-Chloro-phenyl)-5-methyl-isoxazol-4-ylmethoxy]-N-((1R,2R)-2-hydroxy-cyclopentyl)-nicotinamide or 6-[3-(4-chloro-phenyl)-5-methyl-isoxazol-4-ylmethoxy]-N-((1S,2S)-2-hydroxy-cyclopentyl)-nicotinamide As described for example 254, 6-[3-(4-chloro-phenyl)-5-methyl-isoxazol-4-ylmethoxy]-nicotinic acid (300 mg, 0.87 mmol) was converted, using rac trans-2-amino cyclopentanol hydrochloride instead of 2-amino-2-methyl-1-propanol, to the title compound (300 mg, 80%) which was obtained as a white solid. MS: m/e=428.2 [M+H]⁺.

The stereoisomers N-((1S,2S) and (1R,2R)-6-[3-(4-chloro-phenyl)-5-methyl-isoxazol-4-ylmethoxy]-N-2-hydroxy-cyclopentyl)-nicotinamide (300 mg) in ethanol:heptane (1:1, 8 mL) were separated using a 5×50 cm Chiralpak AD column at room temperature using an isopropanol:heptane (3:7) mobile phase with UV detection at 220 nM. The least polar component (−ve sign of rotation) was obtained as a white solid (100 mg).

Example 260

6-[3-(4-Chloro-phenyl)-5-methyl-isoxazol-4-ylmethoxy]-N-((1S,2S)-2-hydroxy-cyclopentyl)-nicotinamide or 6-[3-(4-chloro-phenyl)-5-methyl-isoxazol-4-ylmethoxy]-N-((1R,2R)-2-hydroxy-cyclopentyl)-nicotinamide As described for example 254, 6-[3-(4-chloro-phenyl)-5-methyl-isoxazol-4-ylmethoxy]-nicotinic acid (300 mg, 0.87 mmol) was converted, using rac trans-2-amino cyclopentanol hydrochloride instead of 2-amino-2-methyl-1-propanol, to the title compound (300 mg, 80%) which was obtained as a white solid. MS: m/e=428.2 [M+H]⁺.

The stereoisomers N-((1S,2S) and (1R,2R)-6-[3-(4-chloro-phenyl)-5-methyl-isoxazol-4-ylmethoxy]-N-2-hydroxy-cyclopentyl)-nicotinamide (300 mg) in ethanol:heptane (1:1, 8 mL) were separated using a 5×50 cm Chiralpak AD column at room temperature using an isopropanol:heptane (3:7) mobile phase with UV detection at 220 nM. The most polar component (+ve sign of rotation) was obtained as a white solid (110 mg).

Example 261

6-[3-(2,3-Difluoro-phenyl)-5-methyl-isoxazol-4-ylmethoxy]-N-isopropyl-nicotinamide a) (E)- and/or (Z)-2,3-Difluoro-benzaldehyde oxime As described for example 84a, 2,3-difluorobenzaldehyde (25.0 g, 172 mmol) was converted, instead of 2-fluorobenzaldehyde, to the title compound (26.3 g, 97%) which was obtained as a white solid. 1H-NMR (CDCl$_3$): 7.05-7.30 (m, 2H), 7.45-7.55 (m, 1H), 8.35 (s, 1H), 8.55 (s, 1H).

b) (E)- and/or (Z)-2,3-Difluoro-N-hydroxy-benzenecarboximidoyl chloride

As described for example 84b, (E)- and/or (Z)-2,3-difluoro-benzaldehyde oxime (26.3 g, 167 mmol) was converted, instead of (E)- and/or (Z)-2-fluoro-benzaldehyde oxime, to the title compound (41.4 g, 100%, purity 77%) which was obtained as a yellow liquid. 1H-NMR (CDCl$_3$): 7.10-7.30 (m, 2H), 7.40-7.50 (m, 1H), 8.05 (s, 1H).

c) 3-(2,3-Difluoro-phenyl)-5-methyl-isoxazole-4-carboxylic acid ethyl ester

As described for example 84c, (E)- and/or (Z)-2,3-difluoro-N-hydroxy-benzenecarboximidoyl chloride (20 g, 81 mmol, purity 77%) was converted, instead of (E)- and/or (Z)—N-hydroxy-2-fluoro-benzenecarboximidoyl chloride, to the title compound (17.8 g, 83%) which was obtained as a light yellow liquid. MS: m/e=268.2 [M+H]$^+$.

d) [3-(2,3-Difluoro-phenyl)-5-methyl-isoxazol-4-yl]-methanol

As described for example 84d, 3-(2,3-difluoro-phenyl)-5-methyl-isoxazole-4-carboxylic acid ethyl ester (16.0 g, 59.9 mmol) was converted, instead of 3-(2-fluoro-phenyl)-5-methyl-isoxazole-4-carboxylic acid ethyl ester, to the title compound (4.7 g, 35%) which was obtained as a yellow oil. MS: m/e=226.2 [M+H]$^+$.

e) 6-[3-(2,3-Difluoro-phenyl)-5-methyl-isoxazol-4-ylmethoxy]-nicotinic acid methyl ester As described for example 84e, [3-(2,3-difluoro-phenyl)-5-methyl-isoxazol-4-yl]-methanol (4.70 g, 21 mmol) was converted, instead of [3-(2-fluoro-phenyl)-5-methyl-isoxazol-4-yl]-methanol, to the title compound (3.47 g, 46%) which was obtained as a light yellow solid. MS: m/e=361.1 [M+H]$^+$.

f) 6-[3-(2,3-Difluoro-phenyl)-5-methyl-isoxazol-4-ylmethoxy]-N-isopropyl-nicotinamide As described for example 84f, 6-[3-(2,3-difluoro-phenyl)-5-methyl-isoxazol-4-ylmethoxy]-nicotinic acid methyl ester (200 mg, 0.56 mmol) was converted, instead of [6-[3-(2-fluoro-phenyl)-5-methyl-isoxazol-4-ylmethoxy]-nicotinic acid methyl ester, to the title compound (120 mg, 56%) which was obtained as a colourless oil. MS: m/e=386.5 [M−H]$^−$.

Example 262

6-[3-(2,3-Difluoro-phenyl)-5-methyl-isoxazol-4-ylmethoxy]-N-(tetrahydro-pyran-4-yl)-nicotinamide As described for example 261f, 6-[3-(2,3-difluoro-phenyl)-5-methyl-isoxazol-4-ylmethoxy]-nicotinic acid methyl ester (200 mg, 0.56 mmol) was converted, using 4-aminotetrahydropyran instead of isopropylamine, to the title compound (190 mg, 80%) which was obtained as a white solid. MS: m/e=430.3 [M+H]$^+$.

Example 263

6-[3-(2,4-Difluoro-phenyl)-5-methyl-isoxazol-4-ylmethoxy]-N-isopropyl-nicotinamide a) (E)- and/or (Z)-2,4-Difluoro-benzaldehyde oxime As described for example 84a, 2,4-difluorobenzaldehyde (50.0 g, 344 mmol) was converted, instead of 2-fluorobenzaldehyde, to the title compound (43.8 g, 81%) which was obtained as a white solid. MS: m/e=156.9 [M−H]$^−$.

b) (E)- and/or (Z)-2,4-Difluoro-N-hydroxy-benzenecarboximiodyl chloride

As described for example 84b, (E)- and/or (Z)-2,4-difluoro-benzaldehyde oxime (44.1 g, 281 mmol) was converted, instead of (E)- and/or (Z)-2-fluoro-benzaldehyde oxime, to the title compound (58.8 g, 100%, purity 92%) which was obtained as a yellow solid. MS: m/e=191.1 [M]$^+$.

c) 3-(2,4-Difluoro-phenyl)-5-methyl-isoxazole-4-carboxylic acid ethyl ester

As described for example 84c, (E)- and/or (Z)-2,4-difluoro-N-hydroxy-benzenecarboximiodyl chloride (58.8 g, 281 mmol, purity 77%) was converted, instead of (E)- and/or (Z)—N-hydroxy-2-fluoro-benzenecarboximidoyl chloride, to the title compound (62.2 g, purity 84%) which was obtained as a light brown oil. MS: m/e=268.2 [M+H]$^+$.

d) [3-(2,4-Difluoro-phenyl)-5-methyl-isoxazol-4-yl]-methanol

As described for example 84d, 3-(2,4-difluoro-phenyl)-5-methyl-isoxazole-4-carboxylic acid ethyl ester (61.9 g, 232 mmol) was converted, instead of 3-(2-fluoro-phenyl)-5-methyl-isoxazole-4-carboxylic acid ethyl ester, to the title compound (20.3 g, 39%) which was obtained as a light brown solid. MS: m/e=284.1 [M+OAc]$^−$.

e) 6-[3-(2,4-Difluoro-phenyl)-5-methyl-isoxazol-4-ylmethoxy]-nicotinic acid methyl ester As described for example 84e, [3-(2,4-difluoro-phenyl)-5-methyl-isoxazol-4-yl]-methanol (6.0 g, 26.6 mmol) was converted, instead of [3-(2-fluoro-phenyl)-5-methyl-isoxazol-4-yl]-methanol, to the title compound (5.77 g, 60%) which was obtained as a white solid. MS: m/e=361.1 [M+H]$^+$.

f) 6-[3-(2,4-Difluoro-phenyl)-5-methyl-isoxazol-4-ylmethoxy]-N-isopropyl-nicotinamide As described for example 84f, 6-[3-(2,4-difluoro-phenyl)-5-methyl-isoxazol-4-ylmethoxy]-nicotinic acid methyl ester (200 mg, 0.56 mmol) was converted, instead of [6-[3-(2-fluoro-phenyl)-5-methyl-isoxazol-4-ylmethoxy]-nicotinic acid methyl ester, to the title compound (201 mg, 93%) which was obtained as a colourless oil. MS: m/e=386.1 [M–H]⁻.

Example 264

6-[3-(2,4-Difluoro-phenyl)-5-methyl-isoxazol-4-ylmethoxy]-N-(tetrahydro-pyran-4-yl)-nicotinamide As described for example 263f, 6-[3-(2,4-difluoro-phenyl)-5-methyl-isoxazol-4-ylmethoxy]-nicotinic acid methyl ester (200 mg, 0.56 mmol) was converted, using 4-aminotetrahydropyran instead of isopropylamine, to the title compound (219 mg, 92%) which was obtained as a white solid. MS: m/e=428.1 [M–H]⁻.

Example 265

6-[3-(2,5-Difluoro-phenyl)-5-methyl-isoxazol-4-ylmethoxy]-N-isopropyl-nicotinamide a) 2,5-Difluoro-benzaldehyde oxime As described for example 84a, 2,5-difluorobenzaldehyde (25.0 g, 172 mmol) was converted, instead of 2-fluorobenzaldehyde, to the title compound (26.6 g, 98%) which was obtained as a white solid. 1H-NMR (CDCl₃): 7.05-7.10 (m, 2H), 7.45-7.50 (m, 1H), 8.35 (s, 1H), 8.30-8.60 (br s, 1H).

b) (E)- and/or (Z)-2,5-Difluoro-N-hydroxy-benzenecarboximiodyl chloride

As described for example 84b, (E)- and/or (Z)-2,5-difluoro-benzaldehyde oxime (26.6 g, 169 mmol) was converted, instead of (E)- and/or (Z)-2-fluoro-benzaldehyde oxime, to the title compound (41.8 g, 100%, purity 78%) which was obtained as a yellow solid. 1H-NMR (CDCl₃): 7.05-7.10 (m, 2H), 7.35-7.40 (m, 1H), 8.05 (s, 1H).

c) 3-(2,5-Difluoro-phenyl)-5-methyl-isoxazole-4-carboxylic acid ethyl ester

As described for example 84c, (E)- and/or (Z)-2,5-difluoro-N-hydroxy-benzenecarboximiodyl chloride (20 g, 81 mmol, purity 78%) was converted, instead of (E)—and/or (Z)—N-hydroxy-2-fluoro-benzenecarboximidoyl chloride, to the title compound (20.2 g, 93%) which was obtained as a yellow liquid. MS: m/e=268.2 [M+H]⁺.

d) [3-(2,5-Difluoro-phenyl)-5-methyl-isoxazol-4-yl]-methanol

As described for example 84d, 3-(2,5-difluoro-phenyl)-5-methyl-isoxazole-4-carboxylic acid ethyl ester (18 g, 67.4 mmol) was converted, instead of 3-(2-fluoro-phenyl)-5-methyl-isoxazole-4-carboxylic acid ethyl ester, to the title compound (3.25 g, 21%) which was obtained as a yellow oil. MS: m/e=226.2 [M+H]⁺.

e) 6-[3-(2,5-Difluoro-phenyl)-5-methyl-isoxazol-4-ylmethoxy]-nicotinic acid methyl ester As described for example 84e, [3-(2,5-difluoro-phenyl)-5-methyl-isoxazol-4-yl]-methanol (3.2 g, 14.2 mmol) was converted, instead of [3-(2-fluoro-phenyl)-5-methyl-isoxazol-4-yl]-methanol, to the title compound (1.18 g, 23%) which was obtained as a white solid. MS: m/e=360.9 [M+H]⁺.

f) 6-[3-(2,5-Difluoro-phenyl)-5-methyl-isoxazol-4-ylmethoxy]-N-isopropyl-nicotinamide As described for example 84f, 6-[3-(2,5-difluoro-phenyl)-5-methyl-isoxazol-4-ylmethoxy]-nicotinic acid methyl ester (200 mg, 0.56 mmol) was converted, instead of [6-[3-(2-fluoro-phenyl)-5-methyl-isoxazol-4-ylmethoxy]-nicotinic acid methyl ester, to the title compound (200 mg, 93%) which was obtained as a colourless oil. MS: m/e=386.5 [M–H]⁻.

Example 266

6-[3-(2,5-Difluoro-phenyl)-5-methyl-isoxazol-4-ylmethoxy]-N-(tetrahydro-pyran-4-yl)-nicotinamide As described for example 265f, 6-[3-(2,5-difluoro-phenyl)-5-methyl-isoxazol-4-ylmethoxy]-nicotinic acid methyl ester (200 mg, 0.56 mmol) was converted, using 4-aminotetrahydropyran instead of isopropylamine, to the title compound (170 mg, 71%) which was obtained as a colourless oil. MS: m/e=430.5 [M+H]⁺.

Example 267

6-[3-(3,4-Difluoro-phenyl)-5-methyl-isoxazol-4-ylmethoxy]-N-(2-hydroxy-1,1-dimethyl-ethyl)-nicotinamide As described for example 125f, 6-[3-(3,4-difluoro-phenyl)-5-methyl-isoxazol-4-ylmethoxy]-nicotinic acid methyl ester (200 mg, 0.56 mmol) was converted, using 2-amino-2-methyl-1-propanol instead of 2,2,2-trifluoroethylamine, to the title compound (120 mg, 50%) which was obtained as a colourless oil. MS: m/e=418.3 [M+H]'.

Example 268

6-[3-(3,4-Difluoro-phenyl)-5-methyl-isoxazol-4-ylmethoxy]-N-(3-hydroxy-2,2-dimethyl-propyl)-nicotinamide As described for example 125f, 6-[3-(3,4-difluoro-phenyl)-5-methyl-isoxazol-4-ylmethoxy]-nicotinic acid methyl ester (200 mg, 0.56 mmol) was converted, using 3-amino-2,2-dimethyl-1-propanol instead of 2,2,2-trifluoroethylamine, to the title compound (120 mg, 48%) which was obtained as a colourless oil. MS: m/e=432.2 [M+H]⁺.

Example 269

6-[3-(3,4-Difluoro-phenyl)-5-methyl-isoxazol-4-ylmethoxy]-N-(2-hydroxy-2-methyl-propyl)-nicotinamide As described for example 125f, 6-[3-(3,4-difluoro-phenyl)-5-methyl-isoxazol-4-ylmethoxy]-nicotinic acid methyl ester (200 mg, 0.56 mmol) was converted, using 1-amino-2-methyl-propan-2-ol instead of 2,2,2-trifluoroethylamine, to the title compound (40 mg, 17%) which was obtained as a colourless oil. MS: m/e=418.3 [M+H]$^+$.

Example 270

6-[3-(4-Chloro-2-fluoro-phenyl)-5-methyl-isoxazol-4-ylmethoxy]-N-isopropyl-nicotinamide a) (E)- and/or (Z)-4-Chloro-2-fluoro-benzaldehyde oxime As described for example 84a, 4-chloro-2-fluorobenzaldehyde (5.2 g, 32.5 mmol) was converted, instead of 2-fluorobenzaldehyde, to the title compound (4.7 g, 83%) which was obtained as a white solid. MS: m/e=172.0 [M–H]$^-$.

b) (E)- and/or (Z)-4-Chloro-2-fluoro-N-hydroxy-benzenecarboximiodyl chloride

As described for example 84b, (E)- and/or (Z)-4-chloro-2-fluoro-benzaldehyde oxime (4.7 g, 27.1 mmol) was converted, instead of (E)- and/or (Z)-2-fluoro-benzaldehyde oxime, to the title compound (7.53 g, 100%, purity 75%) which was obtained as a light yellow solid. 1H-NMR (CDCl$_3$): 7.10-7.25 (m, 2H), 7.50-7.60 (m, 1H), 8.05 (s, 1H).

c) 3-(4-Chloro-2-fluoro-phenyl)-5-methyl-isoxazole-4-carboxylic acid ethyl ester As described for example 84c, (E)- and/or (Z)-4-chloro-2-fluoro-N-hydroxy-benzenecarboximiodyl chloride (5.0 g, 18 mmol, purity 75%) was converted, instead of (E)- and/or (Z)—N-hydroxy-2-fluoro-benzenecarboximidoyl chloride, to the title compound (6.5 g, 85%) which was obtained as a yellow liquid. MS: m/e=283.9 [M+H]$^+$.

d) [3-(4-Chloro-2-fluoro-phenyl)-5-methyl-isoxazol-4-yl]-methanol

As described for example 84d, 3-(4-chloro-2-fluoro-phenyl)-5-methyl-isoxazole-4-carboxylic acid ethyl ester (6.3 g, 20 mmol) was converted, instead of 3-(2-fluoro-phenyl)-5-methyl-isoxazole-4-carboxylic acid ethyl ester, to the title compound (2.1 g, 43%) which was obtained as an orange solid. MS: m/e=242.2 [M+H]$^+$.

e) 6-[3-(4-Chloro-2-fluoro-phenyl)-5-methyl-isoxazol-4-ylmethoxy]-nicotinic acid methyl ester As described for example 84e, [3-(4-chloro-2-fluoro-phenyl)-5-methyl-isoxazol-4-yl]-methanol (500 mg, 2.07 mmol) was converted, instead of [3-(2-fluoro-phenyl)-5-methyl-isoxazol-4-yl]-methanol, to the title compound (410 mg, 53%) which was obtained as a colourless oil. MS: m/e=377.2 [M+H]$^+$.

f) 6-[3-(4-Chloro-2-fluoro-phenyl)-5-methyl-isoxazol-4-ylmethoxy]-N-isopropyl-nicotinamide As described for example 84f, 6-[3-(4-chloro-2-fluoro-phenyl)-5-methyl-isoxazol-4-ylmethoxy]-nicotinic acid methyl ester (100 mg, 0.27 mmol) was converted, instead of [6-[3-(2-fluoro-phenyl)-5-methyl-isoxazol-4-ylmethoxy]-nicotinic acid methyl ester, to the title compound (80 mg, 75%) which was obtained as a light yellow oil. MS: m/e=386.5 [M–H]$^-$.

Example 271

6-(5-Methyl-3-pyridin-2-yl-isoxazol-4-ylmethoxy)-nicotinic acid methyl ester a) (E)- and/or (Z)-Pyridine-2-carbaldehyde oxime As described for example 84a, 2-pyridinecarboxaldehyde (53.6 g, 500 mmol) was converted, instead of 2-fluorobenzaldehyde, to the title compound (47.7 g, 78%) which was obtained as an off white solid. MS: m/e=123.3 [M+H]$^+$.

b) 5-Methyl-3-pyridin-2-yl-isoxazole-4-carboxylic acid ethyl ester

To a suspension of N-chlorosuccinimide (6.0 g, 33 mmol) in chloroform (20 mL) was added pyridine (0.26 mL, 3.3 mmol) and a solution of (E)- and/or (Z)-pyridine-2-carbaldehyde oxime (4.0 g, 33 mmol) in chloroform (103 mL) during 15 min at ambient temperature. After stirring for 30 min at this temperature a solution of ethyl(E)-3-(1-pyrrolidino)-2-butenoate (6.0 g, 33 mmol) in chloroform (4 mL) was added. The resulting suspension was warmed to 50° C. and a solution of triethylamine (12 mL, 86 mmol) in chloroform (10 mL) was added dropwise over a period of 1 h. Stirring was continued for 0.5 h at 50° C. and for 30 h at room temperature. The dark brown solution was washed with water (100 mL) and the aqueous layers were extracted with dichloromethane (50 mL) and dried over sodium sulfate and evaporated. Purification by chromatography (SiO$_2$, heptane:ethyl acetate 8:2 to 1:1) afforded the title compound (4.43 g, 58%) as a yellow oil. MS: m/e=233.3 [M+H]$^+$.

c) (5-Methyl-3-pyridin-2-yl-isoxazol-4-yl)-methanol

To a solution of 5-methyl-3-pyridin-2-yl-isoxazole-4-carboxylic acid ethyl ester (4.1 g, 18 mmol) in THF (229 mL) at 0° C. was added lithium aluminum hydride (367 mg, 10 mmol). And the resulting mixture stirred for 1 h at room temperature. Water (1.9 mL) was added carefully followed by aqueous sodium hydroxide (15%, 1.9 mL) and water (0.54 mL). The resulting suspension was stirred for 15 min at ambient temperature and filtered over Hyflo®. Concentration and trituration with heptane afforded the title compound (2.88 g, 86%) as a light yellow solid. MS: m/e=191.3 [M+H]$^+$.

d) 6-(5-Methyl-3-pyridin-2-yl-isoxazol-4-ylmethoxy)-nicotinic acid methyl ester

As described for example 84e, (5-methyl-3-pyridin-2-yl-isoxazol-4-yl)-methanol (2.83 g, 14.9 mmol) was converted, instead of [3-(2-fluoro-phenyl)-5-methyl-isoxazol-4-yl]-methanol, to the title compound (1.63 g, 34%) which was obtained as a white solid. MS: m/e=326.3 [M+H]$^+$.

Example 272

6-(5-Methyl-3-pyridin-2-yl-isoxazol-4-ylmethoxy)-N-(tetrahydro-pyran-4-yl)-nicotinamide As described for example 84f, 6-(5-methyl-3-pyridin-2-yl-isoxazol-4-ylmethoxy)-nicotinic acid methyl ester (97.6 mg, 0.3 mmol) was converted, instead of [6-[3-(2-fluoro-phenyl)-5-methyl-isoxazol-4-ylmethoxy]-nicotinic acid methyl ester, using 4-aminotetrahydropyran instead of 2,2,2-trifluoroethylamine, to the title compound (93 mg, 79%) which was obtained as a white solid. MS: m/e=395.0 [M+H]⁺.

Example 273

N-Isopropyl-6-(5-methyl-3-pyridin-2-yl-isoxazol-4-ylmethoxy)-nicotinamide

As described for example 272, 6-(5-methyl-3-pyridin-2-yl-isoxazol-4-ylmethoxy)-nicotinic acid methyl ester (97.6 mg, 0.3 mmol) was converted, using isopropylamine instead of 4-aminotetrahydropyran, to the title compound (97 mg, 92%) which was obtained as a white solid. MS: m/e=353.4 [M+H]⁺.

Example 274

[6-(5-Methyl-3-pyridin-2-yl-isoxazol-4-ylmethoxy)-pyridin-3-yl]-morpholin-4-yl-methanone As described for example 272, 6-(5-methyl-3-pyridin-2-yl-isoxazol-4-ylmethoxy)-nicotinic acid methyl ester (97.6 mg, 0.3 mmol) was converted, using morpholine instead of 4-aminotetrahydropyran, to the title compound (90 mg, 79%) which was obtained as a white solid. MS: m/e=381.3 [M+H]⁺.

Example 275

6-(5-Methyl-3-pyridin-2-yl-isoxazol-4-ylmethoxy)-N-(2,2,2-trifluoro-ethyl)-nicotinamide As described for example 272, 6-(5-methyl-3-pyridin-2-yl-isoxazol-4-ylmethoxy)-nicotinic acid methyl ester (97.6 mg, 0.3 mmol) was converted, using 2,2,2-trifluoroethylamine instead of 4-aminotetrahydropyran, to the title compound (115 mg, 98%) which was obtained as a white solid. MS: m/e=393.4 [M+H]⁺.

Example 276

(1,1-Dioxo-1,6-thiomorpholin-4-yl)-[6-(5-methyl-3-pyridin-2-yl-isoxazol-4-ylmethoxy)-pyridin-3-yl]-methanone As described for example 272, 6-(5-methyl-3-pyridin-2-yl-isoxazol-4-ylmethoxy)-nicotinic acid methyl ester (97.6 mg, 0.3 mmol) was converted, using thiomorpholine 1,1-dioxide instead of 4-aminotetrahydropyran, to the title compound (41 mg, 32%) which was obtained as a white solid. MS: m/e=429.3 [M+H]⁺.

Example 277

N-Cyclopropylmethyl-6-(5-methyl-3-pyridin-2-yl-isoxazol-4-ylmethoxy)-nicotinamide As described for example 272, 6-(5-methyl-3-pyridin-2-yl-isoxazol-4-ylmethoxy)-nicotinic acid methyl ester (97.6 mg, 0.3 mmol) was converted, using aminomethylcyclopropane instead of 4-aminotetrahydropyran, to the title compound (93 mg, 85%) which was obtained as an off white solid. MS: m/e=365.4 [M+H]⁺.

Example 278

N-Cyclopropyl-6-(5-methyl-3-pyridin-2-yl-isoxazol-4-ylmethoxy)-nicotinamide

As described for example 272, 6-(5-methyl-3-pyridin-2-yl-isoxazol-4-ylmethoxy)-nicotinic acid methyl ester (97.6 mg, 0.3 mmol) was converted, using cyclopropylamine instead of 4-aminotetrahydropyran, to the title compound (86 mg, 82%) which was obtained as a white solid. MS: m/e=365.4 [M+H]⁺.

Example 279

Methyl-6-(5-methyl-3-pyridin-2-yl-isoxazol-4-yl-methoxy)-nicotinamide

As described for example 272, 6-(5-methyl-3-pyridin-2-yl-isoxazol-4-ylmethoxy)-nicotinic acid methyl ester (97.6 mg, 0.3 mmol) was converted, using methylamine (2 M solution in THF) instead of 4-aminotetrahydropyran, to the title compound (35 mg, 36%) which was obtained as a white solid. MS: m/e=325.3 [M+H]⁺.

Example 280

Ethyl-6-(5-methyl-3-pyridin-2-yl-isoxazol-4-yl-methoxy)-nicotinamide

As described for example 272, 6-(5-methyl-3-pyridin-2-yl-isoxazol-4-ylmethoxy)-nicotinic acid methyl ester (97.6 mg, 0.3 mmol) was converted, using ethylamine (2 M solution in THF) instead of 4-aminotetrahydropyran, to the title compound (79 mg, 78%) which was obtained as a white solid. MS: m/e=339.3 [M+H]'.

Example 281

(2-Hydroxy-1,1-dimethyl-ethyl)-6-(5-methyl-3-pyridin-2-yl-isoxazol-4-ylmethoxy)-nicotinamide As described for example 272, 6-(5-methyl-3-pyridin-2-yl-isoxazol-4-ylmethoxy)-nicotinic acid methyl ester (97.6 mg, 0.3 mmol) was converted, using 2-amino-2-methyl-1-propanol instead of 4-aminotetrahydropyran, to the title compound (25 mg, 22%) which was obtained as a white solid. MS: m/e=383.3 [M+H]⁺.

Example 282

[6-(5-Methyl-3-pyridin-2-yl-isoxazol-4-ylmethoxy)-pyridin-3-yl]-thiomorpholin-4-yl-methanone As described for example 272, 6-(5-methyl-3-pyridin-2-yl-isoxazol-4-ylmethoxy)-nicotinic acid methyl ester (97.6 mg, 0.3 mmol) was converted, using thiomorpholine instead

Example 283

6-(5-Methyl-3-pyridin-2-yl-isoxazol-4-ylmethoxy)-nicotinic acid

To a suspension of 6-(5-methyl-3-pyridin-2-yl-isoxazol-4-ylmethoxy)-nicotinic acid methyl ester (330 mg, 1.0 mmol) in THF (3 mL) and methanol (3 mL) was added a solution of lithium hydroxide monohydrate (85.1 mg, 2.0 mmol) in water (3 mL) added and the resulting mixture stirred at room temperature overnight. The mixture was acidified to pH 4 with HCl (1 N, 30 mL) and the resulting mixture was filtered. The solid was dried to afford the title compound (284 mg, 90%) which was obtained as a white solid. MS: m/e=310.5 [M−H]−.

Example 284

(2-Hydroxy-ethyl)-6-(5-methyl-3-pyridin-2-yl-isoxazol-4-ylmethoxy)-nicotinamide

As described for example 98b, 6-(5-methyl-3-pyridin-2-yl-isoxazol-4-ylmethoxy)-nicotinic acid (77.8 mg, 0.25 mmol) was converted, instead of 6-[3-(3-chloro-phenyl)-5-methyl-isoxazol-4-ylmethoxy]-nicotinic acid, using aminoethanol instead of 2,2,2-trifluoroethylamine, to the title compound (21 mg, 24%) which was obtained as a white solid. MS: m/e=355.0 [M+H]+.

Example 285

(2-Methoxy-ethyl)-6-(5-methyl-3-pyridin-2-yl-isoxazol-4-ylmethoxy)-nicotinamide

As described for example 284, 6-(5-methyl-3-pyridin-2-yl-isoxazol-4-ylmethoxy)-nicotinic acid (77.8 mg, 0.25 mmol) was converted, using 2-methoxyethylamine instead of aminoethanol, to the title compound (21 mg, 24%) which was obtained as a white solid. MS: m/e=369.1 [M+H]+.

Example 286

6-[3-(5-Fluoro-pyridin-2-yl)-5-methyl-isoxazol-4-ylmethoxy]-nicotinic acid methyl ester a) 5-Fluoro-pyridine-2-carbaldehyde oxime To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]+.

b) 3-(5-Fluoro-pyridin-2-yl)-5-methyl-isoxazole-4-carboxylic acid ethyl ester

To a suspension of N-chlorosuccinimide (4.63 g, 35 mmol) in chloroform (21 mL) was added pyridine (0.28 mL, 3.5 mmol) and a solution of 5-fluoro-pyridine-2-carbaldehyde oxime (4.86 g, 35 mmol) in chloroform (110 mL) during 15 min at room temperature. After stirring for 30 min at this temperature a solution of ethyl(E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (SiO2, heptane:ethyl acetate=100:0 to 20:80) afforded the title compound (5.83 g, 67%) as yellow oil. MS: m/e=251.1 [M+H]+.

c) [3-(5-Fluoro-pyridin-2-yl)-5-methyl-isoxazol-4-yl]-methanol

To a solution of 3-(5-fluoro-pyridin-2-yl)-5-methyl-isoxazole-4-carboxylic acid ethyl ester (2.5 g, 10 mmol) in dry THF (34 mL), cooled to 0° C., was added lithiumaluminumhydride (209 mg, 2.3 mmol) portionwise. After allowing to warm up to room temperature over 1 h, the mixture was cooled to 0° C. and water (0.2 mL) was added carefully followed by aqueous sodium hydroxide (15%, 0.2 mL) and water (0.6 mL). The resulting suspension was stirred for 4 h at ambient temperature and filtered over Hyflo®. The filtrate was then concentrated and purification by chromatography (SiO2, heptane:ethyl acetate=50:50 to 0:100) afforded the title compound (1.47 g, 71%) as a light yellow solid. MS: m/e=209.1 [M+H]+.

d) 6-[3-(5-Fluoro-pyridin-2-yl)-5-methyl-isoxazol-4-ylmethoxy]-nicotinic acid methyl ester As described for example 84e, [3-(5-fluoro-pyridin-2-yl)-5-methyl-isoxazol-4-yl]-methanol (600 mg, 2.8 mmol) was converted, instead of [3-(2-fluoro-phenyl)-5-methyl-isoxazol-4-yl]-methanol, to the title compound (210 mg, 21%) which was obtained as a white solid. MS: m/e=344.1 [M+H]+.

Example 287

6-[3-(5-Fluoro-pyridin-2-yl)-5-methyl-isoxazol-4-ylmethoxy]-nicotinic acid

As described for example 283, 6-[3-(5-fluoro-pyridin-2-yl)-5-methyl-isoxazol-4-ylmethoxy]-nicotinic acid methyl ester (175 mg, 0.51 mmol) was converted, instead of 6-(5-methyl-3-pyridin-2-yl-isoxazol-4-ylmethoxy)-nicotinic acid methyl ester, to the title compound (154 mg, 92%) which was obtained as a white solid. MS: m/e=328.3 [M−H]−.

Example 288

6-[3-(5-Fluoro-pyridin-2-yl)-5-methyl-isoxazol-4-ylmethoxy]-(tetrahydro-pyran-4-yl)-nicotinamide As described for example 98b, 6-[3-(5-fluoro-pyridin-2-yl)-5-methyl-isoxazol-4-ylmethoxy]-nicotinic acid (69 mg, 0.21 mmol) was converted, instead of 6-[3-(3-chloro-phenyl)-5-methyl-isoxazol-4-ylmethoxy]-nicotinic acid, using 4-aminotetrahydropyran instead of 2,2,2-trifluoroethy-

Example 289

6-[3-(5-Fluoro-pyridin-2-yl)-5-methyl-isoxazol-4-ylmethoxy]-isopropyl-nicotinamide As described for example 288, 6-[3-(5-fluoro-pyridin-2-yl)-5-methyl-isoxazol-4-ylmethoxy]-nicotinic acid (69 mg, 0.21 mmol) was converted, using isopropylamine instead of 4-aminotetrahydropyran, to the title compound (52 mg, 67%) which was obtained as a white solid. MS: m/e=371.1 [M+H]$^+$.

Example 290

Cyclopropyl-6-[3-(5-fluoro-pyridin-2-yl)-5-methyl-isoxazol-4-ylmethoxy]-nicotinamide As described for example 288, 6-[3-(5-fluoro-pyridin-2-yl)-5-methyl-isoxazol-4-ylmethoxy]-nicotinic acid (50 mg, 0.15 mmol) was converted, using cyclopropylamine instead of 4-aminotetrahydropyran, to the title compound (23 mg, 41%) which was obtained as a white solid. MS: m/e=369.0 [M+H]$^+$.

Example 291

6-[3-(5-Fluoro-pyridin-2-yl)-5-methyl-isoxazol-4-ylmethoxy](2-hydroxy-1,1-dimethyl-ethyl)-nicotinamide As described for example 288, 6-[3-(5-fluoro-pyridin-2-yl)-5-methyl-isoxazol-4-ylmethoxy]-nicotinic acid (50 mg, 0.15 mmol) was converted, using 2-amino-2-methyl-1-propanol instead of 4-aminotetrahydropyran, to the title compound (40 mg, 66%) which was obtained as a white solid. MS: m/e=401.2 [M+H]$^+$.

Example 292

Cyclopropylmethyl-6-[3-(5-fluoro-pyridin-2-yl)-5-methyl-isoxazol-4-ylmethoxy]-nicotinamide As described for example 288, 6-[3-(5-fluoro-pyridin-2-yl)-5-methyl-isoxazol-4-ylmethoxy]-nicotinic acid (50 mg, 0.15 mmol) was converted, using aminomethylcyclopropane instead of 4-aminotetrahydropyran, to the title compound (30 mg, 52%) which was obtained as a white solid. MS: m/e=383.2 [M+H]$^+$.

Example 293

(1,1-Dioxo-1,6-thiomorpholin-4-yl)-{6-[3-(5-fluoro-pyridin-2-yl)-5-methyl-isoxazol-4-ylmethoxy]-pyridin-3-yl}-methanone As described for example 288, 6-[3-(5-fluoro-pyridin-2-yl)-5-methyl-isoxazol-4-ylmethoxy]-nicotinic acid (50 mg, 0.15 mmol) was converted, using thiomorpholine 1,1-dioxide instead of 4-aminotetrahydropyran, to the title compound (41 mg, 61%) which was obtained as a white solid. MS: m/e=447.1 [M+H]$^+$.

Example 294

6-[3-(5-Fluoro-pyridin-2-yl)-5-methyl-isoxazol-4-ylmethoxy]-2,2,2-trifluoro-ethyl)-nicotinamide As described for example 288, 6-[3-(5-fluoro-pyridin-2-yl)-5-methyl-isoxazol-4-ylmethoxy]-nicotinic acid (50 mg, 0.15 mmol) was converted, using 2,2,2-trifluoroethylamine instead of 4-aminotetrahydropyran, to the title compound (43 mg, 69%) which was obtained as a white solid. MS: m/e=411.2 [M+H]$^+$.

Example 295

6-[3-(5-Fluoro-pyridin-2-yl)-5-methyl-isoxazol-4-ylmethoxy]-(2-hydroxy-ethyl)-nicotinamide As described for example 288, 6-[3-(5-fluoro-pyridin-2-yl)-5-methyl-isoxazol-4-ylmethoxy]-nicotinic acid (50 mg, 0.15 mmol) was converted, using aminoethanol instead of 4-aminotetrahydropyran, to the title compound (45 mg, 80%) which was obtained as a white solid. MS: m/e=373.1 [M+H]$^+$.

Example 296

{6-[3-(5-Fluoro-pyridin-2-yl)-5-methyl-isoxazol-4-ylmethoxy]-pyridin-3-yl}-morpholin-4-yl-methanone As described for example 288, 6-[3-(5-fluoro-pyridin-2-yl)-5-methyl-isoxazol-4-ylmethoxy]-nicotinic acid (50 mg, 0.15 mmol) was converted, using morpholine instead of 4-aminotetrahydropyran, to the title compound (55 mg, 91%) which was obtained as a colourless gum. MS: m/e=399.1 [M+H]$^+$.

Example 297

Ethyl-6-[3-(5-fluoro-pyridin-2-yl)-5-methyl-isoxazol-4-ylmethoxy]-nicotinamide

As described for example 288, 6-[3-(5-fluoro-pyridin-2-yl)-5-methyl-isoxazol-4-ylmethoxy]-nicotinic acid (50 mg, 0.15 mmol) was converted, using ethylamine (2 M solution in THF) instead of 4-aminotetrahydropyran, to the title compound (45 mg, 83%) which was obtained as a white solid. MS: m/e=357.1 [M+H]$^+$.

Example 298

6-[3-(5-Fluoro-pyridin-2-yl)-5-methyl-isoxazol-4-ylmethoxy]-methyl-nicotinamide

As described for example 288, 6-[3-(5-fluoro-pyridin-2-yl)-5-methyl-isoxazol-4-ylmethoxy]-nicotinic acid (47 mg, 0.14 mmol) was converted, using methylamine (2 M solution

Example 299

6-[3-(5-Fluoro-pyridin-2-yl)-5-methyl-isoxazol-4-ylmethoxy]-N—((S)-2,2,2-trifluoro-1-methyl-ethyl)-nicotinamide As described for example 288, 6-[3-(5-fluoro-pyridin-2-yl)-5-methyl-isoxazol-4-ylmethoxy]-nicotinic acid (100 mg, 0.3 mmol) was converted, using L-2,2,2-trifluoroethylamine instead of 4-aminotetrahydropyran, to the title compound (56 mg, 43%) which was obtained as a white solid. MS: m/e=423.3 [M–H]⁻.

Example 300

6-[3-(5-Chloro-pyridin-2-yl)-5-methyl-isoxazol-4-ylmethoxy]-nicotinic acid methyl ester a) 5-Chloro-pyridine-2-carbaldehyde To a solution of 2-bromo-5-chloropyridine (14.8 g, 77 mmol) in THF (38.5 mL) was added dropwise a solution of i-PrMgCl.LiCl (14% in THF, 81 mL, 85 mmol) at 0-5° C. and the resulting mixture stirred at 0° C. for 1 h. Then DMF (7.7 mL, 100 mmol) was added dropwise at −5° C. and the temperature maintained at 0° C. for 2 h. The reaction mixture was then poured into ice cold saturated brine (500 mL) and then extracted with ethyl acetate (2×300 mL). The combined organic layers were washed with saturated sodiumhydrogencarbonate solution, brine, dried over sodium sulfate, filtered and evaporated. Purification by chromatography (SiO$_2$, heptane:ethyl acetate=1:0 to 9:1) afforded the title compound (6.24 g, 57%) which was obtained as a brown solid. MS: m/e=141.0 [M]⁺.

b) (E)- and/or (Z)-5-Chloro-pyridine-2-carbaldehyde oxime

As described for example 286a, 5-chloro-pyridine-2-carbaldehyde (6.9 g, 4.8 mmol) was converted, instead of 5-fluoro-2-formylpyridine, to the title compound (6.7 g, 89%) which was obtained as a light brown solid. MS: m/e=157.1 [M+H]⁺.

c) 3-(5-Chloro-pyridin-2-yl)-5-methyl-isoxazole-4-carboxylic acid ethyl ester

As described for example 286b, (E)- and/or (Z)-5-chloro-pyridine-2-carbaldehyde oxime (5.6 g, 36 mmol) was converted, instead of 5-fluoro-pyridine-2-carbaldehyde oxime, to the title compound (7.7 g, 80%) which was obtained as a yellow oil. MS: m/e=267.0 [M+H]⁺.

d) [3-(5-Chloro-pyridin-2-yl)-5-methyl-isoxazol-4-yl]-methanol

As described for example 286c, 3-(5-chloro-pyridin-2-yl)-5-methyl-isoxazole-4-carboxylic acid ethyl ester (1.26 g, 4.7 mmol) was converted, instead of 3-(5-fluoro-pyridin-2-yl)-5-methyl-isoxazole-4-carboxylic acid ethyl ester, to the title compound (773 mg, 73%) which was obtained as an off white solid. MS: m/e=224.9 [M+H]⁺.

e) 6-[3-(5-Chloro-pyridin-2-yl)-5-methyl-isoxazol-4-ylmethoxy]-nicotinic acid methyl ester As described for example 84e, [3-(5-chloro-pyridin-2-yl)-5-methyl-isoxazol-4-yl]-methanol (726 mg, 3.2 mmol) was converted, instead of [3-(2-fluoro-phenyl)-5-methyl-isoxazol-4-yl]-methanol, to the title compound (578 mg, 40%) which was obtained as a white solid. MS: m/e=360.3 [M+H]⁺.

Example 301

6-[3-(5-Chloro-pyridin-2-yl)-5-methyl-isoxazol-4-ylmethoxy]-(tetrahydro-pyran-4-yl)-nicotinamide As described for example 84f, 6-[3-(5-chloro-pyridin-2-yl)-5-methyl-isoxazol-4-ylmethoxy]-nicotinic acid methyl ester (108 mg, 0.3 mmol) was converted, instead of [64342-fluoro-phenyl)-5-methyl-isoxazol-4-ylmethoxy]-nicotinic acid methyl ester, using 4-aminotetrahydropyran instead of 2,2,2-trifluoroethylamine, to the title compound (61 mg, 47%) which was obtained as a white solid. MS: m/e=429.5 [M+H]⁺.

Example 302

6-[3-(5-Chloro-pyridin-2-yl)-5-methyl-isoxazol-4-ylmethoxy]-isopropyl-nicotinamide As described for example 301, 6-[3-(5-chloro-pyridin-2-yl)-5-methyl-isoxazol-4-ylmethoxy]-nicotinic acid methyl ester (108 mg, 0.3 mmol) was converted, using isopropylamine instead of 4-aminotetrahydropyran to the title compound (83 mg, 72%) which was obtained as a white solid. MS: m/e=387.1 [M+H]⁺.

Example 303

6-[3-(5-Chloro-pyridin-2-yl)-5-methyl-isoxazol-4-ylmethoxy]-cyclopropyl-nicotinamide As described for example 301, 6-[3-(5-chloro-pyridin-2-yl)-5-methyl-isoxazol-4-ylmethoxy]-nicotinic acid methyl ester (108 mg, 0.3 mmol) was converted, using cyclopropylamine instead of 4-aminotetrahydropyran to the title compound (84 mg, 73%) which was obtained as a white solid. MS: m/e=385.1 [M–H]⁺.

Example 304

6-[3-(5-Chloro-pyridin-2-yl)-5-methyl-isoxazol-4-ylmethoxy]-nicotinic acid

As described for example 283, 6-[3-(5-chloro-pyridin-2-yl)-5-methyl-isoxazol-4-ylmethoxy]-nicotinic acid methyl ester (250 mg, 0.7 mmol) was converted, instead of 6-(5-methyl-3-pyridin-2-yl-isoxazol-4-ylmethoxy)-nicotinic acid methyl ester, to the title compound (83 mg, 35%) which was obtained as a white solid. MS: m/e=344.3 [M–H]⁻.

Example 305

6-[3-(5-Chloro-pyridin-2-yl)-5-methyl-isoxazol-4-ylmethoxy]-(2-hydroxy-1,1-dimethyl-ethyl)-nicotinamide As described for example 98b, 6-[3-(5-chloro-pyridin-2-yl)-5-methyl-isoxazol-4-ylmethoxy]-nicotinic acid (56 mg, 0.16 mmol) was converted, instead of 6-[3-(3-chloro-phenyl)-5-methyl-isoxazol-4-ylmethoxy]-nicotinic acid, using 2-amino-2-methyl-1-propanol instead of 2,2,2-trifluoroethylamine, to the title compound (36 mg, 53%) which was obtained as a white solid. MS: m/e=417.3 [M+H]$^+$.

Example 306

6-[3-(5-Chloro-pyridin-2-yl)-5-methyl-isoxazol-4-ylmethoxy]-cyclopropylmethyl-nicotinamide As described for example 301, [6-[3-(5-chloro-pyridin-2-yl)-5-methyl-isoxazol-4-ylmethoxy]-nicotinic acid methyl ester (108 mg, 0.3 mmol) was converted, using aminomethylcyclopropane instead of 4-aminotetrahydropyran to the title compound (72 mg, 60%) which was obtained as a white solid. MS: m/e=399.3 [M+H]$^+$.

Example 307

{6-[3-(5-Chloro-pyridin-2-yl)-5-methyl-isoxazol-4-ylmethoxy]-pyridin-3-yl}-(1,1-dioxo-1,6-thiomorpholin-4-yl)-methanone As described for example 301, [6-[3-(5-chloro-pyridin-2-yl)-5-methyl-isoxazol-4-ylmethoxy]-nicotinic acid methyl ester (108 mg, 0.3 mmol) was converted, using aminomethylcyclopropane instead of 4-aminotetrahydropyran to the title compound (69 mg, 50%) which was obtained as a white solid. MS: m/e=463.0 [M]$^+$.

Example 308

6-[3-(5-Chloro-pyridin-2-yl)-5-methyl-isoxazol-4-ylmethoxy]-(2,2,2-trifluoro-ethyl)-nicotinamide As described for example 301, [6-[3-(5-chloro-pyridin-2-yl)-5-methyl-isoxazol-4-ylmethoxy]-nicotinic acid methyl ester (108 mg, 0.3 mmol) was converted, using 2,2,2-trifluoroethylamine instead of 4-aminotetrahydropyran to the title compound (64 mg, 50%) which was obtained as a white solid. MS: m/e=427.4 [M+H]$^+$.

Example 309

{6-[3-(5-Chloro-pyridin-2-yl)-5-methyl-isoxazol-4-ylmethoxy]-pyridin-3-yl}-morpholin-4-yl-methanone As described for example 301, [6-[3-(5-chloro-pyridin-2-yl)-5-methyl-isoxazol-4-ylmethoxy]-nicotinic acid methyl ester (108 mg, 0.3 mmol) was converted, using morpholine instead of 4-aminotetrahydropyran to the title compound (18 mg, 15%) which was obtained as a white solid. MS: m/e=415.1 [M+H]$^+$.

Example 310

{6-[3-(5-Chloro-pyridin-2-yl)-5-methyl-isoxazol-4-ylmethoxy]-pyridin-3-yl}-thiomorpholin-4-yl-methanone As described for example 301, [6-[3-(5-chloro-pyridin-2-yl)-5-methyl-isoxazol-4-ylmethoxy]-nicotinic acid methyl ester (108 mg, 0.3 mmol) was converted, using thiomorpholine instead of 4-aminotetrahydropyran to the title compound (76 mg, 59%) which was obtained as a white solid. MS: m/e=431.3 [M+H]$^+$.

Example 311

6-[3-(5-Chloro-pyridin-2-yl)-5-methyl-isoxazol-4-ylmethoxy]-(2-hydroxy-ethyl)-nicotinamide As described for example 301, [6-[3-(5-chloro-pyridin-2-yl)-5-methyl-isoxazol-4-ylmethoxy]-nicotinic acid methyl ester (74 mg, 0.2 mmol) was converted, using thiomorpholine instead of 4-aminotetrahydropyran to the title compound (38 mg, 45%) which was obtained as a white solid. MS: m/e=389.1 [M+H]$^+$.

Example 312

6-(5-Methyl-3-pyrimidin-4-yl-isoxazol-4-yl-methoxy)-nicotinic acid methyl ester a) (E)-4-Dimethylamino-1,1-dimethoxy-but-3-en-2-one A mixture of N,N-dimethylformamide dimethylacetal (86.0 g, 584 mmol) and methylglyoxal 1,1-dimethylacetal (85.6 g, 724 mmol) in isobutanol (500 mL) was heated at 100° C. overnight. The mixture was then cooled and evaporated. Purification by distillation afforded the title product (49.9 g, 48%) as an orange liquid. Bp 123-124° C. at 0.9 mbar. MS: m/e=174.4 [M+H]'.

b) 4-Dimethoxymethyl-pyrimidine

A mixture of (E)-4-dimethylamino-1,1-dimethoxy-but-3-en-2-one (49.6 g, 286 mmol) and formamidine acetate (44.7 g, 429 mmol) was heated at 120° C. for 4 h. After cooling to room temperature the mixture was poured into water and extracted with dichloromethane. The combined organic extracts were then dried over sodium sulfate, filtered and evaporated. Purification by distillation afforded the title product (31 g, 70%) as a colourless liquid. Bp 59-60° C. at 1.3 mbar. MS: m/e=155.0 [M+H]$^+$.

c) Pyrimidine-4-carbaldehyde

A solution of 4-dimethoxymethyl-pyrimidine (30.6 g, 199 mmol) in water (235 mL) and concentrated sulfuric acid (2.9 g, 30 mmol) was heated at 60° C. for 24 h. After cooling to room temperature the pH was set to 8 with saturated aqueous sodium hydrogen carbonate solution. The mixture was then extracted overnight in a continuous extraction (Keberle) for 48 h with chloroform. The chloroform extract was then dried over sodium sulfate, filtered and evaporated. Purification by chromatography (SiO$_2$, dichloromethane:methanol=1:0 to 95:5) afforded the title compound (8.1 g, 26%) which was obtained as a brown oil. MS: m/e=108.0 [M]$^+$.

d) Pyrimidine-4-carbaldehyde oxime

As described for example 286a, pyrimidine-4-carbaldehyde (8.1 g, 51 mmol) was converted, instead of 5-fluoro-2-formylpyridine, to the title compound (2.2 g, 35%) which was obtained as a light brown solid. MS: m/e=124.0 [M+H]$^+$.

e) 5-Methyl-3-pyrimidin-4-yl-isoxazole-4-carboxylic acid ethyl ester

As described for example 286b, pyrimidine-4-carbaldehyde oxime (2.2 g, 18 mmol) was converted, instead of 5-fluoro-pyridine-2-carbaldehyde oxime, to the title compound (2.6 g, 63%) which was obtained as a light brown oil. MS: m/e=233.9 [M+H]$^+$.

f) 5-Methyl-3-pyrimidin-4-yl-isoxazole-4-carboxylic acid

As described for example 58b, 5-methyl-3-pyrimidin-4-yl-isoxazole-4-carboxylic acid ethyl ester (500 mg, 2.1 mmol) was converted, instead of 2-(5-methyl-3-phenyl-isoxazol-4-ylmethoxy)-isonicotinic acid methyl ester, to the title compound (321 mg, 73%) which was obtained as an off white solid. MS: m/e=204.1 [M−H]$^−$.

g) (5-Methyl-3-pyrimidin-4-yl-isoxazol-4-yl)-methanol

To a solution of 5-methyl-3-pyrimidin-4-yl-isoxazole-4-carboxylic acid (300 mg, 1.46 mmol) in THF (4 mL) at −10° C. was added triethylamine (203 µL, 1.46 mmol) and then a solution of ethylchloroformate (139 µL, 1.46 mmol) in THF (1 mL) added keeping the temperature below −5° C. After 1 h the mixture was filtered and the filtrate cooled to −10° C. and a suspension of sodiumborohydride (138 mg, 3.66 mmol) in water (1.5 mL) added over 15 minutes keeping the temperature below −5° C. The mixture was then allowed to warm up to room temperature over 2 h and diluted with aqueous sodium hydroxide (1 N) and extracted with ethylacetate. The combined organic layers were then washed with water and brine, dried over sodium sulfate and evaporated. Purification by chromatography (SiO$_2$, dichloromethane:methanol=9:1) afforded the title product (52.5 mg, 19%) which was obtained as white solid. MS: m/e=190.0 [M−H]$^−$.

hi) 6-(5-Methyl-3-pyrimidin-4-yl-isoxazol-4-yl-methoxy)-nicotinic acid methyl ester To a solution of (5-methyl-3-pyrimidin-4-yl-isoxazol-4-yl)-methanol (313 mg, 1.63 mmol) in THF (20 mL) was added methyl 6-hydroxynicotinate (276 mg, 1.8 mmol) and triphenylphosphine (644 mg, 2.5 mmol) at room temperature under an argon atmosphere. Then diethyl azodicarboxylate (~40% in toluene, 1.1 mL, 2.5 mmol) was added and the reaction mixture was stirred for 30 min at room temperature. Concentration and purification by chromatography (SiO$_2$, heptane:ethyl acetate=100:0 to 1:1) afforded the title compound (95 mg, 18%) as a white solid. MS: m/e=327.3 [M+H]$^+$.
Or alternatively hii) 6-(5-Methyl-3-pyrimidin-4-yl-isoxazol-4-yl-methoxy)-nicotinic acid methyl ester As described for example 84e, (5-methyl-3-pyrimidin-4-yl-isoxazol-4-yl)-methanol (139 mg, 0.73 mmol) was converted, instead of [3-(2-fluoro-phenyl)-5-methyl-isoxazol-4-yl]-methanol, to the title compound (72 mg, 30%) which was obtained as a white solid. MS: m/e=327.5 [M+H]$^+$.

Example 313

N-Isopropyl-6-(5-methyl-3-pyrimidin-4-yl-isoxazol-4-ylmethoxy)-nicotinamide a) 6-(5-Methyl-3-pyrimidin-4-yl-isoxazol-4-yl-methoxy)-nicotinic acid As described for example 283, 6-(5-methyl-3-pyrimidin-4-yl-isoxazol-4-ylmethoxy)-nicotinic acid methyl ester (53 mg, 0.16 mmol) was converted, instead of 6-(5-methyl-3-pyridin-2-yl-isoxazol-4-ylmethoxy)-nicotinic acid methyl ester, to the title compound (42 mg, 83%) which was obtained as a white solid. MS: m/e=311.5 [M−H]$^−$.

b) N-Isopropyl-6-(5-methyl-3-pyrimidin-4-yl-isoxazol-4-ylmethoxy)-nicotinamide

As described for example 98b, 6-(5-methyl-3-pyrimidin-4-yl-isoxazol-4-ylmethoxy)-nicotinic acid (19 mg, 0.06 mmol) was converted, instead of 6-[3-(3-chloro-phenyl)-5-methyl-isoxazol-4-ylmethoxy]-nicotinic acid, using isopropylamine instead of 2,2,2-trifluoroethylamine, to the title compound (16 mg, 73%) which was obtained as a white solid. MS: m/e=354.3 [M+H]$^+$.

Example 314

N-Cyclopropyl-6-(5-methyl-3-pyrimidin-4-yl-isoxazol-4-ylmethoxy)-nicotinamide

As described for example 313b, 6-(5-methyl-3-pyrimidin-4-yl-isoxazol-4-ylmethoxy)-nicotinic acid (19 mg, 0.06 mmol) was converted, using cyclopropylamine instead of isopropylamine, to the title compound (17 mg, 81%) which was obtained as a white solid. MS: m/e=352.5 [M+H]$^+$.

Example 315

N-(2-Hydroxy-1,1-dimethyl-ethyl)-6-(5-methyl-3-pyrimidin-4-yl-isoxazol-4-ylmethoxy)-nicotinamide As described for example 313b, 6-(5-methyl-3-pyrimidin-4-yl-isoxazol-4-ylmethoxy)-nicotinic acid (53 mg, 0.17 mmol) was converted, using cyclopropylamine instead of isopropylamine, to the title compound (39 mg, 60%) which was obtained as a colourless gum. MS: m/e=384.1 [M+H]$^+$.

Example 316

[6-(5-Methyl-3-pyrimidin-4-yl-isoxazol-4-yl-methoxy)-pyridin-3-yl]-morpholin-4-yl-methanone As described for example 313b, 6-(5-methyl-3-pyrimidin-4-yl-isoxazol-4-ylmethoxy)-nicotinic acid (53 mg, 0.17 mmol) was converted, using morpholine instead of isopropylamine, to the title compound (45 mg, 70%) which was obtained as an off white foam. MS: m/e=382.4 [M+H]$^+$.

Example 317

N-Ethyl-6-(5-methyl-3-pyrimidin-4-yl-isoxazol-4-ylmethoxy)-nicotinamide

As described for example 313b, 6-(5-methyl-3-pyrimidin-4-yl-isoxazol-4-ylmethoxy)-nicotinic acid (53 mg, 0.17 mmol) was converted, using ethylamine (2 M solution in THF) instead of isopropylamine, to the title compound (45 mg, 78%) which was obtained as a white solid. MS: m/e=340.0 [M+H]'.

Example 318

N-Methyl-6-(5-methyl-3-pyrimidin-4-yl-isoxazol-4-ylmethoxy)-nicotinamide

As described for example 313b, 6-(5-methyl-3-pyrimidin-4-yl-isoxazol-4-ylmethoxy)-nicotinic acid (53 mg, 0.17 mmol) was converted, using methylamine (2 M solution in THF) instead of isopropylamine, to the title compound (39 mg, 70%) which was obtained as a white solid. MS: m/e=326.3 [M+H]$^+$.

Example 319

[6-(5-Methyl-3-pyrimidin-4-yl-isoxazol-4-yl-methoxy)-pyridin-3-yl]-thiomorpholin-4-yl-methanone As described for example 313b, 6-(5-methyl-3-pyrimidin-4-yl-isoxazol-4-ylmethoxy)-nicotinic acid (53 mg, 0.17 mmol) was converted, using thiomorpholine instead of isopropylamine, to the title compound (47 mg, 70%) which was obtained as a colourless gum. MS: m/e=398.1 [M+H]$^+$.

Example 320

N-(2-Hydroxy-ethyl)-6-(5-methyl-3-pyrimidin-4-yl-isoxazol-4-ylmethoxy)-nicotinamide As described for example 313b, 6-(5-methyl-3-pyrimidin-4-yl-isoxazol-4-ylmethoxy)-nicotinic acid (53 mg, 0.17 mmol) was converted, using ethanolamine instead of isopropylamine, to the title compound (44 mg, 73%) which was obtained as a white solid. MS: m/e=356.3 [M+H]$^+$.

Example 321

N-Isopropyl-6-(3-phenyl-isoxazol-4-ylmethoxy)-nicotinamide a) 3-Phenyl-isoxazole-4-carboxylic acid methyl ester To a mixture of (E)- and/or (Z)—N-hydroxy-benzenecarboximidoyl chloride (12.0 g, 77 mmol) and 4-nitro-benzoic-acid (E)-2-methoxycarbonyl-vinyl ester (9.7 g, 39 mmol) in dichloromethane (200 mL) was added triethylamine (20.9 mL, 150 mml) and the resulting solution stirred overnight at room temperature. The mixture was then diluted with dichloromethane (500 mL) and the organic extract removed and washed with water, dried over sodium sulfate and evaporated. Purification by chromatography (SiO$_2$, heptane:ethyl acetate=100:0 to 4:1) afforded the title product (3.1 g, 40%) which was obtained as a light yellow oil. MS: m/e=204.2 [M+H]$^+$.

b) (3-Phenyl-isoxazol-4-yl)-methanol

As described for example 84d, 3-phenyl-isoxazole-4-carboxylic acid methyl ester (2.95 g, 15 mmol) was converted, instead of 3-(2-fluoro-phenyl)-5-methyl-isoxazole-4-carboxylic acid ethyl ester, to the title compound (1.56 g, 61%) which was obtained as a light green oil. MS: m/e=176.4 [M+H]$^+$.

c) 6-(3-Phenyl-isoxazol-4-ylmethoxy)-nicotinic acid methyl ester

As described for example 84e, (3-phenyl-isoxazol-4-yl)-methanol (700 mg, 4.0 mmol) was converted, instead of [3-(2-fluoro-phenyl)-5-methyl-isoxazol-4-yl]-methanol, to the title compound (288 mg, 23%) which was obtained as a light yellow gum. MS: m/e=311.3 [M+H]$^+$.

d) N-Isopropyl-6-(3-phenyl-isoxazol-4-ylmethoxy)-nicotinamide

As described for example 84f, 6-(3-phenyl-isoxazol-4-ylmethoxy)-nicotinic acid methyl ester (67 mg, 0.21 mmol) was converted, instead of [6-[3-(2-fluoro-phenyl)-5-methyl-isoxazol-4-ylmethoxy]-nicotinic acid methyl ester, using isopropylamine instead of 2,2,2-trifluoroethylamine, to the title compound (59 mg, 81%) which was obtained as an off white solid. MS: m/e=338.2 [M+H]$^+$.

Example 322

6-(3-Phenyl-isoxazol-4-ylmethoxy)-N-(tetrahydro-pyran-4-yl)-nicotinamide

As described for example 321d, 6-(3-phenyl-isoxazol-4-ylmethoxy)-nicotinic acid methyl ester (67 mg, 0.21 mmol) was converted, using 4-aminotetrahydropyran instead of isopropylamine, to the title compound (60 mg, 73%) which was obtained as an off white solid. MS: m/e=380.2 [M+H]$^+$.

Example 323

6-[3-(4-Fluoro-phenyl)-isoxazol-4-ylmethoxy]-N-isopropyl-nicotinamide a) (E)- and/or (Z)-4-Fluoro-benzaldehyde oxime As described for example 84a, 4-fluorobenzaldehyde (24.8 g, 200 mmol) was converted, instead of 2-fluorobenzaldehyde, to the title compound (23.3 g, 84%) which was obtained as a white solid. MS: m/e=139.1 [M]$^+$.

b) (E)- and/or (Z)—N-Hydroxy-4-fluoro-benzenecarboximidoyl chloride

To a solution of (E)- and/or (Z)-4-fluoro-benzaldehyde oxime (100 g, 719 mmol) in DMF (500 mL) was added N-chlorosuccinimide (110 g, 791 mmol) portionwise keeping the temperature below 70° C. The reaction mixture was stirred at room temperature for 2.5 h and then extracted with tert-butyl methyl ether to afford the title compound (125 g, 100%) which was obtained as a yellow oil. MS: m/e=173.1 [M]$^+$.

c) 3-(4-Fluoro-phenyl)-isoxazole-4-carboxylic acid ethyl ester

To a solution of (E)- and/or (Z)—N-hydroxy-4-fluoro-benzenecarboximidoyl chloride (50 g, 241 mmol) in diethylether (1 L) was added a solution of ethyl 3-(N,N-dimethylamino)acrylate (87 mL, 601 mmol) and triethylamine (49 mL, 349 mmol) in diethylether (1 L). The resulting mixture was then stirred for 14 h at room temperature and evaporated. Purification by chromatography (SiO$_2$, heptane:ethyl acetate=100:0 to 4:1) afforded the title product (50.2 g, 88%) which was obtained as a light yellow solid. MS: m/e=236.1 [M+H]$^+$.

d) 3-(4-Fluoro-phenyl)-isoxazole-4-carboxylic acid

To a solution of 3-(4-fluoro-phenyl)-isoxazole-4-carboxylic acid ethyl ester (849 g, 208 mmol) in ethanol (215 mL) was added aqueous sodium hydroxide (2 N, 161 mL, 323 mmol) and the resulting mixture stirred overnight at room temperature. The mixture was then acidified with HCl solution (4 N, 85 mL) to pH 2-3. The precipitate was then filtered off and dissolved in THF (700 mL) and then washed with saturated sodium chloride solution. The aqueous phase was then extracted with ethyl acetate and THF (1:1, 300 mL) and the combined organic phases dried over sodium sulfate and evaporated to afford the title compound (40.8 g, 94%) which was obtained as an orange solid. MS: m/e=206.1 [M−H]⁻.

e) [3-(4-Fluoro-phenyl)-isoxazol-4-yl]-methanol

To a solution of 3-(4-fluoro-phenyl)-isoxazole-4-carboxylic acid (40 g, 193 mmol) in THF (400 mL) at −10° C. was added triethylamine (27.1 mL, 193 mmol) and then a solution of ethylchloroformate (18.8 mL, 193 mmol) in THF (120 mL) added keeping the temperature below −5° C. After 1 h the mixture was filtered and the filtrate cooled to −10° C. and a suspension of sodiumborohydride (19 g, 483 mmol) in water (120 mL) added over 15 minutes keeping the temperature below −5° C. The mixture was then allowed to warm up to room temperature over 2 h and diluted with aqueous sodium hydroxide (1 N, 700 mL) and extracted with tert-butylmethylether. The combined organic layers were then washed with water and brine, dried over sodium sulfate and evaporated. Purification by chromatography (SiO$_2$, heptane:ethyl acetate=1:1) afforded the title product (20.1 g, 54%) which was obtained as white solid. MS: m/e=194.1 [M+H]⁺.

f) 6-[3-(4-Fluoro-phenyl)-isoxazol-4-ylmethoxy]-nicotinic acid methyl ester

As described for example 84e, [3-(4-fluoro-phenyl)-isoxazol-4-yl]-methanol (550 mg, 2.9 mmol) was converted, instead of [3-(2-fluoro-phenyl)-5-methyl-isoxazol-4-yl]-methanol, to the title compound (660 mg, 71%) which was obtained as a white solid. MS: m/e=387.3 [M+OAc]⁻.

g) 6-[3-(4-Fluoro-phenyl)-isoxazol-4-ylmethoxy]-N-isopropyl-nicotinamide

As described for example 84f, 6-[3-(4-fluoro-phenyl)-isoxazol-4-ylmethoxy]-nicotinic acid methyl ester (150 mg, 0.46 mmol) was converted, instead of [6-[3-(2-fluoro-phenyl)-5-methyl-isoxazol-4-ylmethoxy]-nicotinic acid methyl ester, using isopropylamine instead of 2,2,2-trifluoroethylamine, to the title compound (160 mg, 98%) which was obtained as a white solid. MS: m/e=356.3 [M+H]⁺.

Example 324

6-[3-(4-Fluoro-phenyl)-isoxazol-4-ylmethoxy]-N-(tetrahydro-pyran-4-yl)-nicotinamide As described for example 323 g, 6-[3-(4-fluoro-phenyl)-isoxazol-4-ylmethoxy]-nicotinic acid methyl ester (150 mg, 0.46 mmol) was converted, using 4-aminotetrahydropyran instead of isopropylamine, to the title compound (160 mg, 88%) which was obtained as a white solid. MS: m/e=398.3 [M+H]⁺.

Example 325

6-[3-(4-Fluoro-phenyl)-isoxazol-4-ylmethoxy]-N-(2-hydroxy-1-methyl-ethyl)-nicotinamide As described for example 220, 6-[3-(4-fluoro-phenyl)-isoxazol-4-ylmethoxy]-nicotinic acid methyl ester (100 mg, 0.31 mmol) was converted, instead of 6-(5-methyl-3-phenyl-isoxazol-4-ylmethoxy)-nicotinic acid methyl ester, using rac-2-amino-1-propanol instead of 3-amino-1-propanol, to the title compound (80 mg, 71%) which was obtained as a colourless gum. MS: m/e=372.2 [M+H]⁺.

Example 326

6-[3-(4-Fluoro-phenyl)-isoxazol-4-ylmethoxy]-N—((R)-2-hydroxy-1-methyl-ethyl)-nicotinamide As described for example 325, 6-[3-(4-fluoro-phenyl)-isoxazol-4-ylmethoxy]-nicotinic acid methyl ester (60 mg, 0.18 mmol) was converted, using D-alaninol instead of rac-2-amino-1-propanol, to the title compound (28 mg, 41%) which was obtained as a white solid MS: m/e=372.1 [M+H]⁺.

Example 327

6-[3-(4-Fluoro-phenyl)-isoxazol-4-ylmethoxy]-N—((S)-2-hydroxy-1-methyl-ethyl)-nicotinamide As described for example 325, 6-[3-(4-fluoro-phenyl)-isoxazol-4-ylmethoxy]-nicotinic acid methyl ester (60 mg, 0.18 mmol) was converted, using S-(+)-2-amino-1-propanol instead of rac-2-amino-1-propanol, to the title compound (28 mg, 59%) which was obtained as a white solid MS: m/e=370.3 [M−H]⁻.

Example 328

N-Cyclopropylmethyl-6-[3-(4-fluoro-phenyl)-isoxazol-4-ylmethoxy]-nicotinamide

As described for example 324, 6-[3-(4-fluoro-phenyl)-isoxazol-4-ylmethoxy]-nicotinic acid methyl ester (200 mg, 0.61 mmol) was converted, using aminomethylcyclopropane instead of 4-aminotetrahydropyran, to the title compound (70 mg, 31%) which was obtained as a white solid. MS: m/e=368.1 [M+H]⁺.

Example 329

N-Cyclopropyl-6-[3-(4-fluoro-phenyl)-isoxazol-4-ylmethoxy]-nicotinamide

As described for example 324, 6-[3-(4-fluoro-phenyl)-isoxazol-4-ylmethoxy]-nicotinic acid methyl ester (200 mg, 0.61 mmol) was converted, using cyclopropylamine instead of 4-aminotetrahydropyran, to the title compound (60 mg, 28%) which was obtained as a white solid. MS: m/e=343.4 [M+H]⁺.

Example 330

6-[3-(4-Fluoro-phenyl)-isoxazol-4-ylmethoxy]-N-(2,2,2-trifluoro-ethyl)-nicotinamide As described for example 324, 6-[3-(4-fluoro-phenyl)-isoxazol-4-ylmethoxy]-nicotinic acid methyl ester (200 mg, 0.61 mmol) was converted, using 2,2,2-trifluoroethylamine instead of 4-aminotetrahydropyran, to the title compound (100 mg, 41%) which was obtained as a light brown solid. MS: m/e=396.1 [M+H]+.

Example 331

6-[3-(4-Fluoro-phenyl)-isoxazol-4-ylmethoxy]-N-((1S,2S)-2-hydroxy-cyclopentyl)-nicotinamide a) 6-[3-(4-Fluoro-phenyl)-isoxazol-4-ylmethoxy]-nicotinic acid As described for example 324, 6-[3-(4-fluoro-phenyl)-isoxazol-4-ylmethoxy]-nicotinic acid methyl ester (4.0 g, 12.2 mmol) was converted, instead of 6-(5-methyl-3-pyridin-2-yl-isoxazol-4-ylmethoxy)-nicotinic acid methyl ester, to the title compound (3.1 g, 81%) which was obtained as a white solid. MS: m/e=313.3 [M−H]−.

b) 6-[3-(4-Fluoro-phenyl)-isoxazol-4-ylmethoxy]-N-((1S,2S)-2-hydroxy-cyclopentyl)-nicotinamide As described for example 191, 6-(5-methyl-3-phenyl-isoxazol-4-ylmethoxy)-nicotinic acid (200 mg, 0.64 mmol) was converted, instead of 6-(5-methyl-3-phenyl-isoxazol-4-ylmethoxy)-nicotinic acid, using (1S,2S)-2-amino-cyclohexanol hydrochloride (1:1) instead of (1R,2R)-2-amino-cyclohexanol hydrochloride (1:1), to the title compound (180 mg, 71%) which was obtained as a white solid. MS: m/e=398.2 [M−H]−.

Example 332

6-[3-(4-Fluoro-phenyl)-isoxazol-4-ylmethoxy]-N-((1R,2R)-2-hydroxy-cyclopentyl)-nicotinamide or 6-[3-(4-fluoro-phenyl)-isoxazol-4-ylmethoxy]-N-((1S,2S)-2-hydroxy-cyclopentyl)-nicotinamide As described for example 331b, 6-(5-methyl-3-phenyl-isoxazol-4-ylmethoxy)-nicotinic acid (200 mg, 0.64 mmol) was converted, using rac-trans-2-amino-cyclohexanol hydrochloride (1:1) instead of (1S,2S)-2-amino-cyclohexanol hydrochloride (1:1), to the title compound (110 mg, 43%) which was obtained as a colourless oil. MS: m/e=398.2 [M−H]−.

Example 333

6-[3-(4-Fluoro-phenyl)-isoxazol-4-ylmethoxy]-N-(3,3,3-trifluoro-2-hydroxy-propyl)-nicotinamide As described for example 325, 6-[3-(4-fluoro-phenyl)-isoxazol-4-ylmethoxy]-nicotinic acid methyl ester (200 mg, 0.61 mmol) was converted, using 3-amino-1,1,1,-trifluoro-propan-2-ol instead of rac-2-amino-1-propanol, to the title compound (39 mg, 15%) which was obtained as a white solid MS: m/e=426.1 [M+H]+.

Example 334

6-[3-(4-Fluoro-phenyl)-isoxazol-4-ylmethoxy]-N-(2-hydroxy-1-hydroxymethyl-ethyl)-nicotinamide As described for example 325, 6-[3-(4-fluoro-phenyl)-isoxazol-4-ylmethoxy]-nicotinic acid methyl ester (200 mg, 0.61 mmol) was converted, using 2-amino-1,3-propandiol instead of rac-2-amino-1-propanol, to the title compound (117 mg, 49%) which was obtained as a white solid MS: m/e=388.2 [M+H]+.

Example 335

N-(2-Acetylamino-ethyl)-6-[3-(4-fluoro-phenyl)-isoxazol-4-ylmethoxy]-nicotinamide As described for example 331b, 6-(5-methyl-3-phenyl-isoxazol-4-ylmethoxy)-nicotinic acid (100 mg, 0.32 mmol) was converted, using N-acetylethylenediamine instead of (1S,2S)-2-amino-cyclohexanol hydrochloride (1:1), to the title compound (67 mg, 53%) which was obtained as a white solid. MS: m/e=397.0 [M−H]−.

Example 336

6-[3-(4-Fluoro-phenyl)-isoxazol-4-ylmethoxy]-N-(2-methoxy-ethyl)-nicotinamide

As described for example 331b, 6-(5-methyl-3-phenyl-isoxazol-4-ylmethoxy)-nicotinic acid (100 mg, 0.32 mmol) was converted, using 2-methoxyethylamine instead of (1S,2S)-2-amino-cyclohexanol hydrochloride (1:1), to the title compound (89 mg, 75%) which was obtained as a light yellow solid. MS: m/e=370.0 [M+H]−.

Example 337

6-[3-(4-Fluoro-phenyl)-isoxazol-4-ylmethoxy]-N—((R)-2-hydroxy-propyl)-nicotinamide As described for example 331b, 6-(5-methyl-3-phenyl-isoxazol-4-ylmethoxy)-nicotinic acid (100 mg, 0.32 mmol) was converted, using R-(−)-1-amino-2-propanol instead of (1S,2S)-2-amino-cyclohexanol hydrochloride (1:1), to the title compound (75 mg, 64%) which was obtained as a light yellow solid. MS: m/e=370.0 [M−H]−.

Example 338

6-[3-(4-Fluoro-phenyl)-isoxazol-4-ylmethoxy]-N-(2-hydroxy-ethyl)-nicotinamide

As described for example 331b, 6-(5-methyl-3-phenyl-isoxazol-4-ylmethoxy)-nicotinic acid (100 mg, 0.32 mmol) was converted, using ethanolamine instead of (1S,2S)-2-amino-cyclohexanol hydrochloride (1:1), to the title compound (85 mg, 75%) which was obtained as a white solid. MS: m/e=356.2 [M−H]−.

Example 339

6-[3-(4-Fluoro-phenyl)-isoxazol-4-ylmethoxy]-N-(1-hydroxy-cyclopropylmethyl)-nicotinamide As described for example 331b, 6-(5-methyl-3-phenyl-isoxazol-4-ylmethoxy)-nicotinic acid (100 mg, 0.32 mmol) was converted, using 1-(aminomethyl)-cyclopropanol instead of (1S,2S)-2-amino-cyclohexanol hydrochloride (1:1), to the title compound (140 mg, 57%) which was obtained as a white solid. MS: m/e=384.1 [M+H]+.

Example 340

N-(1,1-Dioxo-tetrahydro-1,6-thiophen-3-yl)-6-[3-(4-fluoro-phenyl)-isoxazol-4-ylmethoxy]-nicotinamide As described for example 331b, 6-(5-methyl-3-phenyl-isoxazol-4-ylmethoxy)-nicotinic acid (200 mg, 0.64 mmol) was converted, using 1,1-dioxidotetrahydrothien-3-ylamine instead of (1S,2S)-2-amino-cyclohexanol hydrochloride (1:1), to the title compound (200 mg, 73%) which was obtained as a white solid. MS: m/e=432.2 [M+H]+.

Example 341

6-[3-(4-Fluoro-phenyl)-isoxazol-4-ylmethoxy]-N-((1R,2R)-2-hydroxy-cyclopentyl)-nicotinamide or 6-[3-(4-fluoro-phenyl)-isoxazol-4-ylmethoxy]-N-((1S,2S)-2-hydroxy-cyclopentyl)-nicotinamide The stereoisomers of 6-[3-(4-fluoro-phenyl)-isoxazol-4-ylmethoxy]-N-((1R,2R)-2-hydroxy-cyclopentyl)-nicotinamide or 6-[3-(4-fluoro-phenyl)-isoxazol-4-ylmethoxy]-N-((1S,2S)-2-hydroxy-cyclopentyl)-nicotinamide (example 333, 600 mg) in ethanol:heptane (1:1, 8 mL) were separated using a 5×50 cm Chiralpak AD column at room temperature using an isopropanol:heptane (3:7) mobile phase with UV detection at 220 nM. The least polar component (-ve sign of rotation) was obtained as a white solid (240 mg). The most polar component (+ve sign of rotation) was obtained as a white solid (220 mg).

Example 342

6-[3-(4-Chloro-phenyl)-isoxazol-4-ylmethoxy]-N-(2,2,2-trifluoro-ethyl)-nicotinamide a) (E)- and/or (Z)-4-Chloro-benzaldehyde oxime As described for example 88a, 4-chlorobenzaldehyde (25.0 g, 178 mmol) was converted, instead of 3-fluorobenzaldehyde, to the title compound (27.0 g, 97%) which was obtained as an off white solid. MS: m/e=155.1 [M]+.

b) (E)- and/or (Z)—N-Hydroxy-4-chloro-benzenecarboximidoyl chloride

As described for example 88b, (E)- and/or (Z)-4-chlorobenzaldehyde oxime (27.0 g, 173 mmol) was converted, instead of (E)- and/or (Z)-3-fluoro-benzaldehyde oxime, to the title compound (28.4 g, 86%) which was obtained as a light yellow solid. MS: m/e=189.1 [M]+.

c) 3-(4-Chloro-phenyl)-isoxazole-4-carboxylic acid ethyl ester

As described for example 323c, (E)- and/or (Z)—N-hydroxy-4-chloro-benzenecarboximidoyl chloride (58.0 g, 250.3 mmol) was converted, instead of (E)- and/or (Z)—N-hydroxy-4-fluoro-benzenecarboximidoyl chloride, to the title compound (57 g, 91%) which was obtained as a white solid. MS: m/e=252.1 [M+H]+.

d) 3-(4-Chloro-phenyl)-isoxazole-4-carboxylic acid

As described for example 323d, 3-(4-chloro-phenyl)-isoxazole-4-carboxylic acid ethyl ester (57.0 g, 226.5 mmol) was converted, instead of 3-(4-fluoro-phenyl)-isoxazole-4-carboxylic acid ethyl ester, to the title compound (50.7 g, 92%) which was obtained as a light yellow solid. MS: m/e=222.3 [M–H]−.

e) [3-(4-Chloro-phenyl)-isoxazol-4-yl]-methanol

As described for example 323e, 3-(4-chloro-phenyl)-isoxazole-4-carboxylic acid (40.0 g, 178.9 mmol) was converted, instead of 3-(4-fluoro-phenyl)-isoxazole-4-carboxylic acid, to the title compound (17.3 g, 46%) which was obtained as a light green solid. MS: m/e=210.1 [M+H]'.

f) 6-[3-(4-Chloro-phenyl)-isoxazol-4-ylmethoxy]-nicotinic acid methyl ester

As described for example 323f, [3-(4-chloro-phenyl)-isoxazol-4-yl]-methanol (8.0 g, 42 mmol) was converted, instead of [3-(2-fluoro-phenyl)-5-methyl-isoxazol-4-yl]-methanol, to the title compound (9.4 g, 72%) which was obtained as a light yellow solid. MS: m/e=345.1 [M+H]+.

g) 6-[3-(4-Chloro-phenyl)-isoxazol-4-ylmethoxy]-N-(2,2,2-trifluoro-ethyl)-nicotinamide As described for example 84f, 6-[3-(4-chloro-phenyl)-isoxazol-4-ylmethoxy]-nicotinic acid methyl ester (200 mg, 0.58 mmol) was converted, instead of [6-[3-(2-fluoro-phenyl)-5-methyl-isoxazol-4-ylmethoxy]-nicotinic acid methyl ester, to the title compound (140 mg, 59%) which was obtained as a white solid. MS: m/e=412.1 [M+H]+.

Example 343

6-[3-(4-Chloro-phenyl)-isoxazol-4-ylmethoxy]-N-cyclopropyl-nicotinamide

As described for example 342 g, 6-[3-(4-chloro-phenyl)-isoxazol-4-ylmethoxy]-nicotinic acid methyl ester (200 mg, 0.58 mmol) was converted, using cyclopropylamine instead of 2,2,2-trifluoroethylamine, to the title compound (100 mg, 46%) which was obtained as a white solid. MS: m/e=370.0 [M+H]+.

Example 344

6-[3-(4-Chloro-phenyl)-isoxazol-4-ylmethoxy]-N-isopropyl-nicotinamide

As described for example 344 g, 6-[3-(4-chloro-phenyl)-isoxazol-4-ylmethoxy]-nicotinic acid methyl ester (200 mg, 0.58 mmol) was converted, using isopropylamine instead of 2,2,2-trifluoroethylamine, to the title compound (120 mg, 56%) which was obtained as a white solid. MS: m/e=372.1 [M+H]+.

Example 345

6-[3-(4-Chloro-phenyl)-isoxazol-4-ylmethoxy]-N-(tetrahydro-pyran-4-yl)-nicotinamide As described for example 342 g, 6-[3-(4-chloro-phenyl)-isoxazol-4-ylmethoxy]-nicotinic acid methyl ester (200 mg, 0.58 mmol) was converted, using 4-aminotetrahydropyran instead of 2,2,2-trifluoroethylamine, to the title compound (170 mg, 71%) which was obtained as a white solid. MS: m/e=414.2 [M+H]+.

Example 346

6-[3-(4-Chloro-phenyl)-isoxazol-4-ylmethoxy]-N-(2-hydroxy-ethyl)-nicotinamide a) 6-[3-(4-Chloro-phenyl)-isoxazol-4-ylmethoxy]-nicotinic acid

As described for example 331a, 6-[3-(4-chloro-phenyl)-isoxazol-4-ylmethoxy]-nicotinic acid methyl ester (4.0 g, 11.6 mmol) was converted, instead of 6-[3-(4-fluoro-phenyl)-isoxazol-4-ylmethoxy]-nicotinic acid methyl ester, to the title compound (3.8 g, 100%) which was obtained as a light yellow solid. MS: m/e=331.1 [M−H]−.

b) 6-[3-(4-Chloro-phenyl)-isoxazol-4-ylmethoxy]N-(2-hydroxy-ethyl)-nicotinamide

As described for example 191, 6-[3-(4-chloro-phenyl)-isoxazol-4-ylmethoxy]-nicotinic acid (100 mg, 0.3 mmol) was converted, instead of 6-(5-methyl-3-phenyl-isoxazol-4-ylmethoxy)-nicotinic acid, using ethanolamine instead of (1R,2R)-2-amino-cyclohexanol hydrochloride (1:1), to the title compound (79 mg, 70%) which was obtained as a white solid. MS: m/e=374.0 [M+H]+.

Example 347

6-[3-(4-Chloro-phenyl)-isoxazol-4-ylmethoxy]-N-(2-hydroxy-propyl)-nicotinamide

As described for example 346b, 6-[3-(4-chloro-phenyl)-isoxazol-4-ylmethoxy]-nicotinic acid (200 mg, 0.6 mmol) was converted, using (rac)-1-amino-2-propanol instead of ethanolamine, to the title compound (100 mg, 43%) which was obtained as a colourless gum. MS: m/e=388.1 [M+H]+.

Example 348

6-[3-(4-Chloro-phenyl)-isoxazol-4-ylmethoxy]-N-(3-hydroxy-propyl)-nicotinamide

As described for example 346b, 6-[3-(4-chloro-phenyl)-isoxazol-4-ylmethoxy]-nicotinic acid (200 mg, 0.6 mmol) was converted, using 3-amino-1-propanol instead of ethanolamine, to the title compound (140 mg, 60%) which was obtained as a white solid. MS: m/e=385.9 [M−H]−.

Example 349

6-[3-(4-Chloro-phenyl)-isoxazol-4-ylmethoxy]-N-(2-hydroxy-1,1-dimethyl-ethyl)-nicotinamide

As described for example 346b, 6-[3-(4-chloro-phenyl)-isoxazol-4-ylmethoxy]-nicotinic acid (200 mg, 0.6 mmol) was converted, using 2-amino-2-methyl-1-propanol instead of ethanolamine, to the title compound (110 mg, 45%) which was obtained as a white solid. MS: m/e=402.2 [M+H]+.

Example 350

6-[3-(4-Chloro-phenyl)-isoxazol-4-ylmethoxy]-N-(3-hydroxy-2,2-dimethyl-propyl)-nicotinamide

As described for example 346b, 6-[3-(4-chloro-phenyl)-isoxazol-4-ylmethoxy]-nicotinic acid (200 mg, 0.6 mmol) was converted, using 3-amino-2,2-dimethyl-1-propanol instead of ethanolamine, to the title compound (150 mg, 60%) which was obtained as a white solid. MS: m/e=414.1 [M−H]−.

Example 351

3-({6-[3-(4-Chloro-phenyl)-isoxazol-4-ylmethoxy]-pyridine-3-carbonyl}-amino)-azetidine-1-carboxylic acid tert-butyl ester

As described for example 346b, 6-[3-(4-chloro-phenyl)-isoxazol-4-ylmethoxy]-nicotinic acid (200 mg, 0.6 mmol) was converted, using 3-amino-1-N-Boc-azetidine instead of ethanolamine, to the title compound (200 mg, 68%) which was obtained as a colourless gum. MS: m/e=483.1 [M−H]−.

Example 352

6-[3-(4-Chloro-phenyl)-isoxazol-4-ylmethoxy]-N-((1S,2S)-2-hydroxy-cyclopentyl)-nicotinamide and 6-[3-(4-chloro-phenyl)-isoxazol-4-ylmethoxy]-N-((1R,2R)-2-hydroxy-cyclopentyl)-nicotinamide

As described for example 346b, 6-[3-(4-chloro-phenyl)-isoxazol-4-ylmethoxy]-nicotinic acid (200 mg, 0.6 mmol) was converted, using rac-trans-2-amino-cyclohexanol hydrochloride (1:1) instead of ethanolamine, to the title compound (170 mg, 70%) which was obtained as a colourless gum. MS: m/e=412.1 [M−H]−.

Example 353

6-[3-(4-Chloro-phenyl)-isoxazol-4-ylmethoxy]-N-(2-hydroxy-1-hydroxymethyl-ethyl)-nicotinamide

As described for example 220, 6-[3-(4-chloro-phenyl)-isoxazol-4-ylmethoxy]-nicotinic acid methyl ester (200 mg, 0.58 mmol) was converted, instead of 6-(5-methyl-3-phenyl-isoxazol-4-ylmethoxy)-nicotinic acid methyl ester, using 2-amino-1,3-propandiol instead of 3-amino-1-propanol, to the title compound (90 mg, 38%) which was obtained as a white solid. MS: m/e=402.1 [M−H]−.

Example 354

6-[3-(4-Chloro-phenyl)-isoxazol-4-ylmethoxy]-N—((R)-2-hydroxy-1-methyl-ethyl)-nicotinamide

As described for example 346b, 6-[3-(4-chloro-phenyl)-isoxazol-4-ylmethoxy]-nicotinic acid (200 mg, 0.6 mmol) was converted, using R-(−)-2-amino-1-propanol instead of ethanolamine, to the title compound (80 mg, 34%) which was obtained as a white solid. MS: m/e=385.9 [M−H]−.

Example 355

6-[3-(4-Chloro-phenyl)-isoxazol-4-ylmethoxy]-N—((S)-2-hydroxy-1-methyl-ethyl)-nicotinamide

As described for example 346b, 6-[3-(4-chloro-phenyl)-isoxazol-4-ylmethoxy]-nicotinic acid (200 mg, 0.6 mmol) was converted, using S-(−)-2-amino-1-propanol instead of ethanolamine, to the title compound (70 mg, 30%) which was obtained as a white solid. MS: m/e=385.9 [M−H]⁻.

Example 356

N-(2-Acetylamino-ethyl)-6-[3-(4-chloro-phenyl)-isoxazol-4-ylmethoxy]-nicotinamide As described for example 346b, 6-[3-(4-chloro-phenyl)-isoxazol-4-ylmethoxy]-nicotinic acid (200 mg, 0.6 mmol) was converted, using N-acetylethylenediamine instead of ethanolamine, to the title compound (120 mg, 48%) which was obtained as a white solid. MS: m/e=413.1 [M−H]⁻.

Example 357

6-[3-(4-Chloro-phenyl)-isoxazol-4-ylmethoxy]-N—((S)-2,2,2-trifluoro-1-methyl-ethyl)-nicotinamide As described for example 346b, 6-[3-(4-chloro-phenyl)-isoxazol-4-ylmethoxy]-nicotinic acid (150 mg, 0.45 mmol) was converted, using L-2,2,2-trifluoro-1-(methyl)ethylamine instead of ethanolamine, to the title compound (190 mg, 98%) which was obtained as a white solid. MS: m/e=424.0 [M−H]⁻.

Example 358

6-(3-Pyridin-2-yl-isoxazol-4-ylmethoxy)-N-(tetrahydro-pyran-4-yl)-nicotinamide a) 3-Pyridin-2-yl-isoxazole-4-carboxylic acid ethyl ester To a solution of N-chlorosuccinimide (54.7 g, 409 mmol) in DMF (1 L) was added pyridine-2-carbaldoxime (50 g, 409 mmol) portionwise and the resulting mixture was then stirred for 64 h at room temperature. To this solution was then added ethyl 3-(N,N-dimethylamino)acrylate (58.6 g, 409 mmol) and triethylamine (82.9 mL, 819 mmol) in chloroform (10 mL) and the resulting mixture was then stirred for 14 h at room temperature and poured onto a mixture of ice water and HCl (4 N, 100 mL) and extracted with ethylacetate. The organic extract was then washed with water, saturated aqueous sodium hydrogen carbonate solution, brine, dried with sodium sulfate, filtered and evaporated. Purification by distillation afforded the title product (58.9 g, 66%) which was obtained as a light brown liquid. Bp 125-127° C. at 0.4 mbar. MS: m/e=219.2 [M+H]⁺.

b) 3-Pyridin-2-yl-isoxazole-4-carboxylic acid

As described for example 231, 3-pyridin-2-yl-isoxazole-4-carboxylic acid ethyl ester (9.6 g, 44 mmol), instead of (S)-2-{[6-(5-methyl-3-phenyl-isoxazol-4-ylmethoxy)-pyridine-3-carbonyl]-amino}-3-phenyl-propionic acid methyl ester, was converted to the title compound (6.5 g, 79%) which was obtained as an off white solid. MS: m/e=189.3 [M−H]⁻.

c) (3-Pyridin-2-yl-isoxazol-4-yl)-methanol

As described for example 323e, 3-pyridin-2-yl-isoxazole-4-carboxylic acid (39.0 g, 200 mmol) was converted, instead of 3-(4-fluoro-phenyl)-isoxazole-4-carboxylic acid, to the title compound (26.8 g, 76%) which was obtained as a white solid. MS: m/e=177.2 [M]⁺.

e) 6-(3-Pyridin-2-yl-isoxazol-4-ylmethoxy)-nicotinic acid methyl ester

As described for example 84e, (3-pyridin-2-yl-isoxazol-4-yl)-methanol (800 mg, 4.5 mmol) was converted, instead of [3-(2-fluoro-phenyl)-5-methyl-isoxazol-4-yl]-methanol, to the title compound (547 mg, 39%) which was obtained as a white solid. MS: m/e=311.9 [M+H]⁺.

f) 6-(3-Pyridin-2-yl-isoxazol-4-ylmethoxy)-nicotinic acid

As described for example 358b, 6-(3-pyridin-2-yl-isoxazol-4-ylmethoxy)-nicotinic acid methyl ester (510 mg, 1.6 mmol), instead of 3-pyridin-2-yl-isoxazole-4-carboxylic acid ethyl ester, was converted to the title compound (458 mg, 94%) which was obtained as a white solid. MS: m/e=296.5 [M−H]⁻.

g) 6-(3-Pyridin-2-yl-isoxazol-4-ylmethoxy)-N-(tetrahydro-pyran-4-yl)-nicotinamide As described for example 162b, 6-(3-pyridin-2-yl-isoxazol-4-ylmethoxy)-nicotinic acid (70 mg, 0.24 mmol) was converted using 4-aminotetrahydropyran instead of ethanolamine to the title compound (SiO₂, heptane:ethyl acetate=50:50 to 0:100, 89 mg, 99%) which was obtained as a white solid. MS: m/e=381.5 [M+H]⁺.

Example 359

N-Isopropyl-6-(3-pyridin-2-yl-isoxazol-4-ylmethoxy)-nicotinamide

As described for example 358 g, 6-(3-pyridin-2-yl-isoxazol-4-ylmethoxy)-nicotinic acid (70 mg, 0.24 mmol) was converted using isopropylamine instead of 4-aminotetrahydropyran to the title compound (76 mg, 95%) which was obtained as a white solid. MS: m/e=339.1 [M+H]⁺.

Example 360

N-Cyclopropyl-6-(3-pyridin-2-yl-isoxazol-4-ylmethoxy)-nicotinamide

As described for example 358 g, 6-(3-pyridin-2-yl-isoxazol-4-ylmethoxy)-nicotinic acid (70 mg, 0.24 mmol) was converted using cyclopropylamine instead of 4-aminotetrahydropyran to the title compound (65 mg, 82%) which was obtained as a white solid. MS: m/e=337.3 [M+H]⁺.

Example 361

N-Cyclopropylmethyl-6-(3-pyridin-2-yl-isoxazol-4-ylmethoxy)-nicotinamide

As described for example 358 g, 6-(3-pyridin-2-yl-isoxazol-4-ylmethoxy)-nicotinic acid (70 mg, 0.24 mmol) was converted using aminomethylcyclopropane instead of 4-aminotetrahydropyran to the title compound (80 mg, 97%) which was obtained as a white solid. MS: m/e=351.4 [M+H]⁺.

Example 362

6-(3-Pyridin-2-yl-isoxazol-4-ylmethoxy)-N-(2,2,2-trifluoro-ethyl)-nicotinamide

As described for example 358 g, 6-(3-pyridin-2-yl-isoxazol-4-ylmethoxy)-nicotinic acid (100 mg, 0.34 mmol) was converted using 2,2,2-trifluoroethylamine instead of 4-aminotetrahydropyran to the title compound (83 mg, 65%) which was obtained as a white solid. MS: m/e=379.3 [M+H]$^+$.

Example 363

N-(2-Hydroxy-ethyl)-6-(3-pyridin-2-yl-isoxazol-4-ylmethoxy)-nicotinamide

As described for example 358 g, 6-(3-pyridin-2-yl-isoxazol-4-ylmethoxy)-nicotinic acid (100 mg, 0.34 mmol) was converted using ethanolamine instead of 4-aminotetrahydropyran to the title compound (82 mg, 72%) which was obtained as a white solid. MS: m/e=341.0 [M+H]$^+$.

Example 364

N-Ethyl-6-(3-pyridin-2-yl-isoxazol-4-ylmethoxy)-nicotinamide

As described for example 358 g, 6-(3-pyridin-2-yl-isoxazol-4-ylmethoxy)-nicotinic acid (100 mg, 0.34 mmol) was converted using ethylamine (2 M solution in THF) instead of 4-aminotetrahydropyran to the title compound (88 mg, 81%) which was obtained as a white solid. MS: m/e=325.3 [M+H]$^+$.

Example 365

6-[3-(5-Fluoro-pyridin-2-yl)-isoxazol-4-ylmethoxy]-(tetrahydro-pyran-4-yl)-nicotinamide a) 5-Fluoro-pyridine-2-carbaldehyde oxime To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]$^+$.

b) 3-(5-Fluoro-pyridin-2-yl)-isoxazole-4-carboxylic acid ethyl ester

To a solution of N-chlorosuccinimide (17.34 g, 130 mmol) in DMF (128 mL) was added 5-fluoro-pyridine-2-carbaldehyde oxime (18.2 g, 130 mmol) portionwise over 2 h at room temperature and as the reaction warmed up to 60° C. the mixture was cooled back to room temperature with an icewater bath and the resulting mixture was then stirred for 64 h at room temperature. To this solution was then added ethyl 3-(N,N-dimethylamino)acrylate (18.6 g, 130 mmol) and triethylamine (36.2 mL, 260 mmol) in chloroform (64 mL) and the resulting mixture was then stirred for 1 h at room temperature and poured onto a mixture of ice water and HCl (4 N, 1 L) and extracted with ethylacetate. The organic extract was then washed with water, saturated aqueous sodium hydrogen carbonate solution, brine, dried with sodium sulfate, filtered and evaporated. Purification by chromatography (SiO$_2$, heptane:ethylacetate=100:0 to 1:1) afforded the title product (21.96 g, 72%) which was obtained as a yellow solid. MS: m/e=237.1 [M+H]$^+$.

ci) [3-(5-Fluoro-pyridin-2-yl)-isoxazol-4-yl]-methanol

To a solution of 3-(5-fluoro-pyridin-2-yl)-isoxazole-4-carboxylic acid ethyl ester (1.0 g, 4.23 mmol) in THF (52 mL) was added portionwise lithiumaluminiumhydride (89 mg, 2.33 mmol) at 0° C. and the reaction mixture was stirred at room temperature for 1 h. The mixture was then cooled to 0° C. and water (88 μL) added followed by sodium hydroxide (15% solution, 88 μL) and then again water (264 μL) and the mixture then stirred overnight at room temperature. The precipitate was then filtered off and washed with THF. The combined washings and filtrate were then evaporated. Purification by chromatography (SiO$_2$, heptane:ethyl acetate=100:0 to 1:1) afforded the title compound (249 mg, 30%) which was obtained as a light yellow solid. MS: m/e=195.1 [M+H]$^+$.

Or alternatively via cii) 3-(5-Fluoro-pyridin-2-yl)-isoxazole-4-carboxylic acid

As described for example 358b, 3-(5-fluoro-pyridin-2-yl)-isoxazole-4-carboxylic acid ethyl ester (1.0 g, 4.23 mmol) was converted, instead of 3-pyridin-2-yl-isoxazole-4-carboxylic acid ethyl ester, to the title compound (587 mg, 67%) which was obtained as a dark brown solid. MS: m/e=207.1 [M−H]$^-$.

ciii) [3-(5-Fluoro-pyridin-2-yl)-isoxazol-4-yl]-methanol

As described for example 358c, 3-(5-fluoro-pyridin-2-yl)-isoxazole-4-carboxylic acid (562 mg, 2.7 mmol) was converted, instead of 3-pyridin-2-yl-isoxazole-4-carboxylic acid, to the title compound (367 mg, 70%) which was obtained as an off white solid. MS: m/e=195.2 [M+H]$^+$.

d) 6-[3-(5-Fluoro-pyridin-2-yl)-isoxazol-4-ylmethoxy]-nicotinic acid methyl ester As described for example 84e, [3-(5-fluoro-pyridin-2-yl)-isoxazol-4-yl]-methanol (561 mg, 2.9 mmol) was converted, instead of [3-(2-fluoro-phenyl)-5-methyl-isoxazol-4-yl]-methanol, to the title compound (586 mg, 61%) which was obtained as a white solid. MS: m/e=330.0 [M+H]$^+$.

e) 6-[3-(5-Fluoro-pyridin-2-yl)-isoxazol-4-ylmethoxy]-nicotinic acid

As described for example 365cii, 6-[3-(5-fluoro-pyridin-2-yl)-isoxazol-4-ylmethoxy]-nicotinic acid methyl ester (313 mg, 0.9 mmol) was converted, 3-(5-fluoro-pyridin-2-yl)-isoxazole-4-carboxylic acid ethyl ester, to the title compound (251 mg, 84%) which was obtained as a white solid. MS: m/e=328.3 [M−H]$^-$.

f) 6-[3-(5-Fluoro-pyridin-2-yl)-isoxazol-4-ylmethoxy]-(tetrahydro-pyran-4-yl)-nicotinamide As described for example 98b, 6-[3-(5-fluoro-pyridin-2-yl)-isoxazol-4-ylmethoxy]-nicotinic acid (79 mg, 0.25 mmol) was converted, instead of 6-[3-(3-chloro-phenyl)-5-methyl-isoxazol-4-ylmethoxy]-nicotinic acid, using 4-aminotetrayhdropyran instead of 2,2,2-trifluoroethylamine, to the title compound (79 mg, 79%) which was obtained as an off white solid. MS: m/e=399.1 [M+H]⁺.

Example 366

6-[3-(5-Fluoro-pyridin-2-yl)-isoxazol-4-ylmethoxy]-isopropyl-nicotinamide

As described for example 365f, 6-[3-(5-fluoro-pyridin-2-yl)-isoxazol-4-ylmethoxy]-nicotinic acid (79 mg, 0.25 mmol) was converted, using isopropylamine instead of 4-aminotetrayhdropyran, to the title compound (67 mg, 75%) which was obtained as an off white solid. MS: m/e=357.1 [M+H]⁺.

Example 367

Cyclopropyl-6-[3-(5-fluoro-pyridin-2-yl)-isoxazol-4-ylmethoxy]-nicotinamide

As described for example 365f, 6-[3-(5-fluoro-pyridin-2-yl)-isoxazol-4-ylmethoxy]-nicotinic acid (79 mg, 0.25 mmol) was converted, using cyclopropylamine instead of 4-aminotetrayhdropyran, to the title compound (64 mg, 73%) which was obtained as a white solid. MS: m/e=355.2 [M+H]⁺.

Example 368

6-[3-(5-Fluoro-pyridin-2-yl)-isoxazol-4-ylmethoxy]-(2-hydroxy-1,1-dimethyl-ethyl)-nicotinamide As described for example 365f, 6-[3-(5-fluoro-pyridin-2-yl)-isoxazol-4-ylmethoxy]-nicotinic acid (79 mg, 0.25 mmol) was converted, using 2-amino-2-methyl-1-propanol instead of 4-aminotetrayhdropyran, to the title compound (60 mg, 62%) which was obtained as a white solid. MS: m/e=387.2 [M+H]⁺.

Example 369

6-[3-(5-Fluoro-pyridin-2-yl)-isoxazol-4-ylmethoxy]-(2,2,2-trifluoro-ethyl)-nicotinamide As described for example 365f, 6-[3-(5-fluoro-pyridin-2-yl)-isoxazol-4-ylmethoxy]-nicotinic acid (79 mg, 0.25 mmol) was converted, using 2-amino-2-methyl-1-propanol instead of 4-aminotetrayhdropyran, to the title compound (80 mg, 81%) which was obtained as a white solid. MS: m/e=397.1 [M+H]⁺.

Example 370

6-[3-(5-Fluoro-pyridin-2-yl)-isoxazol-4-ylmethoxy]-(2-hydroxy-ethyl)-nicotinamide As described for example 365f, 6-[3-(5-fluoro-pyridin-2-yl)-isoxazol-4-ylmethoxy]-nicotinic acid (79 mg, 0.25 mmol) was converted, using aminoethanol instead of 4-aminotetrayhdropyran, to the title compound (34 mg, 38%) which was obtained as a white solid. MS: m/e=359.1 [M+H]⁺.

Example 371

Ethyl-6-[3-(5-fluoro-pyridin-2-yl)-isoxazol-4-ylmethoxy]-nicotinamide

As described for example 365f, 6-[3-(5-fluoro-pyridin-2-yl)-isoxazol-4-ylmethoxy]-nicotinic acid (79 mg, 0.25 mmol) was converted, using ethylamine (2 M solution in THF) instead of 4-aminotetrayhdropyran, to the title compound (52 mg, 61%) which was obtained as a white solid. MS: m/e=343.1 [M+H]⁺.

Example 372

6-[3-(5-Fluoro-pyridin-2-yl)-isoxazol-4-ylmethoxy]-methyl-nicotinamide

As described for example 365f, 6-[3-(5-fluoro-pyridin-2-yl)-isoxazol-4-ylmethoxy]-nicotinic acid (79 mg, 0.25 mmol) was converted, using methylamine (2 M solution in THF) instead of 4-aminotetrayhdropyran, to the title compound (55 mg, 67%) which was obtained as a white solid. MS: m/e=329.2 [M+H]⁺.

We claim:
1. A compound of formula I

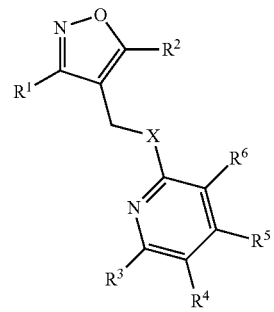

wherein
X is O or NH;
$R^1$ is pyridinyl, optionally substituted with 1, 2 or 3 halo,
$R^2$ is H or $CH_3$ or $CF_3$;
$R^3$, $R^5$ and $R^6$ are H;
$R^4$ is H,
$C_{1-7}$alkyl, optionally substituted with one or more halo, cyano, or hydroxy,
$C_{1-7}$alkoxy, optionally substituted with one or more halo,
CN,
halo,
$NO_2$,
S—$C_{1-7}$alkyl,
S(O)—$C_{1-7}$alkyl
benzyloxy, optionally substituted with one or more E,
—C(O)—$R^a$, wherein $R^a$ is hydroxy, $C_{1-7}$alkoxy, $C_{1-7}$alkyl, phenoxy or phenyl,
3- to 7-membered heterocyclyl, optionally substituted with one or more A,
—C(O)—$NR^bR^c$, wherein $R^b$ and $R^c$ are each independently
H,
$C_{1-7}$alkyl, optionally substituted with one or more halo, methyl, —$(CH_2)_t$-hydroxy, or cyano,
—$(CH_2)_t$—$C_{3-7}$cycloalkyl, optionally substituted by one or more B,
and t is 0, 1, 2, 3, 4, 5 or 6,
—$(CH_2)_u$—O—$C_{1-7}$alkyl, wherein u is 2, 3, 4, 5 or 6,
—$CHR^i$—C(O)$OR^{ii}$, wherein $R^i$ is H, benzyl or $C_{1-4}$alkyl, and $R^{ii}$ is H or $C_{1-7}$alkyl,
—$S(O)_2$—$C_{3-7}$cycloalkyl,
—$(CH_2CH_2O)_vR^{iii}$, wherein v is from 1 to 3, and $R^{iii}$ is H or $C_{1-7}$alkyl, —(CH$_2$)$_w$-heteroaryl or —(CH$_2$)$_w$-aryl, each optionally substituted by one or more E, and wherein w is 0, 1, 2, 3, or 4,
—(CH$_2$)$_x$-heterocyclyl, wherein x is 0, 1, 2, 3 or 4, and wherein heterocyclyl is optionally substituted by one or more
oxo,
C$_{1-7}$alkyl,
C$_{3-7}$cycloalkyl, optionally substituted with one or more B,
CN,
benzyl, optionally substituted with one or more E,
—(CH$_2$)$_y$—C(O)R$^{iv}$, wherein y is 0, 1, 2, 3 or 4, and R$^{iv}$ is hydroxy, or C$_{1-7}$alkoxy,
—(CH$_2$)$_z$—C(O)NR$^v$R$^{vi}$, —(CH$_2$)$_z$NR$^v$R$^{vi}$—C(O)—C$_{1-7}$alkyl or —(CH$_2$)$_z$NR$^v$R$^{vi}$—C(O)—O—C$_{1-7}$alkyl, wherein z is 0, 1, 2, 3 or 4,
and R$^v$ and R$^{vi}$ are independently
hydrogen,
C$_{1-7}$alkyl, optionally substituted by one or more halo, OH or CN,
C$_{3-7}$cycloalkyl, optionally substituted by one or more B,
5- or 6-membered heterocyclyl, optionally substituted by one or more A, or
R$^v$ and R$^{vi}$ together with the nitrogen to which they are bound form a 5- or 6-membered heterocycloalkyl, optionally substituted by one or more A, or
R$^b$ and R$^c$ together with the nitrogen to which they are bound form a heterocyclyl or heteroaryl moiety, optionally substituted with one or more A, or
R$^b$ and R$^c$ together with the nitrogen to which they are bound form a 7- to 12-membered spirocyclic heterocycle, optionally substituted with one or more A;
with the proviso that R$^b$ and R$^c$ are not simultaneously H,
A is hydroxy, oxo, C$_{1-7}$alkyl, C$_{1-7}$alkoxy, C$_{1-7}$hydroxyalkyl, halo, or CN;
B is halo, hydroxy, CN, C$_{1-4}$alkyl, benzyloxy, or C$_{1-4}$haloalkyl; and
E is halo, CN, NO$_2$, hydroxy, C$_{1-7}$alkyl, C$_{1-7}$alkoxy, C$_{1-7}$haloalkyl,
C$_{1-7}$hydroxyalkyl, C$_{1-7}$cyanoalkyl, C$_{1-7}$ haloalkoxy, or C$_{3-7}$cycloalkyl;
or a pharmaceutically acceptable salt thereof.

2. The compound of claim 1, wherein R$^3$ and R$^6$ are H, halo, CN or C$_{1-7}$alkyl.

3. The compound of claim 1, wherein R$^4$ is
H,
C$_{1-7}$alkyl, optionally substituted with one or more halo, cyano, or hydroxy,
C$_{1-7}$alkoxy, optionally substituted with one or more halo, CN,
halo,
NO$_2$,
S—C$_{1-7}$alkyl,
S(O)—C$_{1-7}$alkyl
benzyloxy, optionally substituted with one or more E,
—C(O)—R$^a$, wherein R$^a$ is hydroxy, C$_{1-7}$alkoxy, C$_{1-7}$alkyl, phenoxy or phenyl,
3- to 7-membered heterocyclyl, optionally substituted with one or more A,
—C(O)—NR$^b$R$^c$, wherein R$^b$ and R$^c$ are each independently
H,
C$_{1-7}$alkyl, optionally substituted with one or more halo, methyl, —(CH$_2$)$_t$-hydroxy, or cyano,
—(CH$_2$)$_t$—C$_{3-7}$cycloalkyl, optionally substituted by one or more B, and t is 0, 1, 2, 3, 4, 5 or 6,
—(CH$_2$)$_u$—O—C$_{1-7}$alkyl, wherein u is 2, 3, 4, 5 or 6,
—CHR$^i$—C(O)OR$^{ii}$, wherein R$^i$ is H, benzyl or C$_{1-4}$alkyl, and R$^{ii}$ is H or C$_{1-7}$alkyl,
—S(O)$_2$—C$_{1-7}$alkyl
—S(O)$_2$—C$_{3-7}$cycloalkyl
—(CH$_2$CH$_2$O)$_v$R$^{iii}$, wherein v is from 1 to 3, and R$^{iii}$ is H or C$_{1-7}$alkyl,
—(CH$_2$)$_w$-heteroaryl or —(CH$_2$)$_w$-aryl, each optionally substituted by one or more E, and wherein w is 0, 1, 2, 3, or 4,
—(CH$_2$)$_x$-heterocyclyl, wherein x is 0, 1, 2, 3 or 4, and wherein heterocyclyl is optionally substituted by one or more
oxo,
C$_{1-7}$alkyl,
C$_{3-7}$cycloalkyl, optionally substituted with one or more B,
CN,
benzyl, optionally substituted with one or more E,
—(CH$_2$)$_y$—C(O)R$^{iv}$, wherein y is 0, 1, 2, 3 or 4, and R$^{iv}$ is hydroxy, C$_{1-7}$alkyl, or C$_{1-7}$alkoxy,
—(CH$_2$)$_z$—C(O)NR$^v$R$^{vi}$, —(CH$_2$)$_z$NR$^v$R$^{vi}$—C(O)—C$_{1-7}$alkyl or (CH$_2$)$_z$NR$^v$R$^{vi}$—C(O)—O—C$_{1-7}$alkyl, wherein z is 0, 1, 2, 3 or 4
and R$^v$ and R$^{vi}$ are independently
hydrogen,
C$_{1-7}$alkyl, optionally substituted by one or more halo, OH or CN,
C$_{3-7}$cycloalkyl, optionally substituted by one or more B,
5- or 6-membered heterocyclyl, optionally substituted by one or more A, or
R$^v$ and R$^{vi}$ together with the nitrogen to which they are bound form a 5- or 6-membered heterocycloalkyl, optionally substituted by one or more A, or
R$^b$ and R$^c$ together with the nitrogen to which they are bound form a heterocyclyl or heteroaryl moiety, optionally substituted with one or more A, or
R$^b$ and R$^c$ together with the nitrogen to which they are bound form a 7- to 12-membered spirocyclic heterocycle, optionally substituted with one or more A;
with the proviso that R$^b$ and R$^c$ are not simultaneously H,
A is hydroxy, oxo, C$_{1-7}$alkyl, C$_{1-7}$alkoxy, C$_{1-7}$ haloalkyl, C$_{1-7}$hydroxyalkyl, halo, or CN;
B is halo, hydroxy, CN, C$_{1-4}$alkyl, benzyloxy, or C$_{1-4}$haloalkyl; and
E is halo, CN, NO$_2$, hydroxy, C$_{1-7}$alkyl, C$_{1-7}$alkoxy, C$_{1-7}$haloalkyl, C$_{1-7}$hydroxyalkyl, C$_{1-7}$cyanoalkyl, C$_{1-7}$ haloalkoxy, or C$_{3-7}$cycloalkyl;
or a pharmaceutically acceptable salt thereof.

4. The compound of claim 1, wherein R$^4$ is
—C(O)—NR$^b$R$^c$, wherein R$^b$ and R$^c$ are each independently
H,
C$_{1-7}$ alkyl, optionally substituted with one or more halo, methyl, —(CH$_2$)$_t$-hydroxy, or cyano,
—(CH$_2$)$_t$—C$_{3-7}$cycloalkyl, optionally substituted by one or more B, and t is 0, 1, 2, 3, 4, 5 or 6,
—(CH$_2$)$_u$—O—C$_{1-7}$alkyl, wherein u is 2, 3, 4, 5 or 6,
—CHR$^i$—C(O)OR$^{ii}$, wherein R$^i$ is H, benzyl or C$_{1-4}$alkyl, and R$^{ii}$ is H or C$_{1-7}$alkyl,
—S(O)$_2$—C$_{1-7}$alkyl,
—S(O)$_2$—C$_{3-7}$cycloalkyl,
—(CH$_2$CH$_2$O)$_v$R$^{iii}$, wherein v is from 1 to 3, and R$^{iii}$ is H or C$_{1-7}$alkyl, —(CH$_2$)$_w$-heteroaryl or —(CH$_2$)$_w$-aryl, each optionally substituted by one or more E, and wherein w is 0, 1, 2, 3, or 4, —(CH$_2$)$_x$-heterocyclyl, wherein x is 0, 1, 2, 3 or 4, and wherein heterocyclyl is optionally substituted by one or more oxo, C$_{1-7}$alkyl, C$_{3-7}$cycloalkyl, optionally substituted with one or more B,

CN, benzyl, optionally substituted with one or more E,

—(CH$_2$)$_y$—C(O)R$^{iv}$, wherein y is 0, 1, 2, 3 or 4, and R$^{iv}$ is hydroxy, C$_{1-7}$alkyl, or C$_{1-7}$alkoxy, —(CH$_2$)$_z$—C(O)NR'R$^{vi}$, —(CH$_2$)$_z$NR'R$^{vi}$—C(O)—C$_{1-7}$alkyl or —(CH$_2$)$_z$NR'R$^{vi}$—C(O)—O—C$_{1-7}$alkyl, wherein z is 0, 1, 2, 3 or 4, and R$^v$ and R$^{vi}$ are independently hydrogen, C$_{1-7}$alkyl, optionally substituted by one or more halo, OH or CN, C$_{3-7}$cycloalkyl, optionally substituted by one or more B, 5- or 6-membered heterocyclyl, optionally substituted by one or more A, or R$^v$ and R$^{vi}$ together with the nitrogen to which they are bound form a 5- or 6-membered heterocycloalkyl, optionally substituted by one or more A, or R$^b$ and R$^c$ together with the nitrogen to which they are bound form a heterocyclyl or heteroaryl moiety, optionally substituted with one or more A, or R$^b$ and R$^c$ together with the nitrogen to which they are bound form a 7- to 12-membered spirocyclic heterocycle, optionally substituted with one or more A with the proviso that R$^b$ and R$^c$ are not simultaneously H, A is hydroxy, oxo, C$_{1-7}$alkyl, C$_{1-7}$alkoxy, C$_{1-7}$ haloalkyl, C$_{1-7}$hydroxyalkyl, halo, or CN;

B is halo, hydroxy, CN, C$_{1-4}$ alkyl, benzyloxy, or C$_{1-4}$ haloalkyl; and

E is halo, CN, NO$_2$, hydroxy, C$_{1-7}$alkyl, C$_{1-7}$alkoxy, C$_{1-7}$ haloalkyl, C$_{1-7}$hydroxyalkyl, C$_{1-7}$cyanoalkyl, C$_{1-7}$ haloalkoxy, or C$_{3-7}$cycloalkyl;

or a pharmaceutically acceptable salt thereof.

5. The compound of claim 1, wherein R$^4$ is

H,

C$_{1-7}$alkyl, optionally substituted with one or more halo, cyano, or hydroxy, C$_{1-7}$alkoxy, optionally substituted with one or more halo,

CN, halo,

NO$_2$,

S—C$_{1-7}$alkyl,

S(O)—C$_{1-7}$alkyl, or benzyloxy, optionally substituted with one or more E, and E is halo, CN, NO$_2$, hydroxy, C$_{1-7}$alkyl, C$_{1-7}$alkoxy, C$_{1-7}$ haloalkyl, C$_{1-7}$hydroxyalkyl, C$_{1-7}$cyanoalkyl, C$_{1-7}$ haloalkoxy, or C$_{3-7}$cycloalkyl;

or a pharmaceutically acceptable salt thereof.

6. The compound of claim 1, wherein R$^4$ is

—C(O)—R$^a$, wherein R$^a$ is hydroxy, C$_{1-7}$alkoxy, C$_{1-7}$alkyl, phenoxy or phenyl.

7. The compound of claim 1, wherein R$^4$ is benzyloxy optionally substituted with one or more E and E is halo, CN, NO$_2$, hydroxy, C$_{1-7}$alkyl, C$_{1-7}$alkoxy, C$_{1-7}$ haloalkyl, C$_{1-7}$hydroxyalkyl, C$_{1-7}$cyanoalkyl, C$_{1-7}$ haloalkoxy, or C$_{3-7}$cycloalkyl.

8. The compound of claim 1, wherein R$^4$ is 3- to 7-membered heterocyclyl, optionally substituted with one or more A, wherein A is hydroxy, oxo, C$_{1-7}$alkyl, C$_{1-7}$alkoxy, C$_{1-7}$ haloalkyl, C$_{1-7}$hydroxyalkyl, halo, or CN;

or a pharmaceutically acceptable salt thereof.

9. The compound of claim 1, wherein R$^4$ is oxethenanyl substituted with one OH.

10. The compound of claim 1, wherein R$^5$ is

H,

C$_{1-7}$alkyl, optionally substituted by one or more halo, hydroxy or CN, benzyloxy, optionally substituted with one or more E, 3- to 7-membered heterocyclyl, optionally substituted with one or more A, —C(O)—NR$^b$R$^c$, wherein R$^b$ and R$^c$ are each independently H, or 3-7-membered heterocycloalkyl, optionally substituted with one or more A, and A is hydroxy, oxo, C$_{1-7}$alkyl, C$_{1-7}$alkoxy, C$_{1-7}$ haloalkyl, C$_{1-7}$hydroxyalkyl, halo, or CN;

E is halo, CN, NO$_2$, hydroxy, C$_{1-7}$alkyl, C$_{1-7}$alkoxy, C$_{1-7}$ haloalkyl, C$_{1-7}$hydroxyalkyl, C$_{1-7}$cyanoalkyl, C$_{1-7}$ haloalkoxy, or C$_{3-7}$cycloalkyl.

11. The compound of claim 10, wherein R$^5$ is H or trifluoromethyl.

12. The compound of claim 1, wherein R$^4$ is H.

13. The compound of claim 1, wherein R$^4$ is CN.

14. The compound of claim 1, wherein R$^4$ is halo.

15. The compound of claim 1, wherein R$^4$ is NO$_2$.

16. The compound of claim 1, wherein R$^1$ is phenyl optionally substituted with one or two halo.

17. The compound of claim 1, wherein R$^2$ is methyl or trifluoromethyl.

18. The compound of claim 1, wherein R$^3$ is H, halo, CN, or C$_{1-7}$alkyl.

19. The compound of claim 18, wherein R$^3$ is H, CN, or C$_{1-4}$alkyl.

20. The compound of claim 19, wherein R$^3$ is H, CN, or methyl.

21. The compound of claim 1, wherein R$^6$ is H, halo, CN, or C$_{1-7}$alkyl.

22. The compound of claim 21, wherein R$^6$ is H, halo, or C$_{1-4}$alkyl.

23. The compound of claim 22, wherein R$^6$ is H, Br, or C$_{1-4}$alkyl.

24. The compound of claim 23, wherein R$^6$ is H, Br or methyl.

25. The compound of claim 1, wherein R$^4$ is C(O)NR$^b$R$^c$, wherein R$^b$ and R$^c$ together with the N to which they are bound form a heterocyclyl moiety optionally substituted with one or more A.

26. The compound of claim 1, wherein R$^4$ is C(O)NR$^b$R$^c$, wherein R$^b$ and R$^c$ together with the N to which they are bound form a 7- to 12-membered spirocyclic heterocycle optionally substituted with one or more A.

27. The compound of claim 1, wherein R$^3$, R$^4$, R$^5$, and R$^6$ are not simultaneously H.

28. The compound of claim 1, selected from the group consisting of:

6-(5-methyl-3-pyridin-4-yl-isoxazol-4-ylmethoxy)-N-(2,2,2-trifluoro-ethyl)-nicotinamide;

N-cyclopropylmethyl-6-(5-methyl-3-pyridin-4-yl-isoxazol-4-ylmethoxy)-nicotinamide;

N-cyclopropyl-6-(5-methyl-3-pyridin-4-yl-isoxazol-4-yl-methoxy)-nicotinamide;

N-isopropyl-6-(5-methyl-3-pyridin-4-yl-isoxazol-4-yl-methoxy)-nicotinamide;
6-(5-methyl-3-pyridin-4-yl-isoxazol-4-ylmethoxy)-N-(tetrahydro-pyran-4-yl)-nicotinamide;
[6-(5-methyl-3-pyridin-4-yl-isoxazol-4-ylmethoxy)-pyridin-3-yl]-morpholin-4-yl-methanone;
[6-(5-methyl-3-pyridin-4-yl-isoxazol-4-ylmethoxy)-pyridin-3-yl]-thiomorpholin-4-yl-methanone;
(1,1-dioxo-1λ6-thiomorpholin-4-yl)-[6-(5-methyl-3-pyridin-4-yl-isoxazol-4-ylmethoxy)-pyridin-3-yl]-methanone;
6-(5-methyl-3-pyridin-3-yl-isoxazol-4-ylmethoxy)-nicotinic acid methyl ester;
6-(5-methyl-3-pyridin-3-yl-isoxazol-4-ylmethoxy)-N-(2,2,2-trifluoro-ethyl)-nicotinamide;
N-cyclopropylmethyl-6-(5-methyl-3-pyridin-3-yl-isoxazol-4-ylmethoxy)-nicotinamide;
N-cyclopropyl-6-(5-methyl-3-pyridin-3-yl-isoxazol-4-ylmethoxy)-nicotinamide and a pharmaceutically acceptable salt or ester thereof.

29. The compound of claim 1, selected from the group consisting of:
N-isopropyl-6-(5-methyl-3-pyridin-3-yl-isoxazol-4-ylmethoxy)-nicotinamide;
6-(5-methyl-3-pyridin-3-yl-isoxazol-4-ylmethoxy)-N-(tetrahydro-pyran-4-yl)-nicotinamide;
6-(5-methyl-3-pyridin-2-yl-isoxazol-4-ylmethoxy)-nicotinic acid methyl ester;
6-(5-methyl-3-pyridin-2-yl-isoxazol-4-ylmethoxy)-N!-(tetrahydro-pyran-4-yl)-nicotinamide;
N!-isopropyl-6-(5-methyl-3-pyridin-2-yl-isoxazol-4-ylmethoxy)-nicotinamide;
[6-(5-methyl-3-pyridin-2-yl-isoxazol-4-ylmethoxy)-pyridin-3-yl]-morpholin-4-yl-methanone;
6-(5-methyl-3-pyridin-2-yl-isoxazol-4-ylmethoxy)-#N!-(2, 2, 2-trifluoro-ethyl)-nicotinamide;
(1,1-dioxo-1$l%6&-thiomorpholin-4-yl)-[6-(5-methyl-3-pyridin-2-yl-isoxazol-4-ylmethoxy)-pyridin-3-yl]-methanone;
N!-cyclopropylmethyl-6-(5-methyl-3-pyridin-2-yl-isoxazol-4-ylmethoxy)-nicotinamide;
N!-cyclopropyl-6-(5-methyl-3-pyridin-2-yl-isoxazol-4-ylmethoxy)-nicotinamide;
Methyl-6-(5-methyl-3-pyridin-2-yl-isoxazol-4-ylmethoxy)-nicotinamide;
Ethyl-6-(5-methyl-3-pyridin-2-yl-isoxazol-4-ylmethoxy)-nicotinamide;
(2-hydroxy-1,1-dimethyl-ethyl)-6-(5-methyl-3-pyridin-2-yl-isoxazol-4-ylmethoxy)-nicotinamide;
[6-(5-methyl-3-pyridin-2-yl-isoxazol-4-ylmethoxy)-pyridin-3-yl]-thiomorpholin-4-yl-methanone;
6-(5-methyl-3-pyridin-2-yl-isoxazol-4-ylmethoxy)-nicotinic acid;
(2-hydroxy-ethyl)-6-(5-methyl-3-pyridin-2-yl-isoxazol-4-ylmethoxy)-nicotinamide;
(2-methoxy-ethyl)-6-(5-methyl-3-pyridin-2-yl-isoxazol-4-ylmethoxy)-nicotinamide;
6-[3-(5-fluoro-pyridin-2-yl)-5-methyl-isoxazol-4-ylmethoxy]-nicotinic acid methyl ester and
a pharmaceutically acceptable salt or ester thereof.

30. The compound of claim 1, selected from the group consisting of:
6-[3-(5-fluoro-pyridin-2-yl)-5-methyl-isoxazol-4-ylmethoxy]-nicotinic acid;
6-[3-(5-fluoro-pyridin-2-yl)-5-methyl-isoxazol-4-ylmethoxy]-(tetrahydro-pyran-4-yl)-nicotinamide;
6-[3-(5-fluoro-pyridin-2-yl)-5-methyl-isoxazol-4-ylmethoxy]-isopropyl-nicotinamide;
Cyclopropyl-6-[3-(5-fluoro-pyridin-2-yl)-5-methyl-isoxazol-4-ylmethoxy]-nicotinamide;
6-[3-(5-fluoro-pyridin-2-yl)-5-methyl-isoxazol-4-ylmethoxy](2-hydroxy-1,1-dimethyl-ethyl)-nicotinamide;
Cyclopropylmethyl-6-[3-(5-fluoro-pyridin-2-yl)-5-methyl-isoxazol-4-ylmethoxy]-nicotinamide;
(1,1-dioxo-1$l%6&-thiomorpholin-4-yl)-{6-[3-(5-fluoro-pyridin-2-yl)-5-methyl-isoxazol-4-ylmethoxy]-pyridin-3-yl}-methanone;
6-[3-(5-fluoro-pyridin-2-yl)-5-methyl-isoxazol-4-ylmethoxy]-2,2,2-trifluoro-ethyl)-nicotinamide;
6-[3-(5-fluoro-pyridin-2-yl)-5-methyl-isoxazol-4-ylmethoxy]-(2-hydroxy-ethyl)-nicotinamide;
{6-[3-(5-fluoro-pyridin-2-yl)-5-methyl-isoxazol-4-ylmethoxy]-pyridin-3-yl}-morpholin-4-yl-methanone;
Ethyl-6-[3-(5-fluoro-pyridin-2-yl)-5-methyl-isoxazol-4-ylmethoxy]-nicotinamide;
6-[3-(5-fluoro-pyridin-2-yl)-5-methyl-isoxazol-4-ylmethoxy]-methyl-nicotinamide;
6-[3-(5-fluoro-pyridin-2-yl)-5-methyl-isoxazol-4-ylmethoxy]-#N!-((S)-2,2,2-trifluoro-1-methyl-ethyl)-nicotinamide;
6-[3-(5-chloro-pyridin-2-yl)-5-methyl-isoxazol-4-ylmethoxy]-nicotinic acid methyl ester;
6-[3-(5-chloro-pyridin-2-yl)-5-methyl-isoxazol-4-ylmethoxy]-(tetrahydro-pyran-4-yl)-nicotinamide;
6-[3-(5-chloro-pyridin-2-yl)-5-methyl-isoxazol-4-ylmethoxy]-isopropyl-nicotinamide;
6-[3-(5-chloro-pyridin-2-yl)-5-methyl-isoxazol-4-ylmethoxy]-cyclopropyl-nicotinamide;
6-[3-(5-chloro-pyridin-2-yl)-5-methyl-isoxazol-4-ylmethoxy]-nicotinic acid and
a pharmaceutically acceptable salt or ester thereof.

31. The compound of claim 1, selected from the group consisting of:
6-[3-(5-chloro-pyridin-2-yl)-5-methyl-isoxazol-4-ylmethoxy]-(2-hydroxy-1,1-dimethyl-ethyl)-nicotinamide;
6-[3-(5-chloro-pyridin-2-yl)-5-methyl-isoxazol-4-ylmethoxy]-cyclopropylmethyl-nicotinamide;
{6-[3-(5-chloro-pyridin-2-yl)-5-methyl-isoxazol-4-ylmethoxy]-pyridin-3-yl}-(1,1-dioxo-1$l%6&-thiomorpholin-4-yl)-methanone;
6-[3-(5-chloro-pyridin-2-yl)-5-methyl-isoxazol-4-ylmethoxy]-(2,2,2-trifluoro-ethyl)-nicotinamide;
{6-[3-(5-chloro-pyridin-2-yl)-5-methyl-isoxazol-4-ylmethoxy]-pyridin-3-yl}-morpholin-4-yl-methanone;
{6-[3-(5-chloro-pyridin-2-yl)-5-methyl-isoxazol-4-ylmethoxy]-pyridin-3-yl}-thiomorpholin-4-yl-methanone;
6-[3-(5-chloro-pyridin-2-yl)-5-methyl-isoxazol-4-ylmethoxy]-(2-hydroxy-ethyl)-nicotinamide;
6-(3-pyridin-2-yl-isoxazol-4-ylmethoxy)-N-(tetrahydro-pyran-4-yl)-nicotinamide;
N-isopropyl-6-(3-pyridin-2-yl-isoxazol-4-ylmethoxy)-nicotinamide;
N-cyclopropyl-6-(3-pyridin-2-yl-isoxazol-4-ylmethoxy)-nicotinamide;
N-cyclopropylmethyl-6-(3-pyridin-2-yl-isoxazol-4-ylmethoxy)-nicotinamide;
6-(3-pyridin-2-yl-isoxazol-4-ylmethoxy)-N-(2,2,2-trifluoro-ethyl)-nicotinamide;
N-(2-hydroxy-ethyl)-6-(3-pyridin-2-yl-isoxazol-4-ylmethoxy)-nicotinamide;

N-ethyl-6-(3-pyridin-2-yl-isoxazol-4-ylmethoxy)-nicotinamide;
6-[3-(5-fluoro-pyridin-2-yl)-isoxazol-4-ylmethoxy]-(tetrahydro-pyran-4-yl)-nicotinamide;
6-[3-(5-fluoro-pyridin-2-yl)-isoxazol-4-ylmethoxy]-isopropyl-nicotinamide;
Cyclopropyl-6-[3-(5-fluoro-pyridin-2-yl)-isoxazol-4-ylmethoxy]-nicotinamide;
6-[3-(5-fluoro-pyridin-2-yl)-isoxazol-4-ylmethoxy]-(2-hydroxy-1,1-dimethyl-ethyl)-nicotinamide and
a pharmaceutically acceptable salt or ester thereof.

32. The compound of claim 1, selected from the group consisting of:
6-[3-(5-fluoro-pyridin-2-yl)-isoxazol-4-ylmethoxy]-(2,2,2-trifluoro-ethyl)-nicotinamide;
6-[3-(5-fluoro-pyridin-2-yl)-isoxazol-4-ylmethoxy]-(2-hydroxy-ethyl)-nicotinamide;
Ethyl-6-[3-(5-fluoro-pyridin-2-yl)-isoxazol-4-ylmethoxy]-nicotinamide;
6-[3-(5-fluoro-pyridin-2-yl)-isoxazol-4-ylmethoxy]-methyl-nicotinamide and
a pharmaceutically acceptable salt or ester thereof.

33. The compound of claim 1 wherein said compound is {6-[3-(4-chloro-phenyl)-5-methyl-isoxazol-4-ylmethoxy]-pyridin-3-yl}-morpholin-4-yl-methanone or a pharmaceutically acceptable salt thereof.

34. The compound of claim 1 wherein said compound is [6-(5-methyl-3-pyridin-2-yl-isoxazol-4-ylmethoxy)-pyridin-3-yl]-morpholin-4-yl-methanone or a pharmaceutically acceptable salt thereof.

35. The compound of claim 1 wherein said compound is (1,1-dioxo-1,6-thiomorpholin-4-yl)-{6-[3-(5-fluoro-pyridin-2-yl)-5-methyl-isoxazol-4-ylmethoxy]-pyridin-3-yl}-methanone or a pharmaceutically acceptable salt thereof.

36. The compound of claim 1 wherein said compound is {6-[3-(5-chloro-pyridin-2-yl)-5-methyl-isoxazol-4-ylmethoxy]-pyridin-3-yl}-thiomorpholin-4-yl-methanone or a pharmaceutically acceptable salt thereof.

* * * * *